(12) United States Patent
Park et al.

(10) Patent No.: US 10,573,819 B2
(45) Date of Patent: Feb. 25, 2020

(54) COMPOUND FOR ORGANIC ELECTRONIC ELEMENT, ORGANIC ELECTRONIC ELEMENT COMPRISING THE SAME, AND ELECTRONIC DEVICE THEREOF

(71) Applicant: DUK SAN NEOLUX CO., LTD., Cheonan-si, Chungcheongnam-do (KR)

(72) Inventors: Jonggwang Park, Ulsan (KR); Yeon Hee Choi, Cheonan-si (KR); Yun Suk Lee, Seongnam-si (KR); Kiho So, Cheonan-si (KR); Hyoung Keun Park, Chuncheon-si (KR); Yeonseok Jeong, Gangwon-do (KR); Hak Young Lee, Cheonan-si (KR)

(73) Assignee: DUK SAN NEOLUX CO., LTD., Cheonan-si, Chungcheongnam-do (KR)

( * ) Notice: Subject to any disclaimer, the term of this patent is extended or adjusted under 35 U.S.C. 154(b) by 283 days.

(21) Appl. No.: 15/475,697

(22) Filed: Mar. 31, 2017

(65) Prior Publication Data
US 2017/0288148 A1  Oct. 5, 2017

(30) Foreign Application Priority Data

Apr. 1, 2016 (KR) .................. 10-2016-0039940
Aug. 30, 2016 (KR) .................. 10-2016-0110817

(51) Int. Cl.
| | | |
|---|---|---|
| H01L 51/00 | (2006.01) |
| C07D 333/76 | (2006.01) |
| C09K 11/06 | (2006.01) |
| C07D 487/06 | (2006.01) |
| C07D 409/12 | (2006.01) |
| C07D 409/14 | (2006.01) |
| H01L 51/50 | (2006.01) |

(52) U.S. Cl.
CPC ........ *H01L 51/0061* (2013.01); *C07D 333/76* (2013.01); *C07D 409/12* (2013.01); *C07D 409/14* (2013.01); *C07D 487/06* (2013.01); *C09K 11/06* (2013.01); *H01L 51/006* (2013.01); *H01L 51/0054* (2013.01); *H01L 51/0067* (2013.01); *H01L 51/0068* (2013.01); *H01L 51/0072* (2013.01); *H01L 51/0073* (2013.01); *H01L 51/0074* (2013.01); *C09K 2211/1022* (2013.01); *C09K 2211/1088* (2013.01); *C09K 2211/1092* (2013.01); *H01L 51/5056* (2013.01)

(58) Field of Classification Search
CPC .. C07D 333/76; C07D 409/12; C07D 409/14; C07D 487/06; C09K 11/06; C09K 2211/1022; C09K 2211/1037; C09K 2211/1044; C09K 2211/1088; C09K 2211/1092; H01L 51/0054; H01L 51/0059; H01L 51/006; H01L 51/0061; H01L 51/0067; H01L 51/0068; H01L 51/0072; H01L 51/0073; H01L 51/0074; H01L 51/0081; H01L 51/0085; H01L 51/5056; H01L 51/5064; Y02E 10/549
See application file for complete search history.

(56) References Cited

U.S. PATENT DOCUMENTS

| | | | | |
|---|---|---|---|---|
| 2003/0118866 A1* | 6/2003 | Oh | ............. | H01L 51/0058 428/690 |
| 2012/0298966 A1* | 11/2012 | Zeng | ............. | C07F 7/08 257/40 |
| 2013/0069049 A1* | 3/2013 | Park | ............. | C07D 487/04 257/40 |
| 2015/0380659 A1* | 12/2015 | Ryu | ............. | H01L 51/0059 257/40 |
| 2016/0351816 A1* | 12/2016 | Kim | ............. | H01L 51/0052 |
| 2016/0351817 A1* | 12/2016 | Kim | ............. | H01L 51/0052 |
| 2017/0033289 A1* | 2/2017 | Fuchiwaki | ............. | C07C 211/54 |

FOREIGN PATENT DOCUMENTS

| | | | |
|---|---|---|---|
| CN | 107925008 A | | 4/2018 |
| JP | 2015-147905 A | * | 8/2015 |
| JP | 2016-102858 A | * | 6/2016 |
| KR | 10-2010-0123172 A | | 11/2010 |
| KR | 20130024521 A | * | 3/2013 |
| WO | WO 2016/175533 | * | 3/2016 |

OTHER PUBLICATIONS

Machine translation for WO 2016/175533, publication date Mar. 2016. (Year: 2016).*
Machine translation for JP 2016-102858 A, publication date Jun. 2016. (Year: 2016).*
Machine translation for JP 2015-147905 A, publication date Aug. 2015. (Year: 2015).*
Machine translation for KR 20130024521 A, publication date Mar. 2013 (Year: 2013).*
Chinese Office Action dated May 23, 2019, for corresponding Chinese Patent Application 201710209369.7, 10 pages.

* cited by examiner

*Primary Examiner* — Dawn L Garrett
(74) *Attorney, Agent, or Firm* — Vorys, Sater, Seymour and Pease LLP; Mih Suhn Koh

(57) ABSTRACT

Provided are a compound of Formula 1 and an organic electric element comprising a first electrode, a second electrode, and an organic material layer formed between the first electrode and the second electrode, and electronic device comprising the organic electric element, wherein the driving voltage of the organic electronic device can be lowered, and the luminous efficiency and life span can be improved by comprising the compound represented by Formula 1 in the organic material layer.

13 Claims, 1 Drawing Sheet

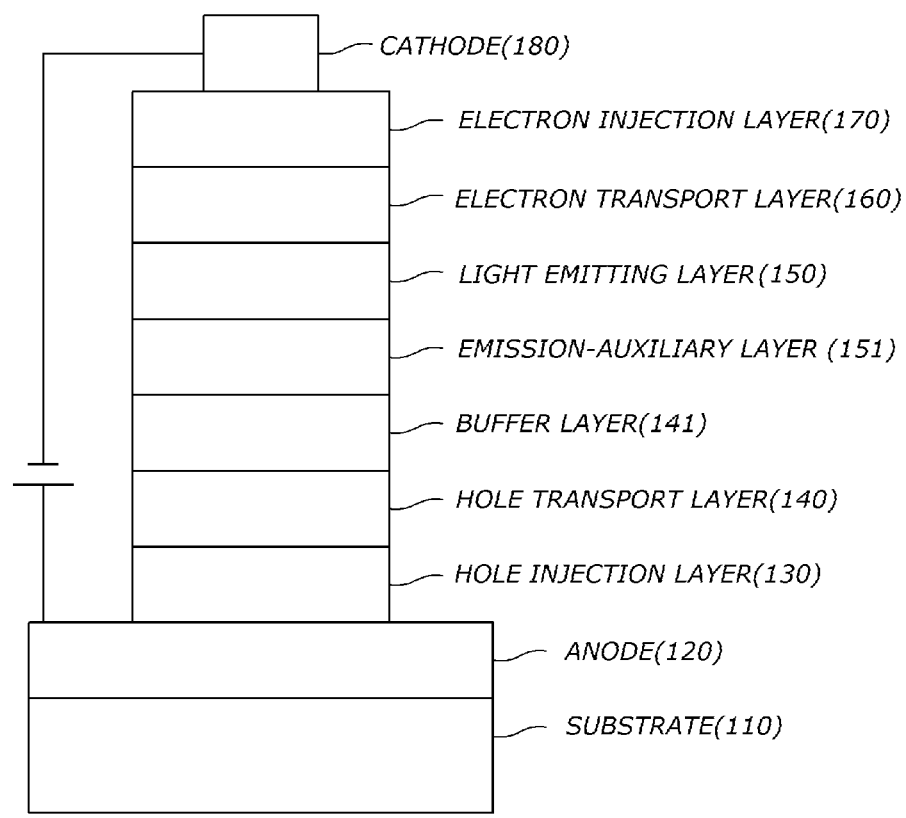

COMPOUND FOR ORGANIC ELECTRONIC ELEMENT, ORGANIC ELECTRONIC ELEMENT COMPRISING THE SAME, AND ELECTRONIC DEVICE THEREOF

CROSS-REFERENCE TO RELATED APPLICATION

This patent application claims benefit of Korean Patent Application No. 10-2016-0039940, filed on Apr. 1, 2016, and Korean Patent Application No. 10-2016-0110817, filed on Aug. 30, 2016, in the Korean Intellectual Property Office, the contents in both of which are hereby incorporated by reference for all purposes as if fully set forth herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer may have a multilayered structure including multiple layers made of different materials in order to improve the efficiency and stability of an organic electric element, and for example, may include a hole injection layer, a hole transport layer, a light emitting layer, an electron transport layer, an electron injection layer, or the like.

A material used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is an important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Recently, in order to solve the problem of light emission in the hole transporting layer of an organic electric element, a method of using a light emission-auxiliary layer between the hole transporting layer and the light emitting layer has been studied, and it is time to develop materials of emission-auxiliary layers for each light-emitting layer since the required material properties are different according to respective pixel-domain (R, G, B) of light emitting layers.

In general, an exciton is formed by recombination of an electron which transfers from an electron transport layer to a light emitting layer and a hole which transfers from a hole transport layer to the light emitting layer.

However, material used in a hole transport layer has a low T1 value because the material should have a low HOMO value, As a result, the exciton generated in the light emitting layer is transferred to the interface of the hole transport layer or the hole transport layer, and thereby emitting light at the interface of the hole-transporting layer or a charge unbalance in the light-emitting layer.

When light is emitted from the interface of the hole transporting layer, the color purity and efficiency of the organic electronic element are lowered and the lifetime is shortened. Therefore, it is strongly desired to develop materials for the emission-auxiliary layer having a HOMO level between the HOMO energy level of the hole transporting layer and the HOMO energy level of the light emitting layer, a high T1 energy value and a hole mobility within a suitable driving voltage range (within a driving voltage range of blue element of a full device).

However, this cannot be achieved simply by the structural properties of the core of the emission-auxiliary layer material. An element having a high efficiency and a long life span can be realized when the characteristics of core and sub-substituents of the emission-auxiliary layer material, the proper combination of between the emission-auxiliary layer and the hole transport layer, and the proper combination of between the emission-auxiliary layer and the light emitting layer.

On the other hand, it is also necessary to develop a hole injection/transport layer materials and an emission-auxiliary layer material having stable characteristics against Joule heat generated when the element is driven, that is, a high glass transition temperature. It has been reported that the low glass transition temperature of the hole transporting layer and the emission-auxiliary layer material lowers the uniformity of the surface when the device is driven and causes the material to deform due to heat generated when the device is driven, as a result, the life span of the device is greatly affected. In addition, an OLED element is mainly formed by a deposition method, and thus it is necessary to develop a material that can withstand a long time in the deposition, that is, a material having high heat resistance characteristics.

That is, in order to sufficiently exhibit the excellent characteristics of the organic electronic device, a material forming the organic material layer, for example, a hole injection material, a hole transport material, a light emitting material, an electron transport material, an electron injection material, an emission-auxiliary layer material or the like, must be supported by a stable and efficient material. However, such a stable and efficient organic material layer material for an organic electric element has not yet been fully developed. Accordingly, there is a continuous need to develop new materials for an organic material layer, specially, there are strong needs to develop materials for an emission-auxiliary layer and a hole transport layer.

SUMMARY

In order to solve one or more of the above-mentioned problems occurring in the prior art, an aspect of the present invention is to provide a compound having efficient electron blocking and hole transporting ability, to provide an organic electronic element with high luminous efficiency, low driving voltage, high heat resistance, color purity and long life span by employing such a compound, and an electronic device including the organic electric element.

In accordance with an aspect of the present invention, the compound represented by the following Formula is provided.

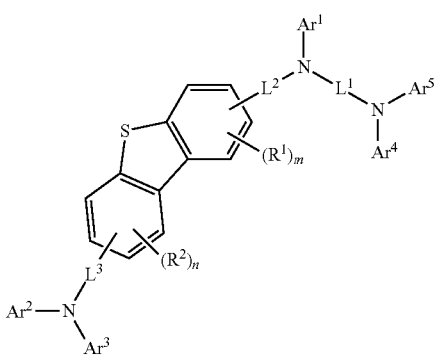

In another aspect of the present invention, organic electric elements containing the compound represented by the formula above and electronic devices including the organic electric element are provided.

According to one or more embodiments of the present invention, luminescence efficiency, high heat-resistant and life span of an organic electric element can be improved because the organic electric element has improved hole transport ability and thermal stability, HOMO energy level and high T1 value that are easy to achieve charge balance in the light emitting layer, and a high refractive index by employing the compound as a material of the organic electric element, wherein the compound is limited in the kind of the amine group, the bonding position and the number of the amine group connected to the dibenzothiophene core.

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), iodine (I) and so on.

Unless otherwise stated, the term "alkyl" or "alkyl group" as used herein has a single bond of 1 to 60 carbon atoms, and means aliphatic functional radicals including a linear alkyl group, a branched chain alkyl group, a cyclo alkyl group (alicyclic), or an alkyl group substituted with a cyclo alkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cyclo alkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below. Also, "substituted fluorenyl group" or "substituted fluorenylene group" means, functional group which at least any one of R, R' and R" is a functional group other than hydrogen and spiro compound which R and R' can be linked together with the carbon to which they are attached to form spiro compound.

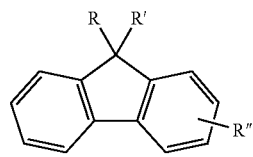

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents at least one of N, O, S, P, and Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes compound below.

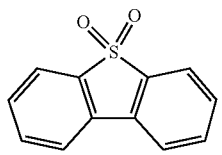 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an aryl alkoxy means an alkoxy substituted with an aryl, an alkoxyl carbonyl means a carbonyl substituted with an alkoxyl, and an aryl carbonyl alkenyl also means an alkenyl substitutes with an aryl carbonyl, wherein the aryl carbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

In the present description, a 'group name' corresponding to an aryl group, an arylene group, a heterocyclic group, and the like exemplified for each symbol and its substituent may be written in the name of functional group reflecting the valence, and may also be described under the name of a parent compound.

For example, in the case of phenanthrene, which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the Formulas used in the present invention are as defined in the index definition of the substituent of the following Formula.

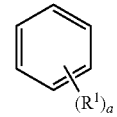

Wherein, when a is an integer of zero, the substituent $R^1$ is absent, that is, hydrogen atoms are bonded to all the carbon constituting the benzene ring, and chemical formulas or compounds may be written without explicitly describing the hydrogen. In addition, one substituent $R^1$ is bonded to any carbon of the carbons forming the benzene ring when "a" is an integer of 1, substituents $R^1$ are bonded, for example, as followings when "a" is an integer of 2 or 3, substituents $R^1$ are bonded to the carbon of the benzene ring in a similar manner when "a" is an integer of 4 to 6, and $R^1$'s may be the same or different from each other when "a" is an integer of 2 or more.

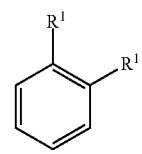

(a=2)

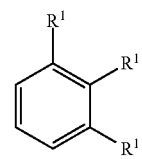

(a=3)

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may not be formed, the organic material layer may further include a hole blocking layer, an electron blocking layer, an emission-auxiliary layer 151, an electron transport auxiliary layer, a buffer layer 141, etc., the electron transport layer 160 and the like may serve as the hole blocking layer, and a hole transport layer 140 and an electron transport layer 160 may be formed of one or more layers.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a material of a hole injection layer 130, a hole transport layer 140, an emission-auxiliary layer 151, an electron transport auxiliary layer, an electron transport layer 160, an electron injection layer 170, as a host material or a dopant material of a light emitting layer 150, or as a material a capping layer material. For example, the inventive compound may be used as material of the light emitting layer 150, the hole transport layer 140, and/or the emission-auxiliary layer 151.

On the other hand, even if the core is the same core, the band gap, the electrical characteristics, the interface characteristics, and the like may be different depending on which substituent is bonded at which position. Therefore, it is necessary to study the selection of the core and the combination of the sub-substituent. Specially, long life span and high efficiency can be simultaneously achieved when the optimal combination of energy levels and T1 values, inherent material properties (mobility, interfacial properties, etc.), and the like among the respective layers of an organic material layer is achieved.

As already described above, in order to solve the emission problem with a hole transport layer in a conventional organic electric element, it is preferable that an emission-auxiliary layer is formed between the hole transport layer and a light emitting layer, and it is time to develop different emission-auxiliary layers according to respective light emitting layers (R, G, B). On the other hand, it is very difficult to infer the characteristics of an emission-auxiliary layer, even if the core of an emission-auxiliary layer is similar, because it is necessary to grasp the correlation between the emission-auxiliary layer and a hole transport layer and a light emitting layer (host).

According to the present invention, energy levels and T1 values between organic material layers, inherent material properties (mobility, interfacial properties, etc.), and the like can be optimized by forming a hole transport layer and/or an emission-auxiliary layer which comprise the compound represented by the Formula 1, and thus it is possible to simultaneously improve the life span and efficiency of the organic electronic element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

And also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

A WOLED (White Organic Light Emitting Device) readily allows for the formation of ultra-high definition images, and is of excellent processability as well as enjoying the advantage of WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R(Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

The compound according to an aspect of the present invention is represented by the following Formula 1.

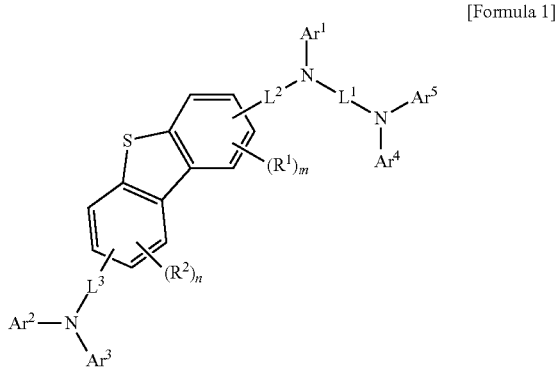

[Formula 1]

In the above formula 1, each symbol is defined as follows.

$L^1$ may be $C_6$-$C_{60}$ arylene group, preferably a $C_6$-$C_{30}$ arylene group, more preferably a $C_6$-$C_{18}$ arylene group, and illustratively phenyl, naphthalene, biphenyl, terphenyl, phenanthrene, triphenylene and the like.

$L^2$ and $L^3$ may be each independently selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; and a fused ring formed by a $C_6$-$C_{60}$ aromatic ring and a $C_3$-$C_{60}$ aliphatic ring.

Where $L^2$ and $L^3$ are an arylene group, $L^2$ and $L^3$ may be each preferably a $C_6$-$C_{30}$ arylene group, more preferably a $C_6$-$C_{18}$ arylene group, and illustratively a phenyl, naphthalene, biphenyl, and the like. Where $L^2$ and $L^3$ are a heterocyclic group, $L^2$ and $L^3$ may be each preferably a $C_2$-$C_{30}$ heterocyclic group, more preferably a $C_2$-$C_{10}$ heterocyclic group, and illustratively pyridine, dibenzothiophene and the like.

$Ar^1$ to $Ar^5$ may be independently selected from the group consisting of a $C_6$-$C_{60}$ aryl group; a $C_2$-$C_{60}$ heterocyclic group containing at least one heteroatom selected from the group consisting of O, N, S, Se, Si and P; a fluorenyl group; a fused ring formed by a $C_6$-$C_{60}$ aromatic ring and a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group. However, carbazole is excluded from $Ar^2$ and $Ar^3$.

Where $Ar^1$ to $Ar^5$ are an aryl group, $Ar^1$ to $Ar^5$ may be each preferably a $C_6$-$C_{60}$ aryl group, more preferably a $C_6$-$C_{18}$ aryl group, and illustratively phenyl, naphthyl, biphenyl, terphenyl, phenanthrene, fluoranthene and the like. Where $Ar^1$ to $Ar^5$ are a heterocyclic group, $Ar^1$ to $Ar^5$ may be each preferably a $C_2$-$C_{60}$ heterocyclic group, more preferably a $C_2$-$C_{18}$ heterocyclic group, and illustratively thiophene, pyridine, indole, isoquinoline, carbazole, indolo carbazole, dibenzofuran, dibenzothiophene, dibenzoselenophene, and the like. Where $Ar^1$ to $Ar^5$ are a fluorenyl group, $Ar^1$ to $Ar^5$ may be each illustratively 9,9-dimethyl-9H-fluorene, 9,9-diphenyl-9H-fluorene, 9,9'-spirobifluorene and the like. Where $Ar^1$ to $Ar^5$ are a fused ring, $Ar^1$ to $Ar^5$ may be each illustratively 1,2-dihydrocyclobutabenzene.

m and n may be each an integer of 0 to 3.

$R^1$ and $R^2$ may be each independently selected from the group consisting of deuterium; tritium; halogen; a cyano group; a nitro group; a $C_6$-$C_{60}$ aryl group; a fluorenyl group; a $C_2$-$C_{60}$ heterocyclic group containing at least one heteroatom selected from the group consisting of O, N, S, Se, Si and P; a fused ring formed by a $C_6$-$C_{60}$ aromatic ring and a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group. When "m" is an integer of 2 or more, neighboring $R^1$s may be linked to each other to form a ring, and when "n" is an integer of 2 or more, neighboring $R^2$s may be linked to each other to form a ring. When "m" is an integer of 2 or more, a plurality of $R^1$s may be the same or different from each other, and when "n" is an integer of 2 or more, a plurality of $R^2$s may be the same or different from each other.

When $R^1$ and $R^2$ are an aryl groups, $R^1$ and $R^2$ may be each preferably $C_6$-$C_{60}$ aryl groups, more preferably $C_6$-$C_{10}$ aryl groups, and may be illustratively phenyl, naphthyl, and the like.

The ring formed by linking adjacent $R^1$s to each other and/or adjacent $R^2$s to each other may be a $C_6$-$C_{60}$ aromatic ring, fluorene, a $C_2$-$C_{60}$ heterocyclic group containing at least one heteroatom selected from the group consisting of O, N, S, Se, Si and P, a fused ring formed by a $C_6$-$C_{60}$ aromatic ring and a $C_3$-$C_{60}$ aliphatic ring, and the like, and illustratively benzene ring. Adjacent $R^1$s and/or adjacent $R^2$s may be linked to each other to form a benzene ring, as a result, naphthalene, phenanthrene, etc. may be formed together with the benzene ring to which $R^1$s and/or $R^2$s are bonded.

$Ar^1$~$Ar^5$, $R^1$, $R^2$, $L^1$~$L^3$, a ring formed by linking adjacent $R^1$s together, and a ring formed by linking adjacent $R^2$s together may be each substituted with one or more substituents selected from the group consisting of deuterium; halogen; a silane group substituted or unsubstituted with a $C_1$-$C_{20}$ alkyl group or a $C_6$-$C_{20}$ aryl group; a phosphine oxide group substituted or unsubstituted with a $C_1$-$C_{20}$ alkyl group or a $C_6$-$C_{20}$ aryl group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Se, Si and P; a $C_3$-$C_{20}$ cycloalkyl group; a $C_7$-$C_{20}$ arylalkyl group; —N($R^a$)($R^b$); a $C_8$-$C_{20}$ arylalkenyl group; and

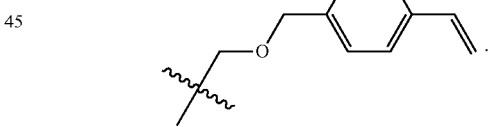

$R^a$ and $R^b$ may be each independently selected from the group consisting of a $C_6$-$C_{60}$ aryl group; a fluorenyl group; a $C_2$-$C_{60}$ heterocyclic group containing at least one heteroatom selected from the group consisting of O, N, S, Se, Si and P. Preferably, $R^a$ and $R^b$ may be each substituted with one or more substituents selected from the group consisting of deuterium; halogen; a silane group substituted or unsubstituted with a $C_1$-$C_{20}$ alkyl group or a $C_6$-$C_{20}$ aryl group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Se, Si and P; a $C_3$-$C_{20}$ cycloalkyl group; a $C_7$-$C_{20}$ arylalkyl group; and a $C_8$-$C_{20}$ arylalkenyl group.

Preferably, the formula 1 may be represented by any one of the following formulas 2 to 5, and more preferably by one of the following formulas 6 to 10.
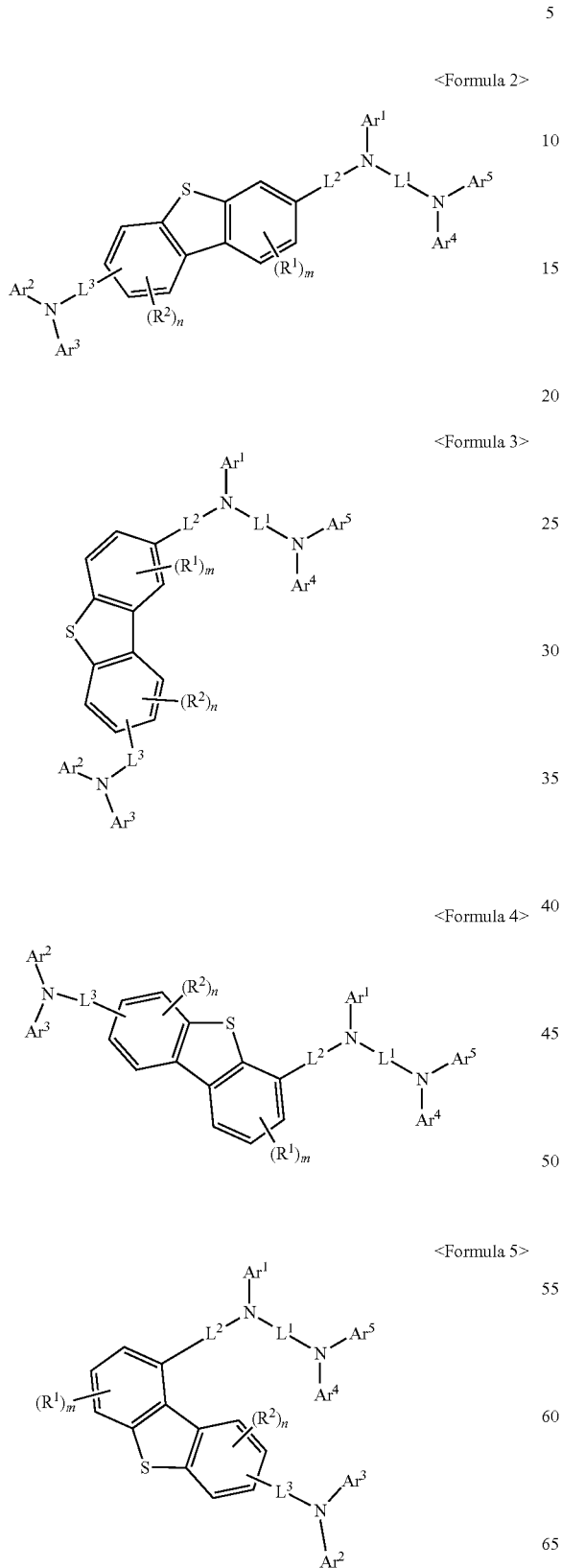
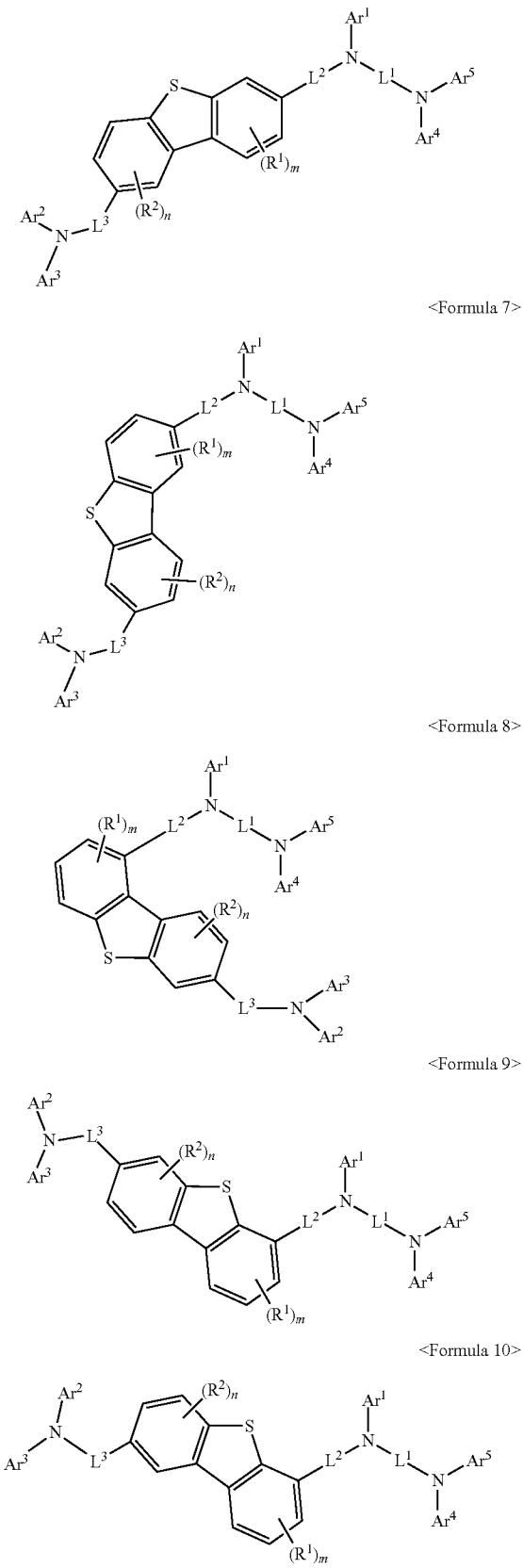

In formulas 2 to 10, $Ar^1 \sim Ar^5$, $R^1$, $R^2$, $L^1 \sim L^3$, m, n, and the like are the same as defined in Formula 1 above.

In formulas 1 to 10, $L^1$ may be represented by any one of the following formulas L1-1 to L1-7.

<Formula L1-1>

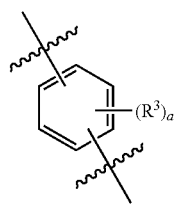

<Formula L1-2>

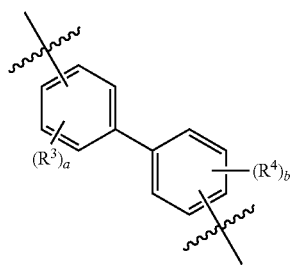

<Formula L1-3>

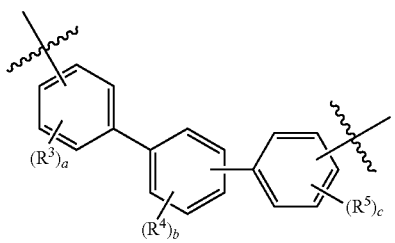

<Formula L1-4>

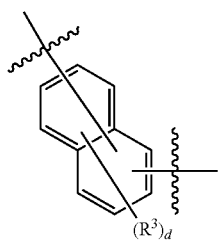

<Formula L1-5>

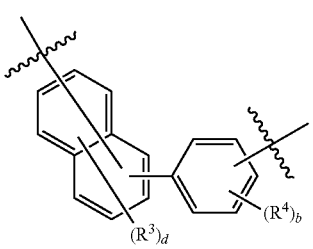

<Formula L1-6>

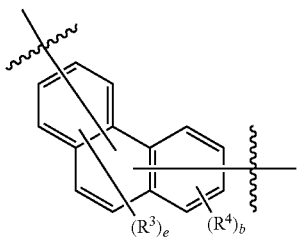

<Formula L1-7>

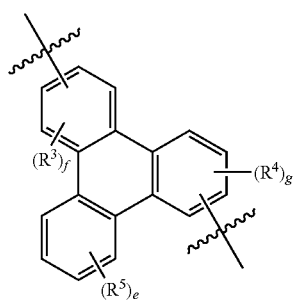

In formulas L1-1 to L1-7, "a" to "c" may be each an integer of 0 to 4, "d" may be an integer of 0 to 6, "e" may be an integer of 0 to 5, "f" and "g" may be each an integer of 0 to 3, $R^3$ to $R^5$ may be each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_6$-$C_{60}$ aromatic ring and a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group, and a plurality of $R^3$ to $R^5$ may be each the same or different from each other when "a" to "g" are each an integer of 2 or more.

When $L^1$ is L1-1, $L^1$ may be preferably any one of the following structures, and in the following structures, $R^3$, a, and the like are the same as defined in Formula L1-1 above.

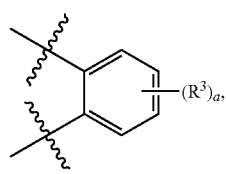

ortho

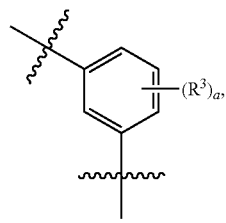

meta

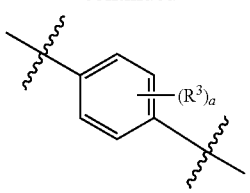

para

Preferably, in the formulas 1 to 10, at least one of $Ar^1$ to $Ar^5$ may be represented by the following formula 11.

<Formula 11>

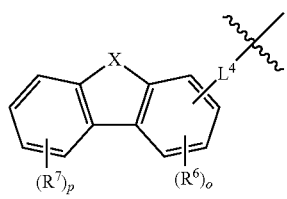

In formula 11, each symbol is defined as follows.

X is S, Se, O, $C(R^c)(R^d)$ or $N(R^e)$ when at least one of $Ar^1$, $Ar^4$ and $Ar^5$ is Formula 11, and X is S, Se, O or $C(R^c)(R^d)$ when at least one of $Ar^2$ and $Ar^3$ is Formula 11.

$R^c$ to $R^e$ may be each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_6$-$C_{60}$ aromatic ring and a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group, and $R^c$ and $R^d$ may be linked to each other to form a spiro compound.

$L^4$ may be selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; and a fused ring formed by a $C_6$-$C_{20}$ aromatic ring and a $C_3$-$C_{20}$ aliphatic ring.

"o" may be an integer of 0 to 3, "p" may be an integer of 0 to 4, and $R^6$ and $R^7$ may be each independently selected from the group consisting of deuterium; tritium; halogen; a cyano group; a nitro group; a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_6$-$C_{60}$ aromatic ring and a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group. When "o" and "p" are each an integer of 2 or more, a plurality of $R^6$s and $R^7$s may be each the same or different from each other, and adjacent $R^6$s and/or adjacent $R^6$s may be linked to each other to form a ring.

More preferably, at least one of $Ar^1$, $Ar^2$ and $Ar^5$ is the above Formula 11, wherein X may be S in the Formula 11.

When at least one of $Ar^1$ to $Ar^5$ is the above Formula 11, preferably, Formula 1 may be represented by any one of the following formulas 1-1 to 1-3

<Formula 1-1>

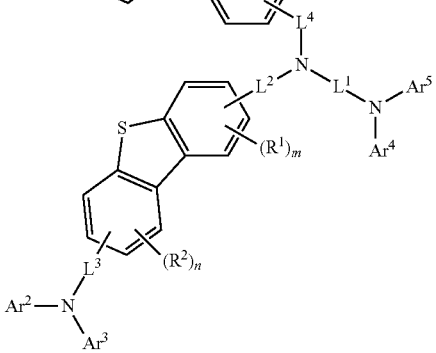

<Formula 1-2>

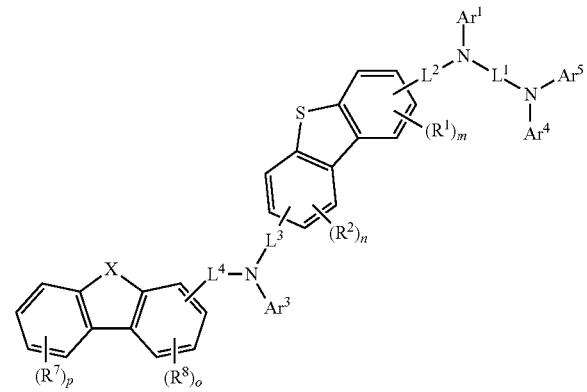

<Formula 1-3>

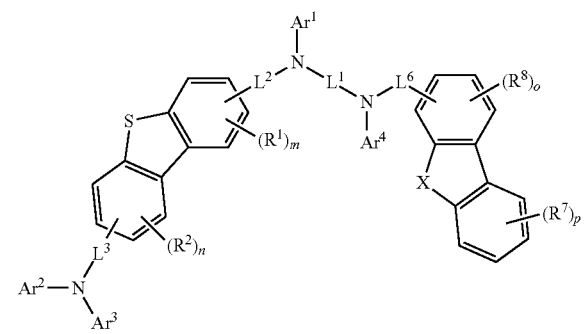

X is S, Se, O, $C(R^c)(R^d)$ or $N(R^e)$ in formulas 1-1 and 1-3, X is S, Se, O or $C(R^c)(R^d)$ in formulas 1-2, $Ar^1$ to $Ar^5$, $L^1$ to $L^3$, $R^1$, $R^2$, m, n, and the like are each the same as defined in Formula 1 above, and $L^4$, $R^c$ to $R^e$, $R^6$, $R^7$, o and p are each the same as defined in Formula 11 above.

Specifically, the compound represented by Formula 1 may be any one of the following compounds.

P-1
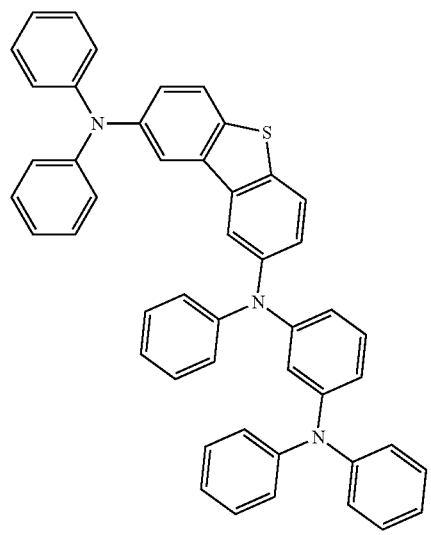
P-2
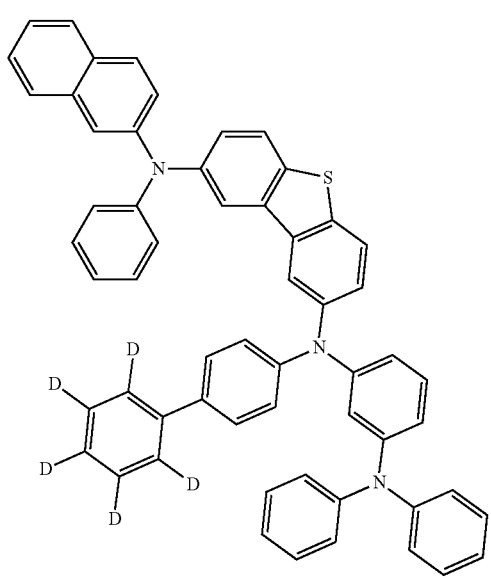
P-3
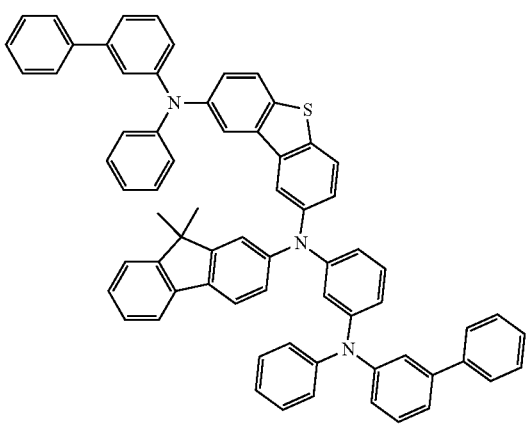
P-4
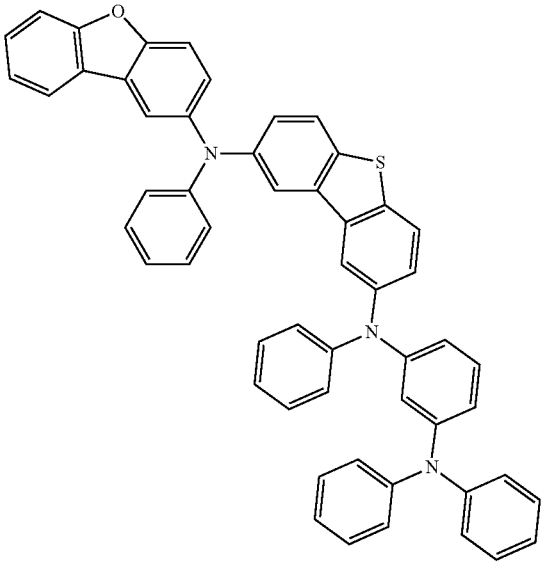
P-5
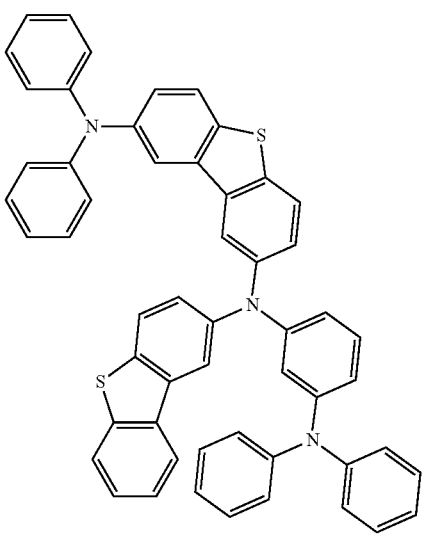
P-6
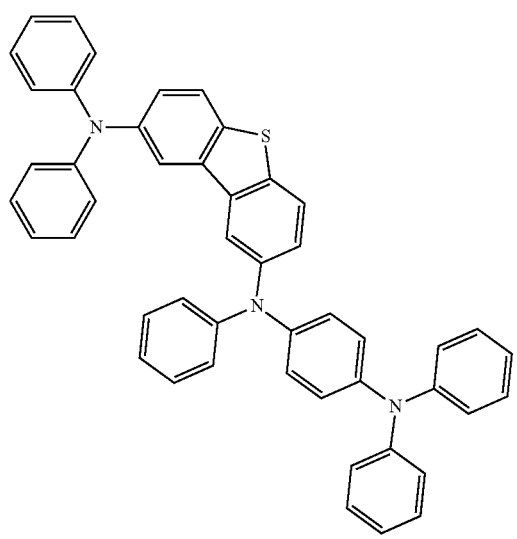

P-7
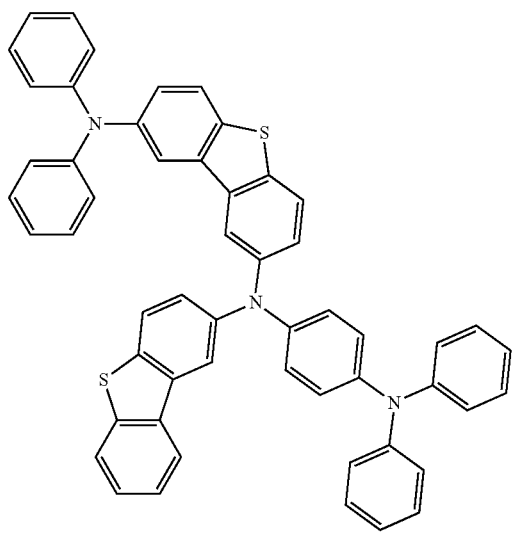
P-8
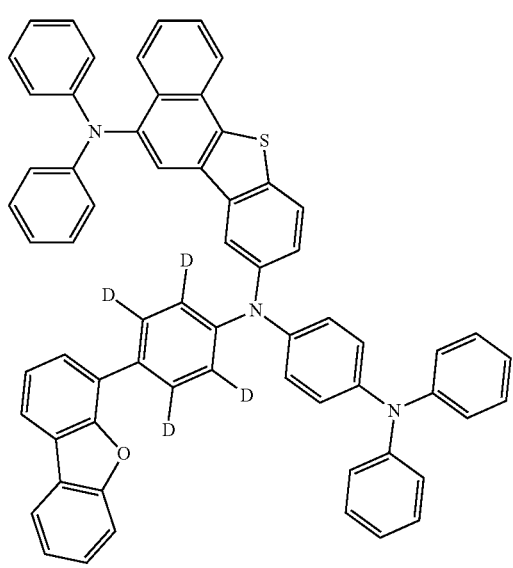
P-9
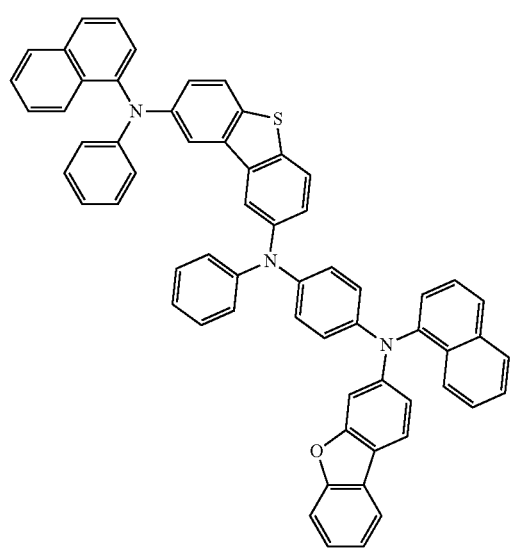
P-10
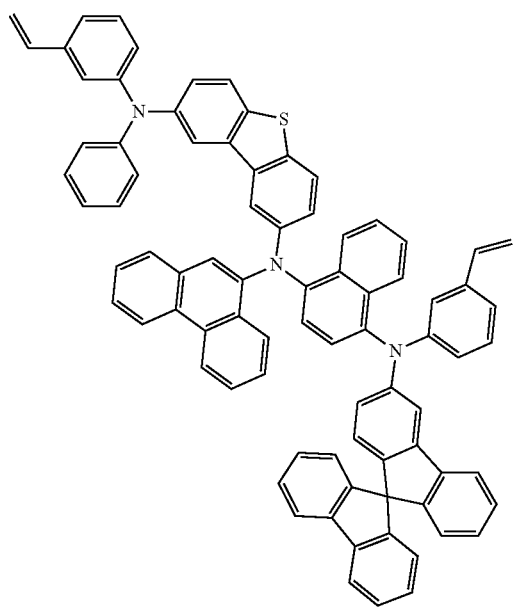
P-11
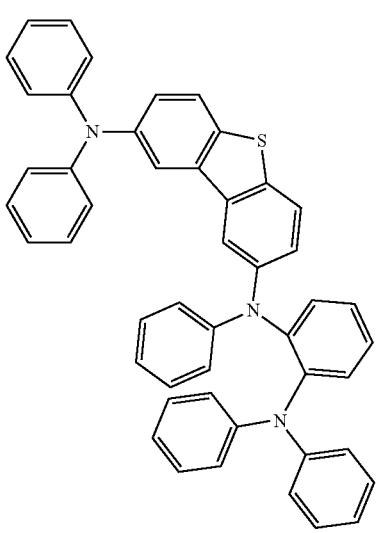
P-12
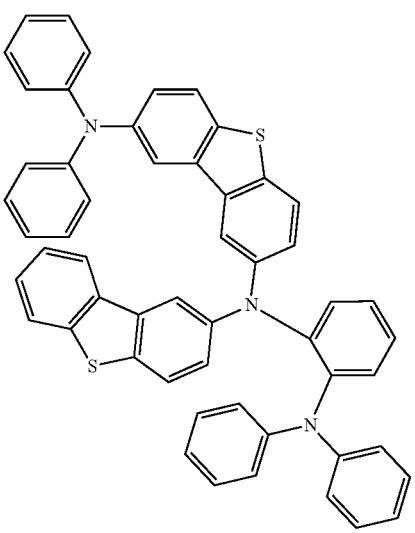

P-13
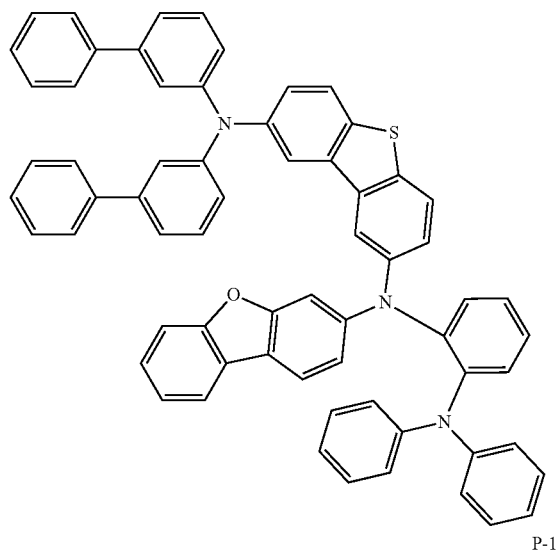
P-14
P-15
P-16
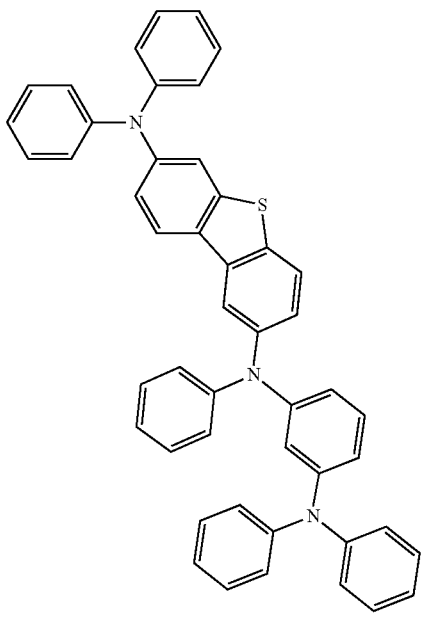
P-17
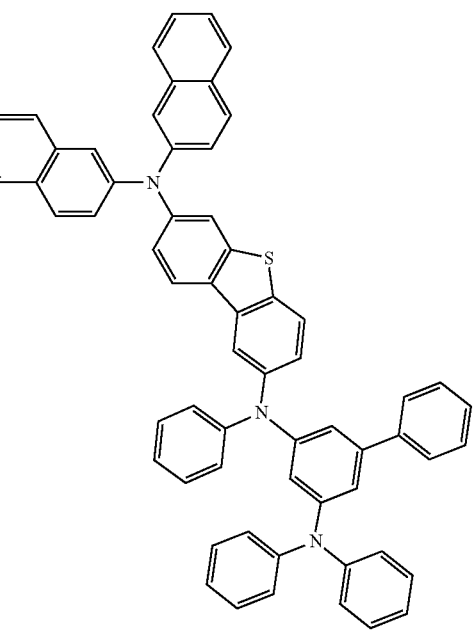

P-18
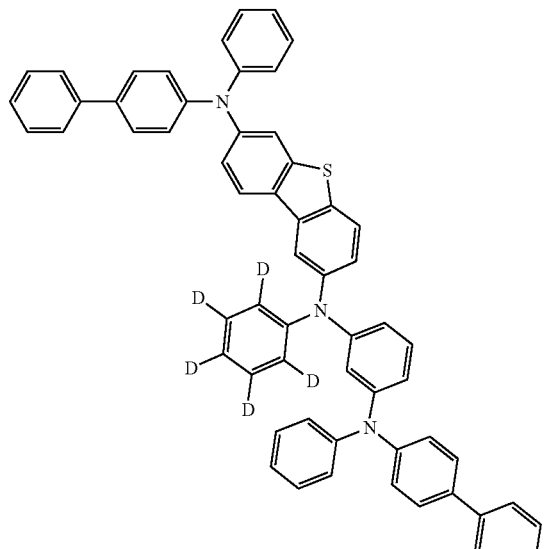
P-19
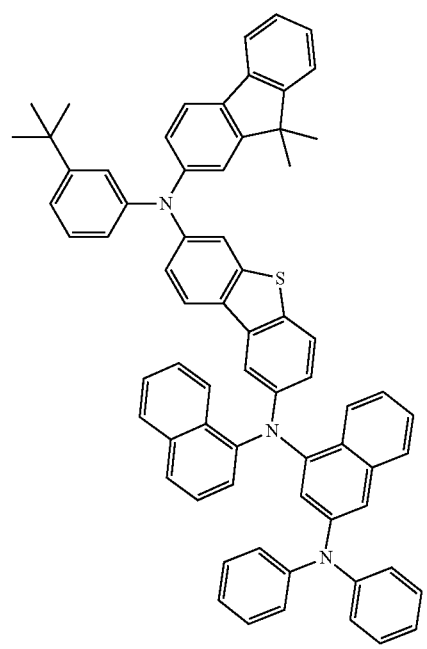
P-20
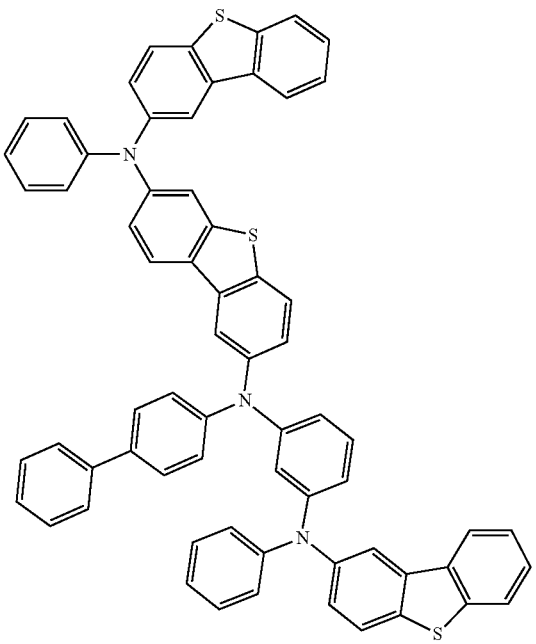
P-21
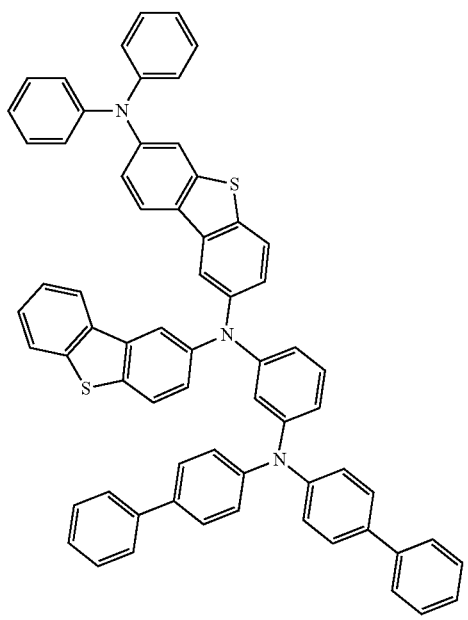

P-22
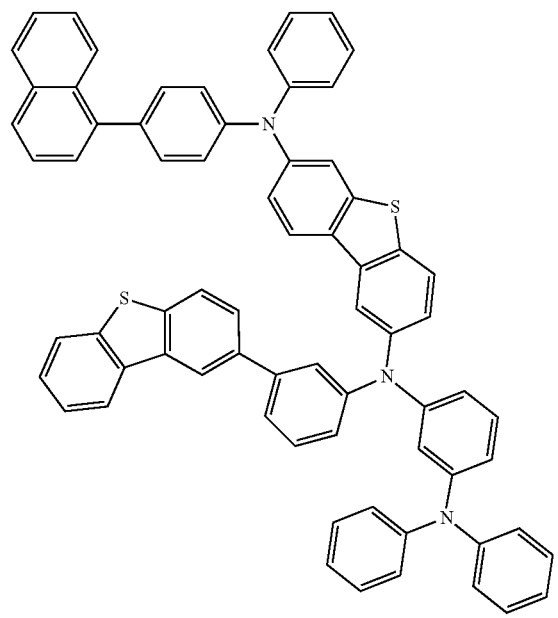
P-24
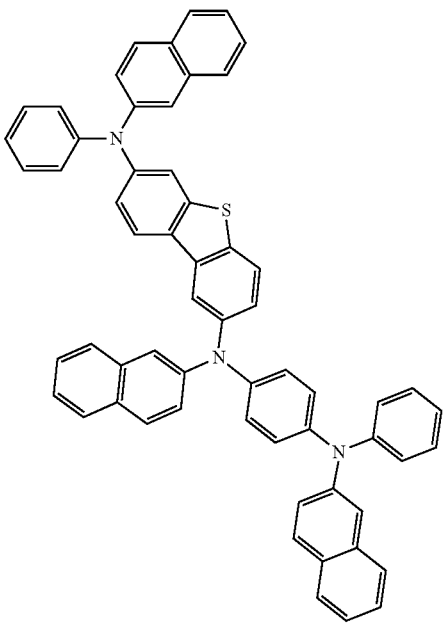
P-23
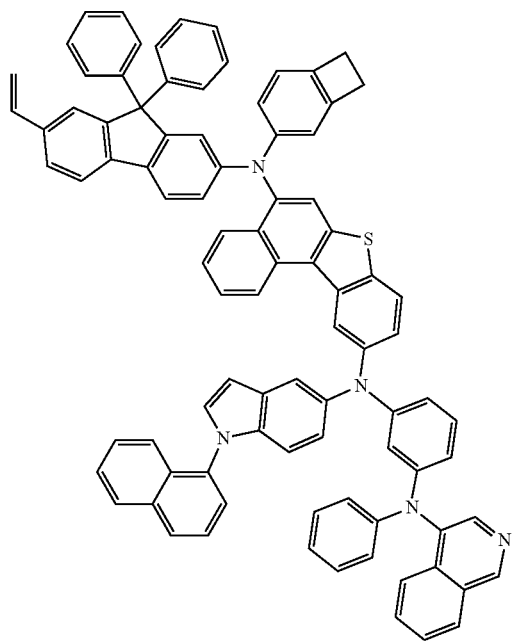
P-25
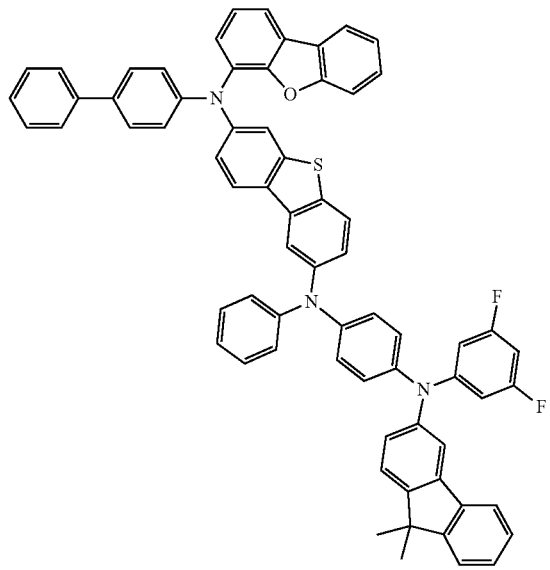

P-26
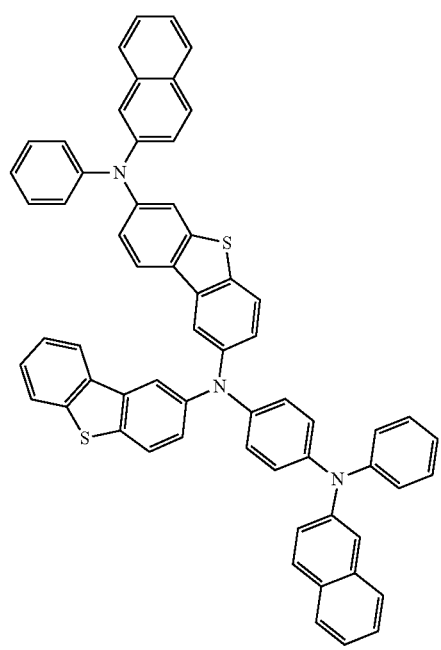
P-27
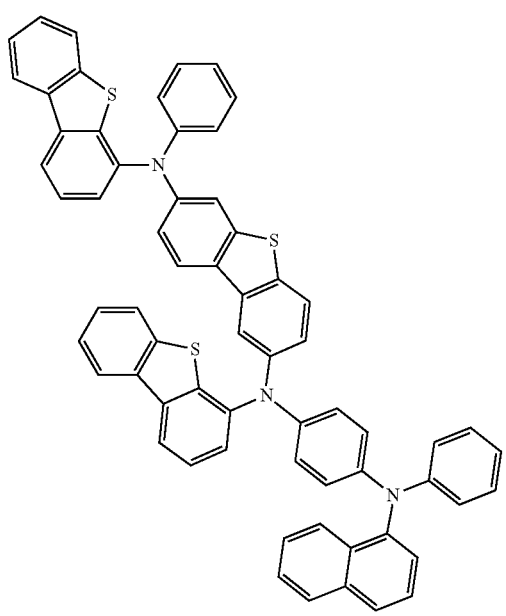
P-28
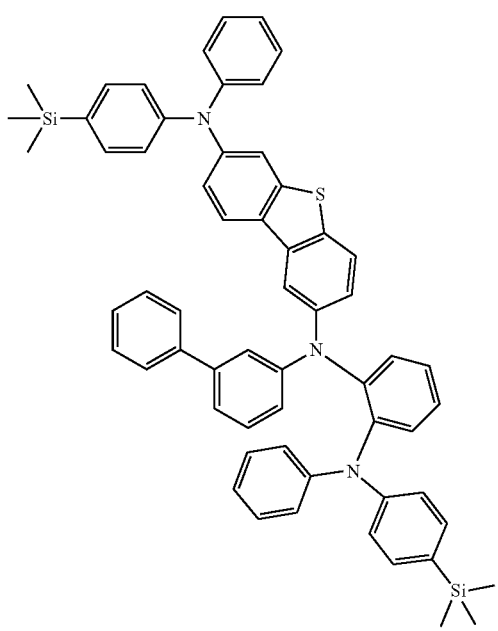
P-29
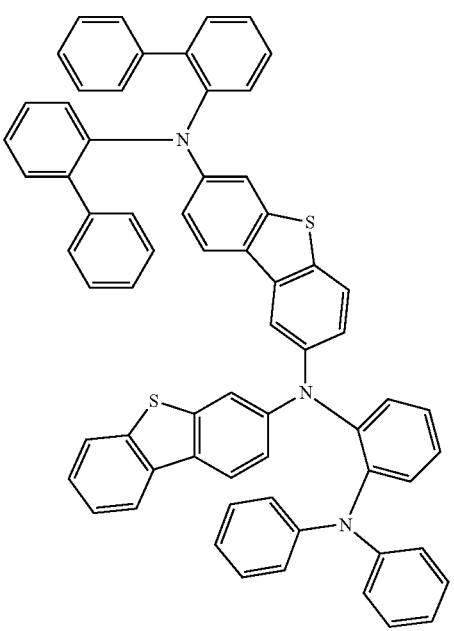

P-30
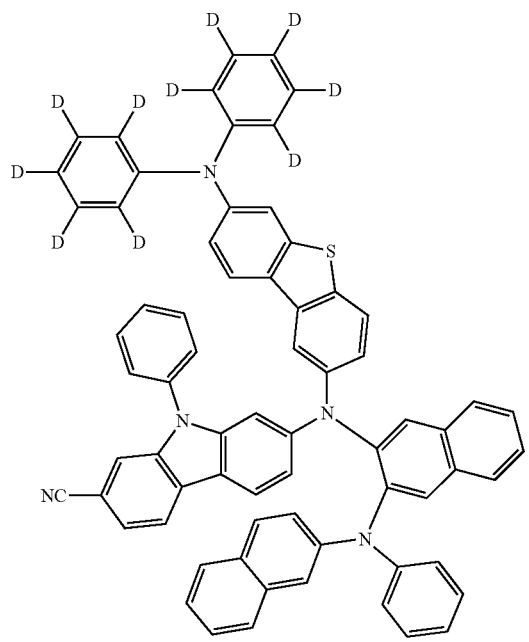
P-31
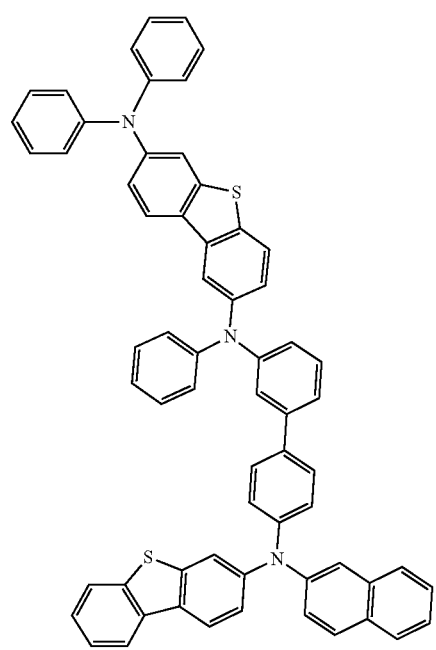
P-32
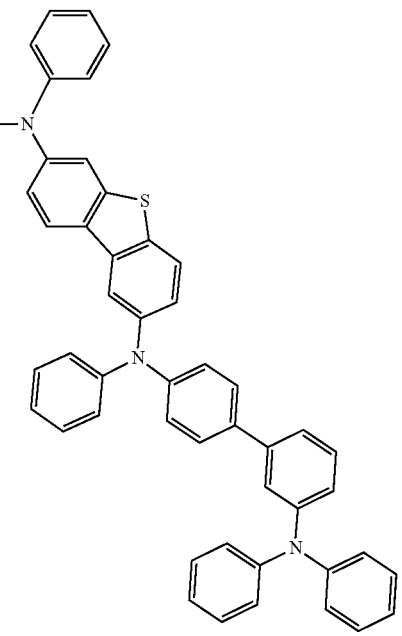
P-33
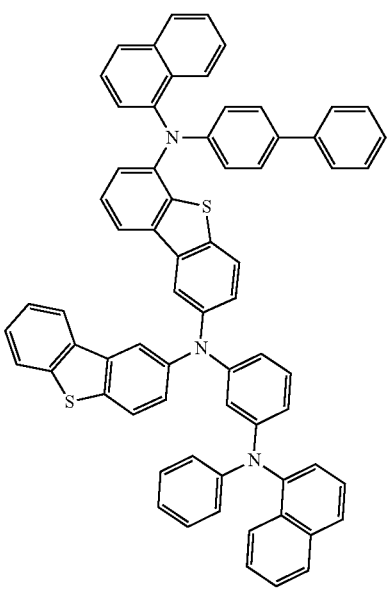

P-34
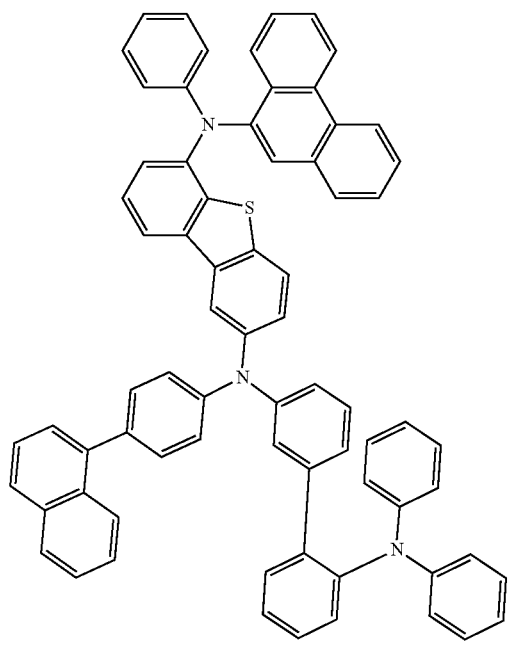
P-36
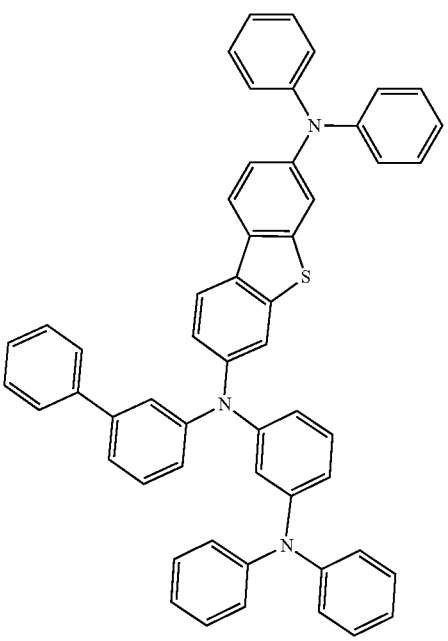
P-35
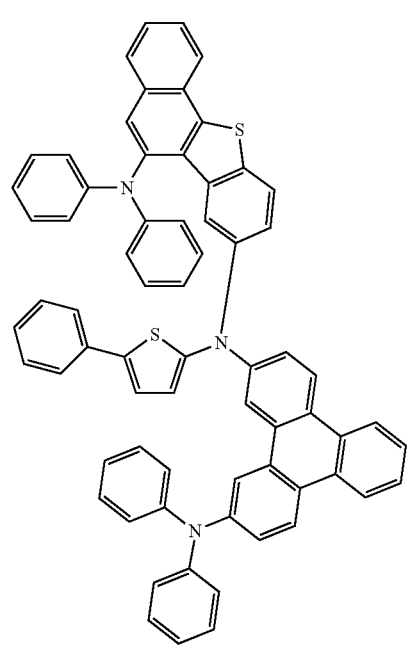
P-37
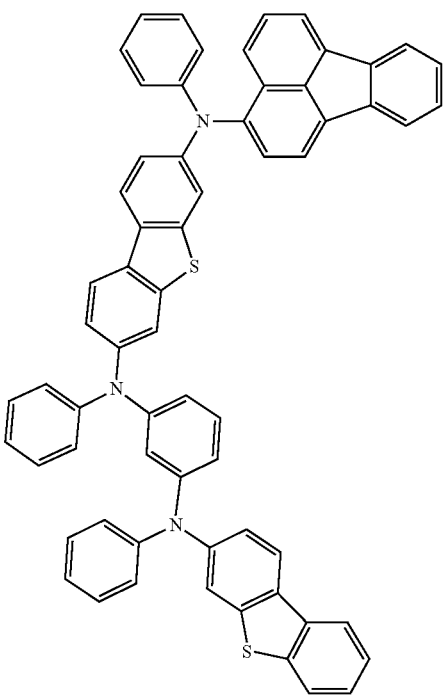

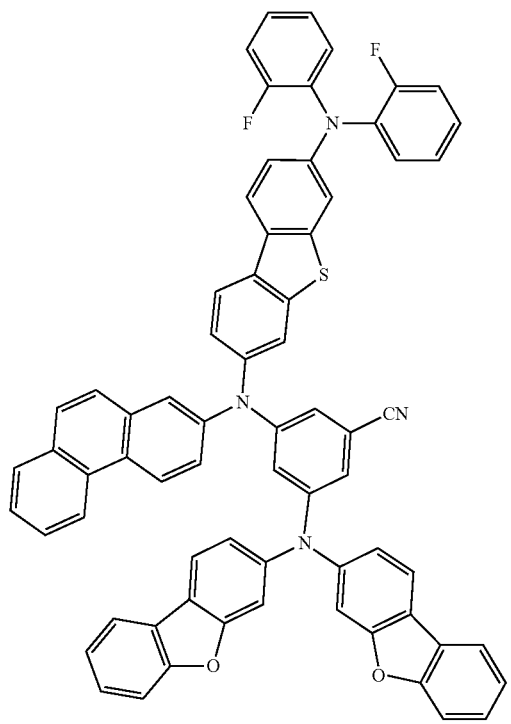
P-38
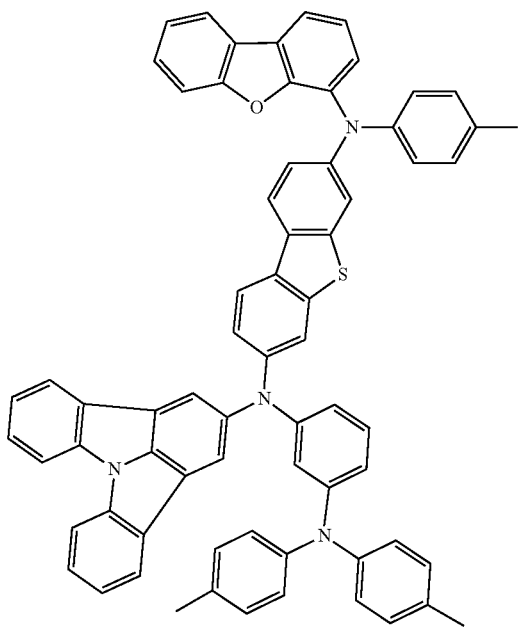
P-40
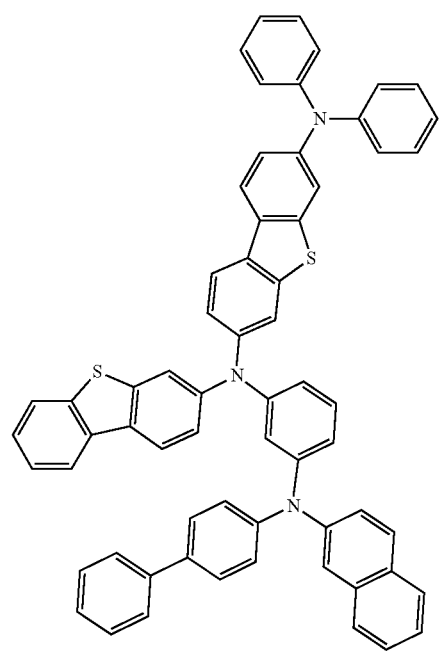
P-39
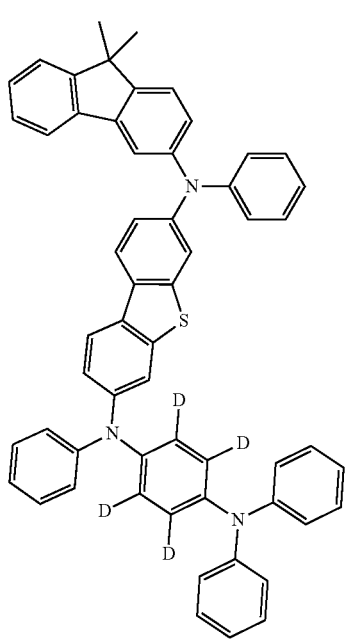
P-41

P-42
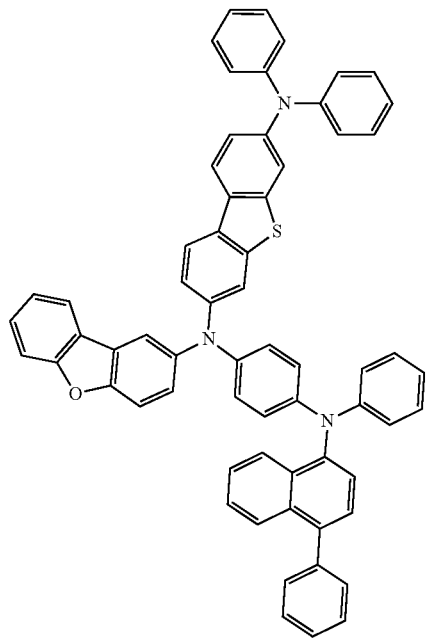
P-44
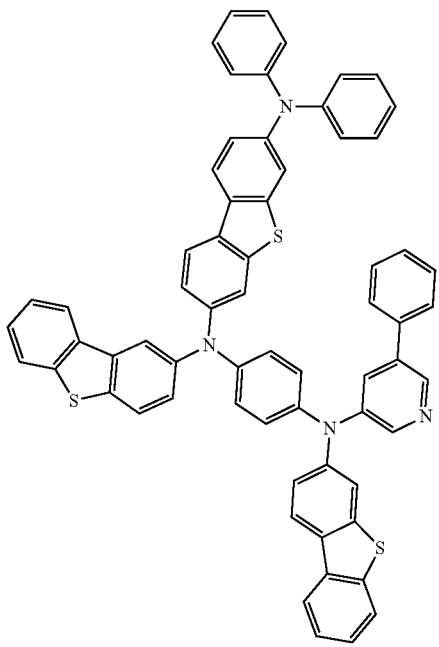
P-43
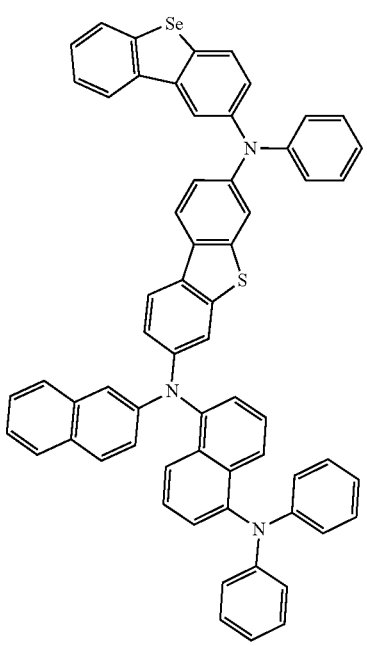
P-45
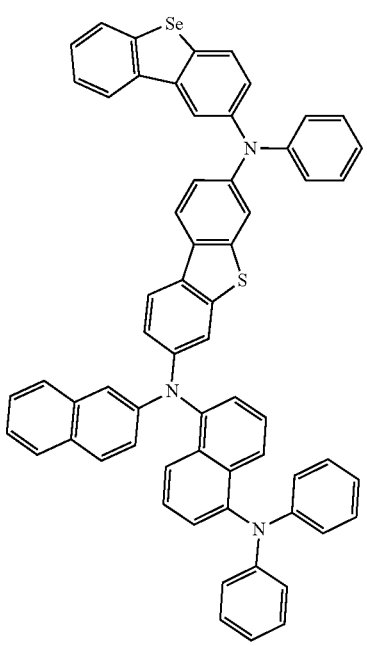

P-46
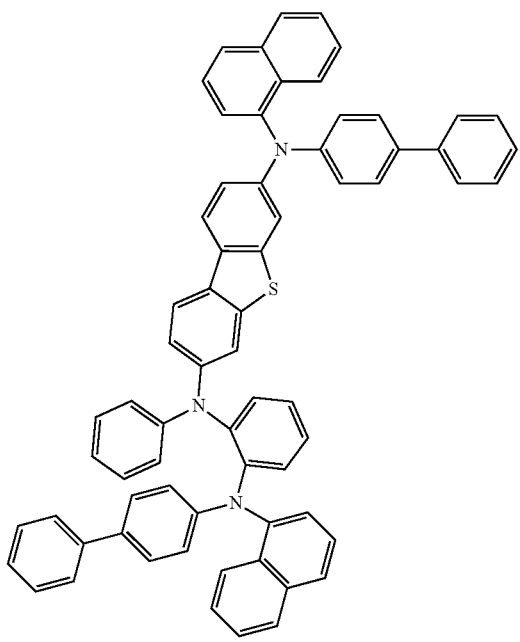
P-48
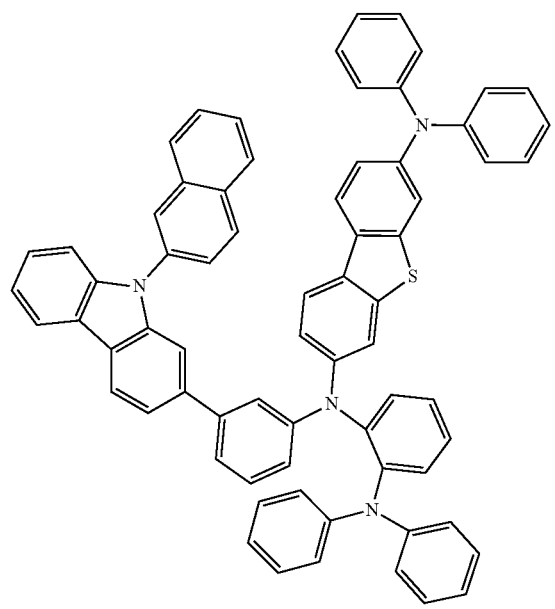
P-47
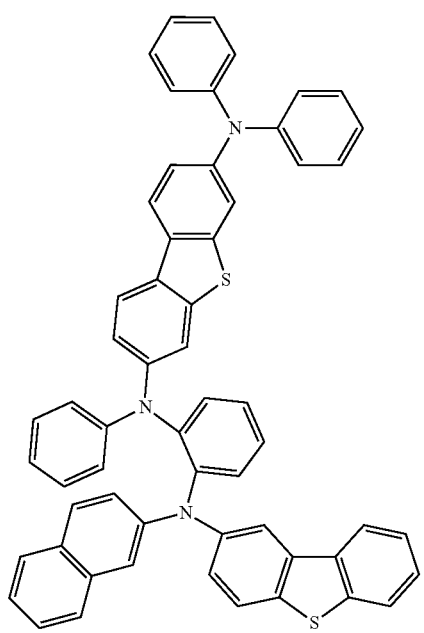
P-49
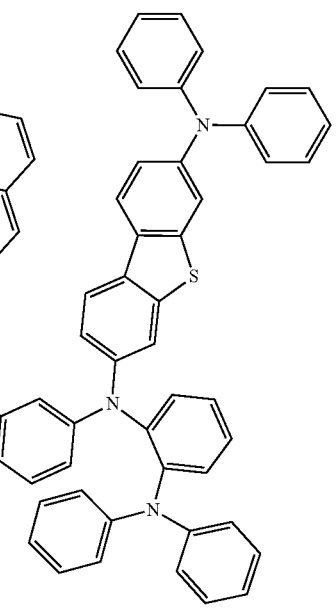

P-50
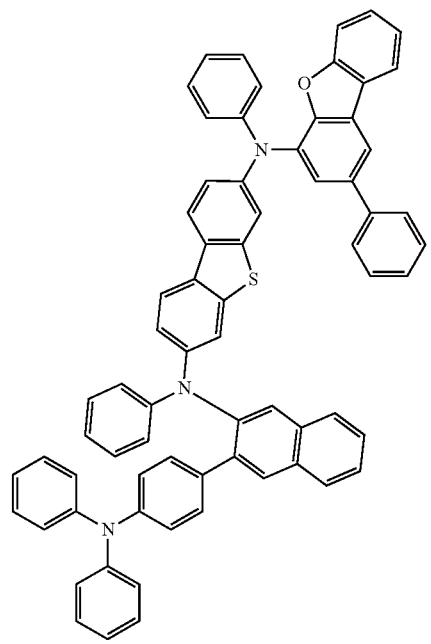
P-52
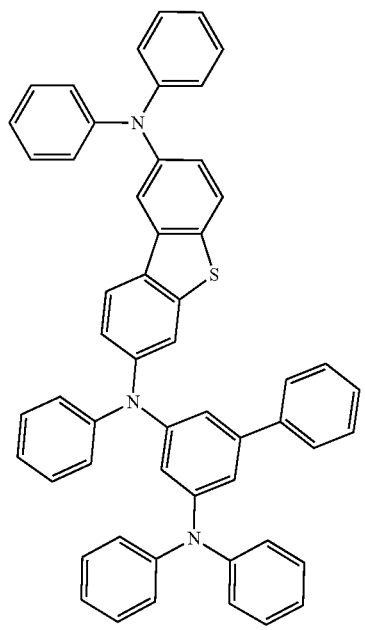
P-51
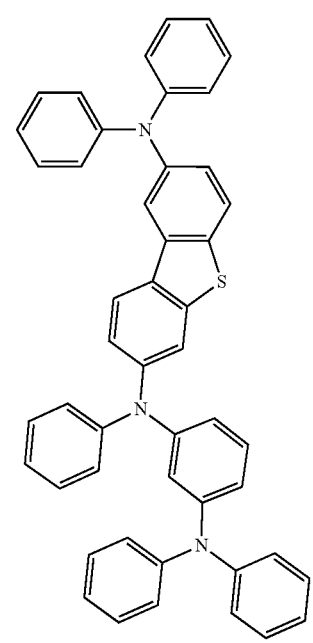
P-53
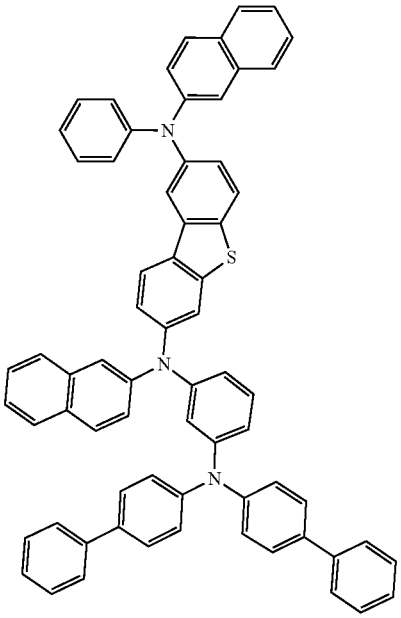

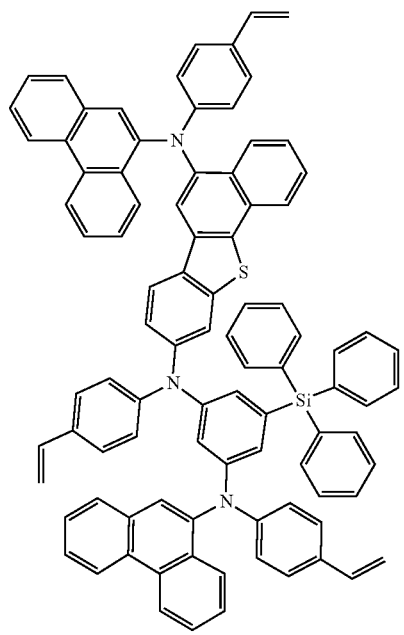 P-54
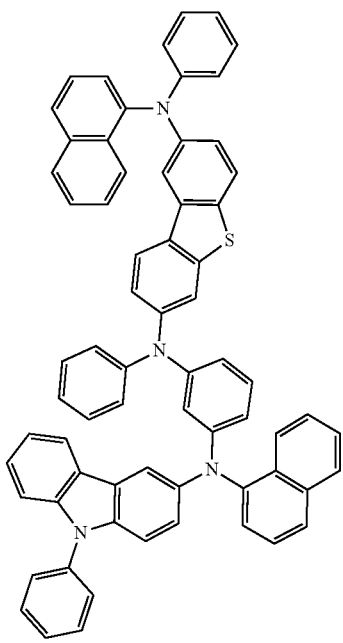 P-56
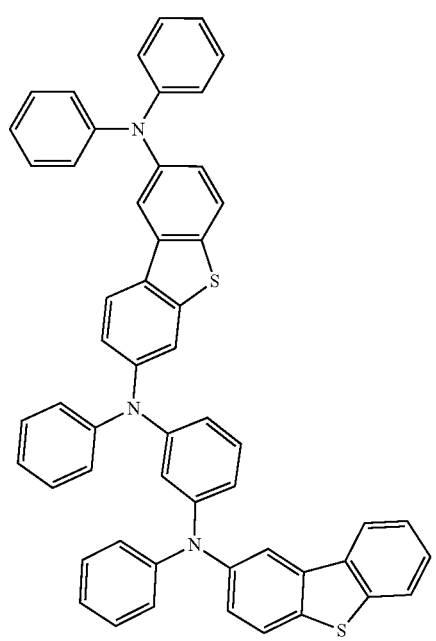 P-55
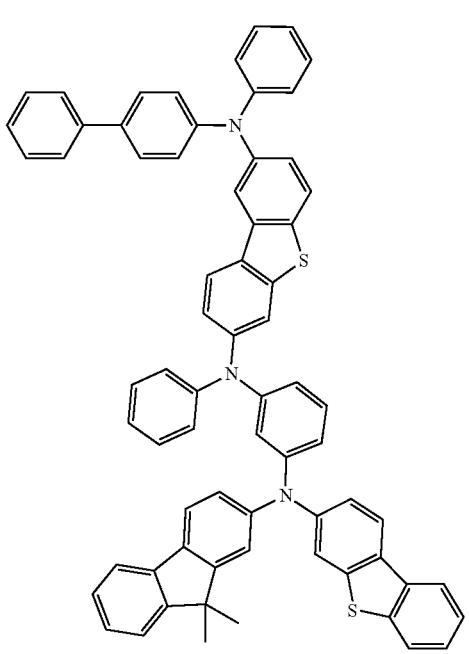 P-57

P-58
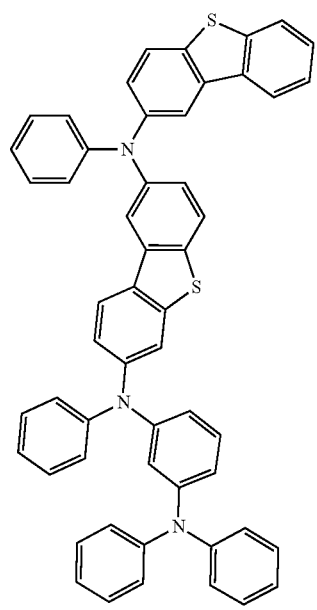
P-60
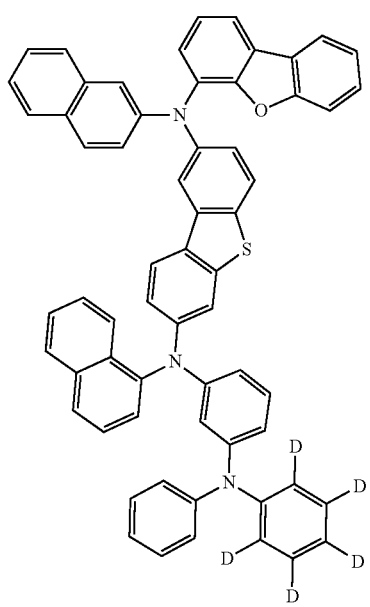
P-59
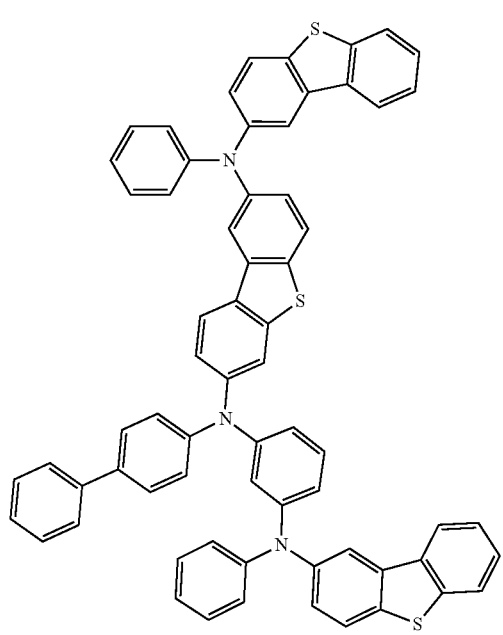
P-61
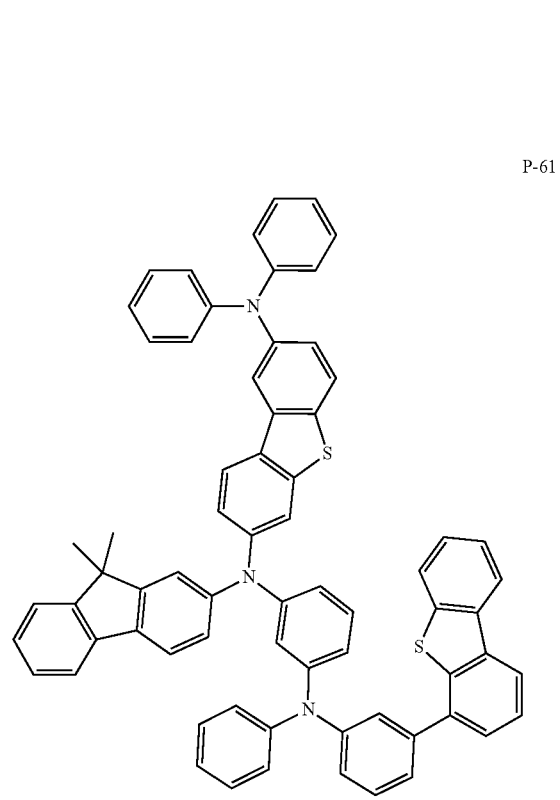

P-62
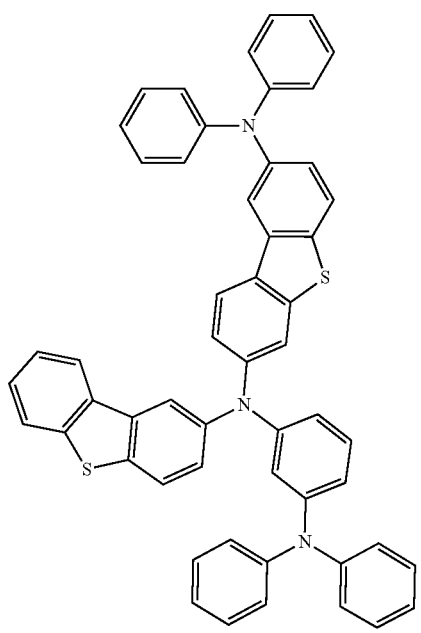
P-64
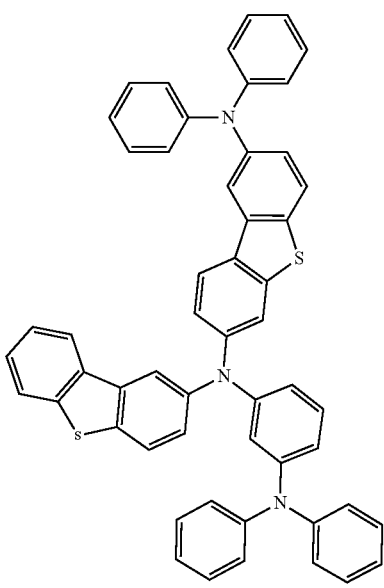
P-63
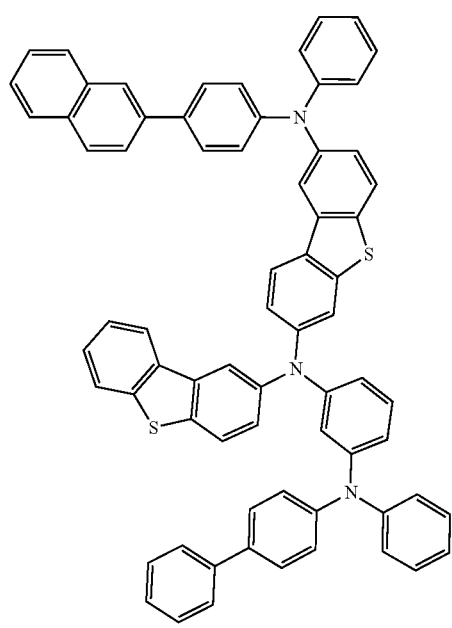
P-65
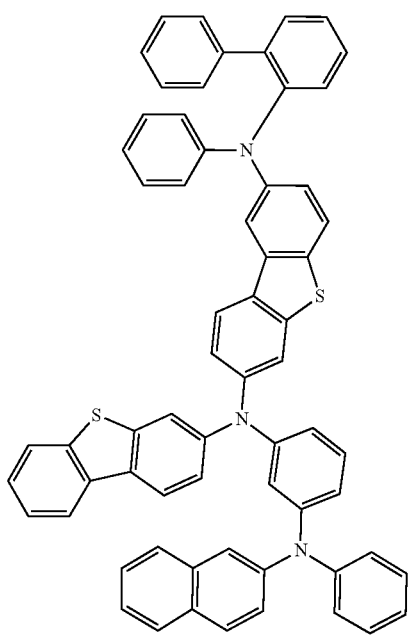

P-66
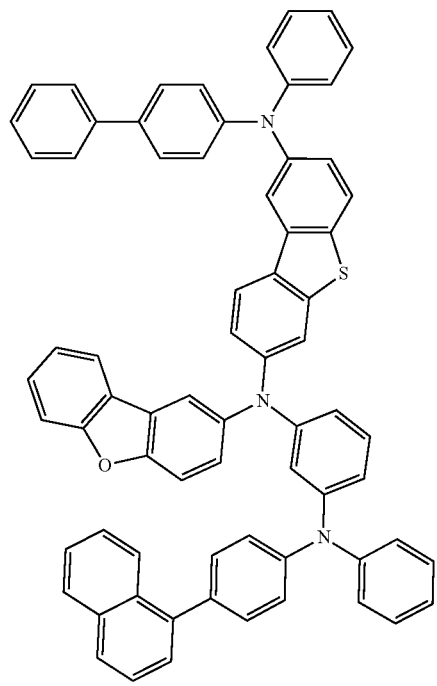
P-68
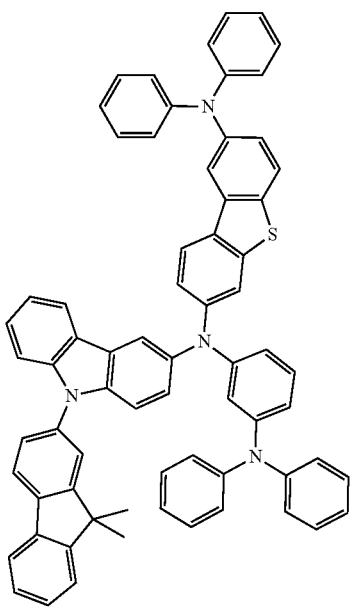
P-67
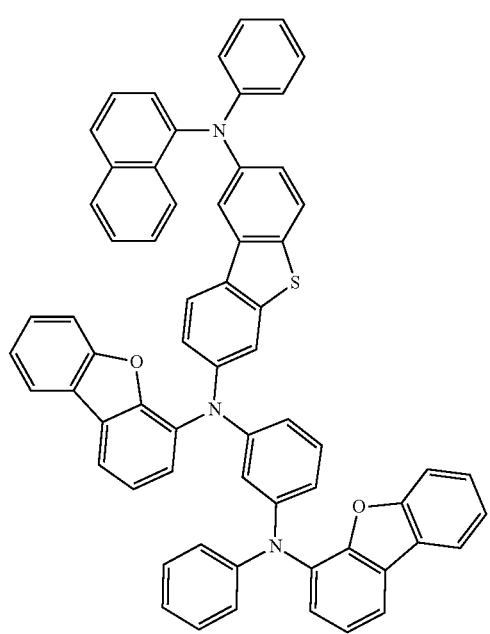
P-69
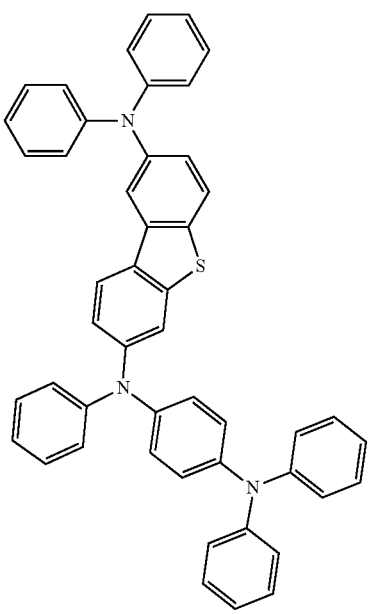

P-70
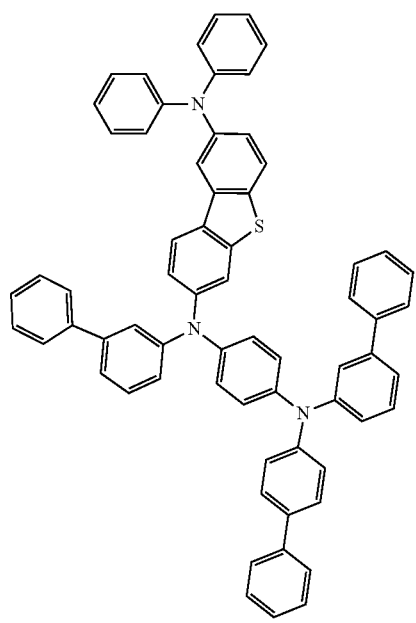
P-72
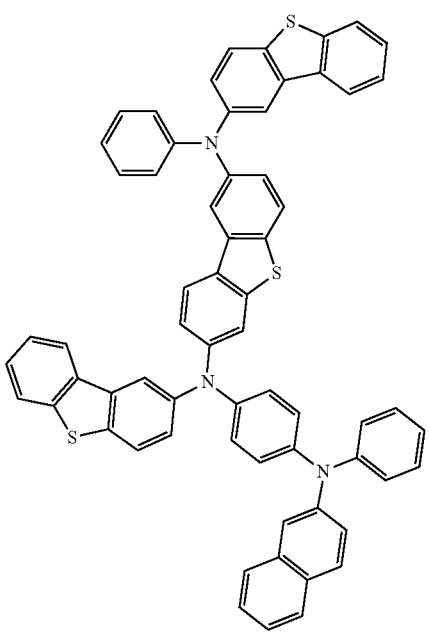
P-71
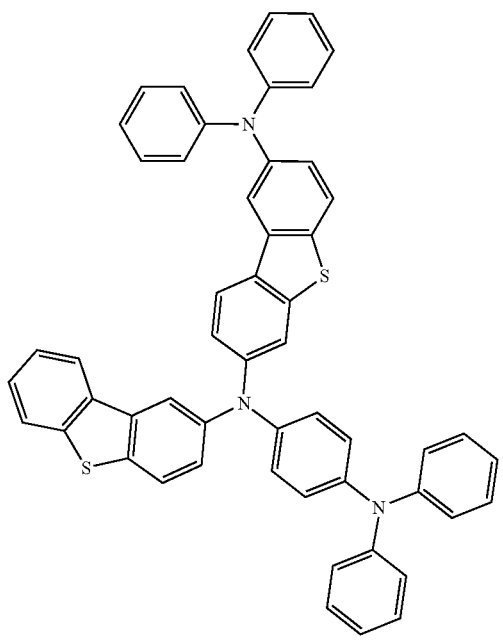
P-73
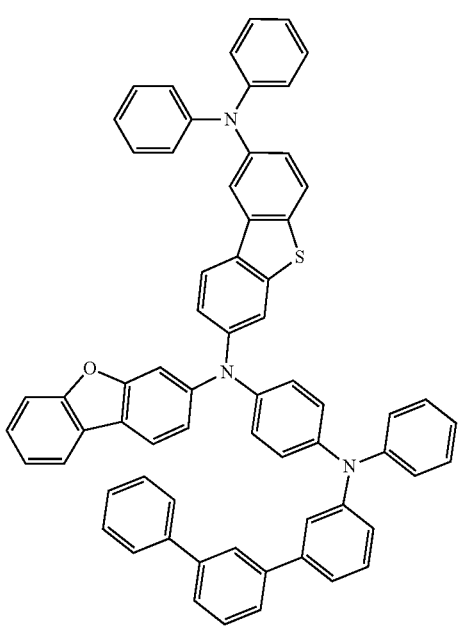

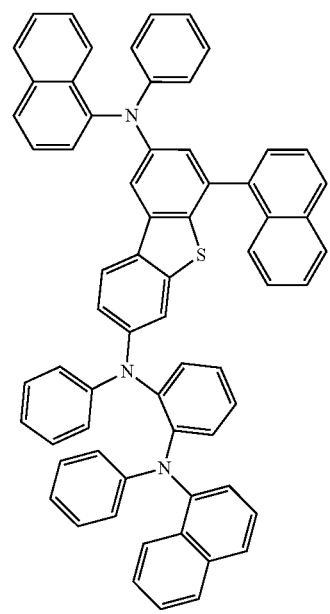
P-74
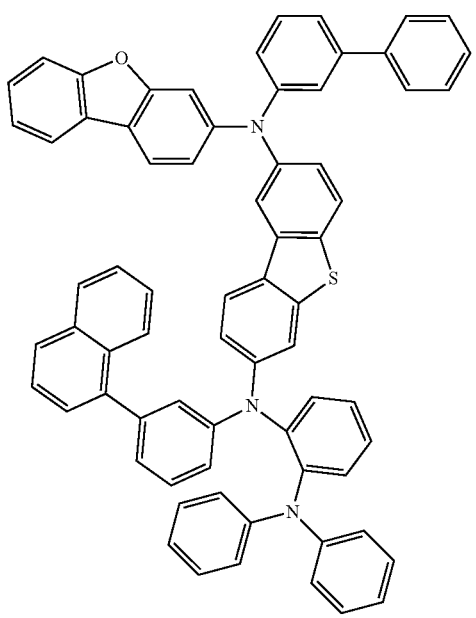
P-76
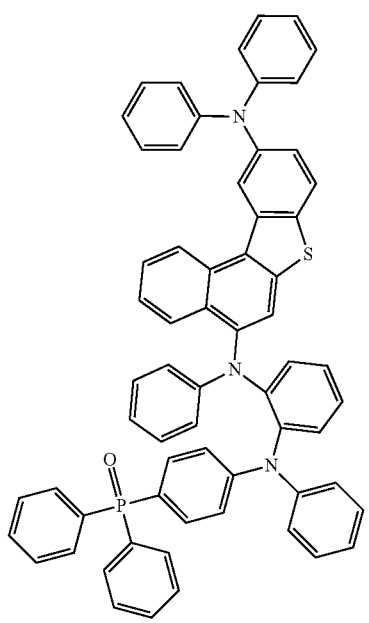
P-75
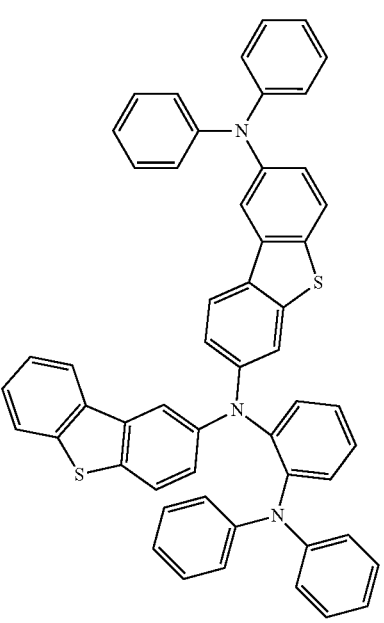
P-77

P-78
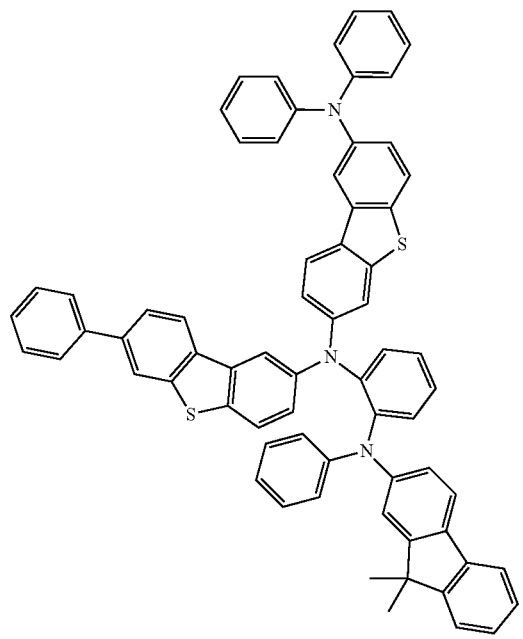
P-79
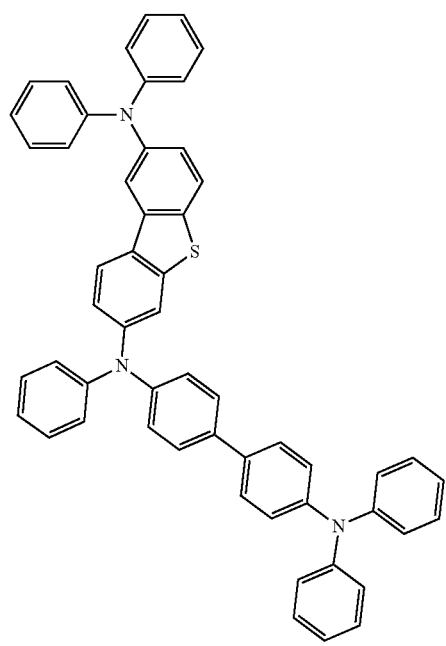
P-80
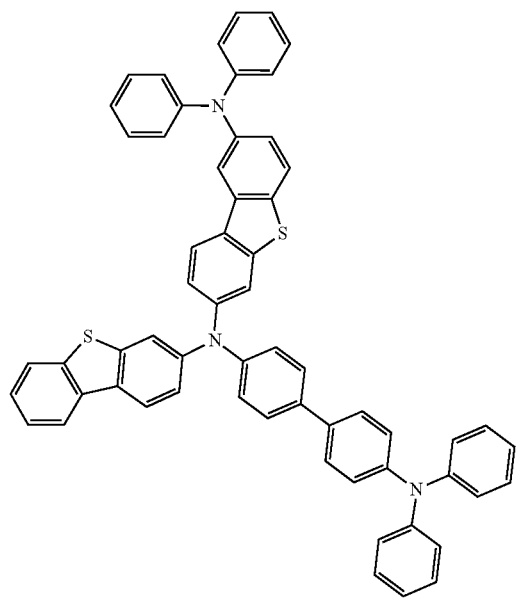
P-81
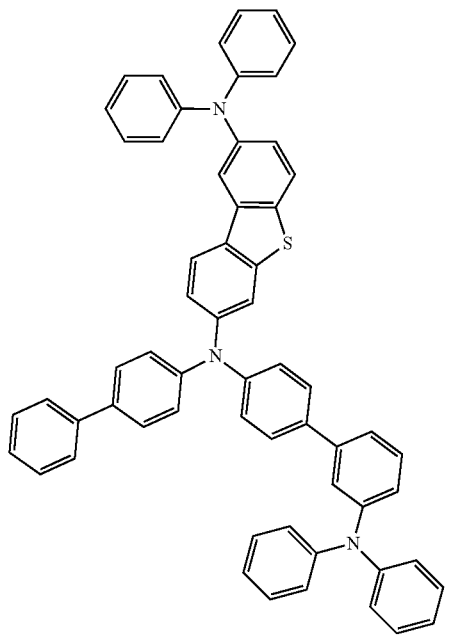

P-82
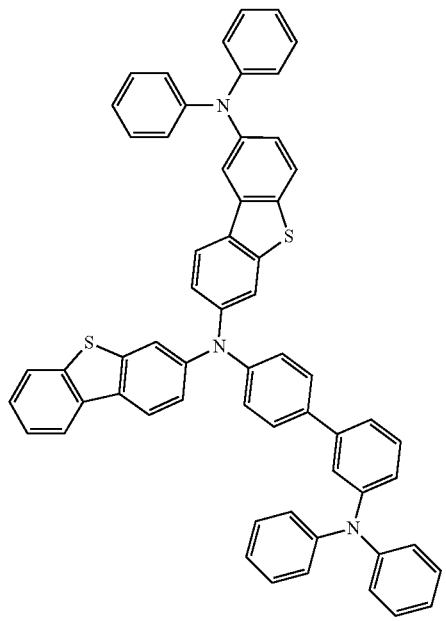
P-84
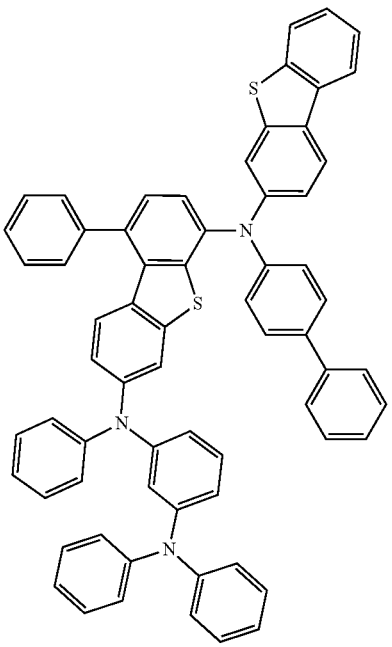
P-83
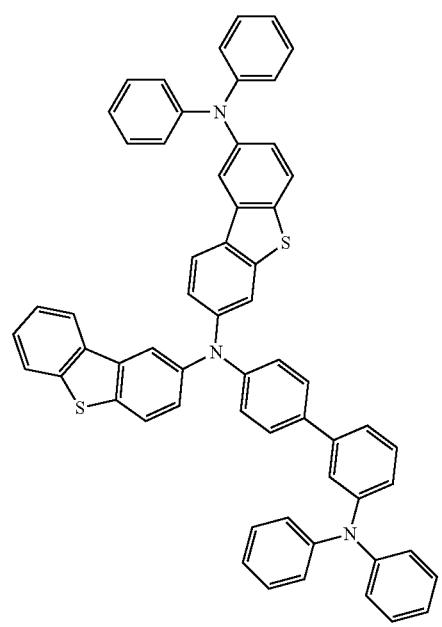
P-85
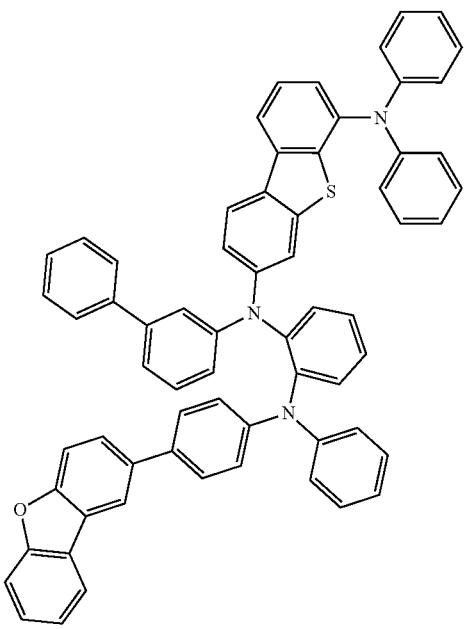

P-86
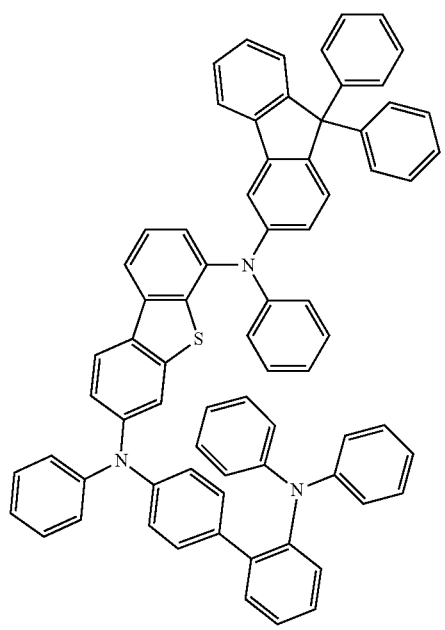
P-88
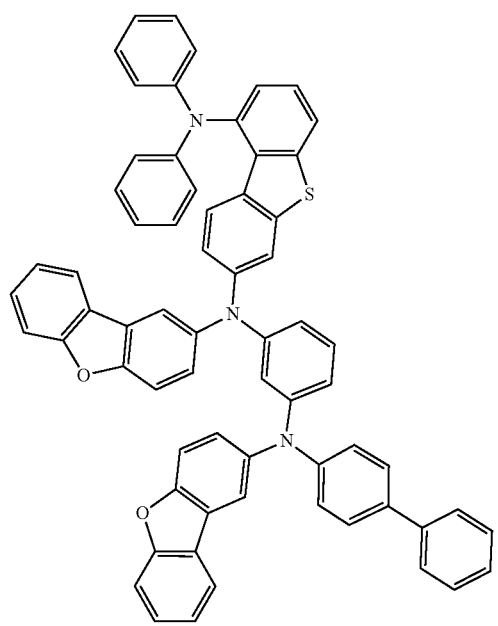
P-87
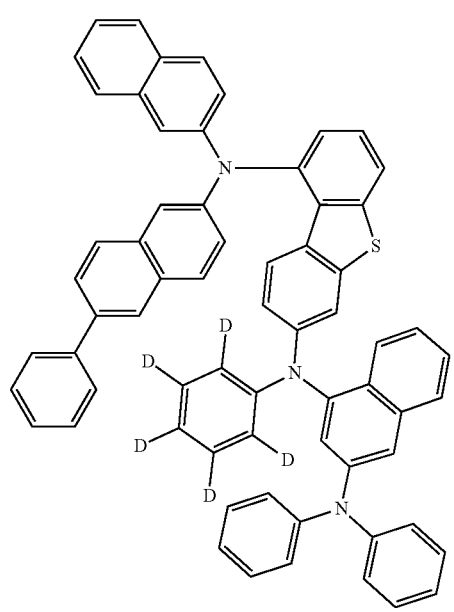
P-89
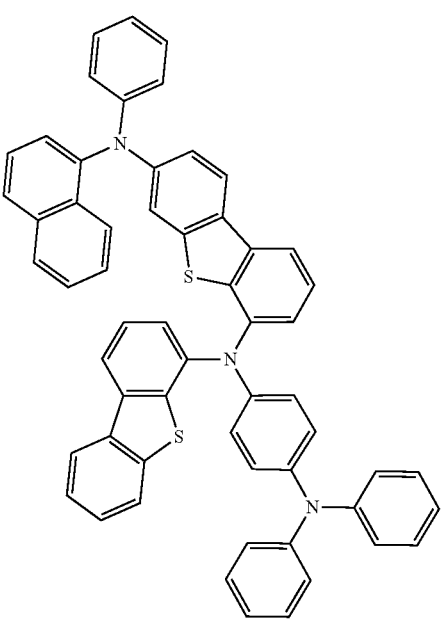

P-90
P-91
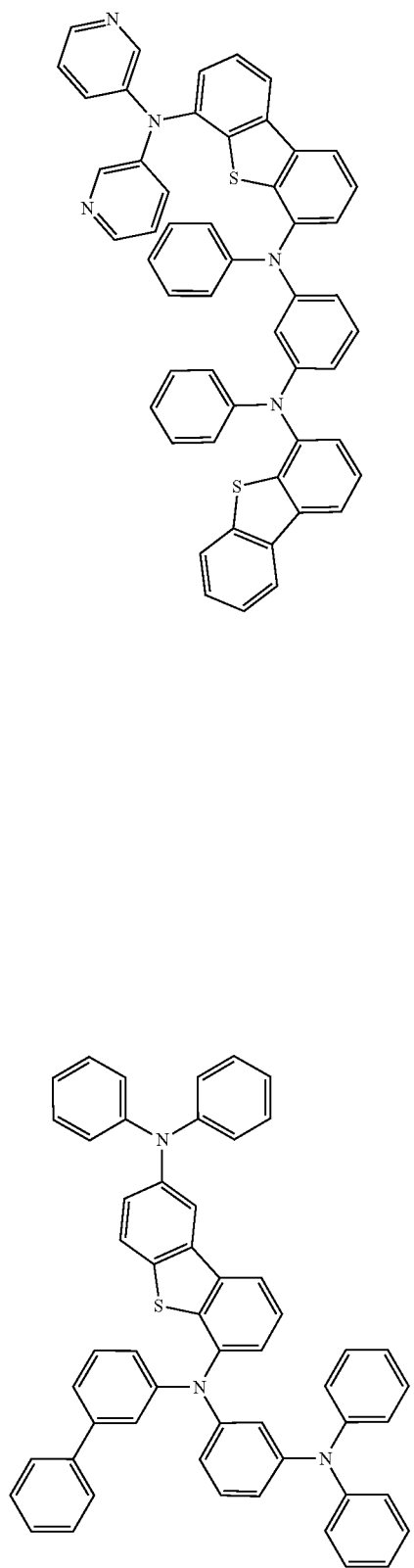
P-92
P-93
P-94
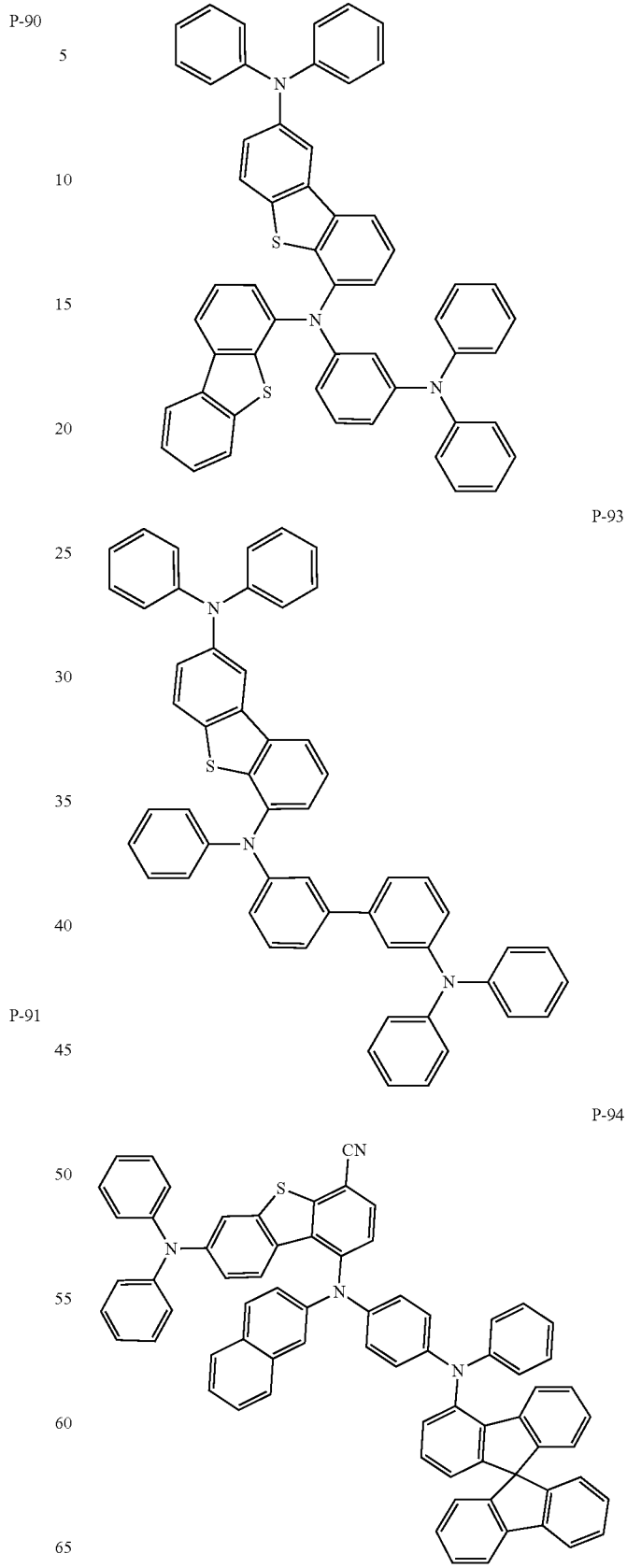

P-95
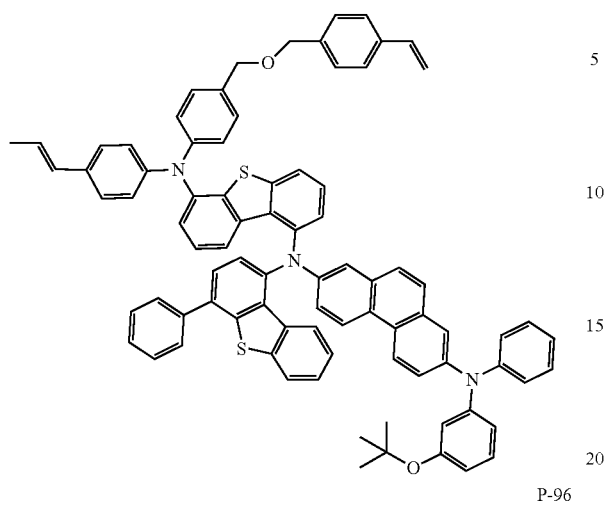
P-96
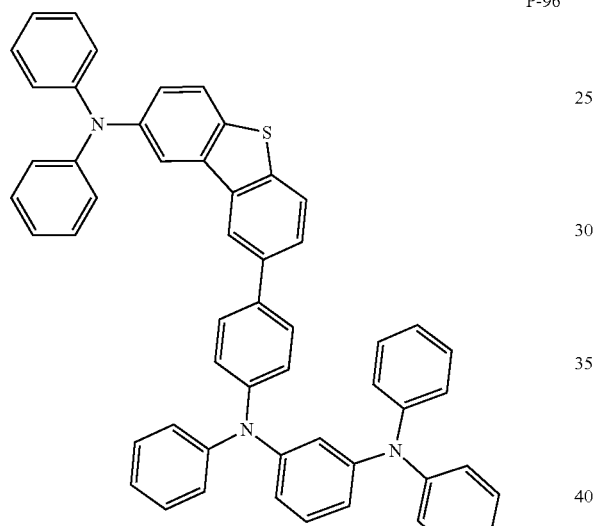
P-97
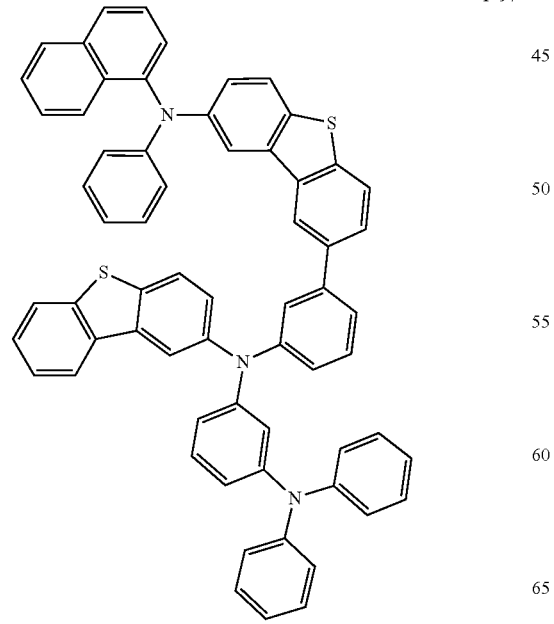
P-98
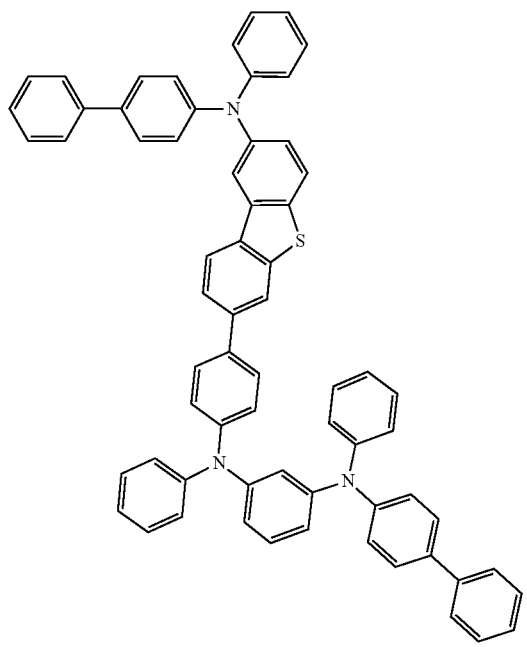
P-99
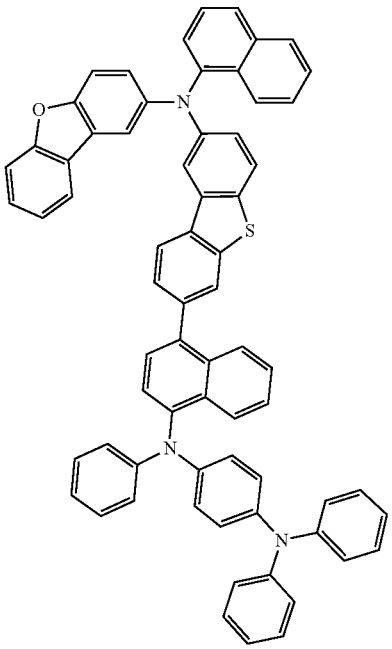

P-100
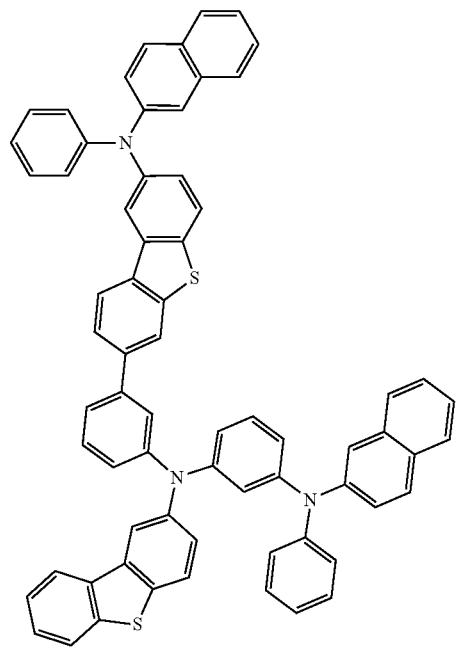
P-101
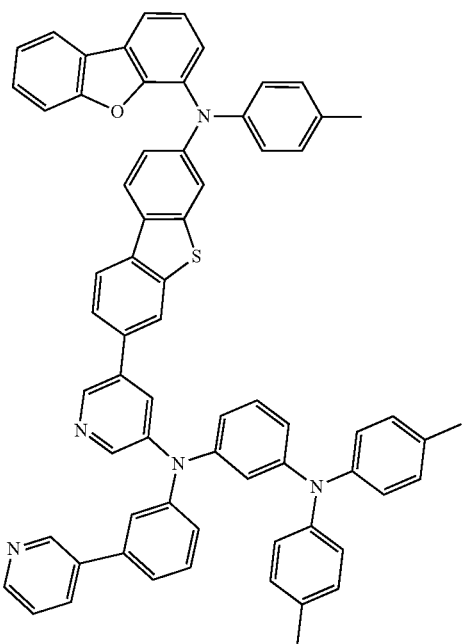
P-102
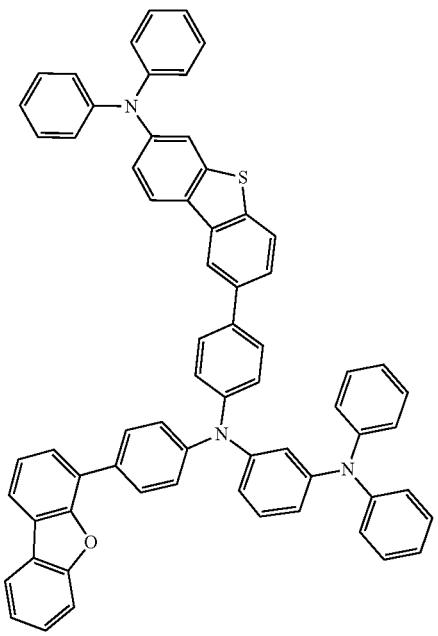
P-103
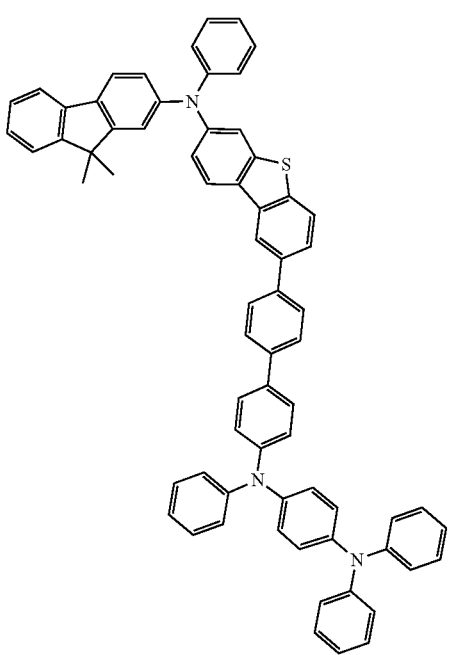

P-104
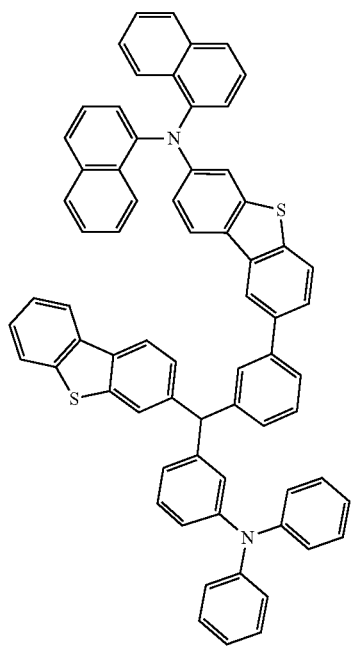
P-105
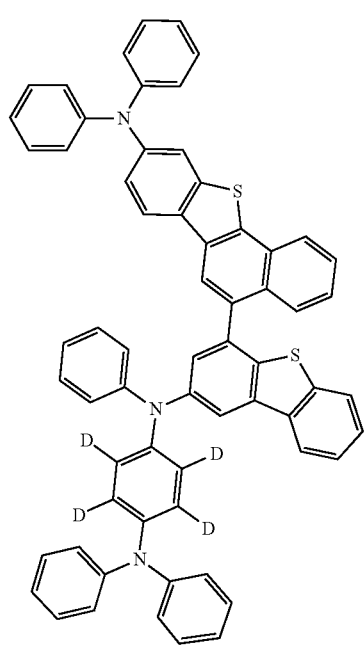
P-106
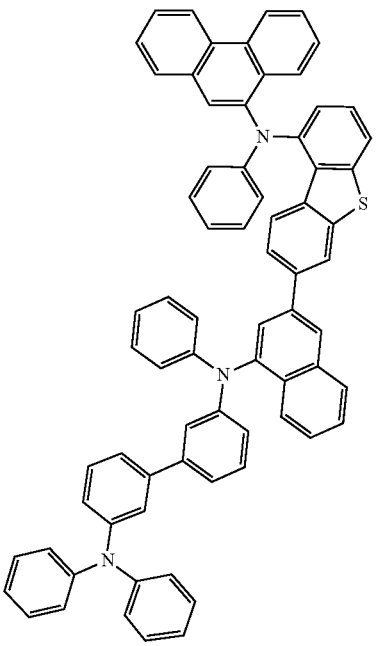
P-107
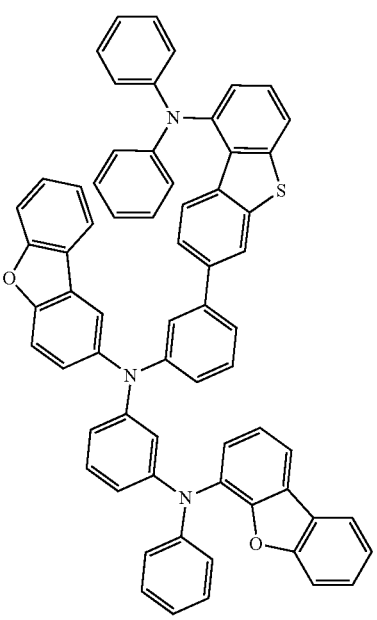

P-108

P-109

P-110

P-111

P-112
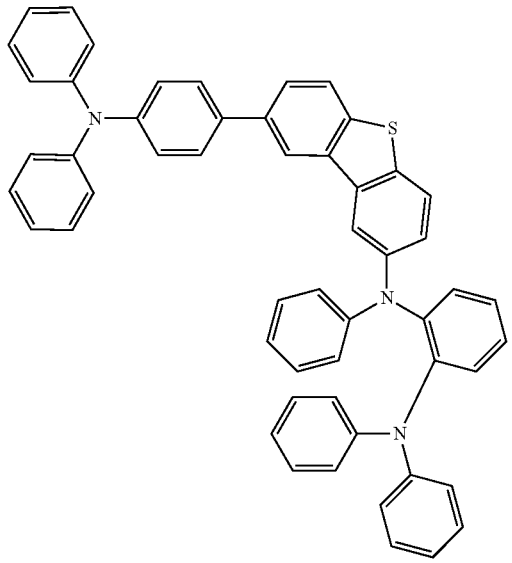
P-114
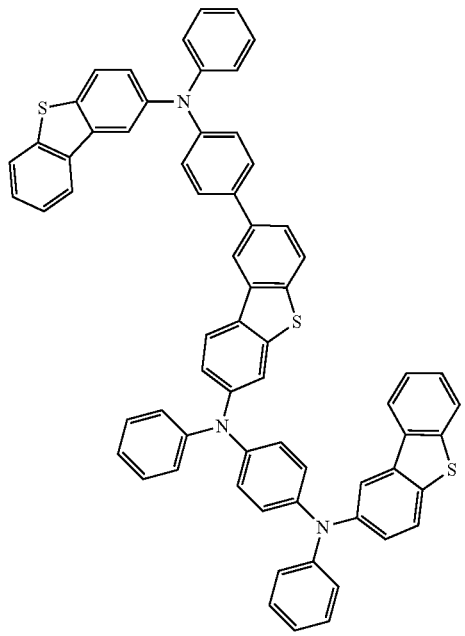
P-113
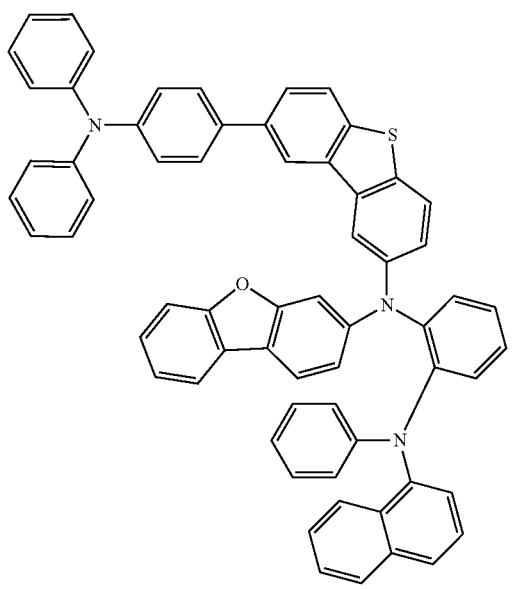
P-115
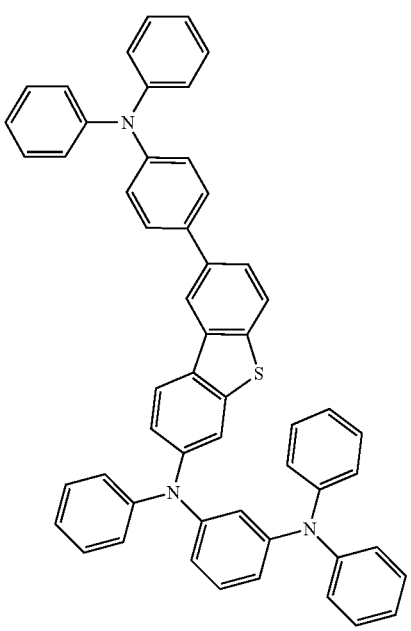

P-116
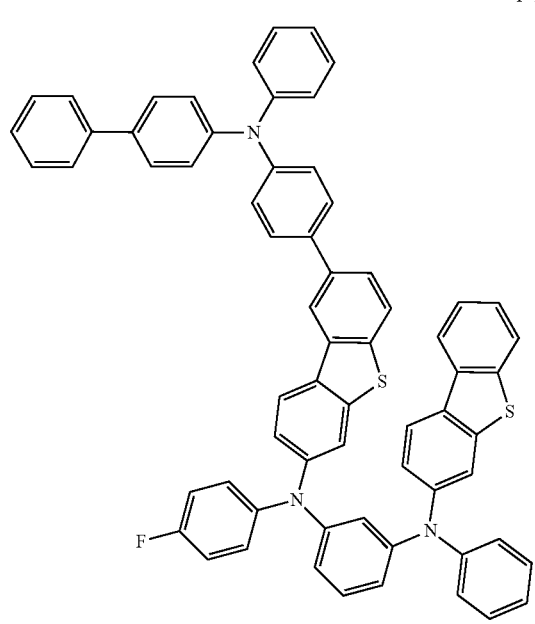
P-117
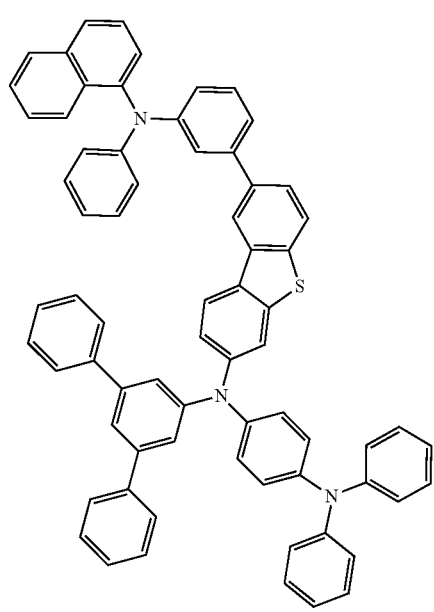
P-118
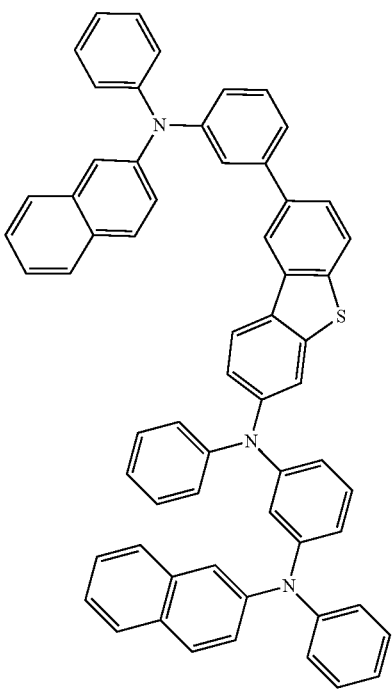
P-119
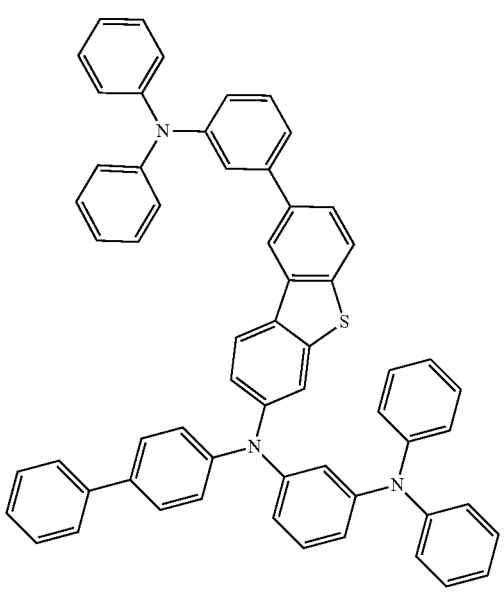

P-120
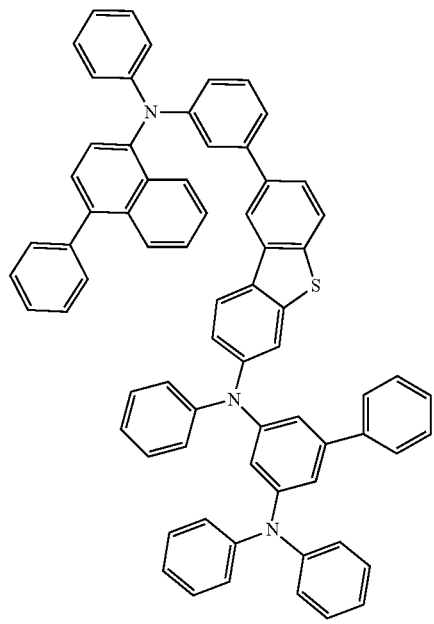
P-122
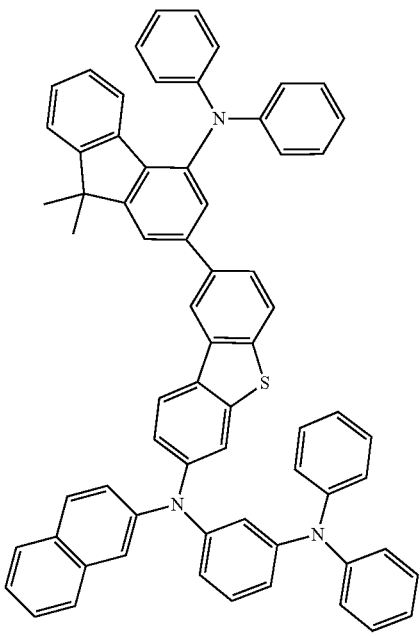
P-121
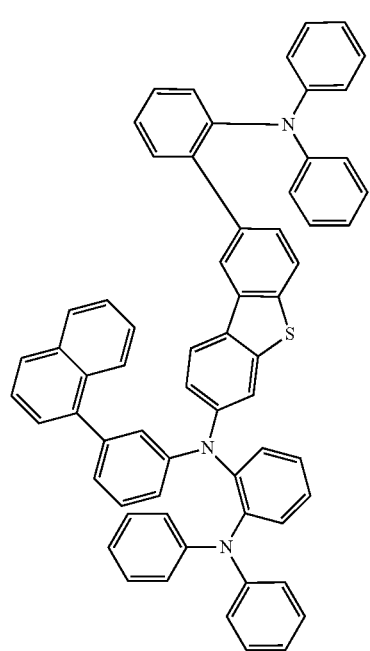
P-123
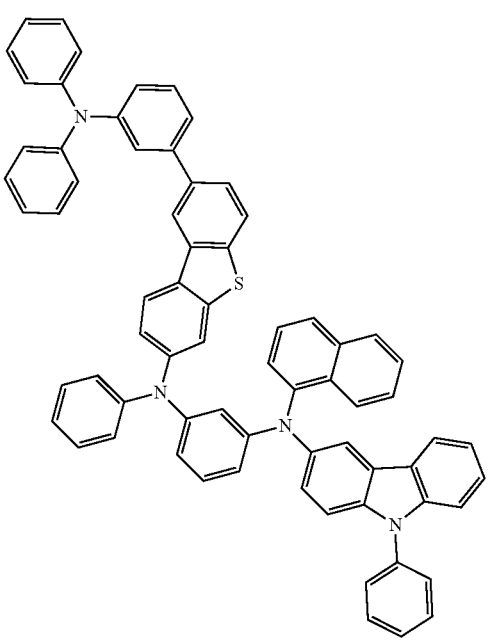

P-124
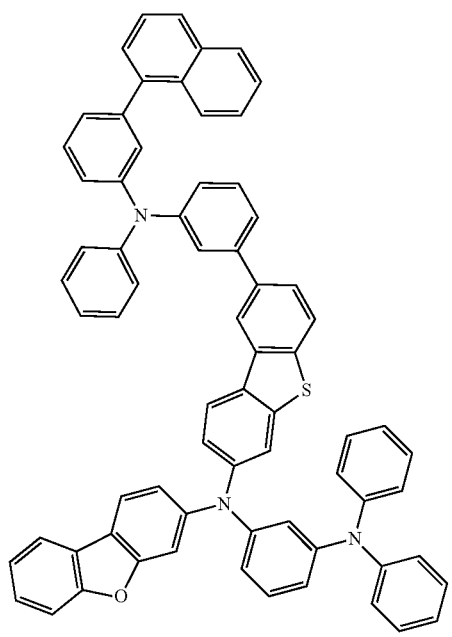
P-126
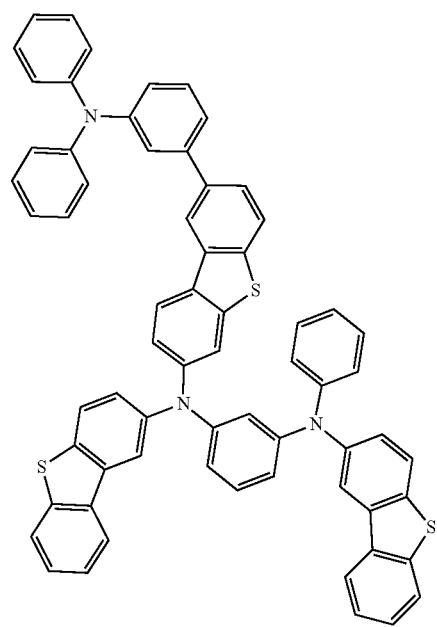
P-125
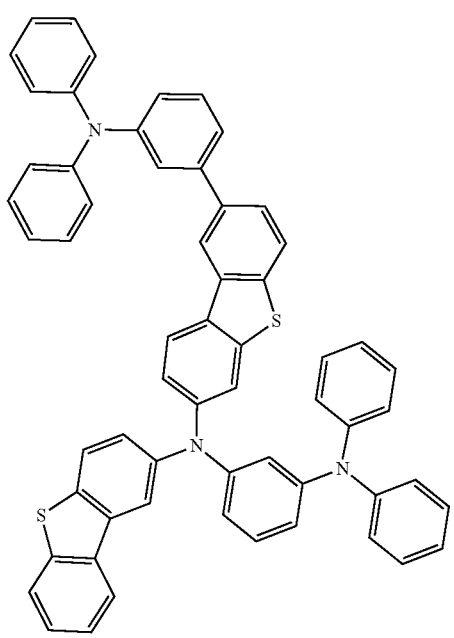
P-127
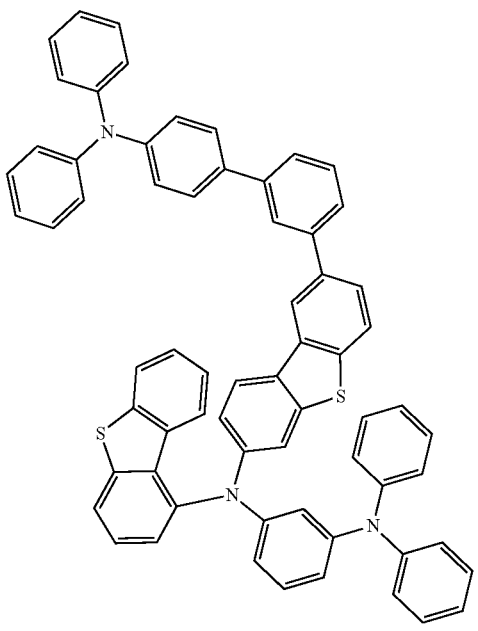

P-128
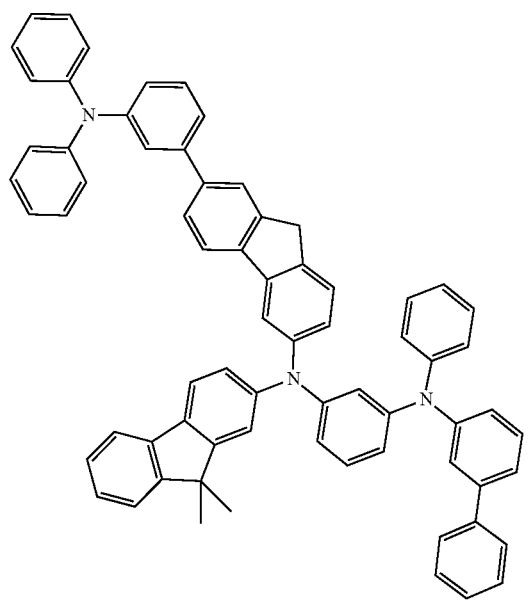
P-130
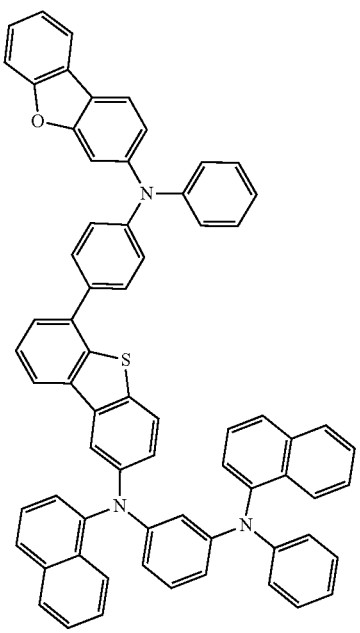
P-129
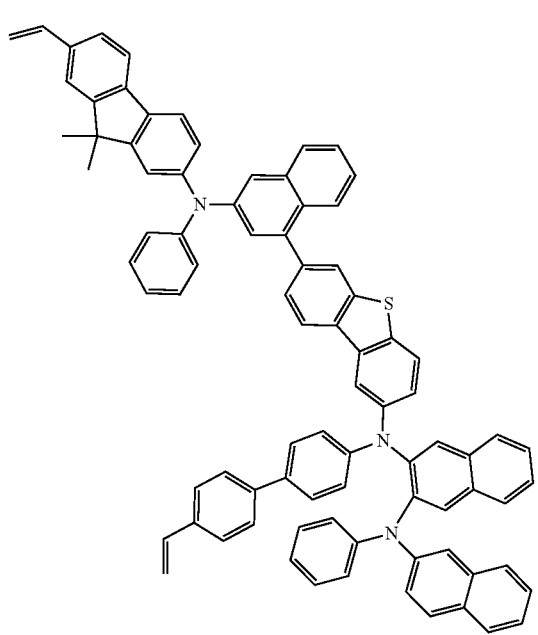
P-131
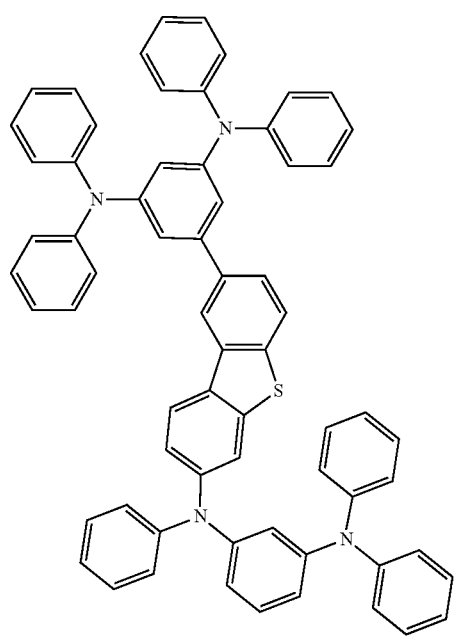

P-132
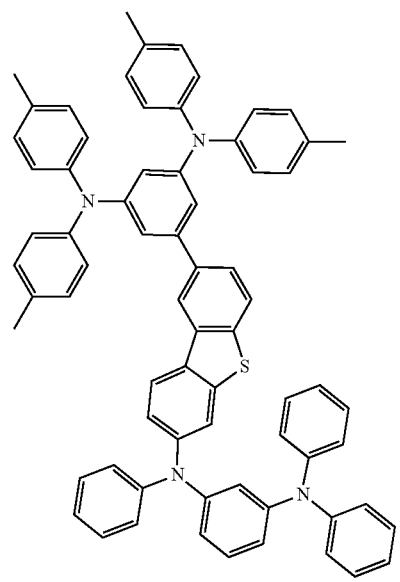
P-134
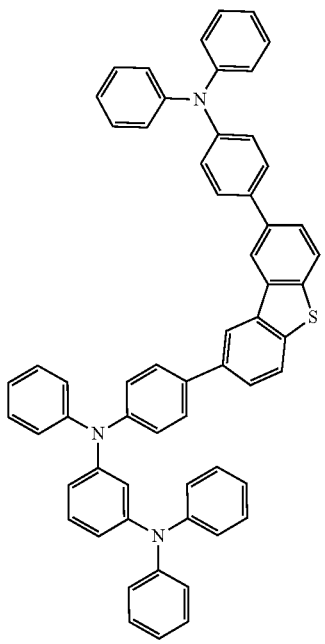
P-133
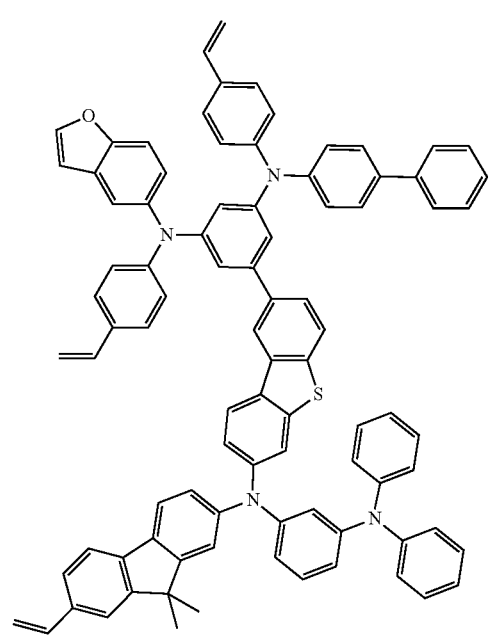
P-135
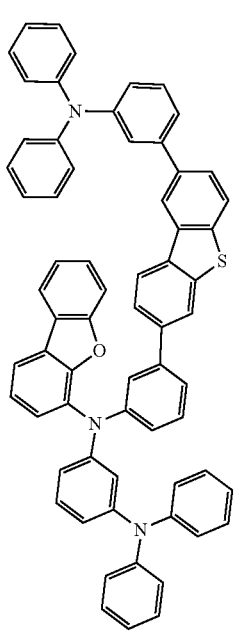

In another aspect of the present invention, the present invention provides an organic electric element comprising a first electrode, a second electrode, and an organic material layer formed between the first electrode and the second electrode. Here, the organic material layer comprises the compound represented by Formulas 1 to 10.

Preferably, the organic material layer may comprise at least one layer of a hole injection layer, a hole transport layer, an emission-auxiliary layer, a light emitting layer, an electron transport-auxiliary layer, a electron transport layer and a electron injection layer, and at least one layer of a hole injection layer, a hole transport layer, an emission-auxiliary layer, a light emitting layer, an electron transport-auxiliary layer, a electron transport layer and a electron injection layer contains the compounds as a single compound or a mixture of two or more kinds. More preferably, the organic material layer may comprise a light emitting layer and an emission-auxiliary layer, the light emitting layer comprises a phosphorescent red light emitting material, and the compound is contained in the light emitting-auxiliary layer.

In another aspect of the present invention, the present invention provides an electronic device comprising a display device, wherein a display device comprises an organic electric element according to the present invention, and a control unit for controlling the display device. Preferably, the organic electric element may be any one of an organic light emitting diode, an organic solar cell, an organic photo conductor, an organic transistor, and an element for monochromatic or white illumination.

Hereinafter, Synthesis method of the compound represented by Formula 1 according to one embodiment of the present invention and Preparation method of an organic electric element will be described in detail by way of examples. However, the present invention is not limited to the following examples.

SYNTHESIS EXAMPLE

The compound (final products) represented by Formula 1 according to the present invention are synthesized by reacting Sub 1 and Sub 2 as shown in Reaction Scheme 1, but are not limited thereto.

$Ar^1$ to $Ar^5$, $L^1$ to $L^3$, $R^1$, $R^2$, m, n, and the like are the same as defined in Formula 1.

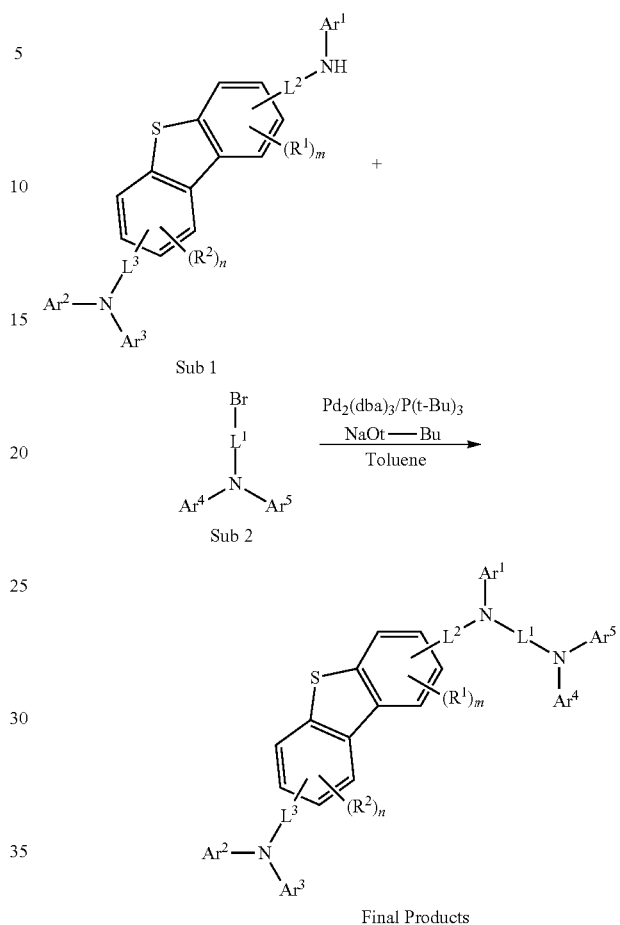

I. Synthesis of Sub 1

Sub 1 of the above Reaction Scheme 1 is synthesized by the following Reaction Scheme 2, but is not limited thereto. $Hal^1$ is I, Br or Cl, and $Hal^2$ is Br or Cl.

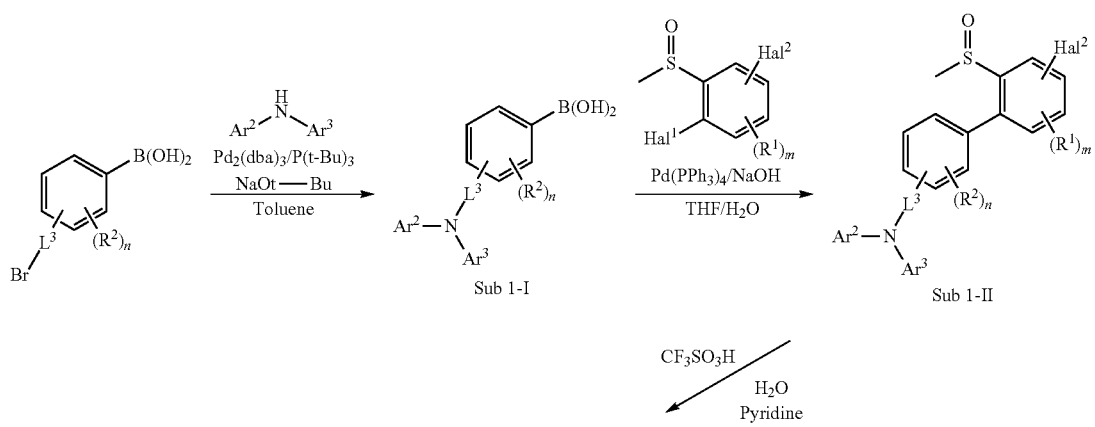

83
84
-continued
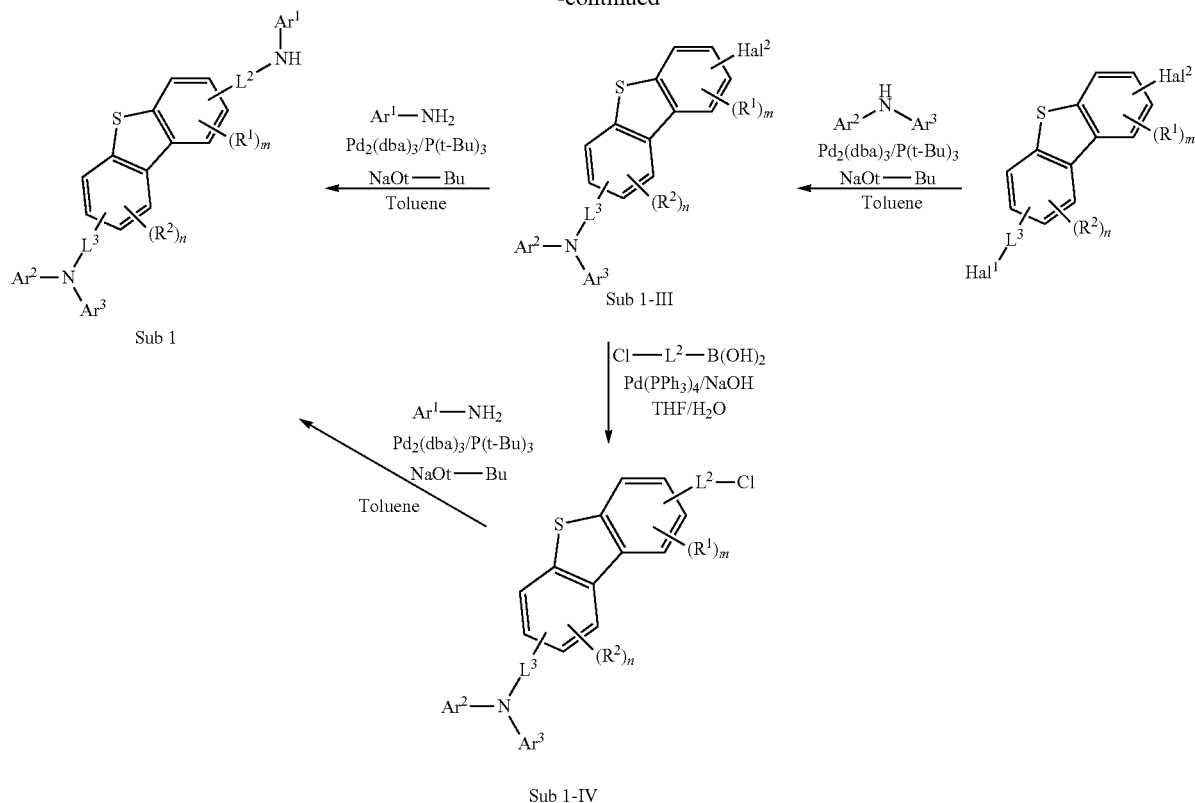
In the Reaction Scheme 2, the amine(HN—Ar²Ar³) reactant was synthesized by using the synthesis method disclosed in Korean Patent No. 10-1251451 (published on Apr. 5, 2013) of the present applicant.
Synthesis Examples of compounds belonging to Sub 1 are as follows.
1. Synthesis Examples of Sub 1-1 and Sub 1-83
<Reaction Scheme 3>
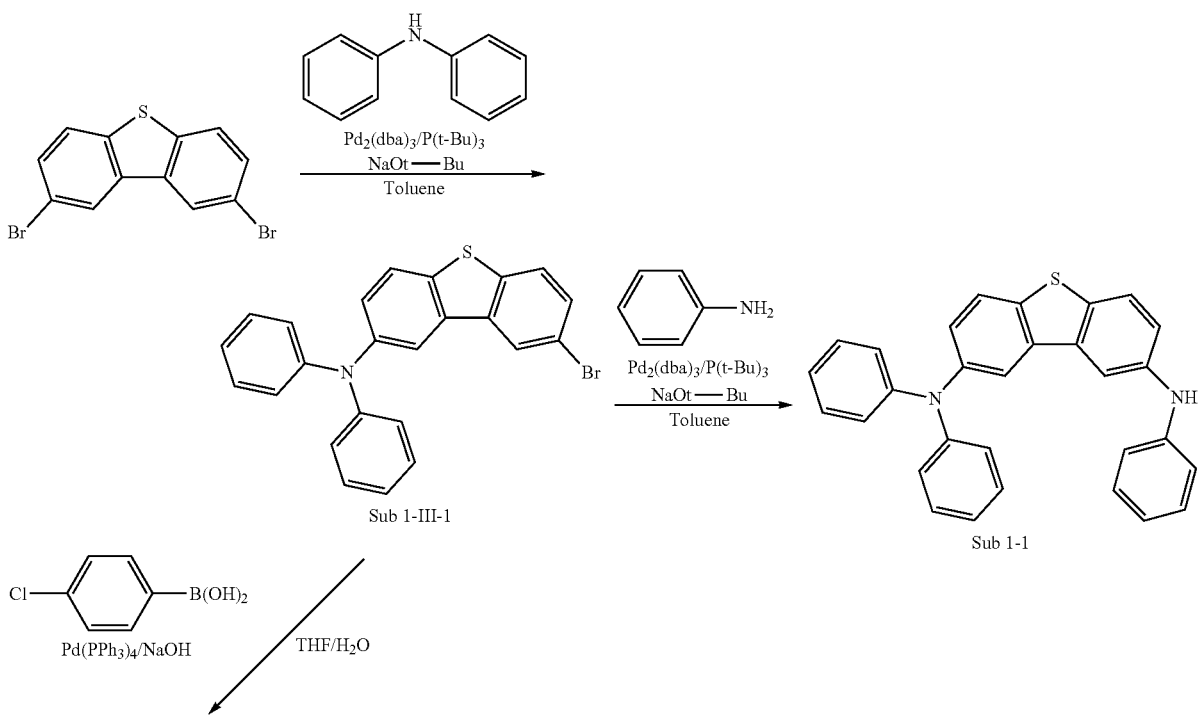

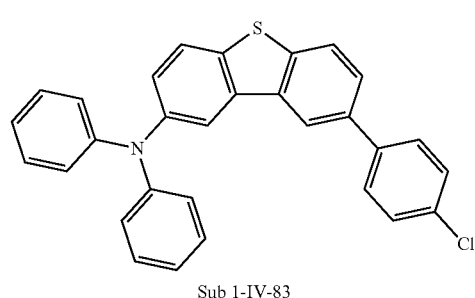

Sub 1-IV-83

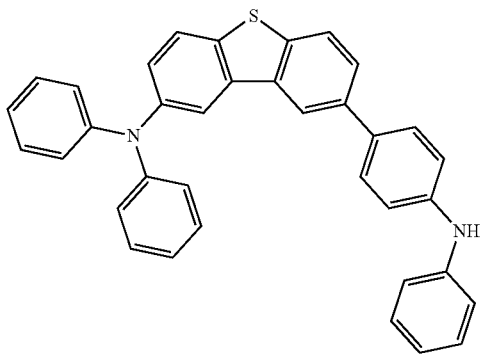

Sub 1-83

(1) Synthesis of Sub 1-III-1

After the starting material diphenylamine (CAS Registry Number: 122-39-4) (17.24 g, 101.87 mmol) was dissolved in toluene (850 ml) in a round bottom flask, 2,8-dibromodibenzo[b,d]thiophene (CAS Registry Number: 31574-87-5) (52.27 g, 152.81 mmol), $Pd_2(dba)_3$ (2.80 g, 3.06 mmol), 50% $P(t\text{-Bu})_3$ (4.0 ml, 8.15 mmol) and NaOt-Bu (29.37 g, 305.62 mmol) are added, and stirred at 70° C. After completion of the reaction, the reaction product was extracted with $CH_2Cl_2$ and water. The organic layer was dried over $MgSO_4$ and concentrated. The resulting compound was purified by silicagel column and recrystallized to obtain 28.06 g of the product (yield: 64%).

(2) Synthesis of Sub 1-1

Sub 1-III-1 (12.22 g, 28.39 mmol) obtained in the above synthesis, toluene (200 ml), toluene (200 ml), aniline (CAS Registry Number: 62-53-3) (2.91 g, 31.23 mmol), $Pd_2(dba)_3$ (0.78 g, 0.85 mmol), 50% $P(t\text{-Bu})_3$ (1.1 ml, 2.27 mmol) and NaOt-Bu (8.19 g, 85.18 mmol) were placed in a round bottom flask and stirred at 40° C. After completion of the reaction, the reaction product was extracted with $CH_2Cl_2$ and water. The organic layer was dried over $MgSO_4$ and concentrated. The resulting compound was purified by silicagel column and recrystallized to obtain 10.43 g of the product (yield: 83%).

(3) Synthesis of Sub 1-IV-83

After Sub 1-III-1 (14.59 g, 33.90 mmol) obtained in the above synthesis was dissolved in THF (120 ml) in a round bottom flask, 4-chlorophenyl)boronic acid (CAS Registry Number: 1679-18-1) (5.83 g, 37.29 mmol), $Pd(PPh_3)_4$ (1.57 g, 1.36 mmol), NaOH (4.07 g, 101.71 mmol) and water (60 ml) are added, and stirred at 80° C. After completion of the reaction, the reaction product was extracted with $CH_2Cl_2$ and water. The organic layer was dried over $MgSO_4$ and concentrated. The resulting compound was purified by silicagel column and recrystallized to obtain 10.34 g of the product (yield: 66%).

(4) Synthesis of Sub 1-83

Aniline (CAS Registry Number: 62-53-3) (2.29 g, 24.62 mmol), $Pd_2(dba)_3$ (0.61 g, 0.67 mmol), 50% $P(t\text{-Bu})_3$ (0.9 ml, 1.79 mmol), NaOt-Bu (6.45 g, 67.14 mmol) and toluene (160 ml) are added to Sub 1-IV-83 (10.34 g, 22.38 mmol) obtained in the above synthesis, and 9.40 g (yield: 81%) of the product was obtained by using the same manner as described above for the synthesis of compound Sub 1-1.

2. Synthesis Example of Sub 1-20

<Reaction Scheme 4>

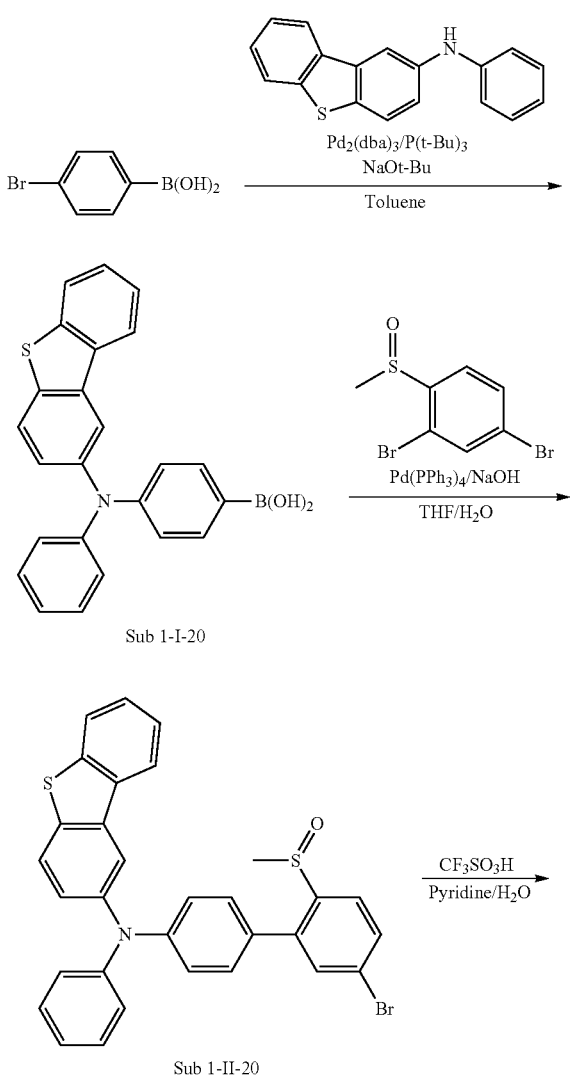

Sub 1-I-20

Sub 1-II-20

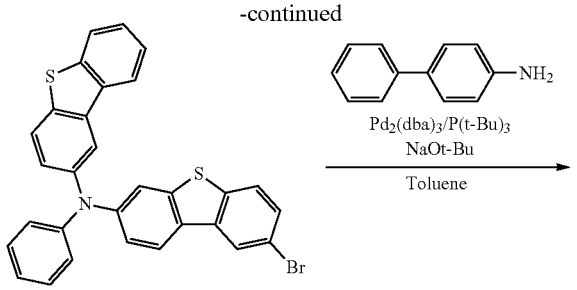

Sub 1-III-20

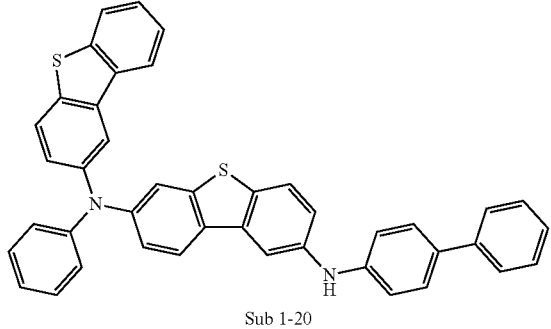

Sub 1-20

(1) Synthesis of Sub 1-I-20

After the starting material (4-bromophenyl)boronic acid (CAS Registry Number: 5467-74-3) (15.17 g, 75.54 mmol) was dissolved in toluene (755 ml) in a round bottom flask, N-phenyldibenzo[b,d]thiophen-2-amine (CAS Registry Number: 1300028-91-4) (20.80 g, 75.54 mmol), Pd$_2$(dba)$_3$ (2.08 g, 2.27 mmol), 50% P(t-Bu)$_3$ (2.2 ml, 4.53 mmol) and NaOt-Bu (21.78 g, 226.61 mmol) are added, and stirred at 100° C. After completion of the reaction, the reaction product was extracted with CH$_2$Cl$_2$ and water. The organic layer was dried over MgSO$_4$ and concentrated. The resulting compound was purified by silicagel column and recrystallized to obtain 25.68 g of the product (yield: 86%).

(2) Synthesis of Sub 1-II-20

After Sub 1-I-20 (25.68 g, 64.97 mmol) obtained in the above synthesis was dissolved in THF (230 ml) in a round bottom flask, 2,4-dibromo-1-(methylsulfinyl)benzene (CAS Registry Number: 1820757-87-6) (21.30 g, 71.46 mmol), Pd(PPh$_3$)$_4$ (3.00 g, 2.60 mmol), NaOH (7.80 g, 194.90 mmol) and water (115 ml) are added, and stirred at 80° C. After completion of the reaction, the reaction product was extracted with CH$_2$Cl$_2$ and water. The organic layer was dried over MgSO$_4$ and concentrated. The resulting compound was purified by silicagel column and recrystallized to obtain 25.12 g of the product (yield: 68%).

(3) Synthesis of Sub 1-III-20

After Sub 1-II-20 (25.12 g, 44.18 mmol) obtained in the above synthesis were placed in a round bottom flask with triflic acid (58.6 ml, 662.74 mmol), and stirred for 24 hours. Then, pyridine aqueous solution (775 ml, pyridine:H$_2$O=1:5) was slowly added dropwise and the mixture was refluxed and stirred for 30 minutes. After completion of the reaction, the reaction product was extracted with CH$_2$Cl$_2$ and water. The organic layer was dried over MgSO$_4$ and concentrated. The resulting compound was purified by silicagel column and recrystallized to obtain 11.62 g of the product (yield: 49%).

(4) Synthesis of Sub 1-20

[1,1'-biphenyl]-4-amine (CAS Registry Number: 92-67-1) (4.03 g, 23.82 mmol), Pd$_2$(dba)$_3$ (0.59 g, 0.65 mmol), 50% P(t-Bu)$_3$ (0.8 ml, 1.73 mmol), NaOt-Bu (6.24 g, 64.98 mmol), toluene (150 ml) are added to Sub 1-III-20 (11.62 g, 21.66 mmol) obtained in the above synthesis, and 10.83 g (yield: 80%) of the product was obtained by using the same manner as described above for the synthesis of compound Sub 1-1.

3. Synthesis Example of Sub 1-28

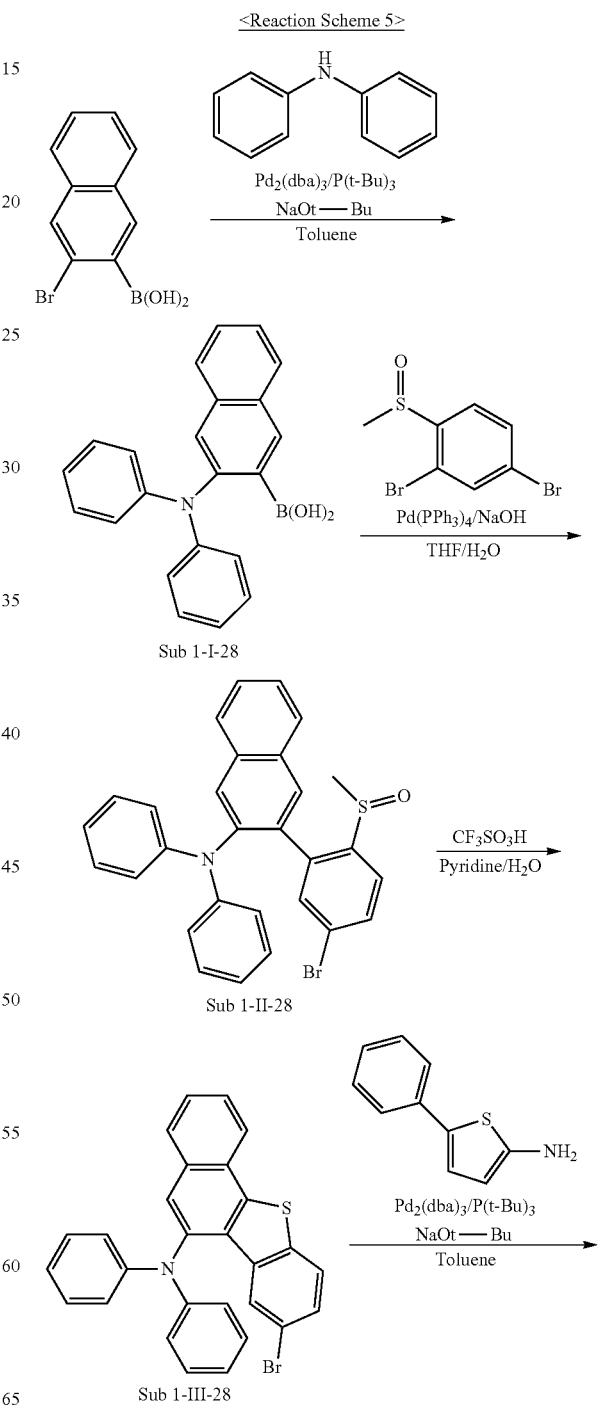

-continued

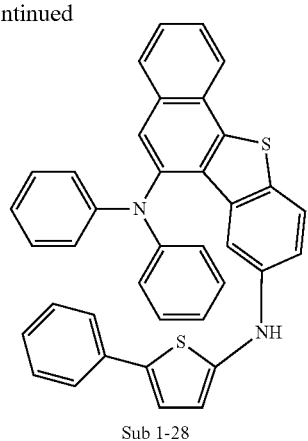

Sub 1-28

(1) Synthesis of Sub 1-I-28

Diphenylamine (CAS Registry Number: 122-39-4) (19.78 g, 116.90 mmol), $Pd_2(dba)_3$ (3.21 g, 3.51 mmol), 50% $P(t-Bu)_3$ (3.4 ml, 7.01 mmol), NaOt-Bu (33.71 g, 350.71 mmol) and toluene (1170 ml) are added to the starting material (3-bromonaphthalen-2-yl)boronic acid (CAS Registry Number: 1301205-62-8) (29.33 g, 116.90 mmol), and 29.34 g (yield: 74%) of the product was obtained by using the same manner as described above for the synthesis of compound Sub 1-I-20.

(2) Synthesis of Sub 1-II-28

2,4-dibromo-1-(methylsulfinyl)benzene (CAS Registry Number: 1820757-87-6) (28.35 g, 95.15 mmol), $Pd(PPh_3)_4$ (4.00 g, 3.46 mmol), NaOH (10.38 g, 259.49 mmol), THF (300 ml) and water (150 ml) are added to Sub 1-I-28 (29.34 g, 86.50 mmol) obtained in the above synthesis, and 24.82 g (yield: 56%) of the product was obtained by using the same manner as described above for the synthesis of compound Sub 1-II-20.

(3) Synthesis of Sub 1-III-28

Triflic acid (64.3 ml, 726.48 mmol) and pyridine aqueous (850 ml, pyridine:$H_2O$=1:5) are added to Sub 1-II-28 (24.82 g, 48.43 mmol) obtained in the above synthesis, and 11.63 g (yield: 50%) of the product was obtained by using the same manner as described above for the synthesis of compound Sub 1-III-20.

(4) Synthesis of Sub 1-28

5-phenylthiophen-2-amine (CAS Registry Number: 14770-85-5) (4.67 g, 26.63 mmol), $Pd_2(dba)_3$ (0.67 g, 0.73 mmol), 50% $P(t-Bu)_3$ (0.9 ml, 1.94 mmol), NaOt-Bu (6.98 g, 72.62 mmol) and toluene (170 ml) are added to Sub 1-III-28 (11.63 g, 24.21 mmol) obtained in the above synthesis, and 8.77 g (yield: 63%) of the product was obtained by using the same manner as described above for the synthesis of compound Sub 1-1.

4. Synthesis Examples of Sub 1-44 and Sub 1-96

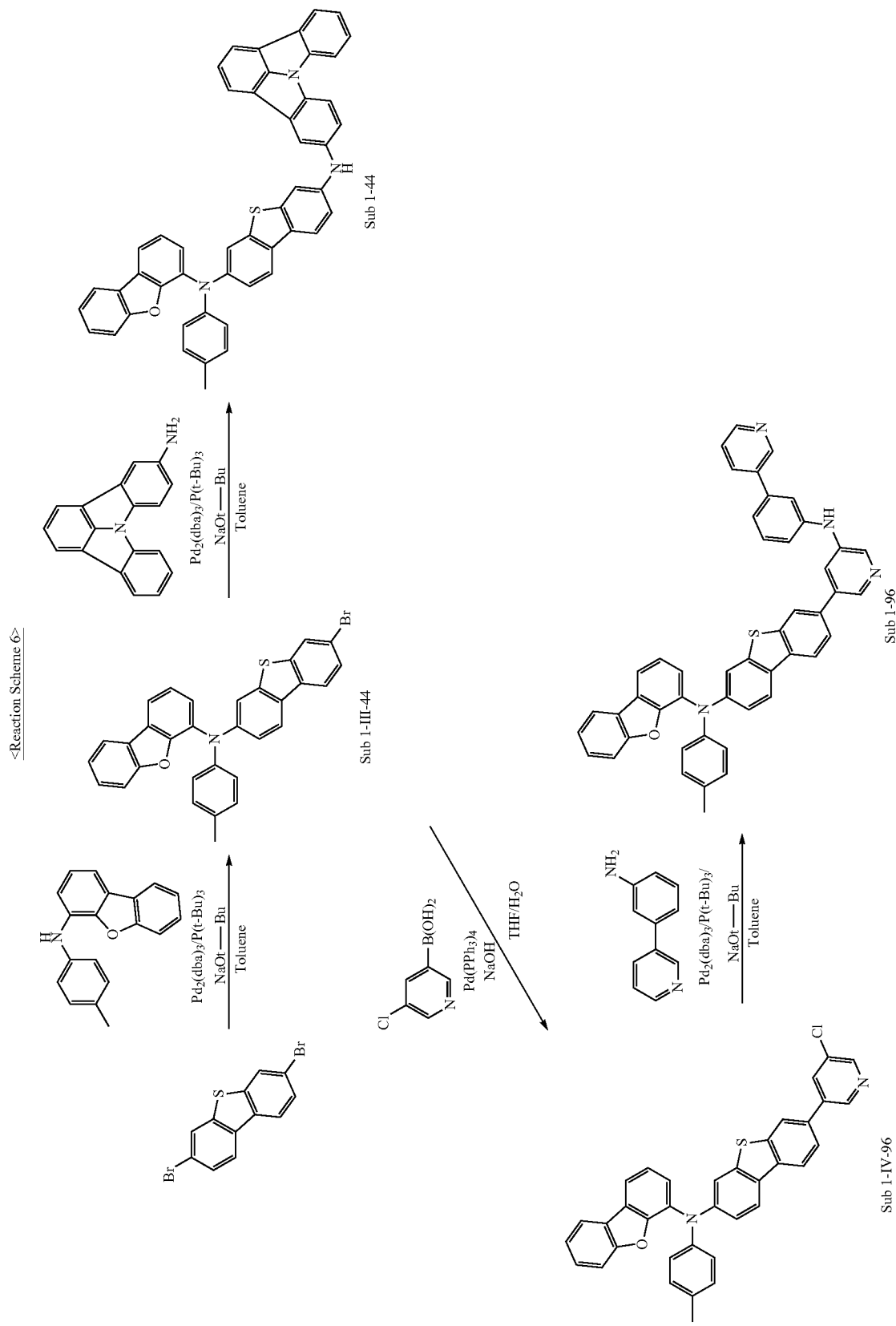

(1) Synthesis of Sub 1-III-44

3,7-dibromodibenzo[b,d]thiophene (CAS Registry Number: 83834-10-0) (61.94 g, 181.09 mmol), $Pd_2(dba)_3$ (3.32 g, 3.62 mmol) 50% $P(t-Bu)_3$ (4.7 ml, 9.66 mmol), NaOt-Bu (34.81 g, 362.19 mmol) and toluene (100 ml) are added to the starting material N-(p-tolyl)dibenzo[b,d]furan-4-amine (CAS Registry Number: 1609080-05-8) (33.00 g, 120.73 mmol), and 38.07 g (yield: 59%) of the product was obtained by using the same manner as described above for the synthesis of compound Sub 1-III-1.

(2) Synthesis of Sub 1-44

Indolo[3,2,1-jk]carbazol-5-amine (CAS Registry Number: 1191512-09-0) (5.50 g, 21.45 mmol), $Pd_2(dba)_3$ (0.54 g, 0.58 mmol) 50% $P(t-Bu)_3$ (0.8 ml, 1.56 mmol), NaOt-Bu (5.62 g, 58.49 mmol) and toluene (135 ml) are added to Sub 1-III-44 (10.42 g, 19.50 mmol) obtained in the above synthesis, and 9.96 g (yield: 72%) of the product was obtained by using the same manner as described above for the synthesis of compound Sub 1-1.

(3) Synthesis of Sub 1-IV-96

(5-chloropyridin-3-yl)boronic acid (CAS Registry Number: 872041-85-5) (8.91 g, 56.60 mmol), $Pd(PPh_3)_4$ (2.38 g, 2.06 mmol), NaOH (6.17 g, 154.36 mmol), THF (180 ml) and water (90 ml) are added to Sub 1-III-44 (27.50 g, 51.45 mmol) obtained in the above synthesis, and 14.88 g (yield: 51%) of the product was obtained by using the same manner as described above for the synthesis of compound Sub 1-IV-83.

(4) Synthesis of Sub 1-96

3-(pyridin-3-yl)aniline (CAS Registry Number: 57976-57-5) (4.91 g, 28.86 mmol), $Pd_2(dba)_3$ (0.72 g, 0.79 mmol), 50% $P(t-Bu)_3$ (1.0 ml, 2.10 mmol), NaOt-Bu (7.57 g, 78.72 mmol) and toluene (185 ml) are added to Sub 1-IV-96 (14.88 g, 26.24 mmol) obtained in the above synthesis, and 9.93 g (yield: 54%) of the product was obtained by using the same manner as described above for the synthesis of compound Sub 1-1.

5. Synthesis Examples of Sub 1-46 and Sub 1-73

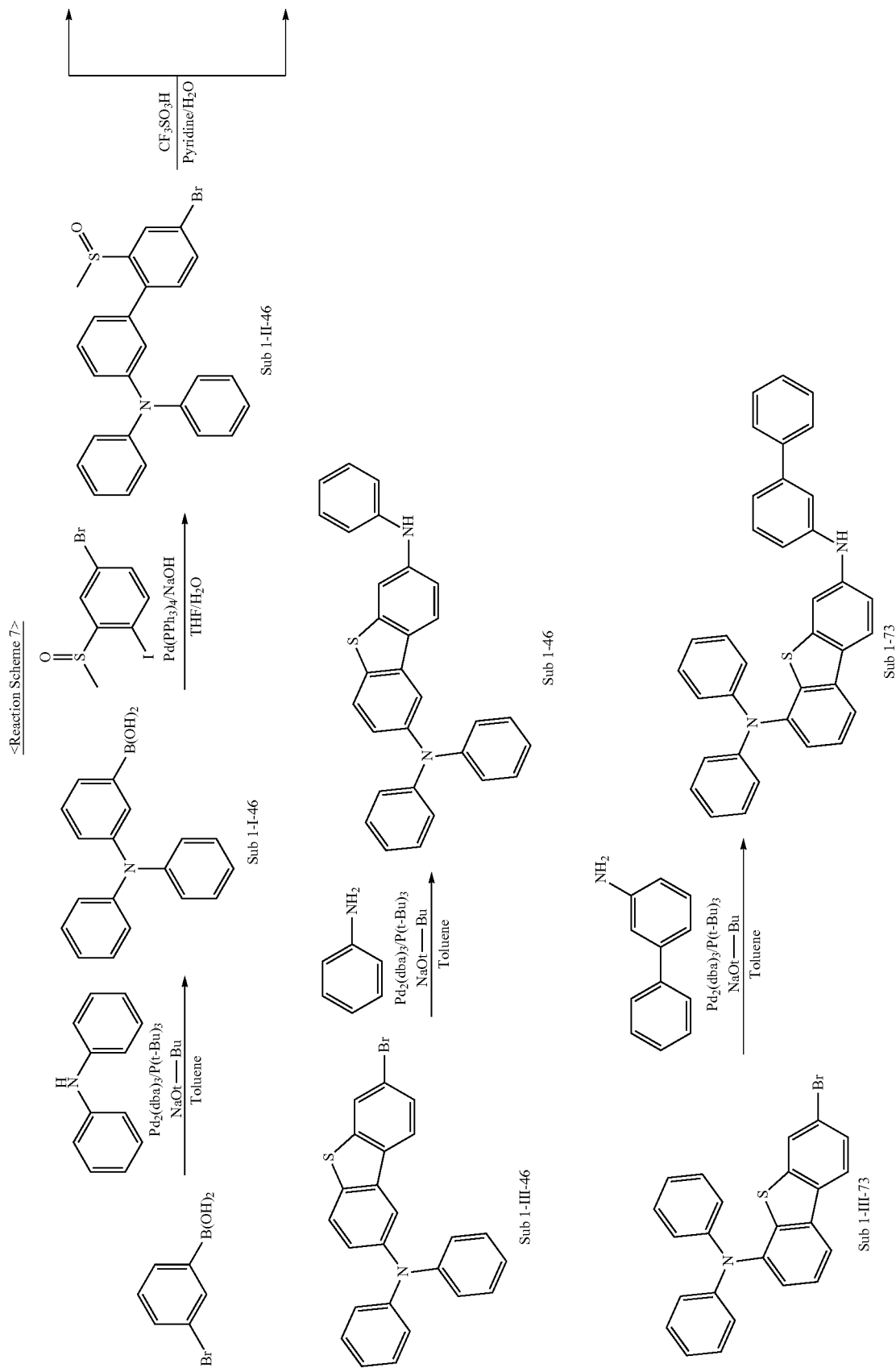

(1) Synthesis of Sub 1-I-46

Diphenylamine (CAS Registry Number: 122-39-4) (32.29 g, 190.81 mmol), Pd$_2$(dba)$_3$ (5.24 g, 5.72 mmol), 50% P(t-Bu)$_3$ (5.6 ml, 11.45 mmol), NaOt-Bu (55.02 g, 572.42 mmol) and toluene (1270 ml) are added to the starting material (3-bromophenyl)boronic acid (CAS Registry Number: 89598-96-9) (38.32 g, 190.81 mmol), and 50.20 g (yield: 91%) of the product was obtained by using the same manner as described above for the synthesis of compound Sub 1-I-20.

(2) Synthesis of Sub 1-II-46

4-bromo-1-iodo-2-(methylsulfinyl)benzene (CAS Registry Number: 1638151-06-0) (65.89 g, 190.98 mmol), Pd(PPh$_3$)$_4$ (8.03 g, 6.94 mmol), NaOH (20.83 g, 520.85 mmol), THF (610 ml) and water (305 ml) are added to Sub 1-I-46 (50.20 g, 173.62 mmol) obtained in the above synthesis, and 60.21 g (yield: 75%) of the product was obtained by using the same manner as described above for the synthesis of compound Sub 1-II-20.

(3) Synthesis of Sub 1-III-46 and Sub 1-III-73

Triflic acid (115.2 ml, 1302.09 mmol) and pyridine aqueous (1520 ml, pyridine:H$_2$O=1:5) are added to Sub 1-II-46 (60.21 g, 130.21 mmol) obtained in the above synthesis, and 23.54 g (yield: 42%) of the product Sub 1-III-46 and 20.73 g (yield: 37%) of the product Sub 1-III-71 were obtained by using the same manner as described above for the synthesis of compound Sub 1-111-20.

(4) Synthesis of Sub 1-46

Aniline (CAS Registry Number: 62-53-3) (2.74 g, 29.47 mmol), Pd$_2$(dba)$_3$ (0.74 g, 0.80 mmol), 50% P(t-Bu)$_3$ (1.0 ml, 2.14 mmol), NaOt-Bu (7.72 g, 80.37 mmol) and toluene (190 ml) are added to Sub 1-III-46 (11.53 g, 26.79 mmol) obtained in the above synthesis, and 10.08 g (yield: 85%) of the product was obtained by using the same manner as described above for the synthesis of compound Sub 1-1.

(5) Synthesis of Sub 1-73

[1,1'-biphenyl]-3-amine (CAS Registry Number: 2243-47-2) (4.39 g, 25.97 mmol), Pd$_2$(dba)$_3$ (0.65 g, 0.71 mmol), 50% P(t-Bu)$_3$ (0.9 ml, 1.89 mmol), NaOt-Bu (6.81 g, 70.82 mmol) and toluene (165 ml) are added to Sub 1-III-73 (10.16 g, 23.61 mmol) obtained in the above synthesis, and 9.80 g (yield: 80%) of the product was obtained by using the same manner as described above for the synthesis of compound Sub 1-1.

6. Synthesis Example of Sub 1-60

<Reaction Scheme 8>

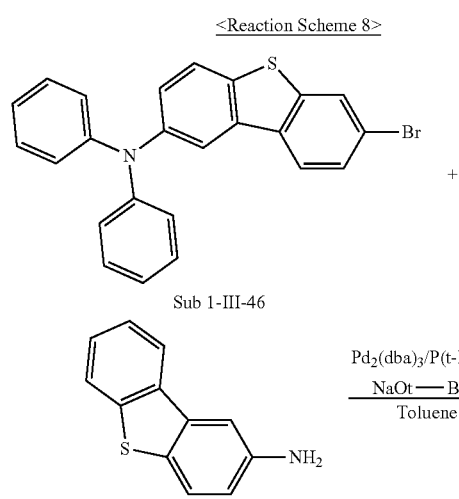

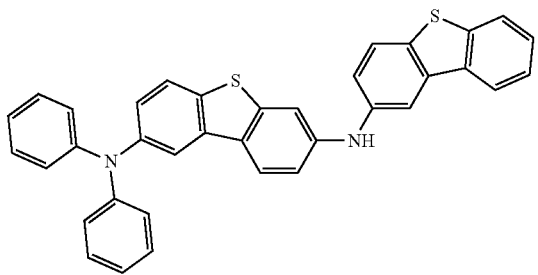

Sub 1-60

Dibenzo[b,d]thiophen-2-amine (CAS Registry Number: 7428-91-3) (5.98 g, 30.01 mmol), Pd$_2$(dba)$_3$ (0.75 g, 0.82 mmol), 50% P(t-Bu)$_3$ (1.1 ml, 2.18 mmol), NaOt-Bu (7.87 g, 81.84 mmol) and toluene (190 ml) are added to Sub 1-III-46 (11.74 g, 27.28 mmol) obtained in the above synthesis, and 10.63 g (yield: 71%) of the product was obtained by using the same manner as described above for the synthesis of compound Sub 1-1.

7. Synthesis Example of Sub 1-79

<Reaction Scheme 9>

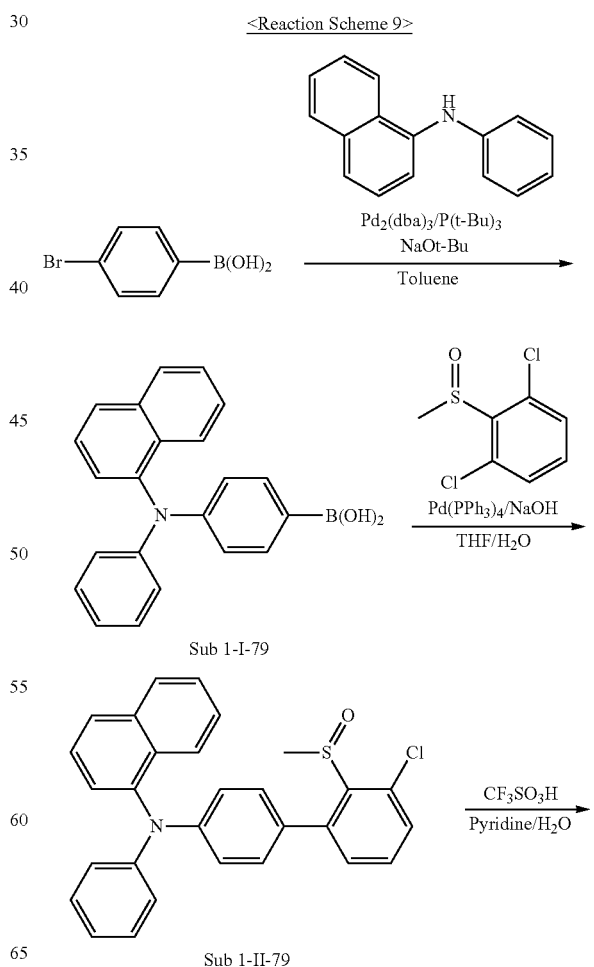

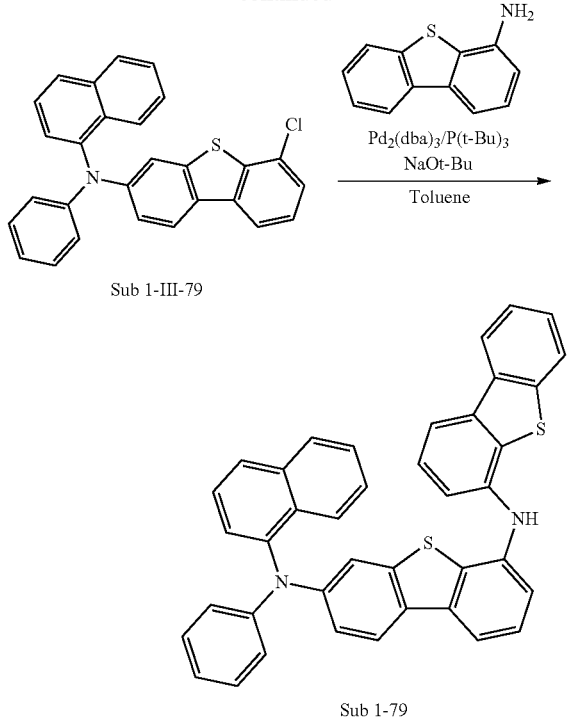

Sub 1-III-79

Sub 1-79

(1) Synthesis of Sub 1-I-79

N-phenylnaphthalen-1-amine (CAS Registry Number: 90-30-2) (24.57 g, 112.04 mmol), Pd$_2$(dba)$_3$ (3.08 g, 3.36 mmol), 50% P(t-Bu)$_3$ (3.3 ml, 6.72 mmol), NaOt-Bu (32.30 g, 336.11 mmol) and toluene (1120 ml) are added to the starting material (4-bromophenyl)boronic acid (CAS Registry Number: 5467-74-3) (22.50 g, 112.04 mmol), and 35.34 g (yield: 93%) of the product was obtained by using the same manner as described above for the synthesis of compound Sub 1-I-20.

(2) Synthesis of Sub 1-II-79

1,3-dichloro-2-(methylsulfinyl)benzene (CAS Registry Number: 122199-98-8) (23.96 g, 114.60 mmol), Pd(PPh$_3$)$_4$ (4.82 g, 4.17 mmol), NaOH (12.50 g, 312.56 mmol), THF (360 ml) and water (180 ml) are added to Sub 1-I-79 (35.34 g, 104.19 mmol) obtained in the above synthesis, and 25.36 g (yield: 52%) of the product was obtained by using the same manner as described above for the synthesis of compound Sub 1-II-20.

(3) Synthesis of Sub 1-III-79

Triflic acid (71.9 ml, 812.80 mmol) and pyridine aqueous (950 ml, pyridine:H$_2$O=1:5) are added to Sub 1-II-79 (25.36 g, 54.19 mmol) obtained in the above synthesis, and 11.10 g (yield: 47%) of the product was obtained by using the same manner as described above for the synthesis of compound Sub 1-III-20.

(4) Synthesis of Sub 1-79

Dibenzo[b,d]thiophen-4-amine (CAS Registry Number: 72433-66-0) (5.58 g, 28.01 mmol), Pd$_2$(dba)$_3$ (0.70 g, 0.76 mmol), 50% P(t-Bu)$_3$ (1.0 ml, 2.04 mmol), NaOt-Bu (7.34 g, 76.38 mmol) and toluene (180 ml) are added to Sub 1-III-79 (11.10 g, 25.46 mmol) obtained in the above synthesis, and 10.37 g (yield: 68%) of the product was obtained by using the same manner as described above for the synthesis of compound Sub 1-1.

8. Synthesis Examples of Sub 1-109 and Sub 1-114

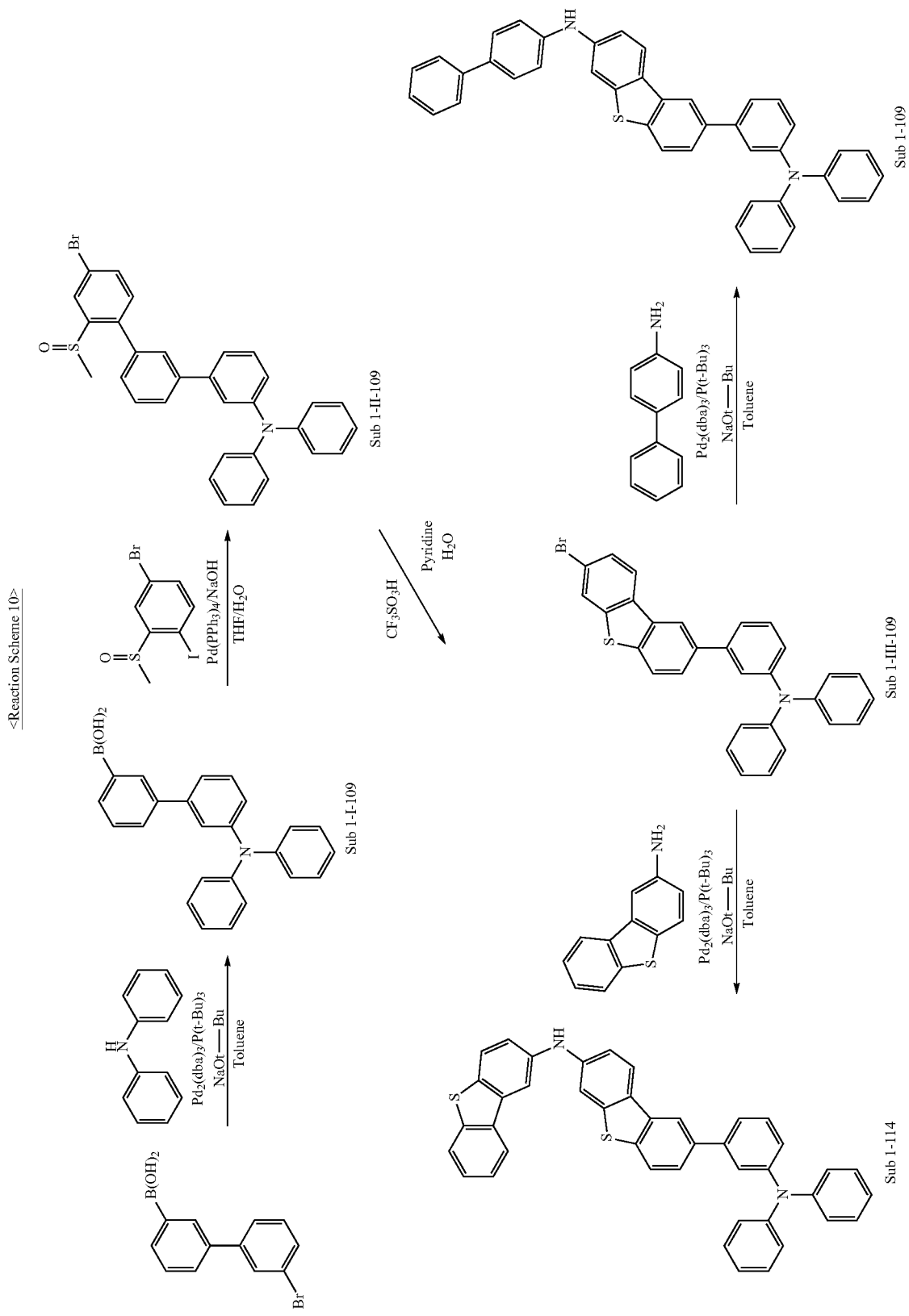

(1) Synthesis of Sub 1-I-109 Diphenylamine (CAS Registry Number: 122-39-4) (44.64 g, 263.79 mmol), Pd$_2$(dba)$_3$ (7.25 g, 7.91 mmol), 50% P(t-Bu)$_3$ (7.7 ml, 15.83 mmol), NaOt-Bu (76.06 g, 791.38 mmol) and toluene (1760 ml) are added to the starting material (3'-bromo-[1,1'-biphenyl]-3-yl)boronic acid (CAS Registry Number: 1048990-21-1) (73.05 g, 263.79 mmol), and 86.71 g (yield: 90%) of the product was obtained by using the same manner as described above for the synthesis of compound Sub 1-I-20.

(2) Synthesis of Sub 1-II-109

4-bromo-1-iodo-2-(methylsulfinyl)benzene (CAS Registry Number: 1638151-06-0) (90.09 g, 261.15 mmol), Pd(PPh$_3$)$_4$ (10.97 g, 9.50 mmol), NaOH (28.49 g, 712.22 mmol), THF (830 ml) and water (415 ml) are added to Sub 1-I-109 (86.71 g, 237.41 mmol) obtained in the above synthesis, and 95.88 g (yield: 75%) of the product was obtained by using the same manner as described above for the synthesis of compound Sub 1-II-20.

(3) Synthesis of Sub 1-III-109

Triflic acid (157.6 ml, 1780.50 mmol) and pyridine aqueous (2080 ml, pyridine:H$_2$O=1:5) are added to Sub 1-II-109 (95.88 g, 178.05 mmol) obtained in the above synthesis, and 36.97 g (yield: 41%) of the product was obtained by using the same manner as described above for the synthesis of compound Sub 1-111-20.

(4) Synthesis of Sub 1-109

[1,1'-biphenyl]-4-amine (CAS Registry Number: 92-67-1) (3.75 g, 22.18 mmol), Pd$_2$(dba)$_3$ (0.55 g, 0.60 mmol), 50% P(t-Bu)$_3$ (0.8 ml, 1.61 mmol), NaOt-Bu (5.81 g, 60.48 mmol) and toluene (140 ml) are added to Sub 1-III-109 (10.21 g, 20.16 mmol) obtained in the above synthesis, and 9.47 g (yield: 79%) of the product was obtained by using the same manner as described above for the synthesis of compound Sub 1-1.

(5) Synthesis of Sub 1-114

Dibenzo[b,d]thiophen-2-amine (CAS Registry Number: 7428-91-3) (4.58 g, 23.00 mmol), Pd$_2$(dba)$_3$ (0.57 g, 0.63 mmol), 50% P(t-Bu)$_3$ (0.8 ml, 1.67 mmol), NaOt-Bu (6.03 g, 62.73 mmol) and toluene (145 ml) are added to Sub 1-III-109 (10.59 g, 20.91 mmol) obtained in the above synthesis, and 9.80 g (yield: 75%) of the product was obtained by using the same manner as described above for the synthesis of the compound Sub 1-1.

9. Synthesis Example of Sub 1-119

<Reaction Scheme 11>

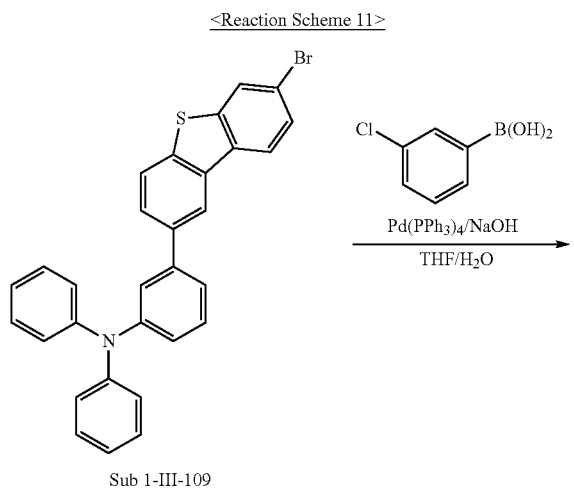

Sub 1-III-109

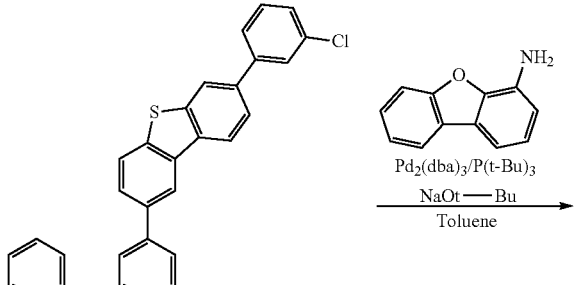

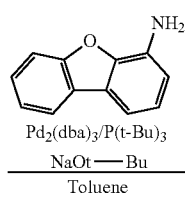

Sub 1-IV-119

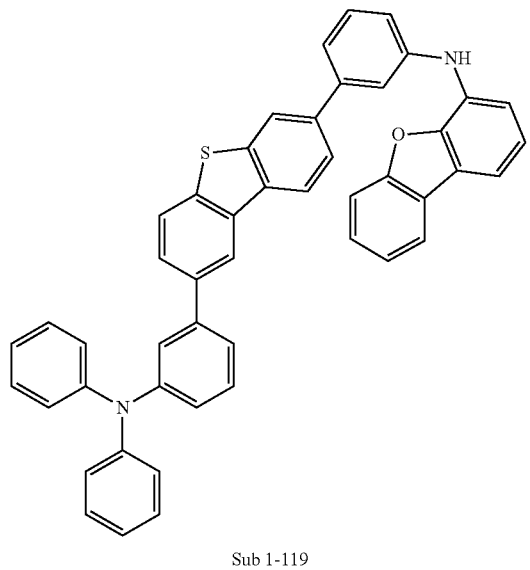

Sub 1-119

(1) Synthesis of Sub 1-IV-119

(3-chlorophenyl)boronic acid (CAS Registry Number: 63503-60-6) (5.37 g, 34.34 mmol), Pd(PPh$_3$)$_4$ (1.44 g, 1.25 mmol), NaOH (3.75 g, 93.65 mmol), THF (110 ml) and water (55 ml) are added to Sub 1-III-109 (15.81 g, 31.22 mmol) obtained in the above synthesis, and 10.58 (yield: 63%) of the product was obtained by using the same manner as described above for the synthesis of compound Sub 1-IV-83.

(2) Synthesis of Sub 1-119

Dibenzo[b,d]furan-4-amine (CAS Registry Number: 50548-43-1) (3.96 g, 21.63 mmol), Pd$_2$(dba)$_3$ (0.54 g, 0.59 mmol), 50% P(t-Bu)$_3$ (0.8 ml, 1.57 mmol), NaOt-Bu (5.67 g, 58.98 mmol) and toluene (140 ml) are added to Sub 1-IV-119 (10.58 g, 19.66 mmol) obtained in the above synthesis, and 9.29 (yield: 69%) of the product was obtained by using the same manner as described above for the synthesis of compound Sub 1-1.

The compound belonging to Sub 1 may be, but not limited to, the following compounds, and Table 1 shows FD-MS (Field Desorption-Mass Spectrometry) values of some compounds belonging to Sub 1.

105 106
-continued
Sub 1-1
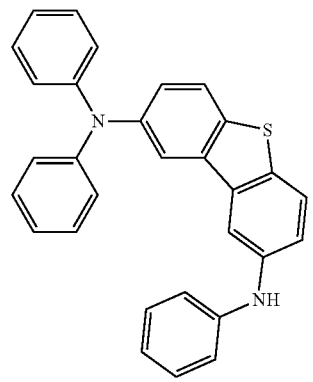
Sub 1-5
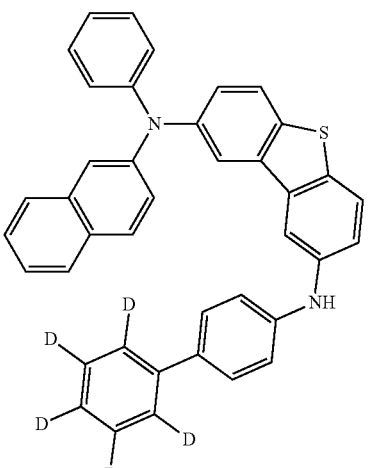
Sub 1-2
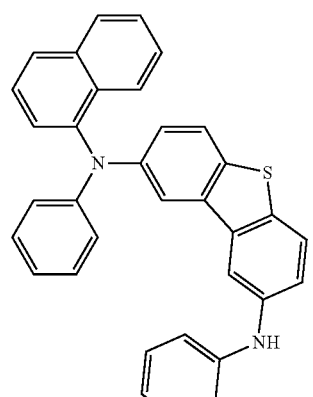
Sub 1-6
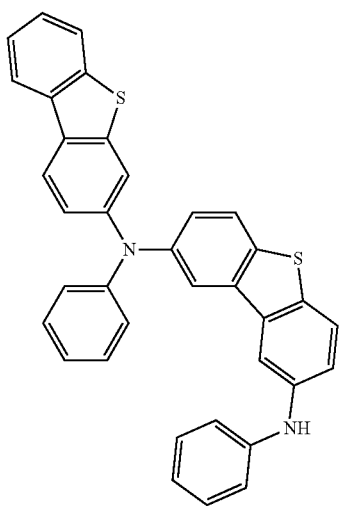
Sub 1-3
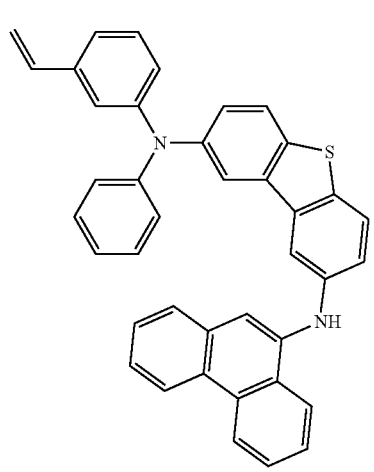
Sub 1-7
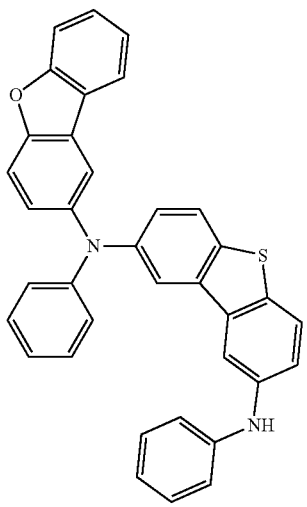
Sub 1-4
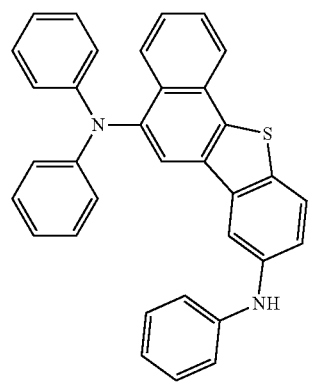

Sub 1-8
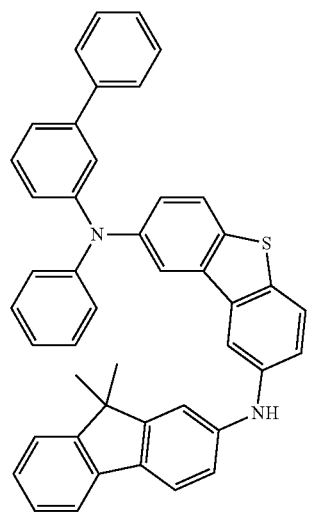
Sub 1-9
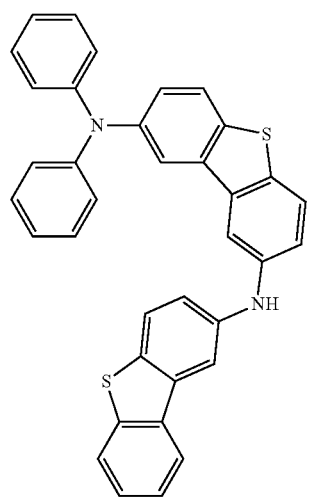
Sub 1-10
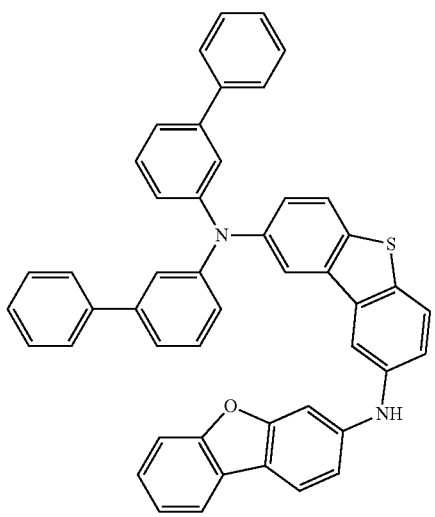
Sub 1-11
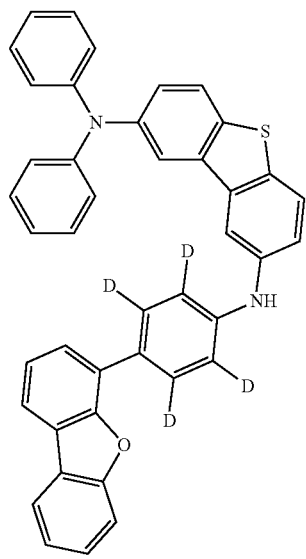
Sub 1-12
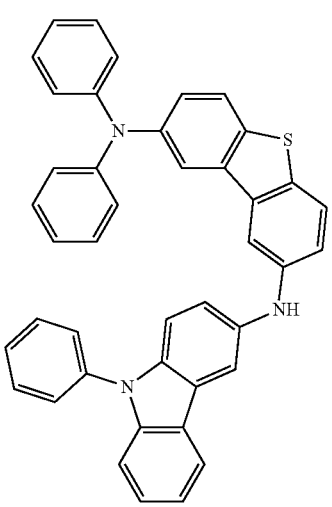
Sub 1-13
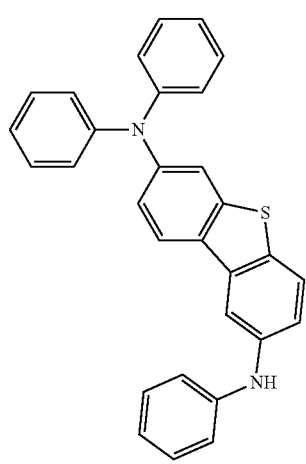

Sub 1-14
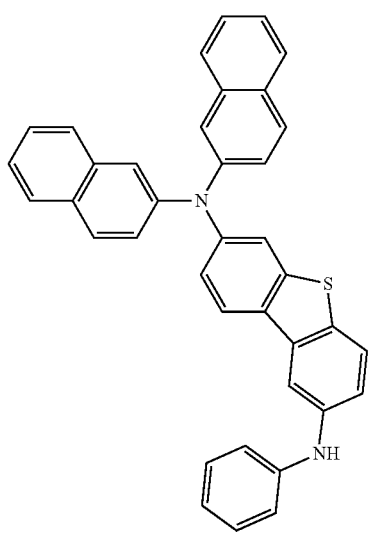
Sub 1-15
Sub 1-16
Sub 1-17
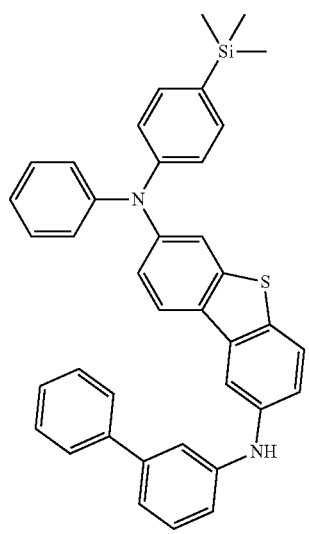
Sub 1-18
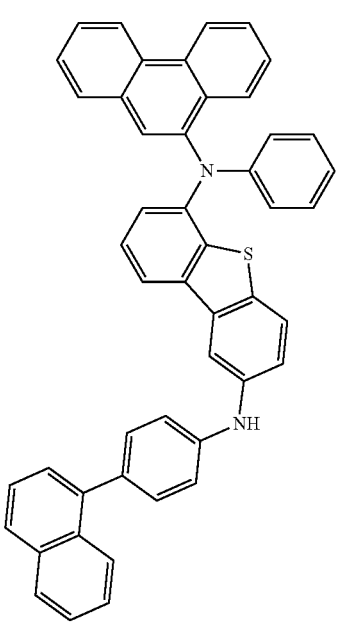

Sub 1-19
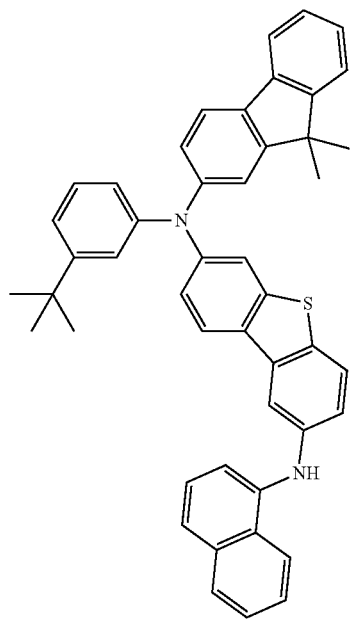
Sub 1-20
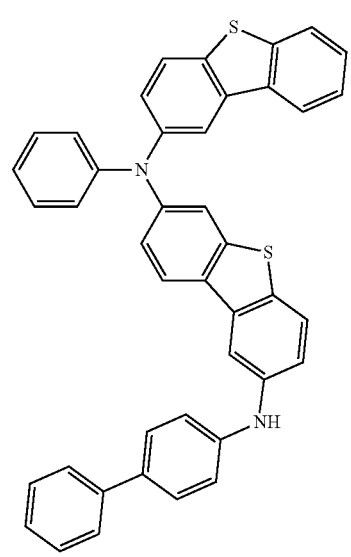
Sub 1-21
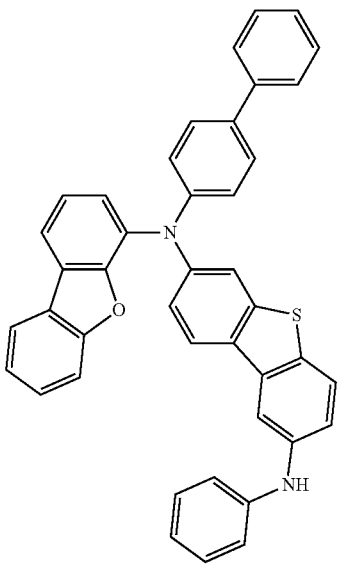
Sub 1-22
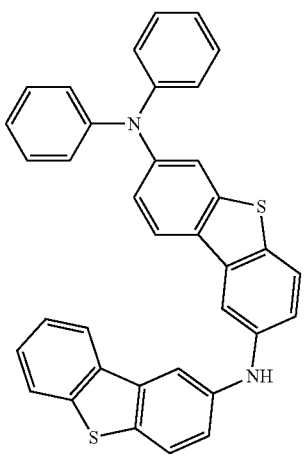
Sub 1-23
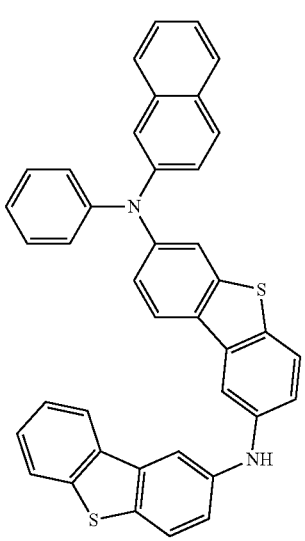

Sub 1-24
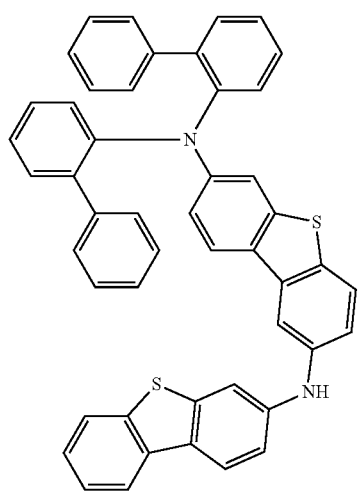
Sub 1-25
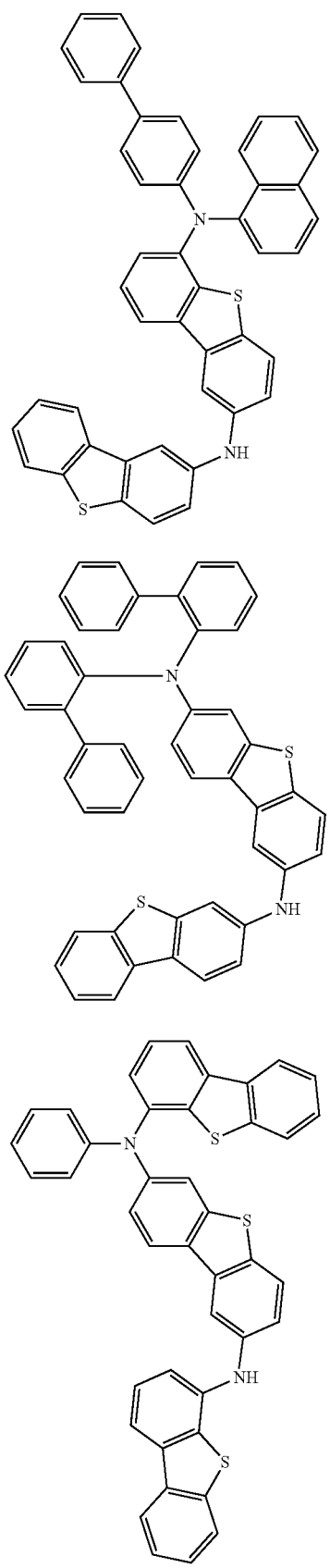
Sub 1-26
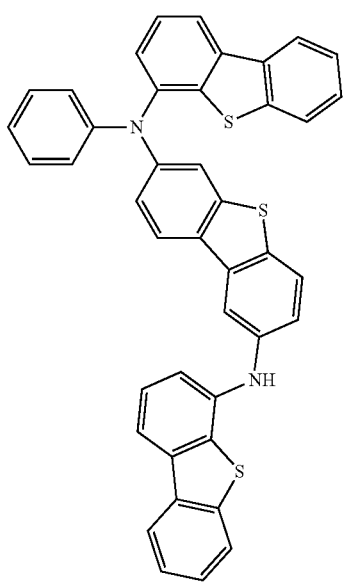
Sub 1-27
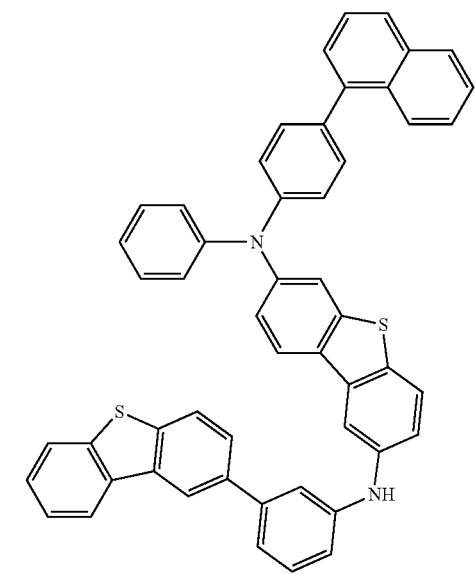
Sub 1-28
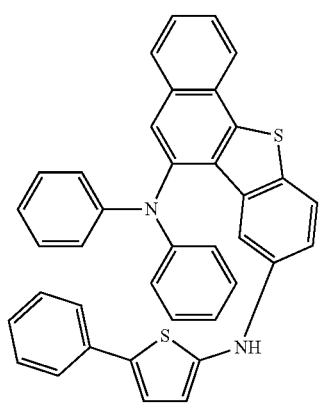
Sub 1-29
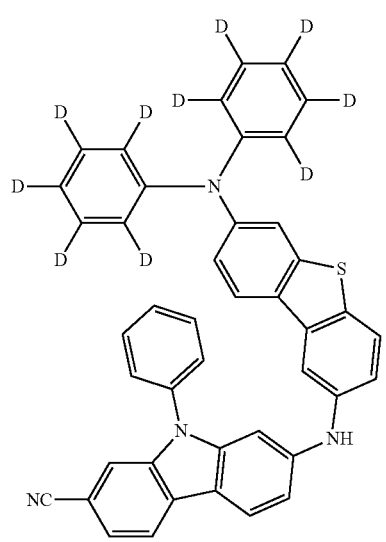

115
-continued
Sub 1-30
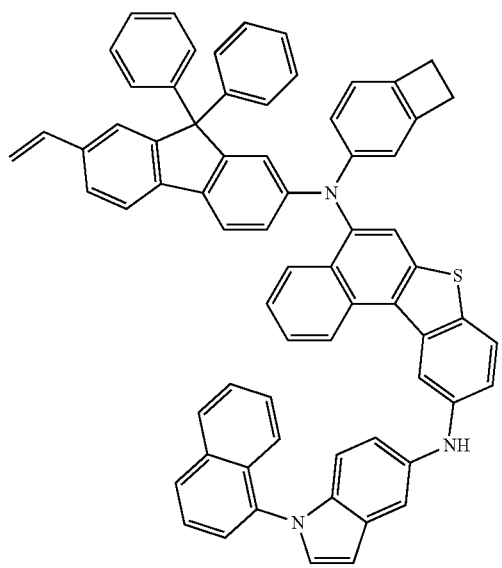
Sub 1-31
Sub 1-32
116
-continued
Sub 1-33
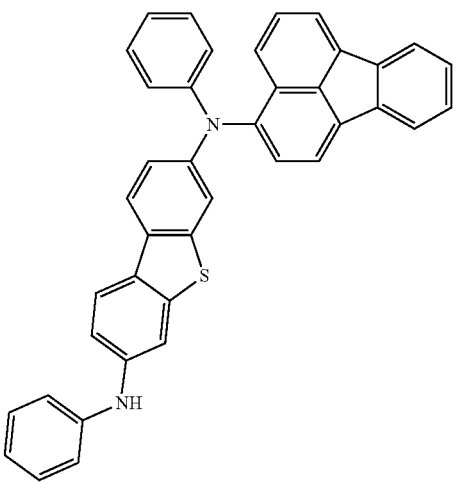
Sub 1-34
Sub 1-35

-continued
Sub 1-36
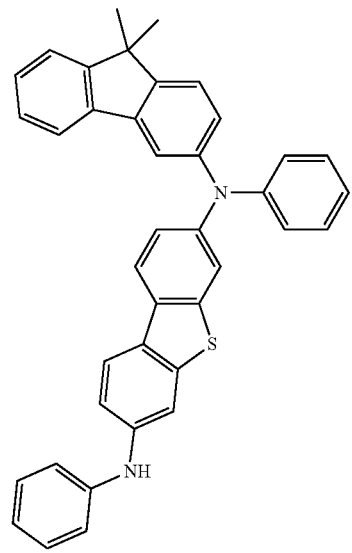
Sub 1-37
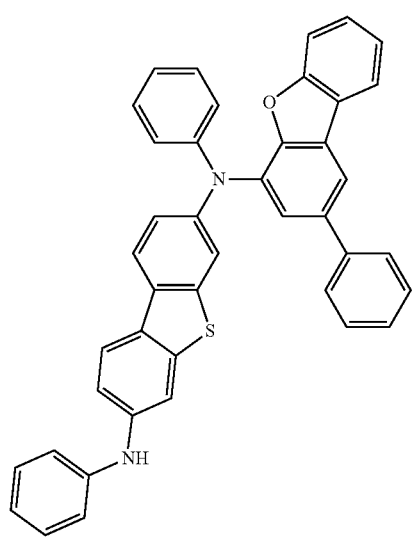
Sub 1-38
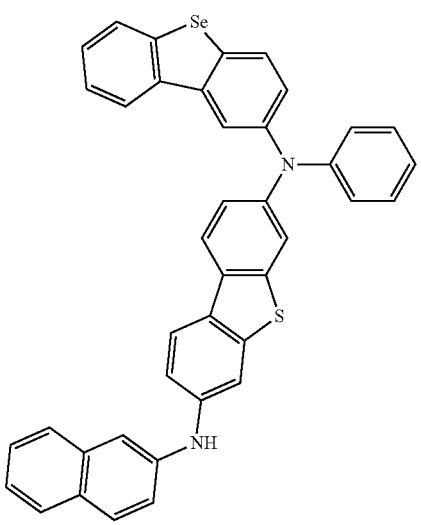
-continued
Sub 1-39
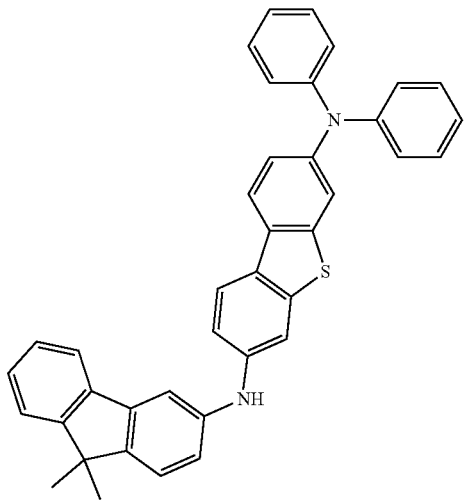
Sub 1-40
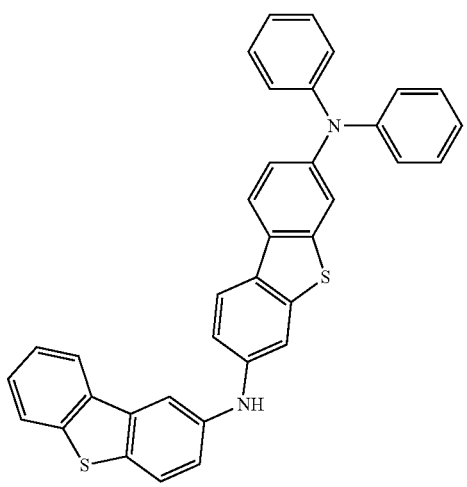
Sub 1-41
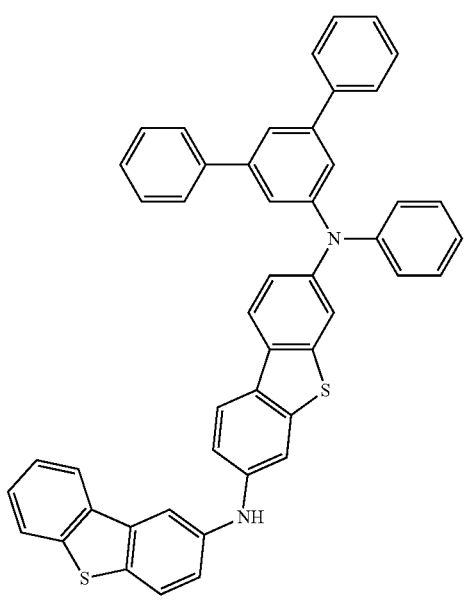

Sub 1-42
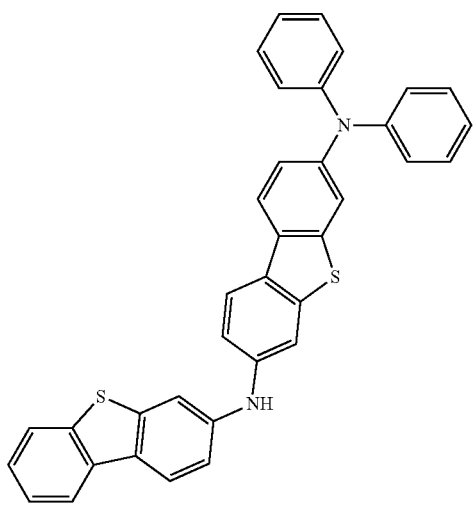
Sub 1-43
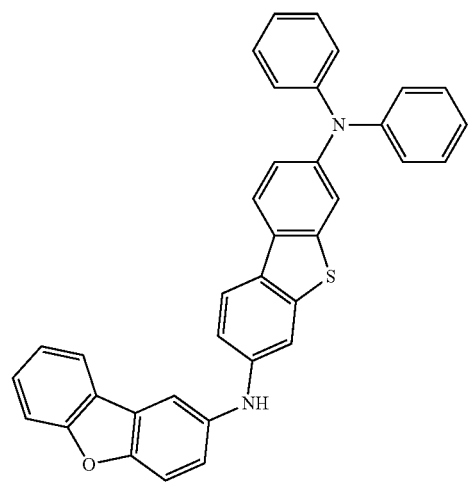
Sub 1-44
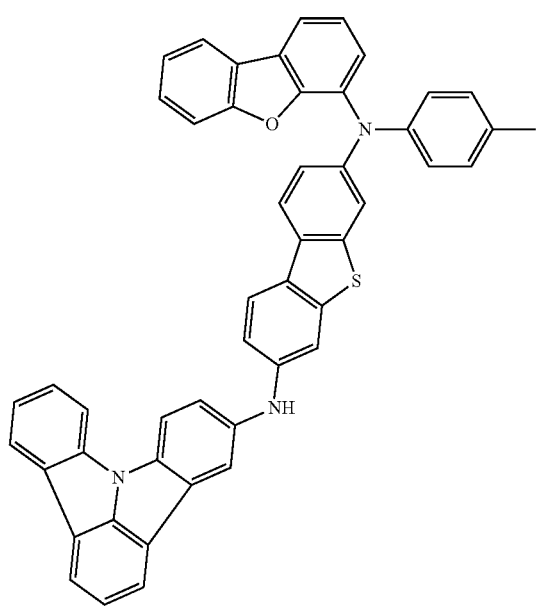
Sub 1-45
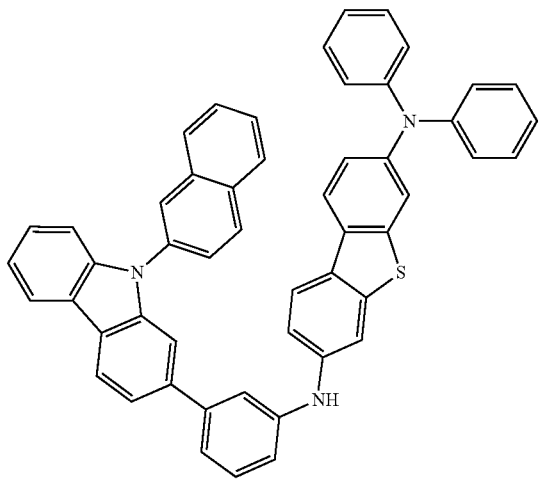
Sub 1-46
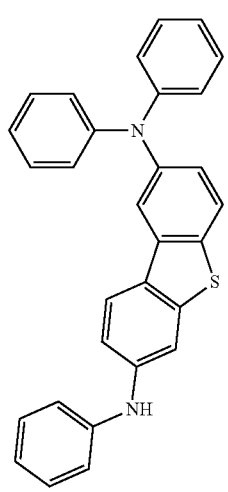
Sub 1-47
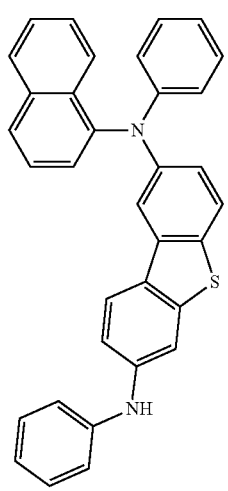

-continued
Sub 1-48
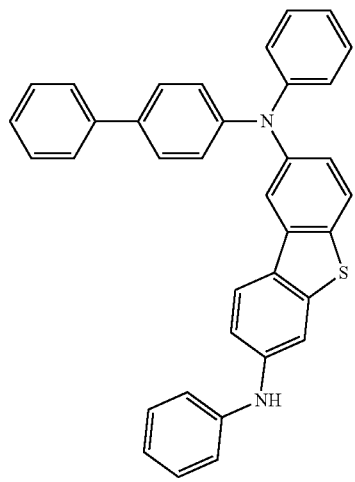
Sub 1-49
Sub 1-50
-continued
Sub 1-51
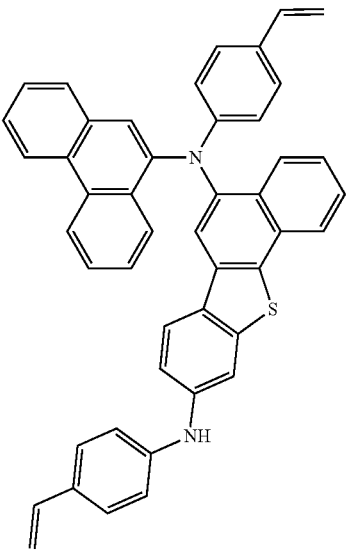
Sub 1-52
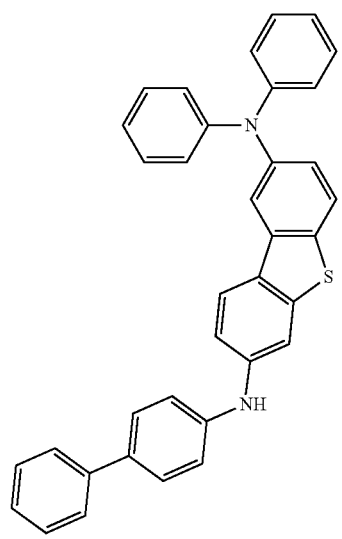
Sub 1-53
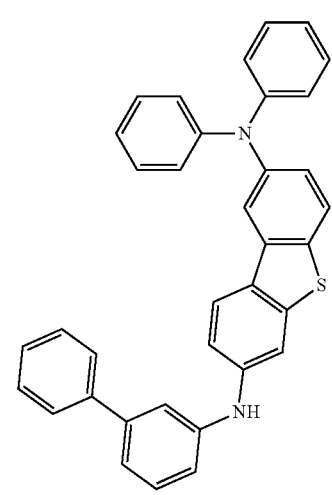

-continued
Sub 1-54
Sub 1-55
Sub 1-56
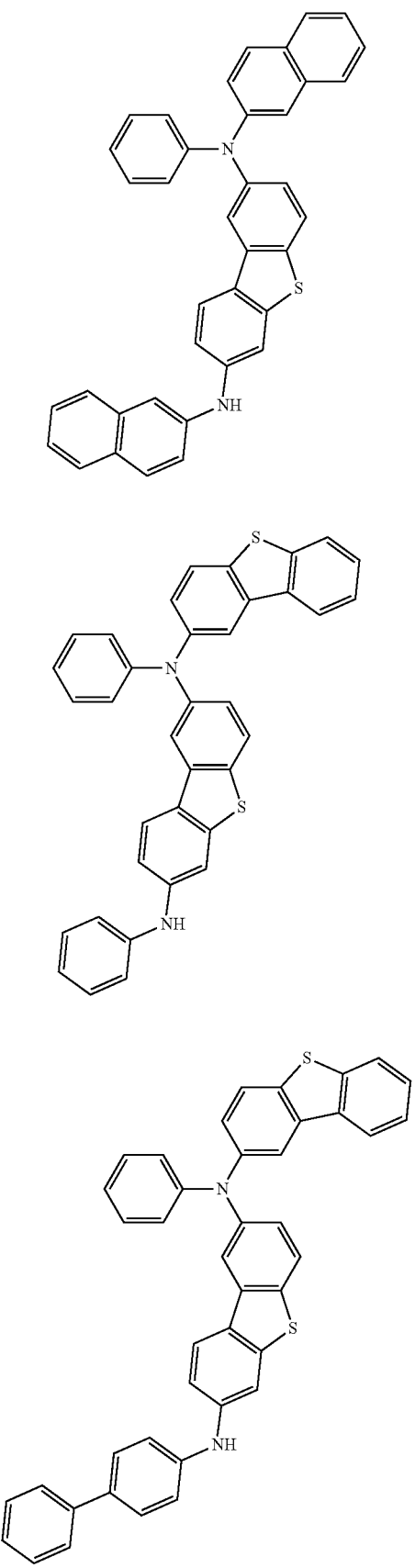
Sub 1-57
Sub 1-58
Sub 1-59
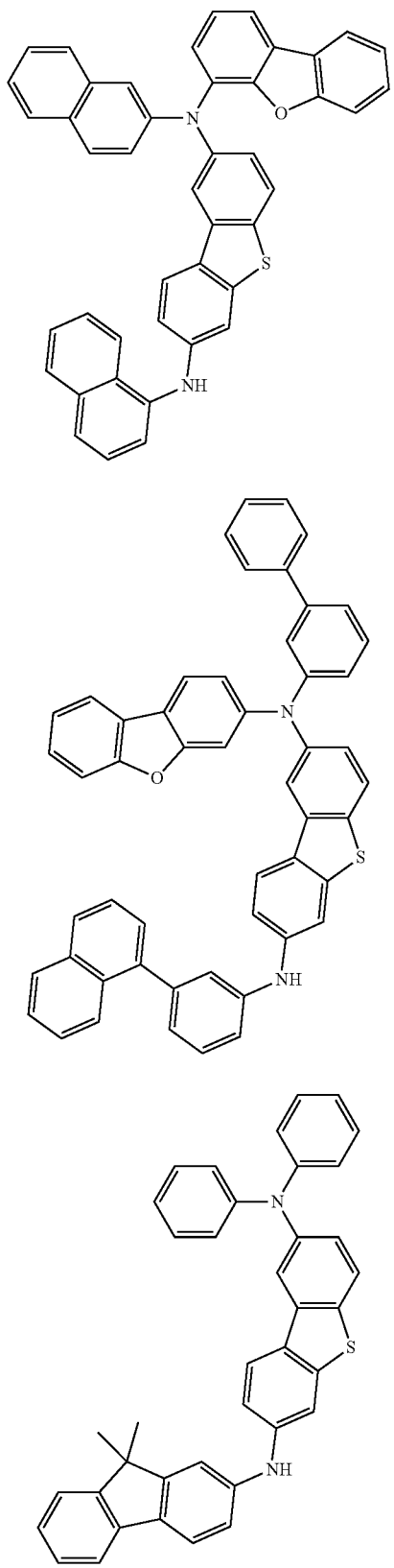

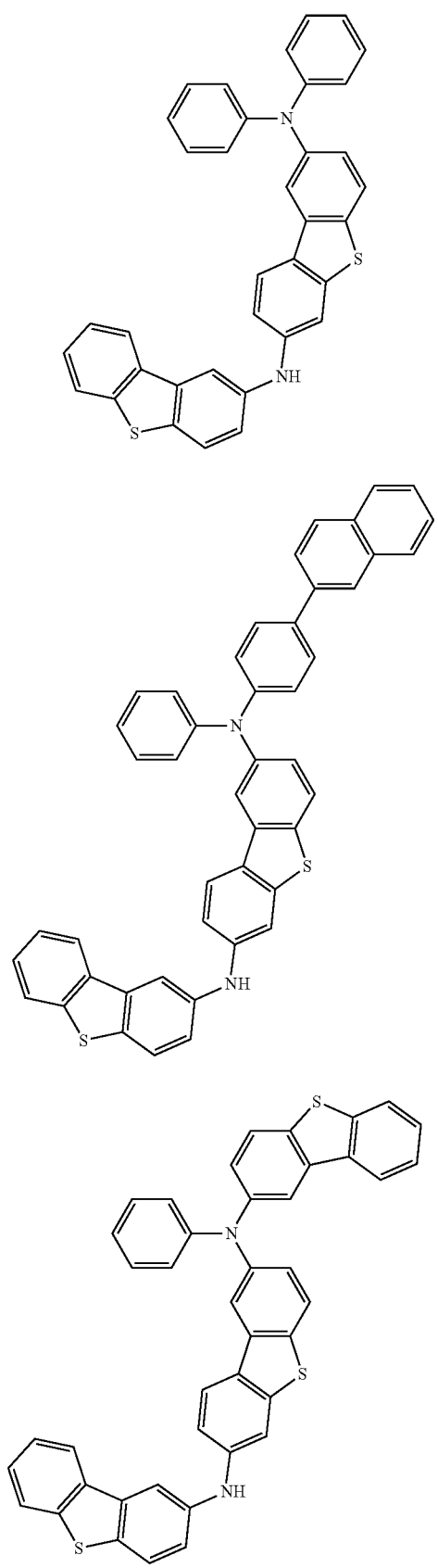
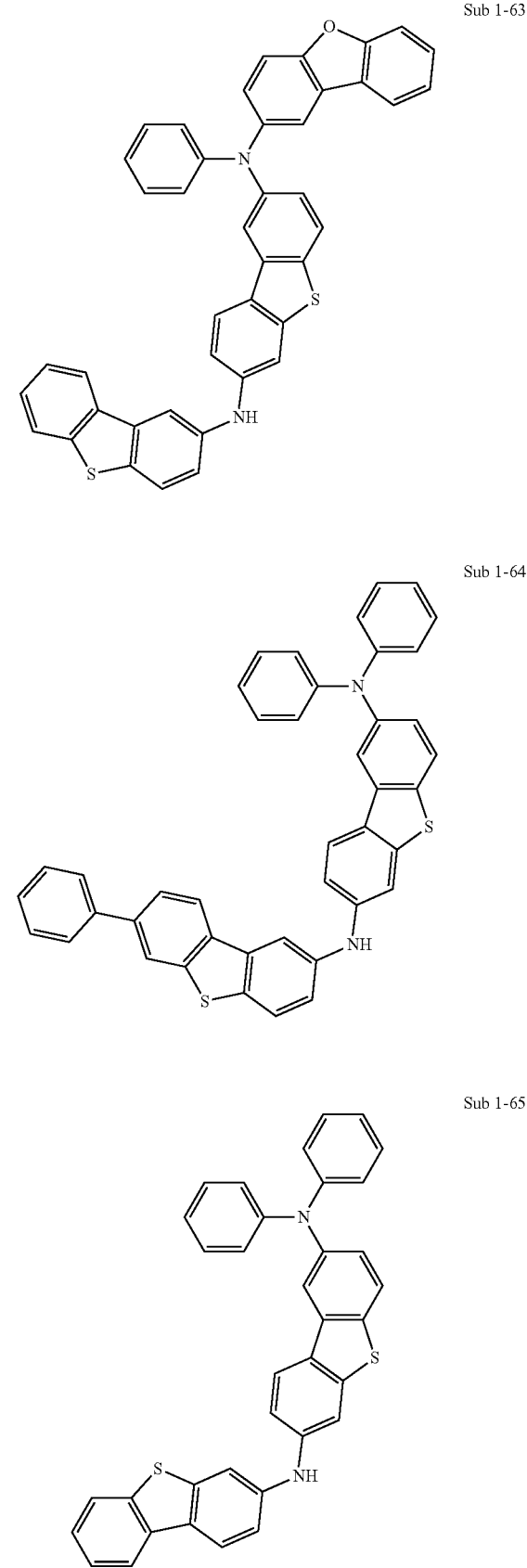

Sub 1-66
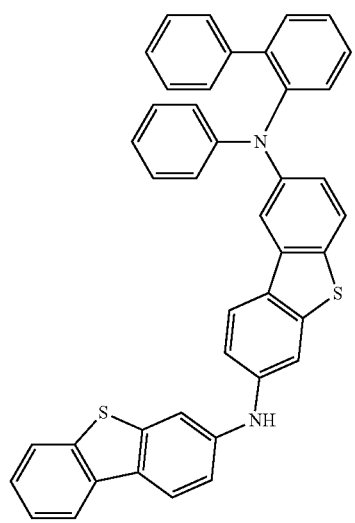
Sub 1-67
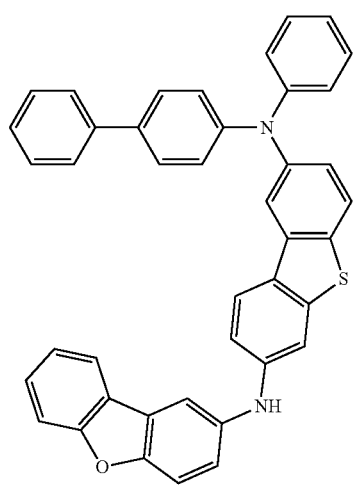
Sub 1-68
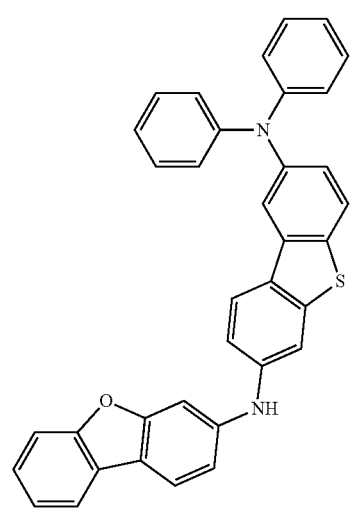
Sub 1-69
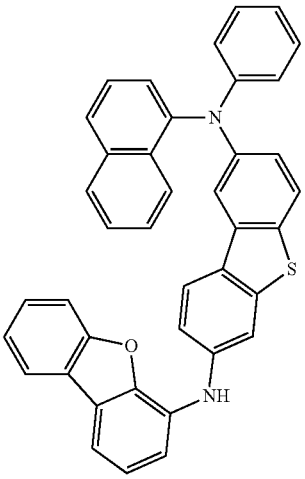
Sub 1-70
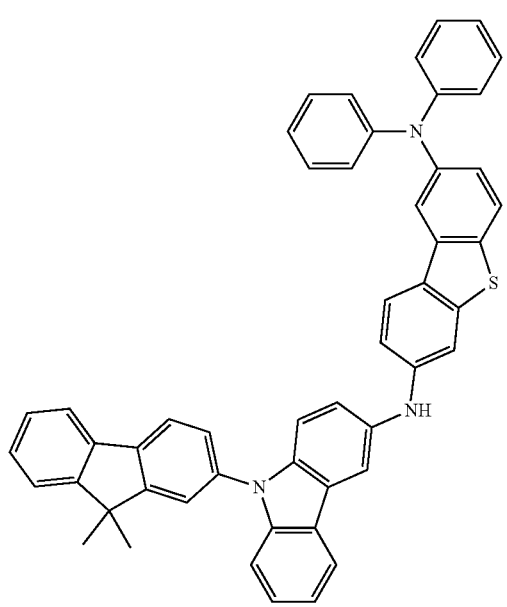
Sub 1-71
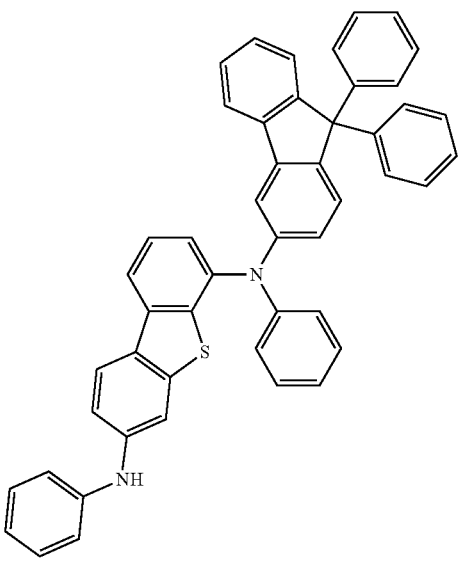

Sub 1-72
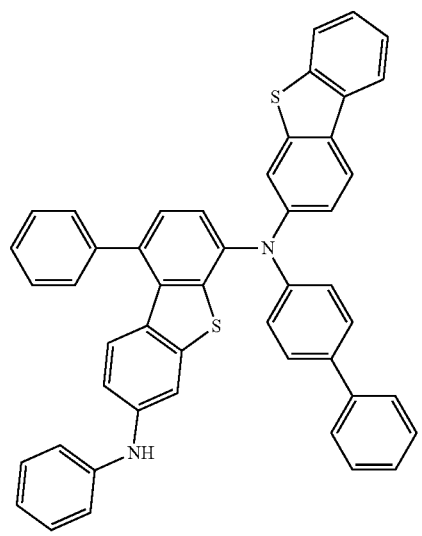
Sub 1-73
Sub 1-74
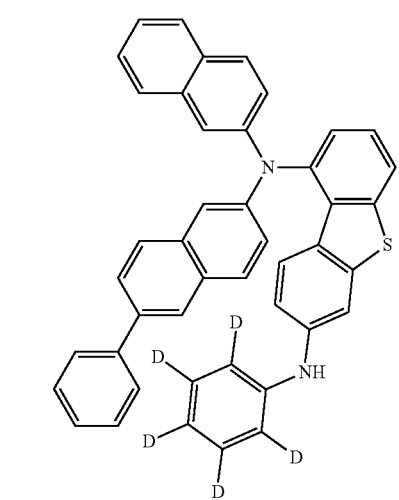
Sub 1-75
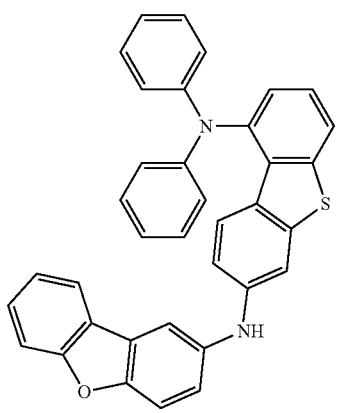
Sub 1-76
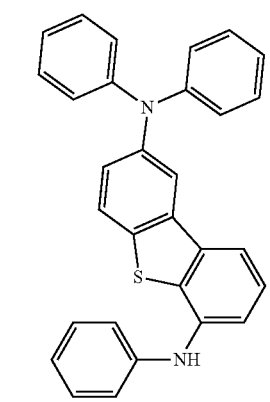
Sub 1-77
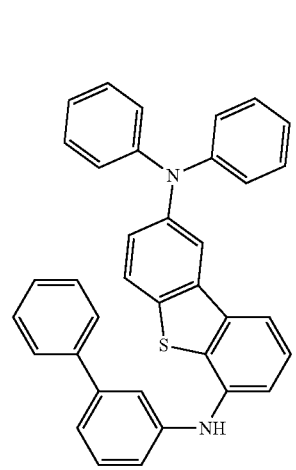

Sub 1-78
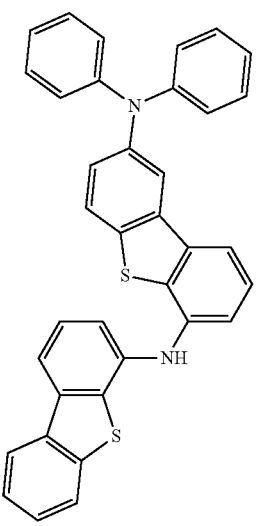
Sub 1-79
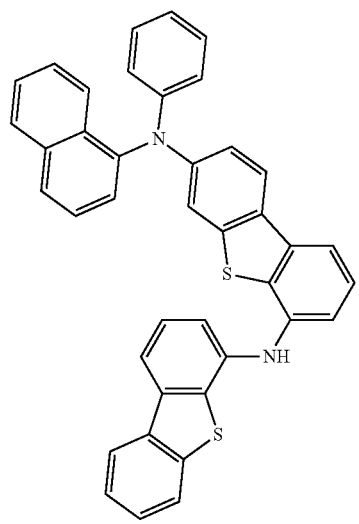
Sub 1-80
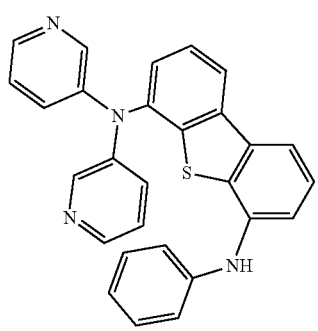
Sub 1-81
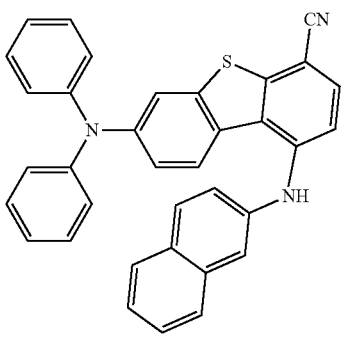
Sub 1-82
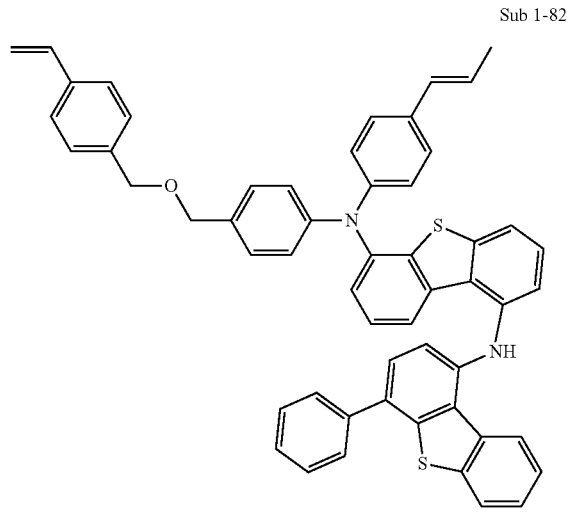
Sub 1-83
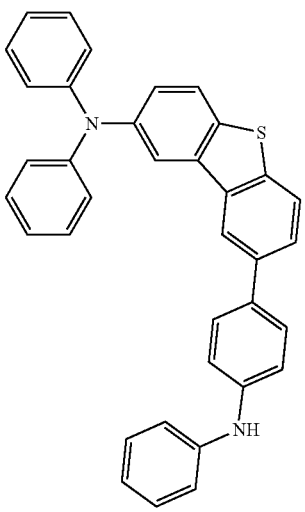

Sub 1-84
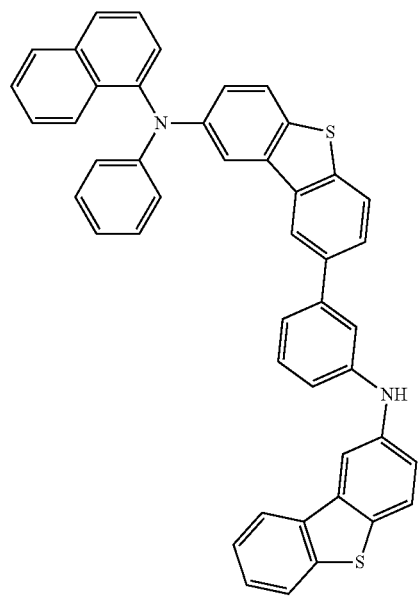
Sub 1-87
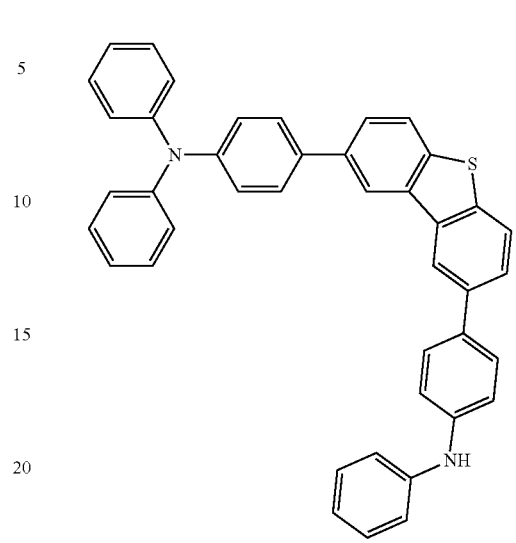
Sub 1-85
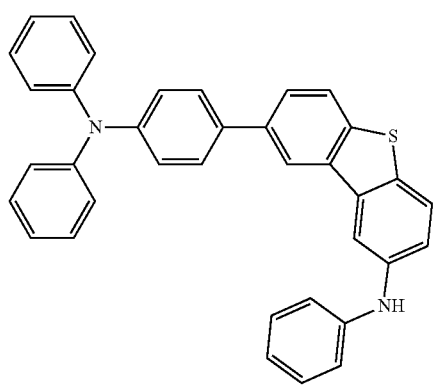
Sub 1-86
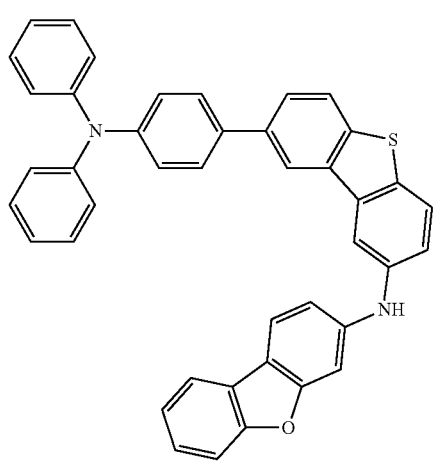
Sub 1-88
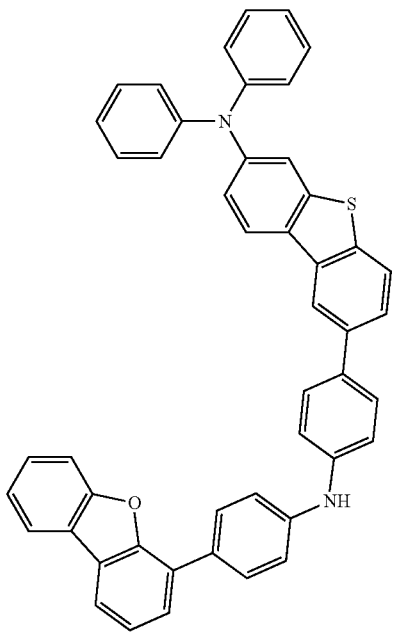

Sub 1-89
Sub 1-90
Sub 1-91
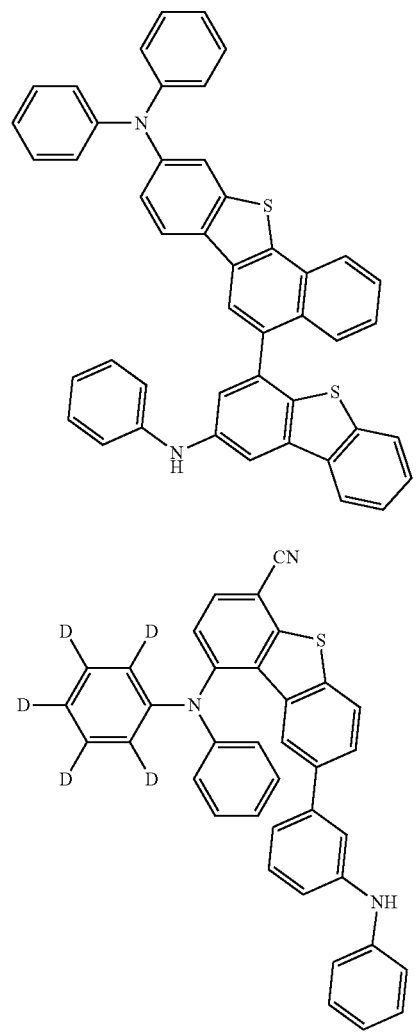
Sub 1-92
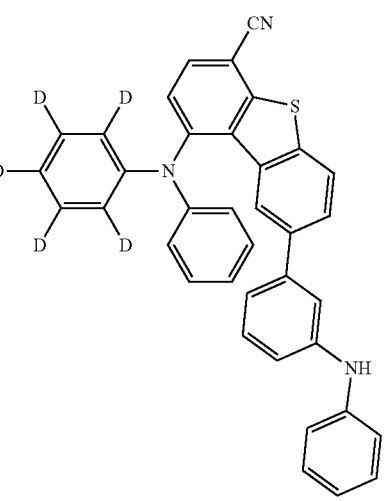
Sub 1-93
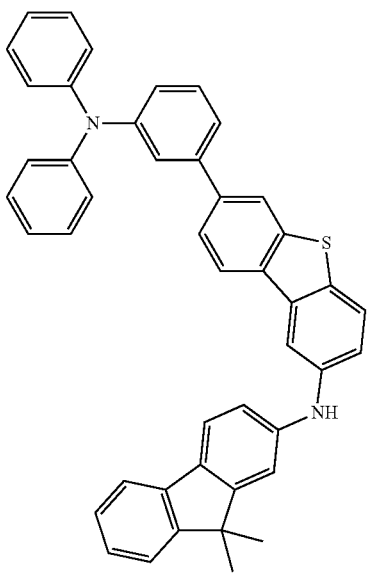

Sub 1-94
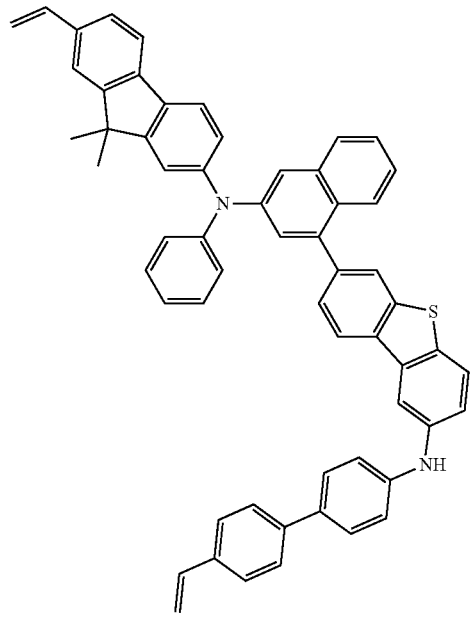
Sub 1-96
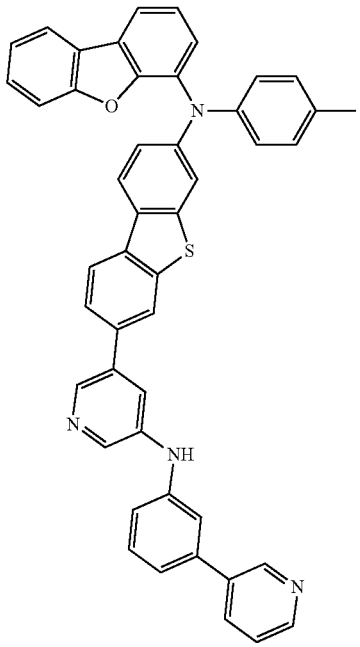
Sub 1-95
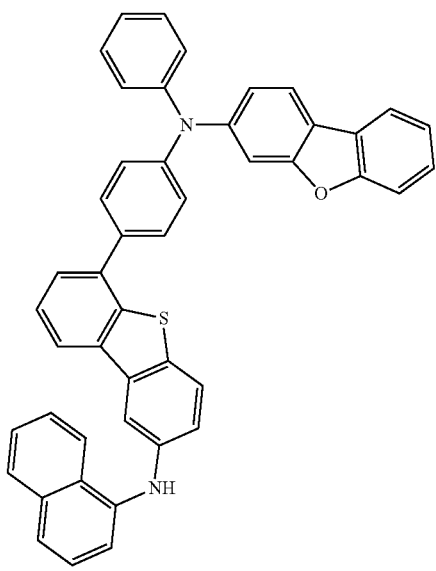
Sub 1-97
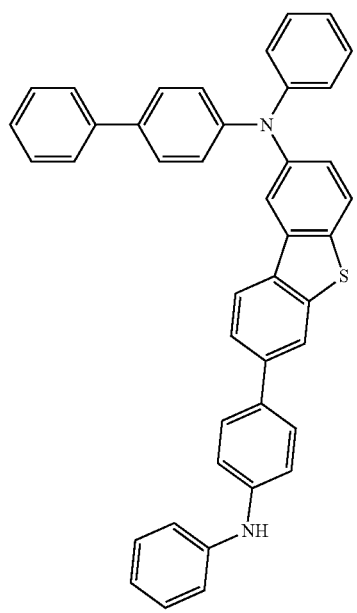

Sub 1-98

Sub 1-99

Sub 1-100

Sub 1-101

Sub 1-102
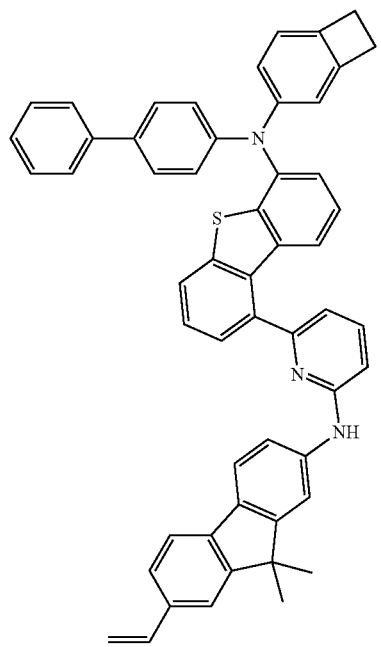
Sub 1-104
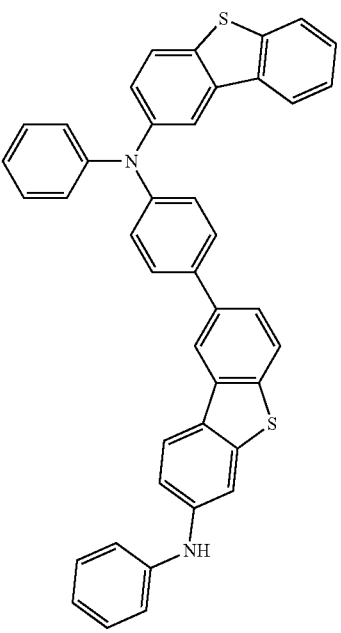
Sub 1-103
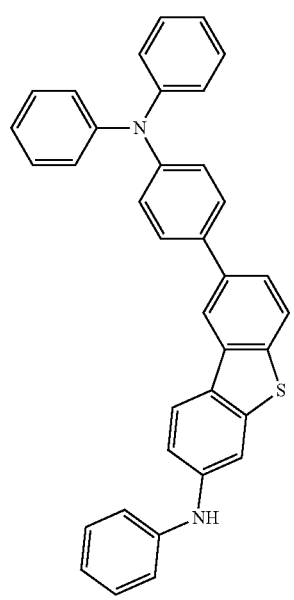
Sub 1-105
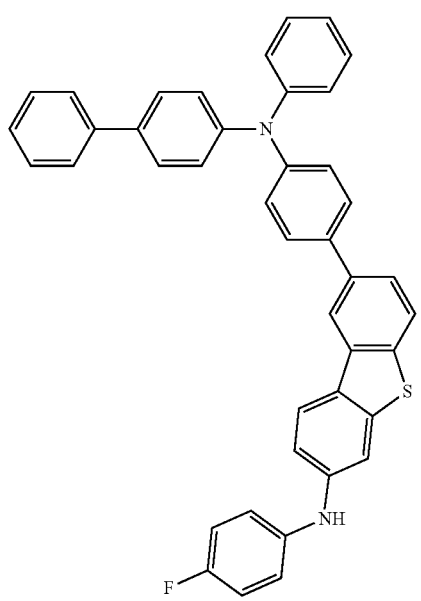

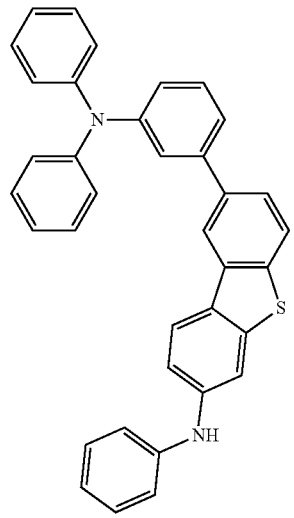
Sub 1-106
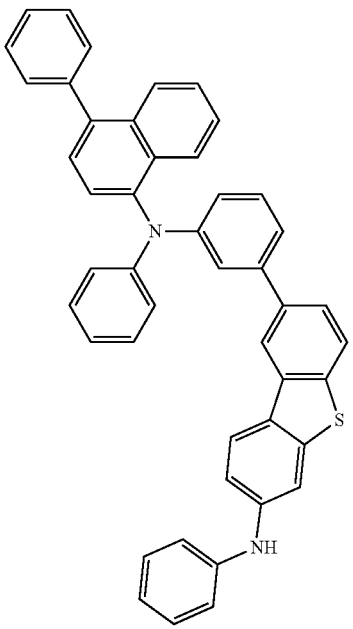
Sub 1-108
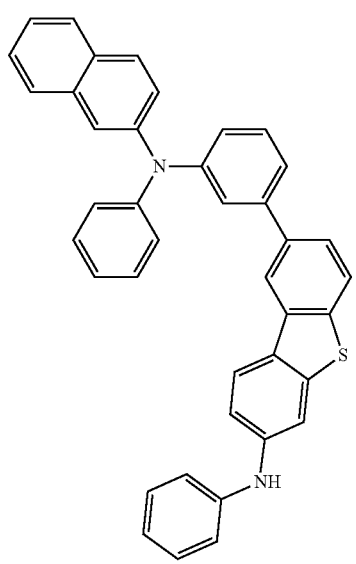
Sub 1-107
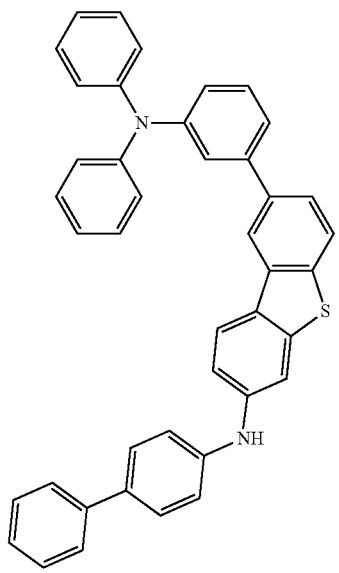
Sub 1-109

Sub 1-110
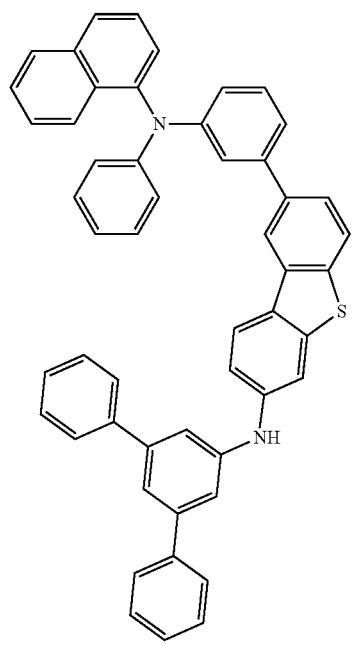
Sub 1-112
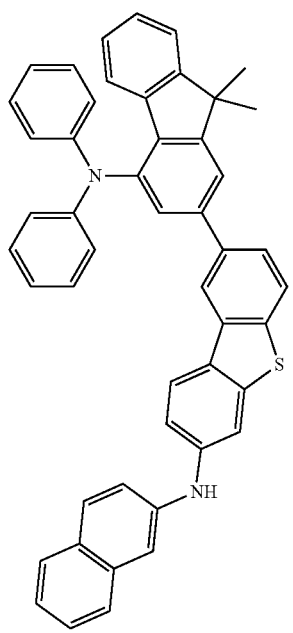
Sub 1-111
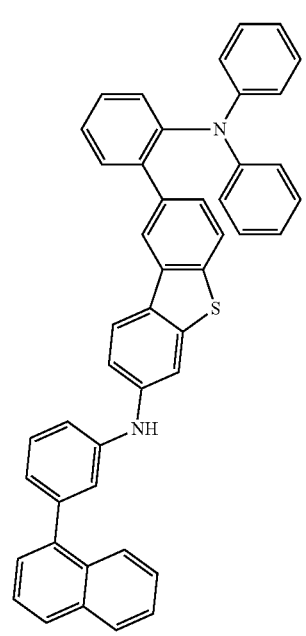
Sub 1-113
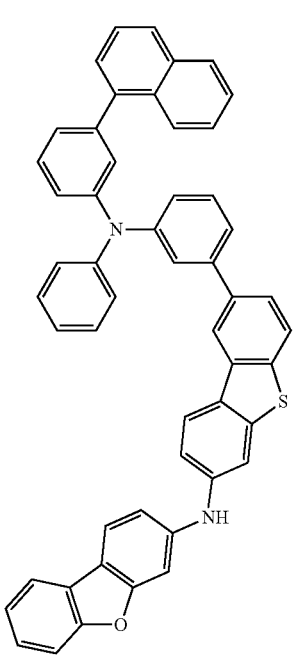

Sub 1-114
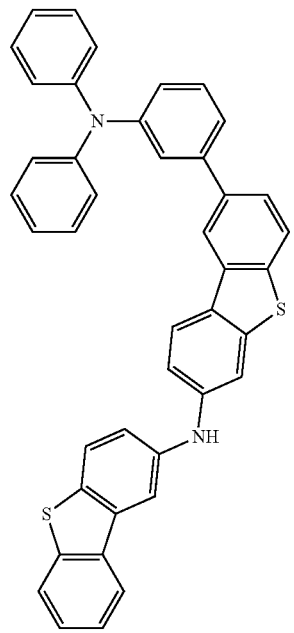
Sub 1-116
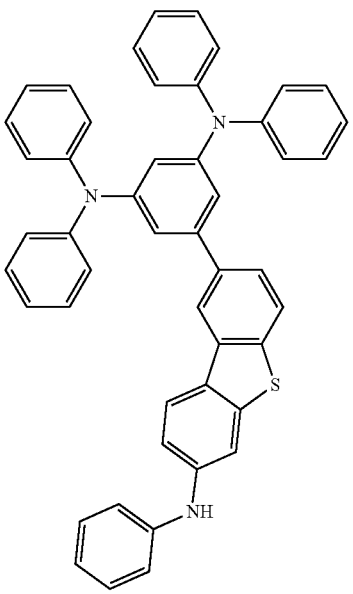
Sub 1-115
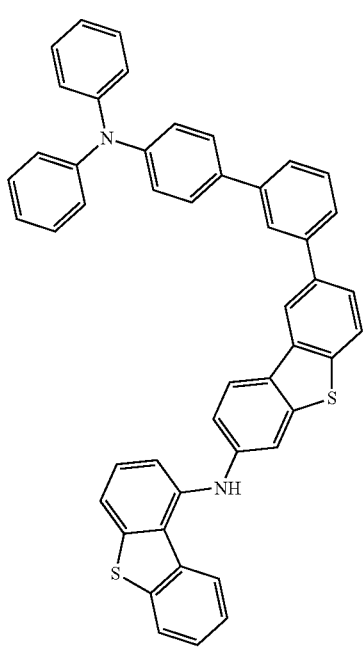
Sub 1-117

-continued

Sub 1-118

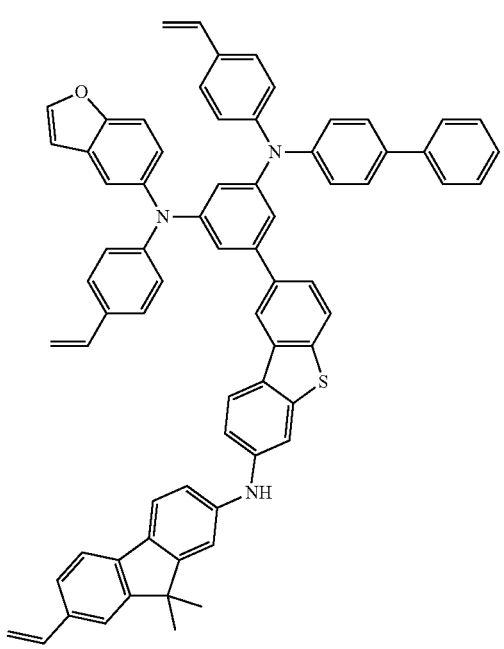

Sub 1-119

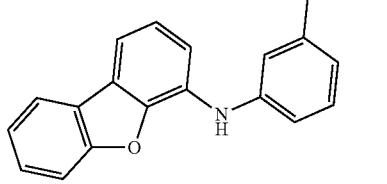

II. Synthesis of Sub 2

Sub 2 of the above Reaction Scheme 1 may be synthesized by the reaction route of Reaction Scheme 12, but is not limited thereto. $Hal^3$ is I or Br.

<Reaction Scheme 12>

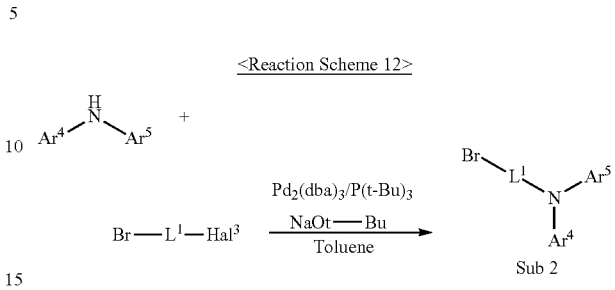

In Reaction Scheme 12, the amine($HN-Ar^4Ar^5$) reactant was synthesized by using the synthesis method disclosed in Korean Patent No. 10-1251451 (published on Apr. 5, 2013) of the present applicant.

Synthesis examples of compounds belonging to Sub 2 are as follows.

1. Synthesis Example of Sub 2-1

<Reaction Scheme 13>

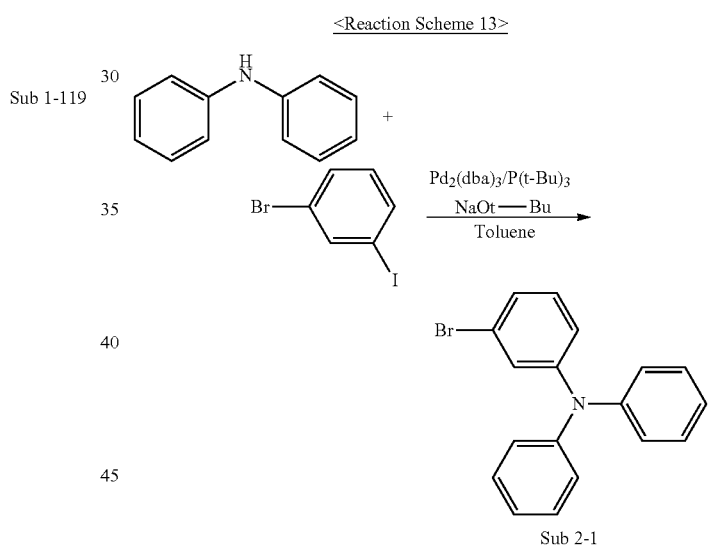

Sub 2-1

After the starting material diphenylamine (CAS Registry Number: 122-39-4) (7.93 g, 43.86 mmol) was dissolved in toluene (390 ml) in a round bottom flask, 1-bromo-3-iodobenzene (CAS Registry Number: 591-18-4) (19.89 g, 70.29 mmol), $Pd_2(dba)_3$ (1.29 g, 1.41 mmol), 50% $P(t-Bu)_3$ (1.8 ml, 3.75 mmol) and NaOt-Bu (13.51 g, 140.58 mmol)

TABLE 1

| Compound | FD-MS | Compound | FD-MS |
|---|---|---|---|
| Sub 1-1 | m/z = 442.15($C_{30}H_{22}N_2S$ = 442.58) | Sub 1-20 | m/z = 624.17($C_{42}H_{28}N_2S_2$ = 624.82) |
| Sub 1-28 | m/z = 574.15($C_{38}H_{26}N_2S_2$ = 574.76) | Sub 1-44 | m/z = 709.22($C_{49}H_{31}N_3OS$ = 709.87) |
| Sub 1-46 | m/z = 442.15($C_{30}H_{22}N_2S$ = 442.58) | Sub 1-60 | m/z = 548.14($C_{36}H_{24}N_2S_2$ = 548.72) |
| Sub 1-73 | m/z = 518.18($C_{36}H_{26}N_2S$ = 518.68) | Sub 1-79 | m/z = 598.15($C_{40}H_{26}N_2S_2$ = 598.78) |
| Sub 1-83 | m/z = 518.18($C_{36}H_{26}N_2S$ = 518.68) | Sub 1-96 | m/z = 700.23($C_{47}H_{32}N_4OS$ = 700.86) |
| Sub 1-109 | m/z = 594.21($C_{42}H_{30}N_2S$ = 594.78) | Sub 1-114 | m/z = 624.17($C_{42}H_{28}N_2S_2$ = 624.82) |
| Sub 1-119 | m/z = 684.22($C_{48}H_{32}N_2OS$ = 684.86) | | | are added, and stirred at 70° C. After completion of the reaction, the reaction product was extracted with CH₂Cl₂ and water. The organic layer was dried over MgSO₄ and concentrated. The resulting compound was purified by silicagel column and recrystallized to obtain 10.48 g (yield: 69%) of the product.

2. Synthesis Example of Sub 2-3

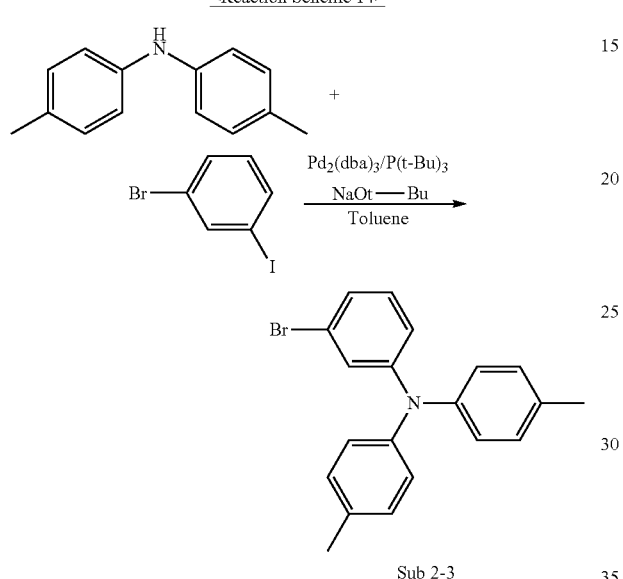

Sub 2-3

1-bromo-3-iodobenzene (CAS Registry Number: 591-18-4) (18.84 g, 66.61 mmol), Pd₂(dba)₃ (1.22 g, 1.33 mmol), 50% P(t-Bu)₃ (1.7 ml, 3.55 mmol), NaOt-Bu (12.80 g, 133.21 mmol) and toluene (370 ml) are added to the starting material di-p-tolylamine (CAS Registry Number: 620-93-9) (8.76 g, 44.40 mmol), and 10.17 g (yield: 65%) of the product was obtained by using the same manner as described above for the synthesis of compound Sub 2-1.

3. Synthesis Example of Sub 2-4

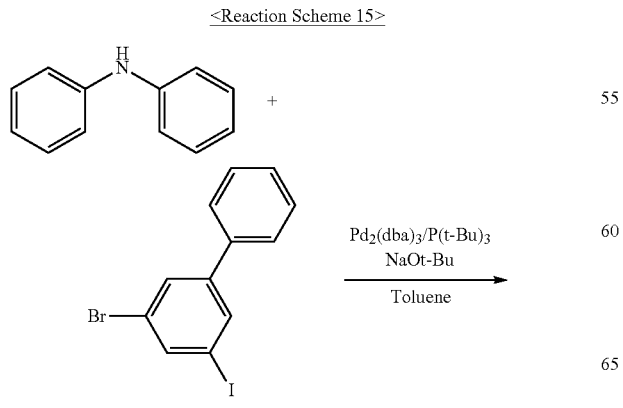

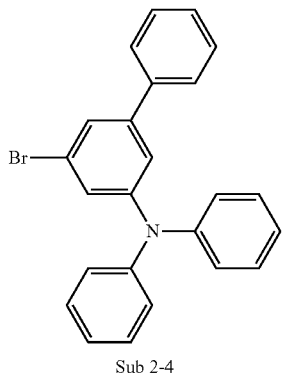

Sub 2-4

3-bromo-5-iodo-1,1'-biphenyl (CAS Registry Number: 136649-44-0) (20.08 g, 55.93 mmol), Pd₂(dba)₃ (1.02 g, 1.12 mmol), 50% P(t-Bu)₃ (1.5 ml, 2.98 mmol), NaOt-Bu (10.75 g, 111.86 mmol) and toluene (310 ml) are added to the starting material diphenylamine (CAS Registry Number: 122-39-4) (6.31 g, 37.29 mmol), and 10.90 g (yield: 73%) of the product was obtained by using the same manner as described above for the synthesis of compound Sub 2-1.

4. Synthesis Example of Sub 2-13

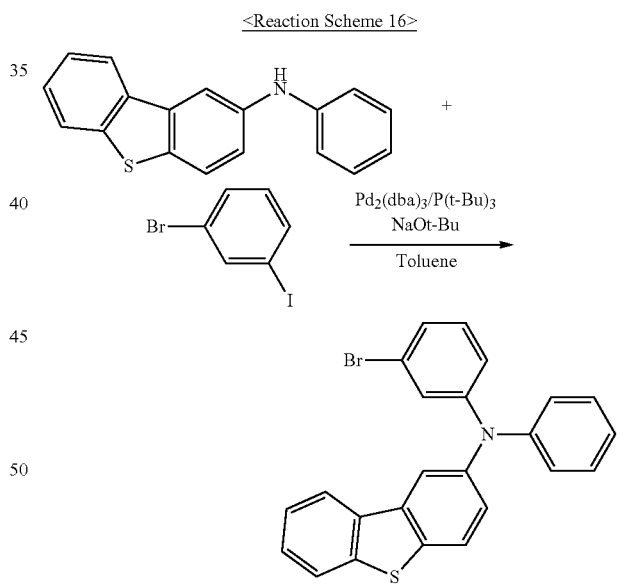

Sub 2-13

1-bromo-3-iodobenzene (CAS Registry Number: 591-18-4) (14.52 g, 51.31 mmol), Pd₂(dba)₃ (0.94 g, 1.03 mmol), 50% P(t-Bu)₃ (1.3 ml, 2.74 mmol), NaOt-Bu (9.86 g, 102.63 mmol) and toluene (285 ml) are added to the starting material N-phenyldibenzo[b,d]thiophen-2-amine (CAS Registry Number: 1300028-91-4) (9.42 g, 34.21 mmol), and 10.31 g (yield: 70%) of the product was obtained by using the same manner as described above for the synthesis of compound Sub 2-1.

5. Synthesis Example of Sub 2-29

<Reaction Scheme 17>

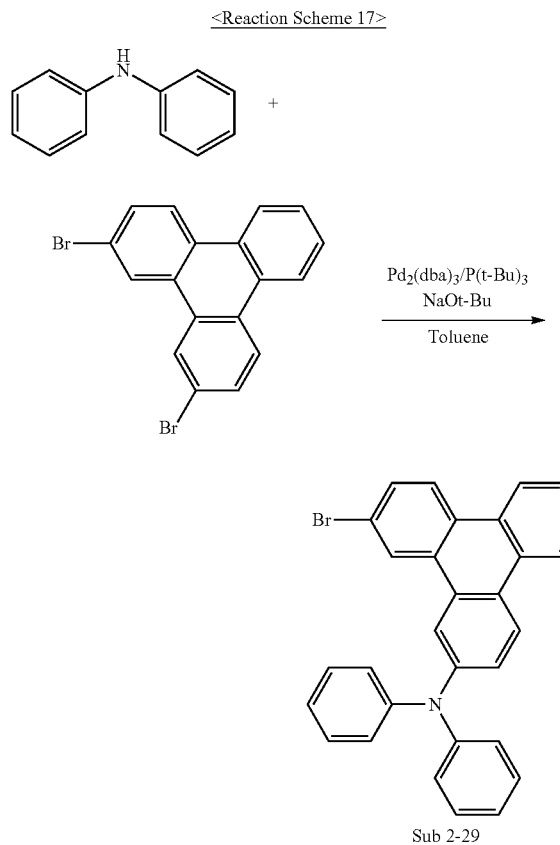

Sub 2-29

2,11-dibromotriphenylene (CAS Registry Number: 24253-51-8) (14.68 g, 38.03 mmol), Pd$_2$(dba)$_3$ (0.70 g, 0.76 mmol), 50% P(t-Bu)$_3$ (1.0 ml, 2.03 mmol), NaOt-Bu (7.31 g, 76.05 mmol) and toluene (210 ml) are added to the starting material diphenylamine (CAS Registry Number: 122-39-4) (4.29 g, 25.35 mmol), and 9.02 g (yield: 75%) of the product was obtained by using the same manner as described above for the synthesis of compound Sub 2-1.

6. Synthesis Example of Sub 2-30

<Reaction Scheme 18>

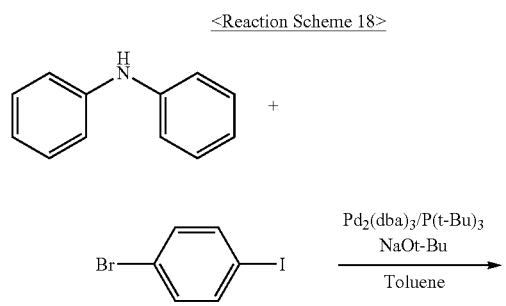

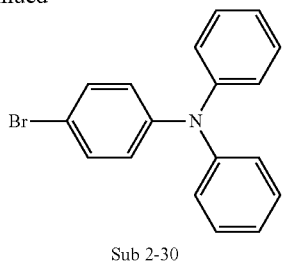

Sub 2-30

1-bromo-4-iodobenzene (CAS Registry Number: 589-87-7) (19.26 g, 68.07 mmol), Pd$_2$(dba)$_3$ (1.25 g, 1.36 mmol), 50% P(t-Bu)$_3$ (1.8 ml, 3.63 mmol), NaOt-Bu (13.08 g, 136.15 mmol) and toluene (380 ml) are added to the starting material diphenylamine (CAS Registry Number: 122-39-4) (7.68 g, 45.38 mmol), and 10.59 g (yield: 72%) of the product was obtained by using the same manner as described above for the synthesis of compound Sub 2-1.

7. Synthesis Example of Sub 2-43

<Reaction Scheme 19>

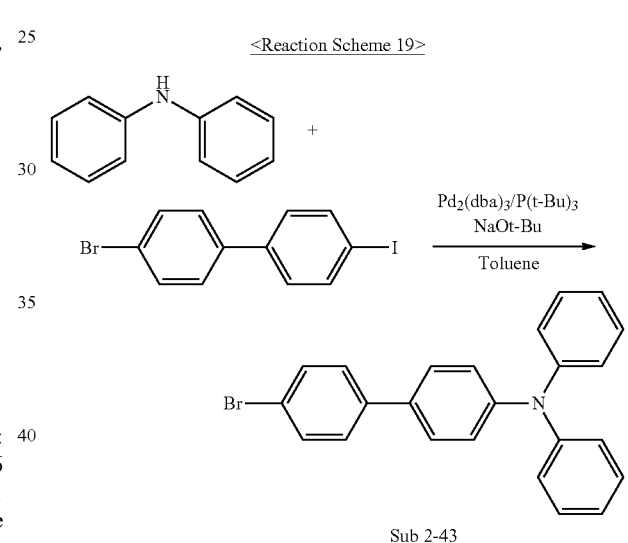

Sub 2-43

4-bromo-4'-iodo-1,1'-biphenyl (CAS Registry Number: 105946-82-5) (20.91 g, 58.23 mmol), Pd$_2$(dba)$_3$ (1.07 g, 1.16 mmol), 50% P(t-Bu)$_3$ (1.5 ml, 3.11 mmol) NaOt-Bu (11.19 g, 116.47 mmol) and toluene (325 ml) are added to the starting material diphenylamine (CAS Registry Number: 122-39-4) (6.57 g, 38.82 mmol), and 10.10 g (yield: 65%) of the product was obtained by using the same manner as described above for the synthesis of compound Sub 2-1.

8. Synthesis Example of Sub 2-52

<Reaction Scheme 20>

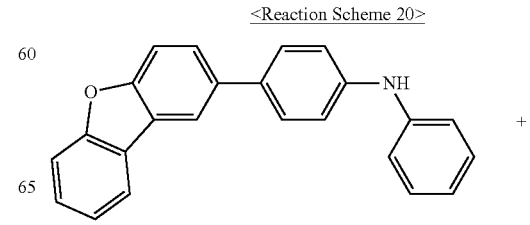

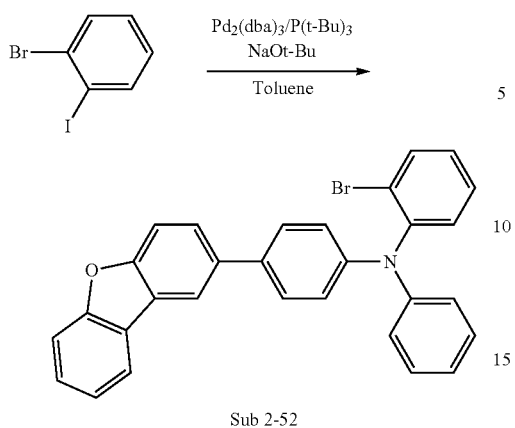

Sub 2-52

1-bromo-2-iodobenzene (CAS Registry Number: 583-55-1) (15.76 g, 55.72 mmol), Pd$_2$(dba)$_3$ (1.02 g, 1.11 mmol), 50% P(t-Bu)$_3$ (1.4 ml, 2.97 mmol), NaOt-Bu (10.71 g, 111.45 mmol) and toluene (310 ml) are added to the starting material 4-(dibenzo[b,d]furan-2-yl)-N-phenylaniline (CAS Registry Number: 1381976-37-9) (12.46 g, 37.15 mmol), and 9.66 g (yield: 53%) of the product was obtained by using the same manner as described above for the synthesis of compound Sub 2-1.

The compounds belonging to Sub 2 may be, but not limited to, the following compounds, and Table 2 shows FD-MS (Field Desorption-Mass Spectrometry) values of some compounds belonging to Sub 2.

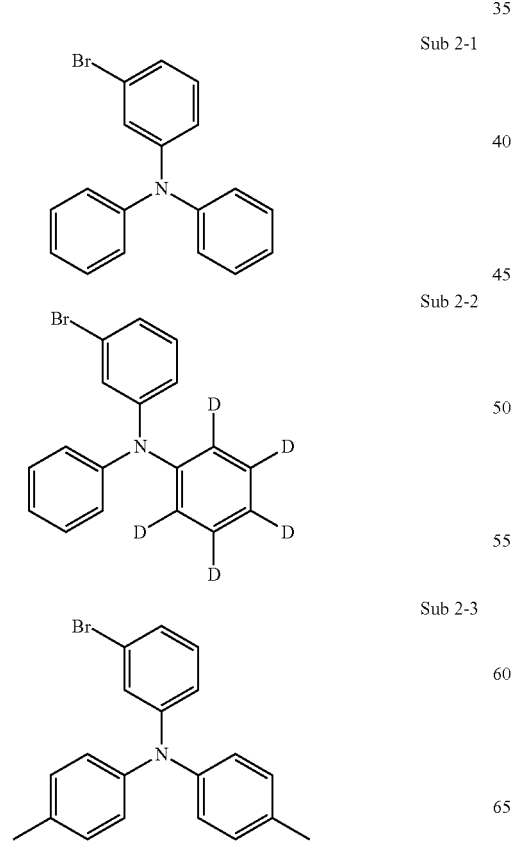

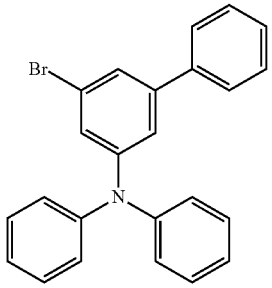

Sub 2-4

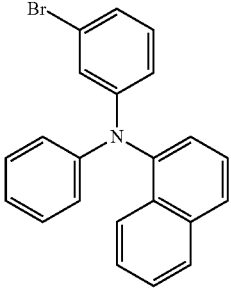

Sub 2-5

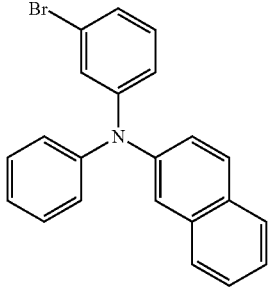

Sub 2-6

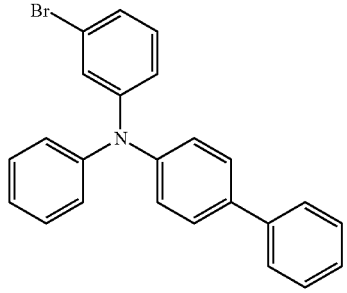

Sub 2-7

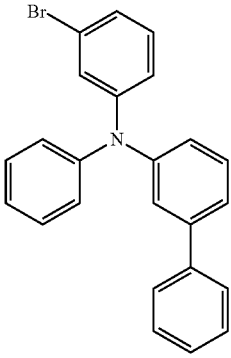

Sub 2-8

-continued
Sub 2-9
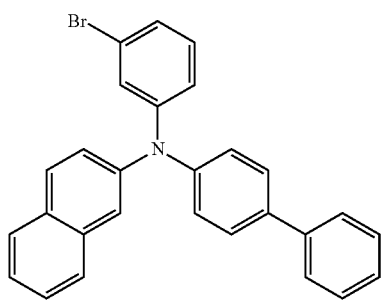
Sub 2-10
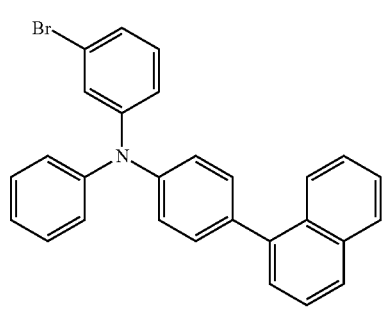
Sub 2-11
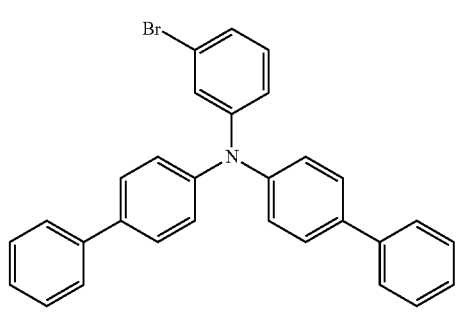
Sub 2-12
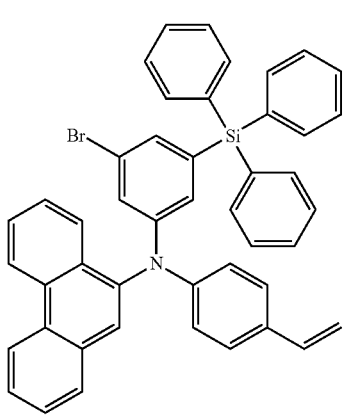
-continued
Sub 2-13
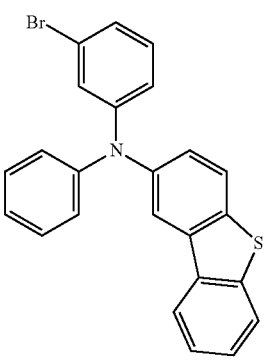
Sub 2-14
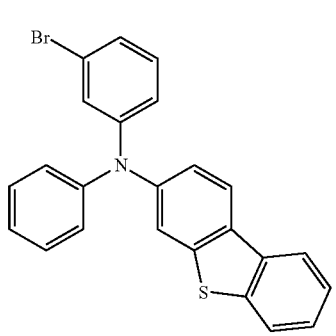
Sub 2-15
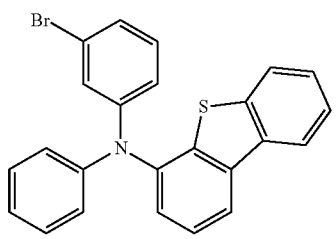
Sub 2-16
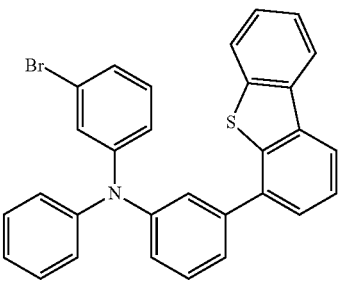
Sub 2-17
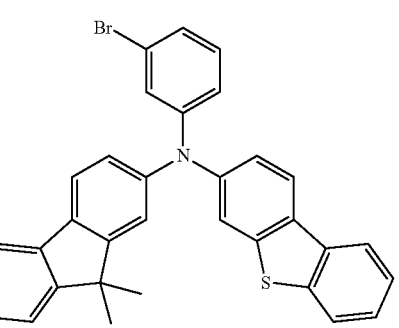

Sub 2-18
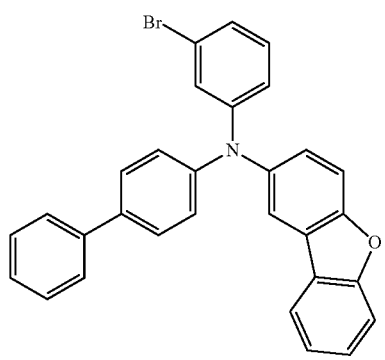
Sub 2-19
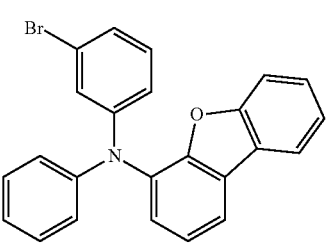
Sub 2-20
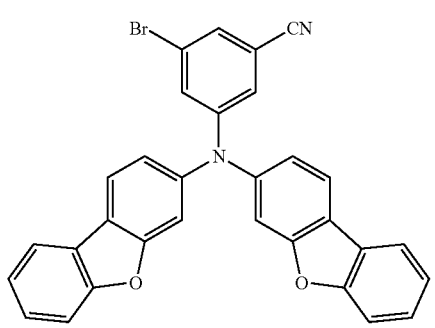
Sub 2-21
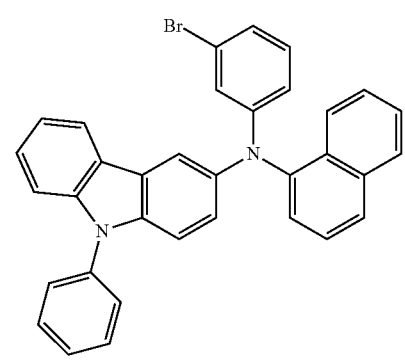
Sub 2-22
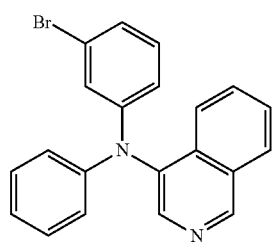
Sub 2-23
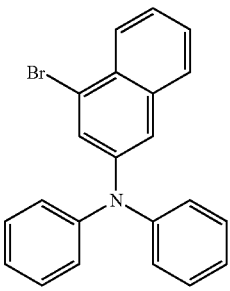
Sub 2-24
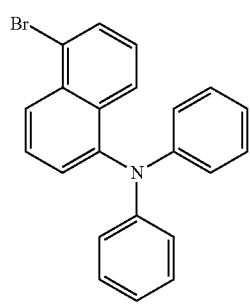
Sub 2-25
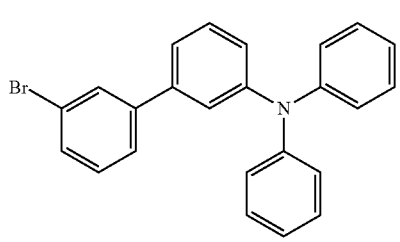
Sub 2-26
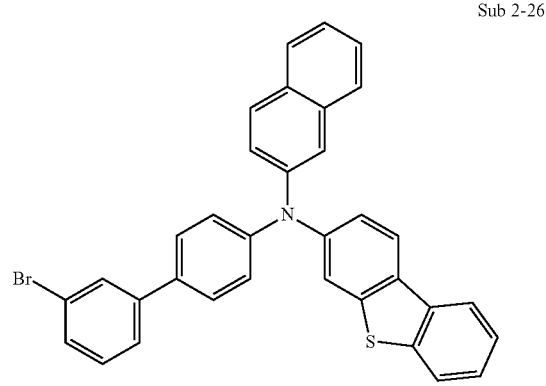
Sub 2-27
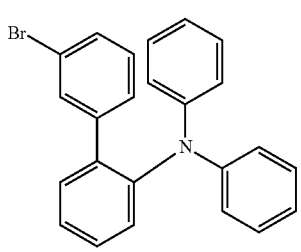

-continued
Sub 2-28
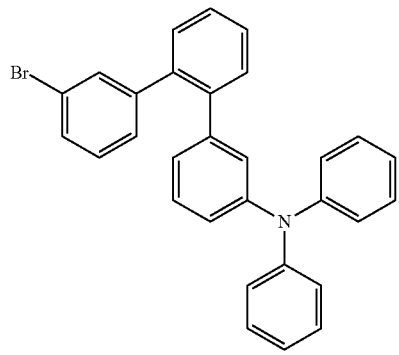
Sub 2-29
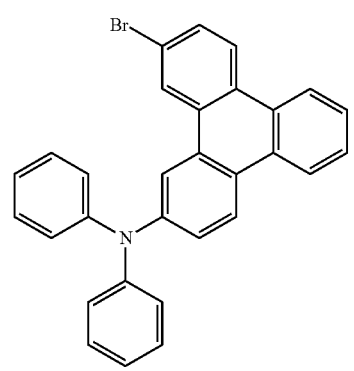
Sub 2-30
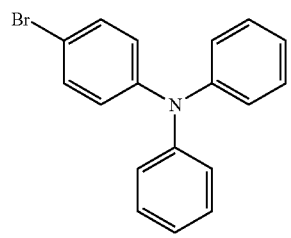
Sub 2-31
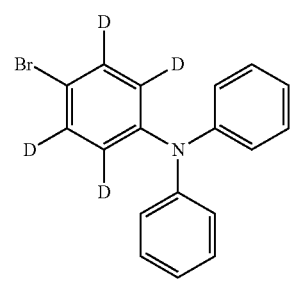
Sub 2-32
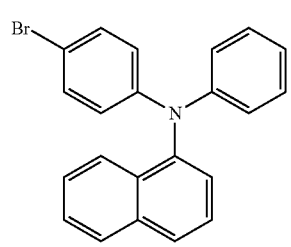
-continued
Sub 2-33
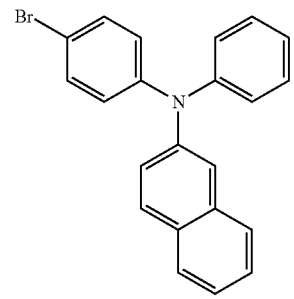
Sub 2-34
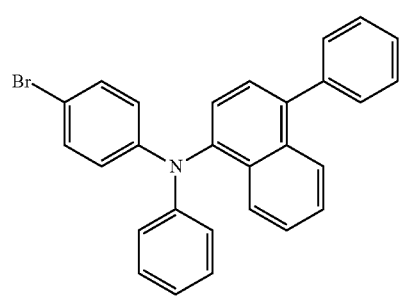
Sub 2-35
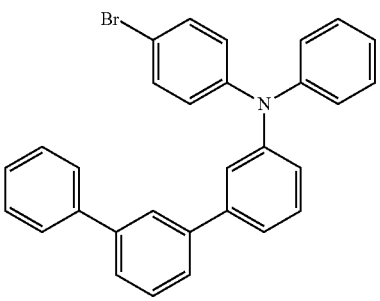
Sub 2-36
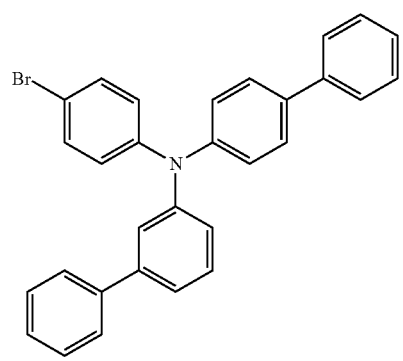
Sub 2-37
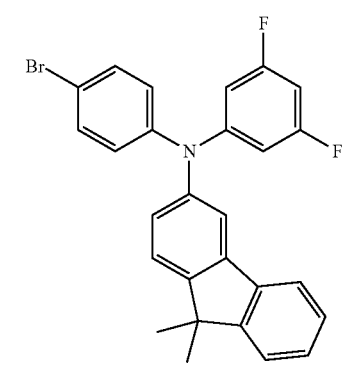

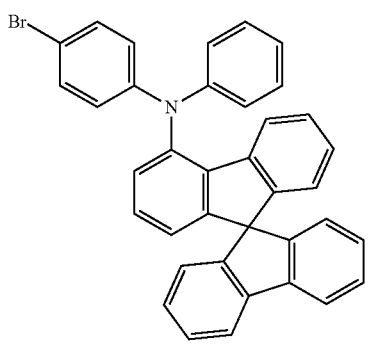
Sub 2-38
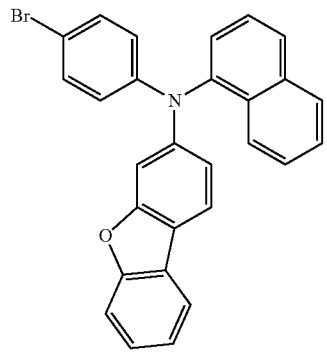
Sub 2-39
Sub 2-40
Sub 2-41
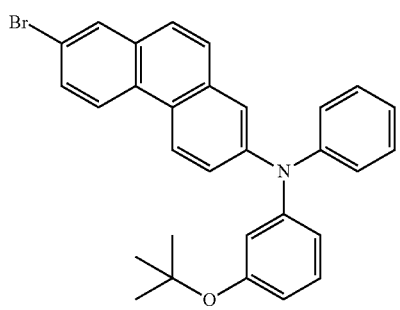
Sub 2-42
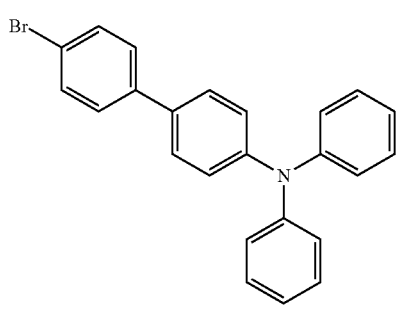
Sub 2-43
Sub 2-44
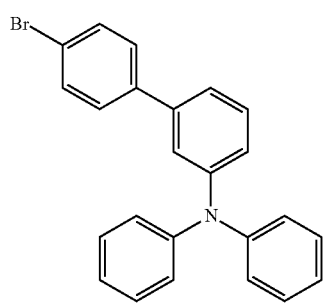
Sub 2-45
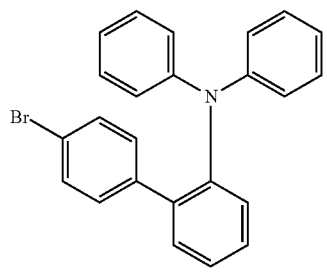
Sub 2-46
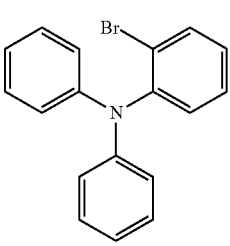

Sub 2-47
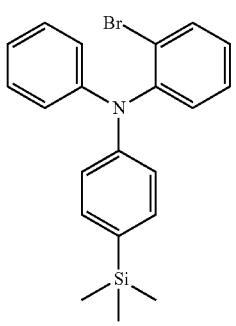
Sub 2-48
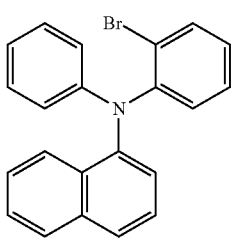
Sub 2-49
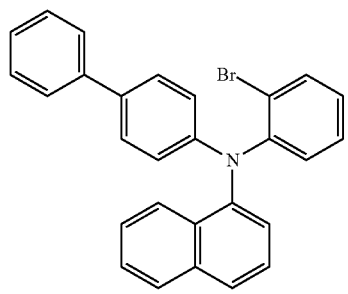
Sub 2-50
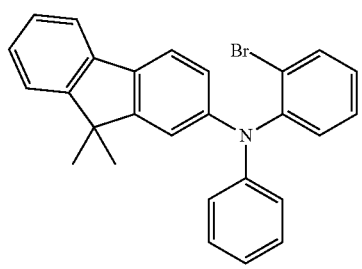
Sub 2-51
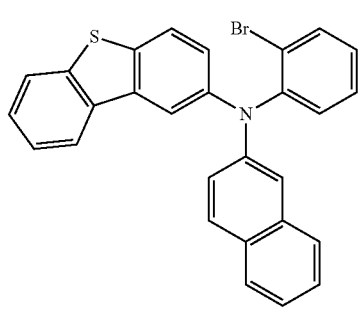
Sub 2-52
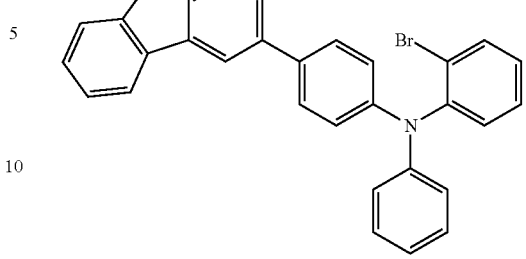
Sub 2-53
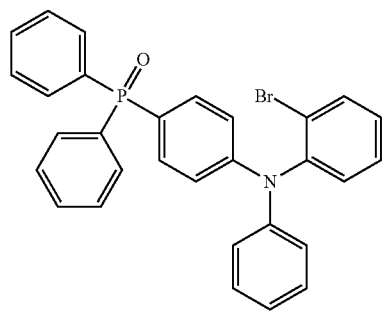
Sub 2-54
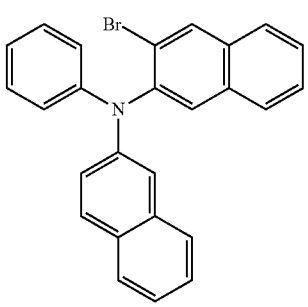
Sub 2-55
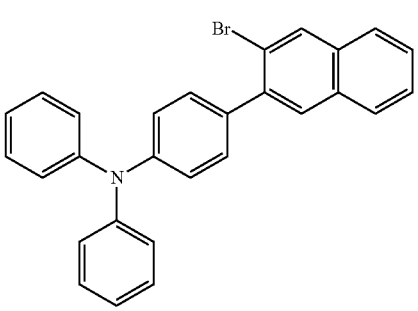
Sub 2-56
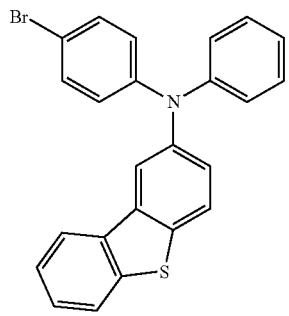

TABLE 2

| Compound | FD-MS | Compound | FD-MS |
|---|---|---|---|
| Sub 2-1 | m/z = 323.03($C_{18}H_{14}BrN$ = 324.22) | Sub 2-3 | m/z = 351.06($C_{20}H_{18}BrN$ = 352.28) |
| Sub 2-4 | m/z = 399.06($C_{24}H_{18}BrN$ = 400.32) | Sub 2-13 | m/z = 429.02($C_{24}H_{16}BrNS$ = 430.36) |
| Sub 2-29 | m/z = 473.08($C_{30}H_{20}BrN$ = 474.40) | Sub 2-30 | m/z = 323.03($C_{18}H_{14}BrN$ = 324.22) |
| Sub 2-43 | m/z = 399.06($C_{24}H_{18}BrN$ = 400.32) | Sub 2-52 | m/z = 489.07($C_{30}H_{20}BrNO$ = 490.40) |

III. Synthesis of Product

After Sub 1 (1 eq.) was dissolved in toluene in a round bottom flask, Sub 2 (1 eq.), $Pd_2(dba)_3$ (0.03 eq.), $(t-Bu)_3P$ (0.06 eq.) and NaOt-Bu (3 eq.) are added, and stirred at 100° C. After completion of the reaction, the reaction product was extracted with $CH_2Cl_2$ and water. The organic layer was dried over $MgSO_4$ and concentrated. The resulting compound was purified by silicagel column and recrystallized to obtain a final product.

1. Synthesis Example of P-1

After Sub 1-1 (3.96 g, 8.95 mmol) obtained in the above synthesis was dissolved in toluene (90 ml) in a round bottom flask, Sub 2-1 (2.90 g, 8.95 mmol), $Pd_2(dba)_3$ (0.25 g, 0.27 mmol), 50% $P(t-Bu)_3$ (0.3 ml, 0.54 mmol) and NaOt-Bu (2.58 g, 26.84 mmol) are added, and stirred at 100° C. After completion of the reaction, the reaction product was extracted with $CH_2Cl_2$ and water. The organic layer was dried over $MgSO_4$ and concentrated. The resulting compound was purified by silicagel column and recrystallized to obtain 5.65 g of the product (yield: 92%).

2. Synthesis Example of P-20

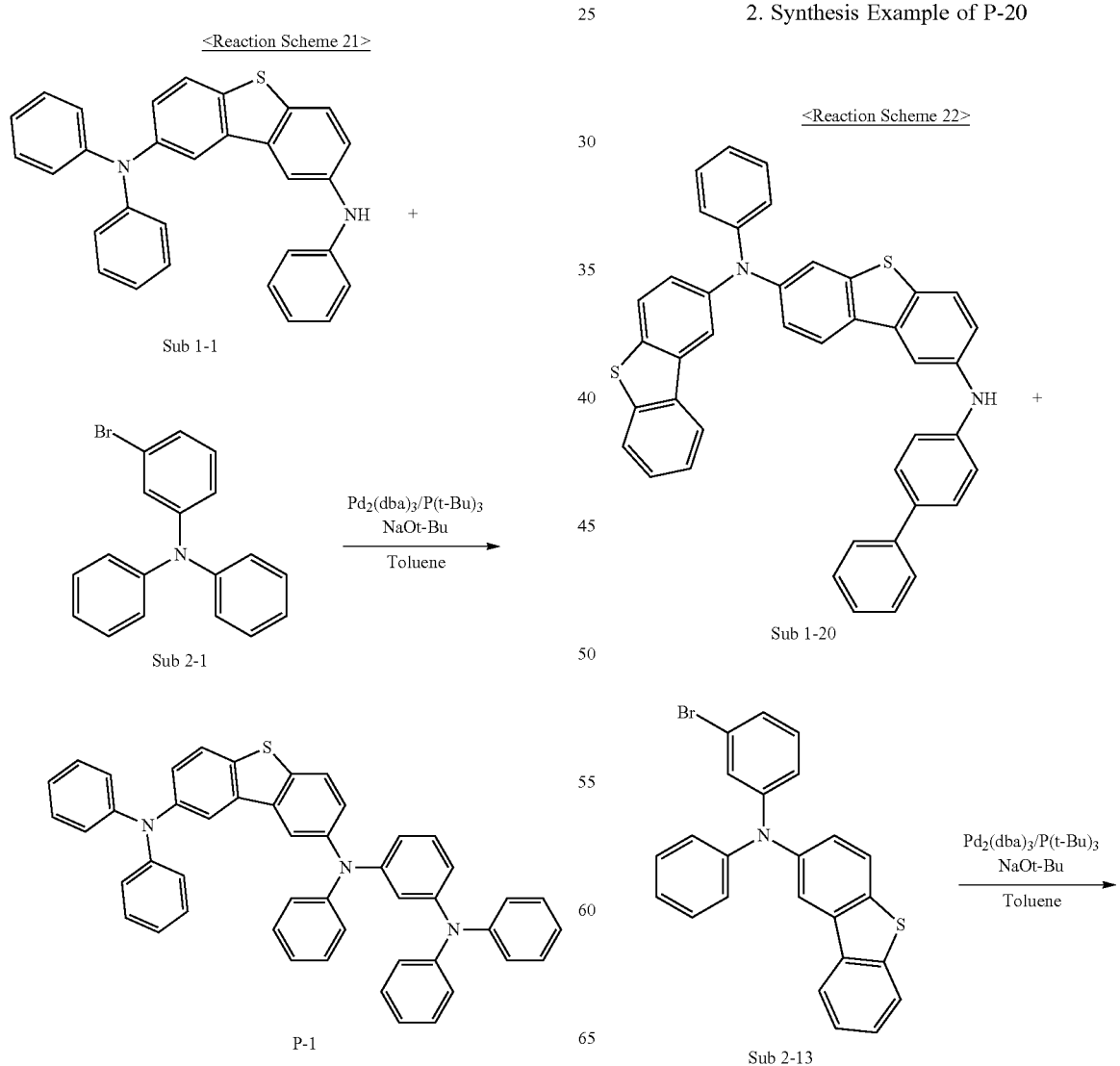

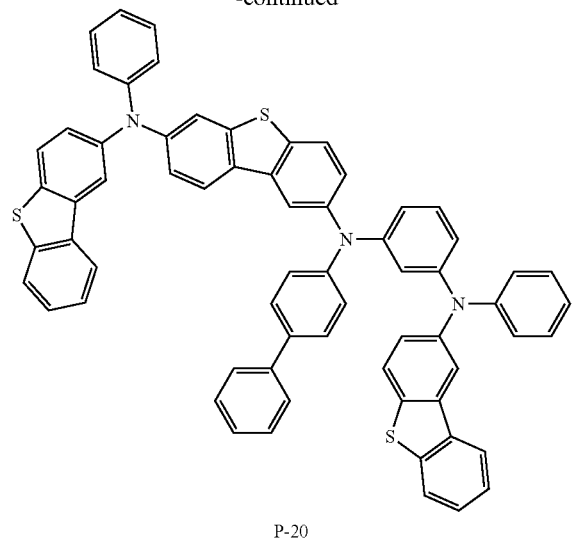

P-20

Sub 2-13 (2.62 g, 6.10 mmol), Pd$_2$(dba)$_3$ (0.17 g, 0.18 mmol), 50% P(t-Bu)$_3$ (0.2 ml, 0.37 mmol), NaOt-Bu (1.76 g, 18.29 mmol) and toluene (60 ml) are added to Sub 1-20 (3.81 g, 6.10 mmol) obtained in the above synthesis, and 5.11 g (yield: 86%) of the product was obtained by using the same manner as described above for the synthesis of compound P-1.

3. Synthesis Example of P-35

<Reaction Scheme 23>

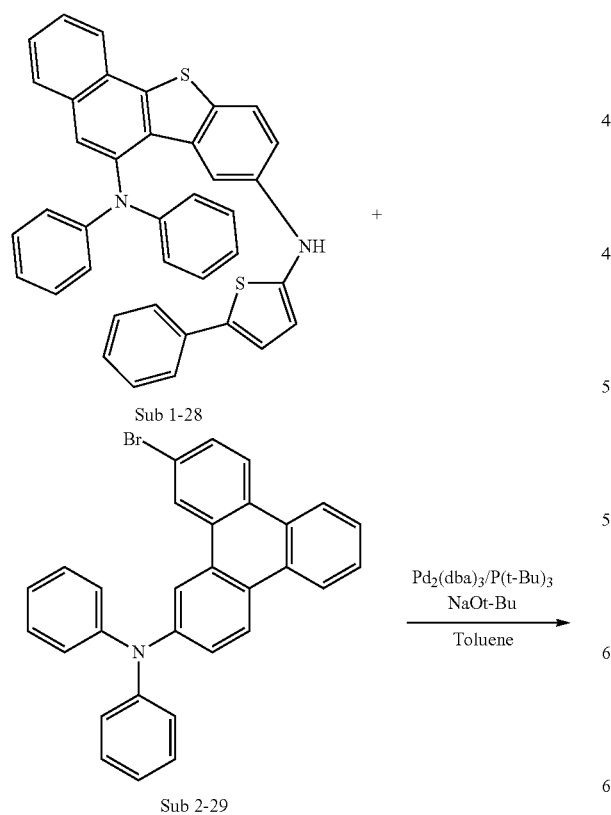

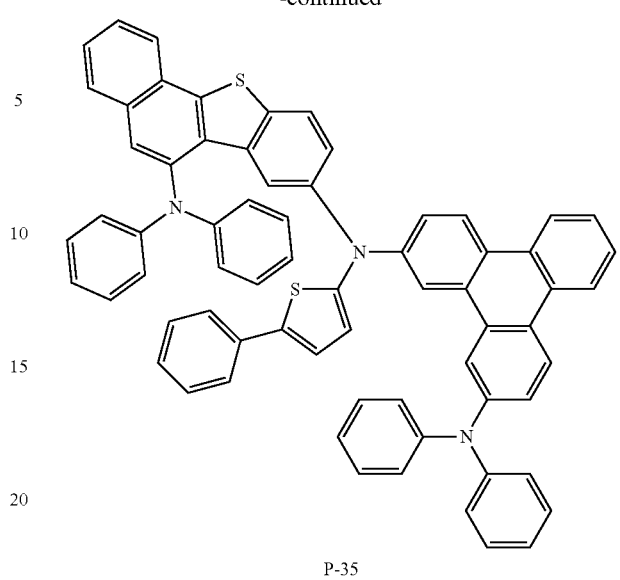

P-35

Sub 2-29 (3.33 g, 7.01 mmol), Pd$_2$(dba)$_3$ (0.19 g, 0.21 mmol), 50% P(t-Bu)$_3$ (0.2 ml, 0.42 mmol), NaOt-Bu (2.02 g, 21.03 mmol) and toluene (70 ml) are added to Sub 1-28 (4.03 g, 7.01 mmol) obtained in the above synthesis, and 4.89 g (yield: 72%) of the product was obtained by using the same manner as described above for the synthesis of compound P-1.

4. Synthesis Example of P-40

<Reaction Scheme 24>

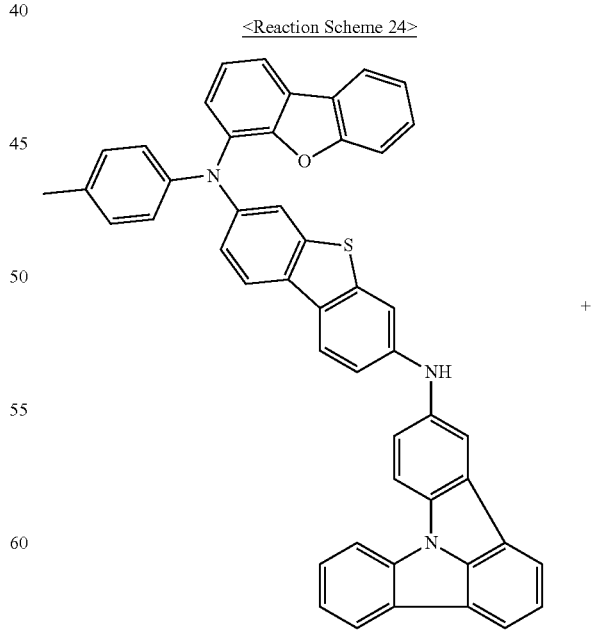

-continued

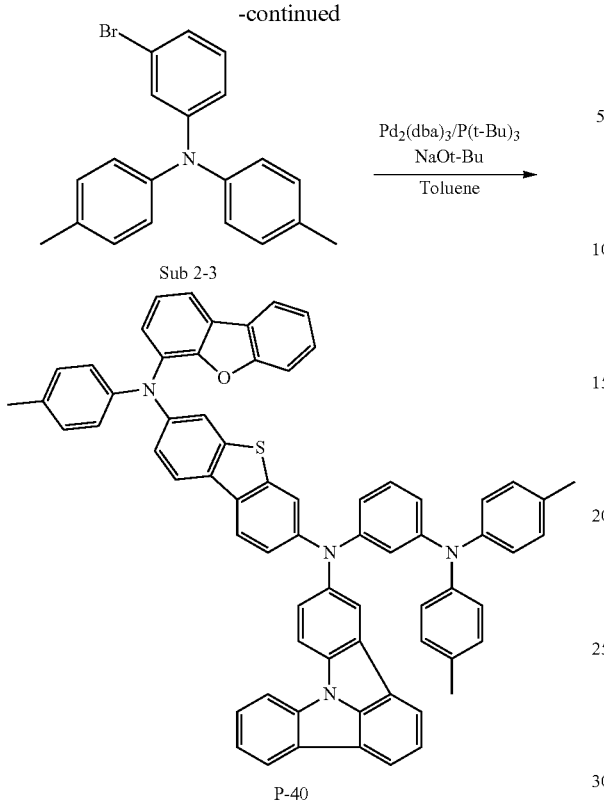

Sub 2-3

P-40

Sub 2-3 (2.32 g, 6.58 mmol), Pd$_2$(dba)$_3$ (0.18 g, 0.20 mmol), 50% P(t-Bu)$_3$ (0.2 ml, 0.39 mmol), NaOt-Bu (1.90 g, 19.74 mmol) and toluene (65 ml) are added to Sub 1-44 (4.67 g, 6.58 mmol) obtained in the above synthesis, and 4.97 g (yield: 77) of the product was obtained by using the same manner as described above for the synthesis of compound P-1.

5. Synthesis Example of P-52

<Reaction Scheme 25>

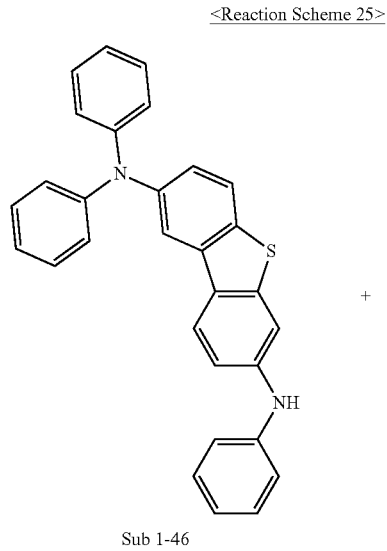

Sub 1-46

-continued

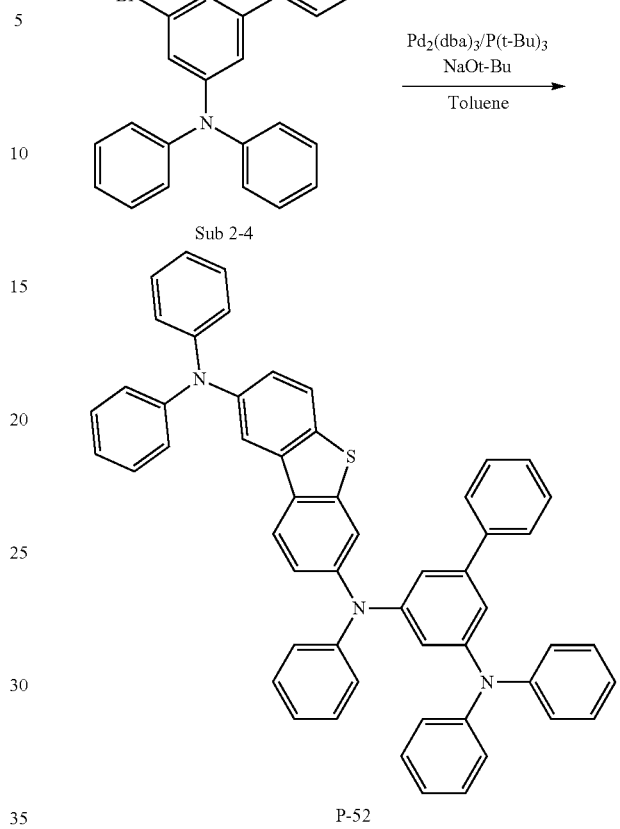

Sub 2-4

P-52

Sub 2-4 (3.20 g, 8.00 mmol), Pd$_2$(dba)$_3$ (0.22 g, 0.24 mmol), 50% P(t-Bu)$_3$ (0.2 ml, 0.48 mmol), NaOt-Bu (2.31 g, 24.00 mmol) and toluene (80 ml) are added to Sub 1-46 (3.54 g, 8.00 mmol) obtained in the above synthesis, and 5.42 g (yield: 89) of the product was obtained by using the same manner as described above for the synthesis of compound P-1.

6. Synthesis Example of P-71

<Reaction Scheme 26>

Sub 1-60

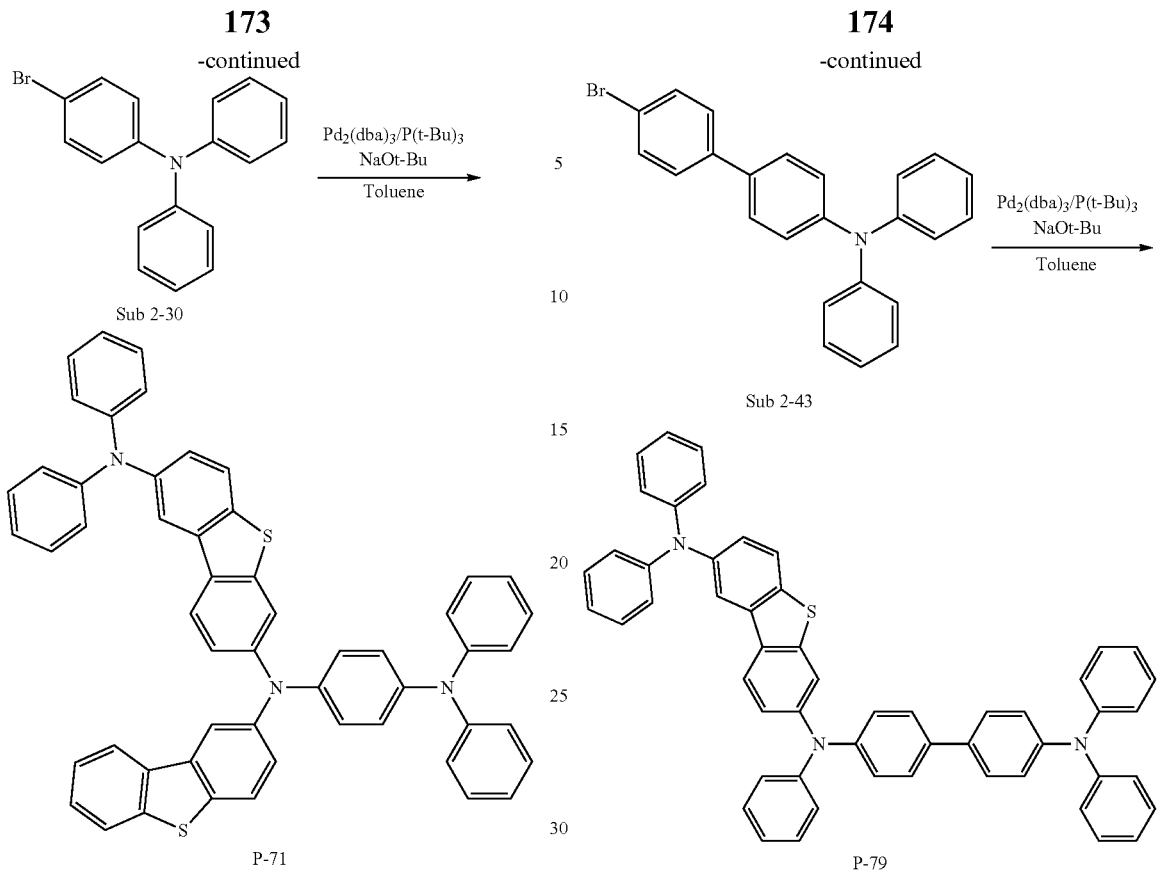

Sub 2-30 (2.42 g, 7.47 mmol), Pd$_2$(dba)$_3$ (0.21 g, 0.22 mmol), 50% P(t-Bu)$_3$ (0.2 ml, 0.45 mmol), NaOt-Bu (2.15 g, 22.42 mmol) and toluene (75 ml) are added to Sub 1-60 (4.10 g, 7.47 mmol) obtained in the above synthesis, and 5.33 g (yield: 90%) of the product was obtained by using the same manner as described above for the synthesis of compound P-1.

7. Synthesis Example of P-79

Sub 2-43 (2.91 g, 7.28 mmol), Pd$_2$(dba)$_3$ (0.20 g, 0.22 mmol), 50% P(t-Bu)$_3$ (0.2 ml, 0.44 mmol), NaOt-Bu (2.10 g, 21.83 mmol) and toluene (75 ml) are added to Sub 1-46 (3.22 g, 7.28 mmol) obtained in the above synthesis, and 4.71 g (yield: 85%) of the product was obtained by using the same manner as described above for the synthesis of compound P-1.

8. Synthesis Example of P-85

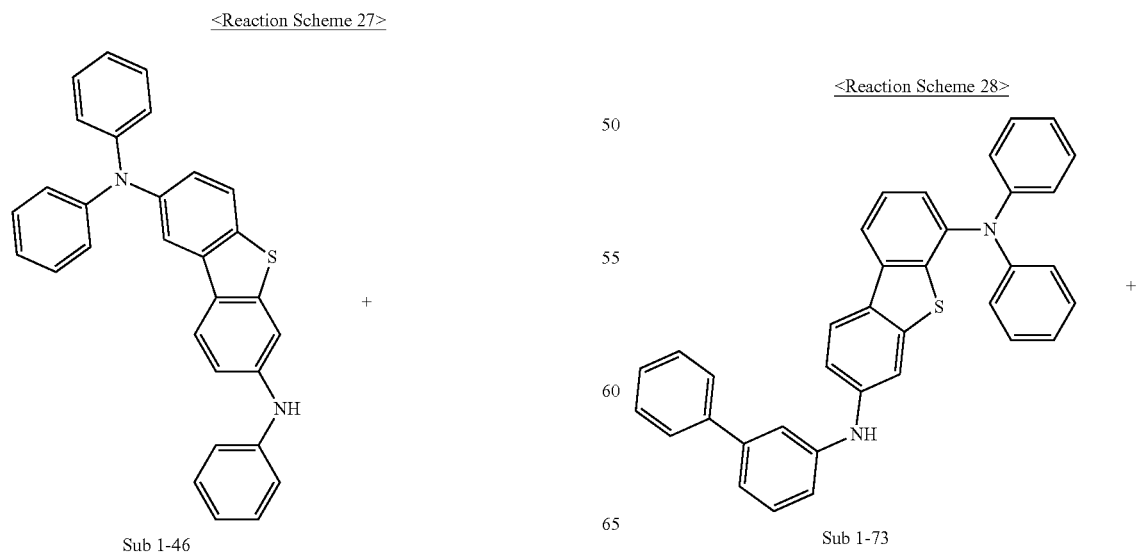

-continued

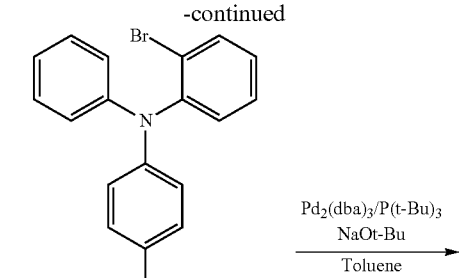

Sub 2-52

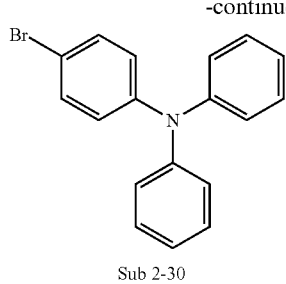

Sub 2-30

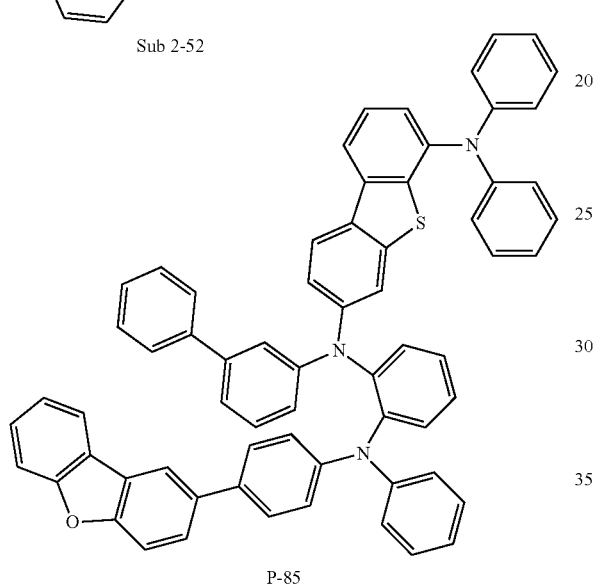

P-85

Sub 2-52 (3.84 g, 7.83 mmol), Pd$_2$(dba)$_3$ (0.22 g, 0.23 mmol), 50% P(t-Bu)$_3$ (0.2 ml, 0.47 mmol), NaOt-Bu (2.26 g, 23.48 mmol) and toluene (80 ml) are added to Sub 1-73 (4.06 g, 7.83 mmol) obtained in the above synthesis, and 5.30 g (yield: 73%) of the product was obtained by using the same manner as described above for the synthesis of compound P-1.

9. Synthesis Example of P-89

<Reaction Scheme 29>

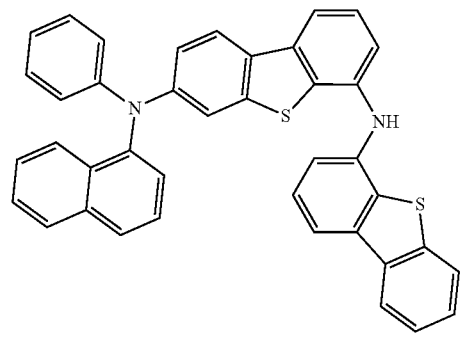

Sub 1-79

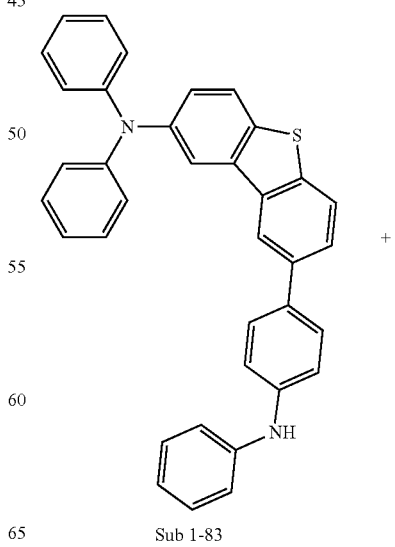

P-89

Sub 2-30 (2.29 g, 7.06 mmol), Pd$_2$(dba)$_3$ (0.19 g, 0.21 mmol), 50% P(t-Bu)$_3$ (0.2 ml, 0.42 mmol), NaOt-Bu (2.04 g, 21.19 mmol) and toluene (70 ml) are added to Sub 1-79 (4.23 g, 7.06 mmol) obtained in the above synthesis, and 5.29 g (yield: 89%) of the product was obtained by using the same manner as described above for the synthesis of compound P-1.

10. Synthesis Example of P-96

<Reaction Scheme 30>

Sub 1-83

-continued

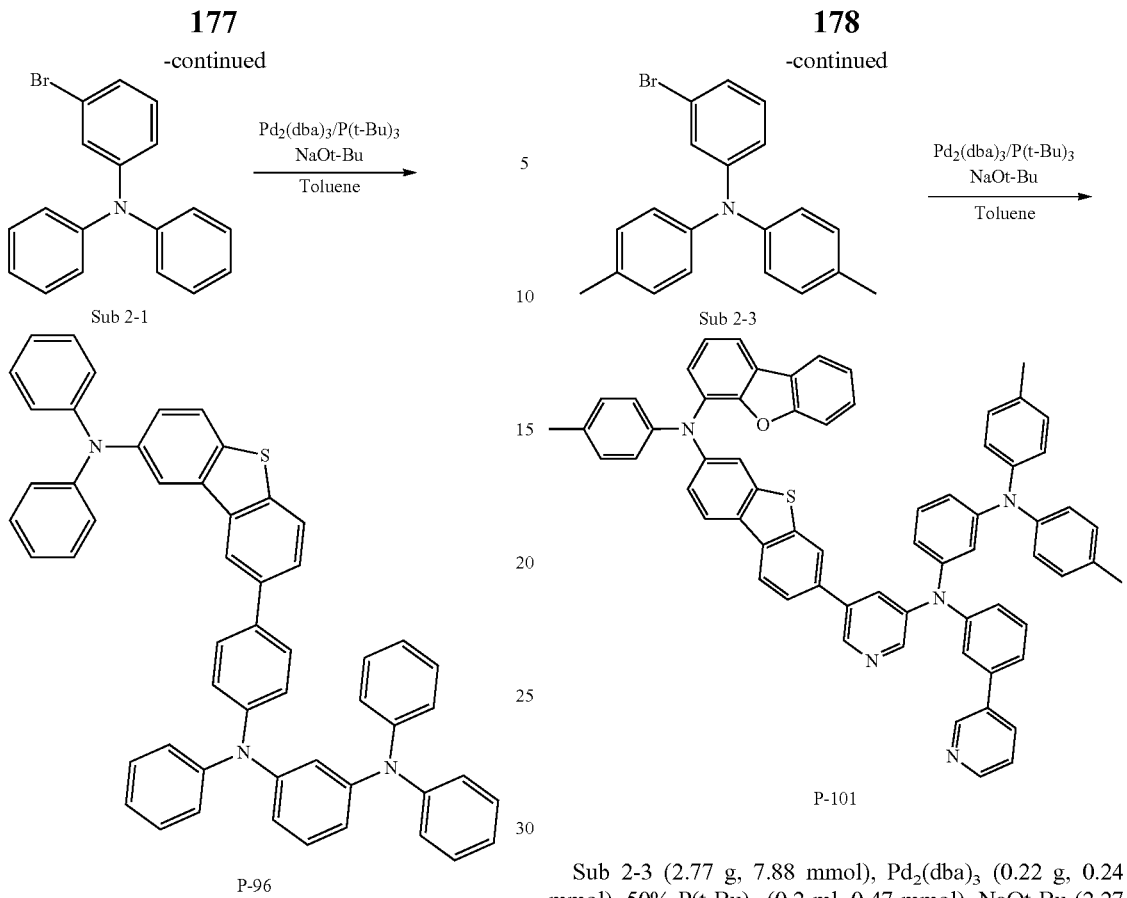

Sub 2-1 (2.91 g, 8.97 mmol), Pd₂(dba)₃ (0.25 g, 0.27 mmol), 50% P(t-Bu)₃ (0.3 ml, 0.54 mmol), NaOt-Bu (2.58 g, 26.90 mmol) and toluene (90 ml) are added to Sub 1-83 (4.65 g, 8.97 mmol) obtained in the above synthesis, and 5.87 g (yield: 86%) of the product was obtained by using the same manner as described above for the synthesis of compound P-1.

11. Synthesis Example of P-101

Sub 2-3 (2.77 g, 7.88 mmol), Pd₂(dba)₃ (0.22 g, 0.24 mmol), 50% P(t-Bu)₃ (0.2 ml, 0.47 mmol), NaOt-Bu (2.27 g, 23.63 mmol) and toluene (80 ml) are added to Sub 1-96 (5.52 g, 7.88 mmol) obtained in the above synthesis, and 4.90 g (yield: 64%) of the product was obtained by using the same manner as described above for the synthesis of compound P-1.

12. Synthesis Example of P-119

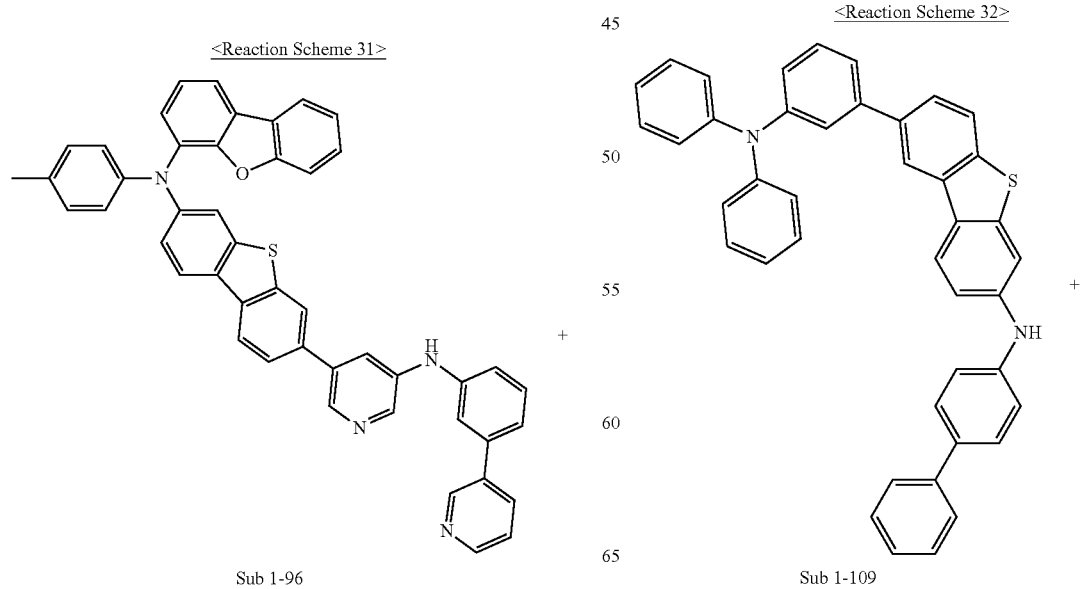

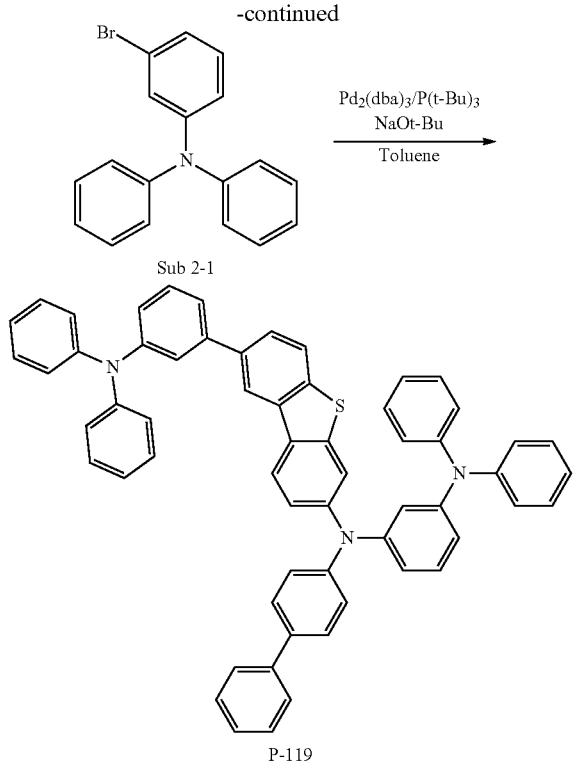

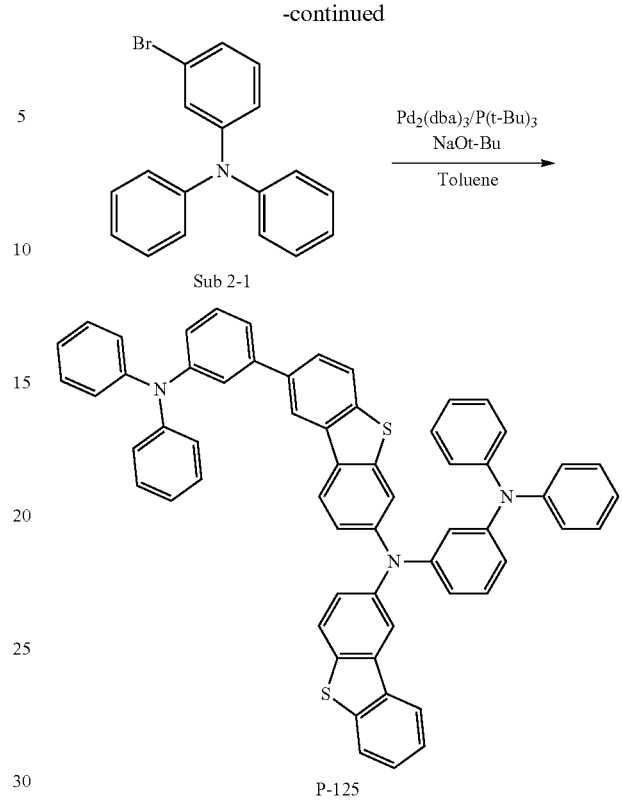

Sub 2-1 (2.79 g, 8.61 mmol), Pd₂(dba)₃ (0.24 g, 0.26 mmol), 50% P(t-Bu)₃ (0.3 ml, 0.52 mmol), NaOt-Bu (2.48 g, 25.82 mmol) and toluene (85 ml) are added to Sub 1-109 (5.12 g, 8.61 mmol) obtained in the above synthesis, and 5.56 g (yield: 77%) of the product was obtained by using the same manner as described above for the synthesis of compound P-1.

13. Synthesis Example of P-125

Sub 2-1 (2.78 g, 8.58 mmol), Pd₂(dba)₃ (0.24 g, 0.26 mmol), 50% P(t-Bu)₃ (0.3 ml, 0.51 mmol), NaOt-Bu (2.47 g, 25.74 mmol) and toluene (85 ml) are added to Sub 1-114 (5.36 g, 8.58 mmol) obtained in the above synthesis, and 5.29 g (yield: 71%) of the product was obtained by using the same manner as described above for the synthesis of compound P-1.

14. Synthesis Example of P-135

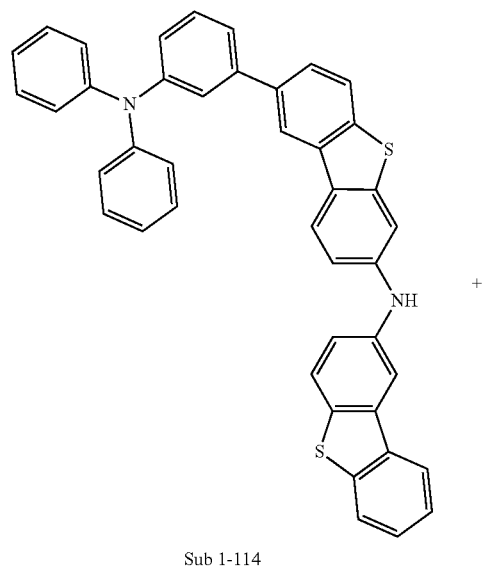

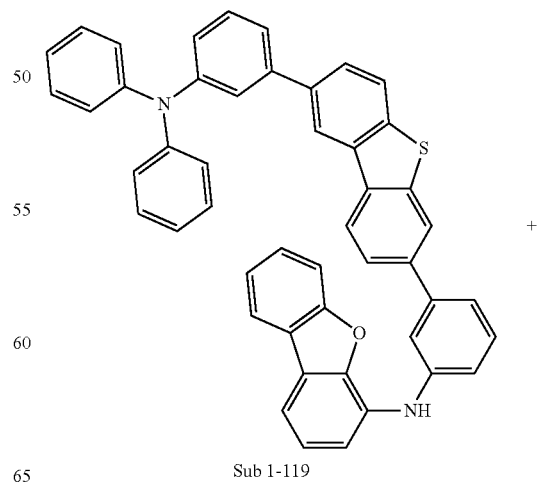

-continued

Sub 2-1

[Structure: Sub 2-1, brominated triphenylamine]

Pd₂(dba)₃/P(t-Bu)₃
NaOt-Bu
Toluene
→

P-135

[Structure: P-135]

Sub 2-1 (2.66 g, 8.19 mmol), Pd$_2$(dba)$_3$ (0.23 g, 0.25 mmol), 50% P(t-Bu)$_3$ (0.2 ml, 0.49 mmol), NaOt-Bu (2.36 g, 24.57 mmol) and toluene (80 ml) are added to Sub 1-119 (5.61 g, 8.19 mmol) obtained in the above synthesis, and 5.17 g (yield: 68%) of the product was obtained by using the same manner as described above for the synthesis of compound P-1.

The FD-MS values of some compounds of the present invention prepared according to the above synthesis examples are shown in Table 3 below.

TABLE 3

| Compound | FD-MS | Compound | FD-MS |
|---|---|---|---|
| P-1 | m/z = 685.26($C_{48}H_{35}N_3S$ = 685.89) | P-20 | m/z = 973.26($C_{66}H_{43}N_3S_3$ = 974.27) |
| P-35 | m/z = 967.31($C_{68}H_{45}N_3S_2$ = 968.25) | P-40 | m/z = 980.35($C_{69}H_{48}N_4OS$ = 981.23) |
| P-52 | m/z = 761.29($C_{54}H_{39}N_3S$ = 761.99) | P-71 | m/z = 791.24($C_{54}H_{37}N_3S_2$ = 792.03) |
| P-79 | m/z = 761.29($C_{54}H_{39}N_3S$ = 761.99) | P-85 | m/z = 927.33($C_{66}H_{45}N_3OS$ = 928.17) |
| P-89 | m/z = 841.26($C_{58}H_{39}N_3S_2$ = 842.09) | P-96 | m/z = 761.29($C_{54}H_{39}N_3S$ = 761.99) |
| P-101 | m/z = 971.37($C_{67}H_{49}N_5OS$ = 972.22) | P-119 | m/z = 837.32($C_{60}H_{43}N_3S$ = 838.09) |
| P-125 | m/z = 867.27($C_{60}H_{41}N_3S_2$ = 868.13) | P-135 | m/z = 927.33($C_{66}H_{45}N_3OS$ = 928.17) |

In the above, an exemplary synthesis example of the present invention represented by the general formula 1 are described, but all of them are based on Buchwald-Hartwig cross coupling reaction, Suzuki cross-coupling reaction, Intramolecular acid-induced cyclization reaction (*J. mater. Chem.* 1999, 9, 2095). Therefore, it will be understood by those skilled in the art that the above reaction proceeds even when other substituents (Ar$^1$ to Ar$^5$, L$^1$ to L$^3$, R$^1$, R$^2$, m and n) defined in Formula 1 are bonded, in addition to the substituents specified in the specific synthesis example. For example, the reaction of Sub 1 and Sub 2→Final Product in Reaction Scheme 1, the reactions of starting materials→Sub 1-I, starting materials→Sub 1-III, Sub 1-III→Sub 1, and Sub 1-IV→Sub 1 in Reaction Scheme 2, and the reaction of starting materials→Sub 2 reaction in Reaction Scheme 12 are all based on the Buchwald-Hartwig cross coupling reaction, the reactions of Sub 1-I→Sub 1-II, and Sub 1-III→Sub 1-IV in Reaction Scheme 2 are based on the Suzuki cross-coupling reaction, the reaction of Sub 1-II→Sub 1-III is based on the Intramolecular acid-induced cyclization reaction (*J. mater. Chem.* 1999, 9, 2095). The above reactions will proceed even if a substituent not specifically mentioned is attached.

Fabrication and Evaluation of Organic Electronic Element

Example 1 Green OLED (a Hole Transport Layer)

Organic light emitting diodes (OLEDs) were fabricated according to a conventional method by using a compound of the present invention as a hole transport layer material.

First, an ITO layer (anode) was formed on a glass substrate, and then 4,4',4"-tris[2-naphthyl(phenyl)amino]triphenylamine (hereinafter, "2-TNATA") was vacuum-deposited on the ITO layer to form a hole injection layer with a thickness of 60 nm.

Subsequently, compound P-1 of the present invention was vacuum-deposited with a thickness of 60 nm on the hole injection layer to form a hole transport layer.

Subsequently, a light emitting layer with a thickness of 30 nm was formed on the hole transport layer by using 4,4'-N,N'-dicarbazole-biphenyl (hereinafter, "CBP") as a host material and tris(2-phenylpyridine)-iridium (hereinafter, "Ir (ppy)$_3$") as a dopant material in a weight ratio of 90:10.

Next, ((1,1'-bisphenyl)-4-olato)bis(2-methyl-8-quinolinolato)aluminum (hereinafter, "BAlq") was vacuum-deposited with a thickness of 10 nm on the light emitting layer to form a hole blocking layer, and tris(8-quinolinolato)aluminum (hereinafter, "Alq$_3$") was formed with a thickness of 40 nm to form an electron transport layer.

Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

Example 2 to Example 33 Green OLED (a Hole Transport Layer)

The OLEDs were fabricated in the same manner as described in Example 1 except that the compounds P-6 to P-134 of the present invention described in Table 4 instead of the compound P-1 of the present invention were used as the hole transport layer material.

Comparative Example 1 to Comparative Example 6 Green OLED (a Hole Transport Layer)

The OLEDs were fabricated in the same manner as described in Example 1 except that the following Comparative Compounds 1 to 6 described in Table 4 instead of the compound P-1 of the present invention were used as the hole transport layer material.

<Comp. compd 1>

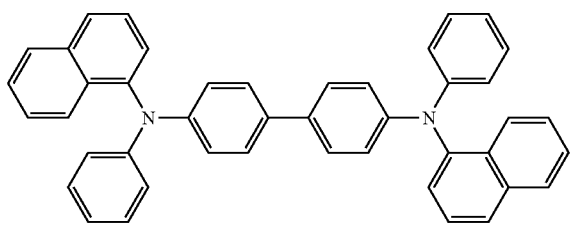

<Comp. compd 2>

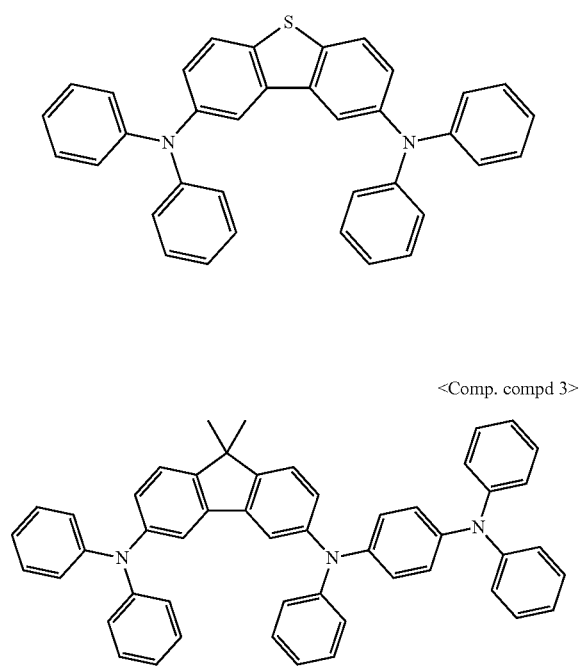

<Comp. compd 3>

<Comp. compd 4>

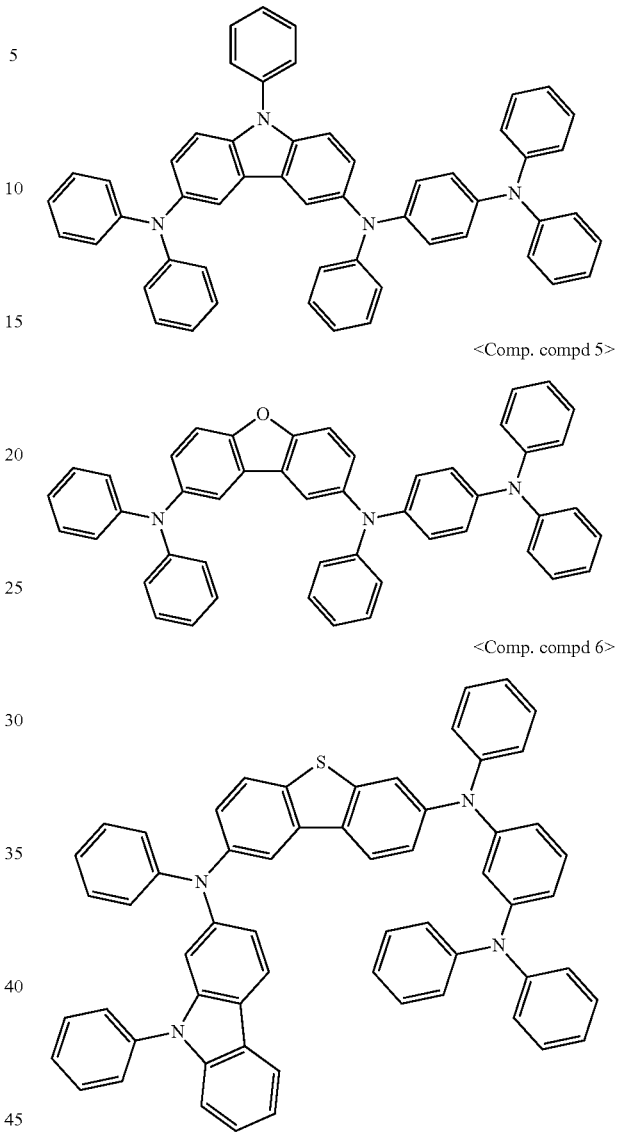

<Comp. compd 5>

<Comp. compd 6>

Electruminescence (EL) characteristics were measured with a PR-650 (Photoresearch) by applying a forward bias DC voltage to the OLEDs prepared in Examples 1 to 33 of the present invention and Comparative Examples 1 to 6. And, the T95 life span was measured using a life span measuring apparatus manufactured by Macscience Inc. at reference brightness of 5000 cd/m². The measurement results are shown in Table 4 below.

TABLE 4

| | Compound | Voltage (V) | Current Density (mA/cm²) | Brightness (cd/m²) | Efficiency (cd/A) | Lifetime T(95) | CIE x | y |
|---|---|---|---|---|---|---|---|---|
| comp. Ex(1) | comp. Com1 | 6.0 | 21.5 | 5000 | 23.3 | 57.4 | 0.33 | 0.62 |
| comp. Ex(2) | comp. Com2 | 5.9 | 18.9 | 5000 | 26.4 | 80.8 | 0.33 | 0.62 |
| comp. Ex(3) | comp. Com3 | 5.8 | 18.3 | 5000 | 27.3 | 72.1 | 0.33 | 0.61 |
| comp. Ex(4) | comp. Com4 | 5.9 | 18.0 | 5000 | 27.7 | 86.6 | 0.33 | 0.62 |
| comp. Ex(5) | comp. Com5 | 5.8 | 16.5 | 5000 | 30.3 | 94.8 | 0.33 | 0.62 |
| comp. Ex(6) | comp. Com6 | 5.7 | 16.2 | 5000 | 30.9 | 106.1 | 0.32 | 0.62 |
| Ex.(1) | Com.(P-1) | 5.8 | 14.0 | 5000 | 35.6 | 120.9 | 0.33 | 0.61 |
| Ex.(2) | Com.(P-6) | 5.6 | 12.8 | 5000 | 39.1 | 131.8 | 0.33 | 0.62 |

TABLE 4-continued

|  | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex.(3) | Com.(P-7) | 5.6 | 12.4 | 5000 | 40.4 | 134.6 | 0.33 | 0.62 |
| Ex.(4) | Com.(P-8) | 5.7 | 12.7 | 5000 | 39.5 | 131.6 | 0.33 | 0.61 |
| Ex.(5) | Com.(P-9) | 5.7 | 12.6 | 5000 | 39.8 | 132.3 | 0.33 | 0.61 |
| Ex.(6) | Com.(P-11) | 5.8 | 14.5 | 5000 | 34.5 | 117.3 | 0.33 | 0.62 |
| Ex.(7) | Com.(P-24) | 5.7 | 12.0 | 5000 | 41.6 | 136.6 | 0.33 | 0.62 |
| Ex.(8) | Com.(P-26) | 5.6 | 11.6 | 5000 | 43.1 | 142.5 | 0.33 | 0.62 |
| Ex.(9) | Com.(P-27) | 5.6 | 11.8 | 5000 | 42.4 | 144.0 | 0.33 | 0.61 |
| Ex.(10) | Com.(P-41) | 5.7 | 13.2 | 5000 | 37.9 | 128.4 | 0.33 | 0.61 |
| Ex.(11) | Com.(P-42) | 5.7 | 13.0 | 5000 | 38.3 | 133.5 | 0.33 | 0.62 |
| Ex.(12) | Com.(P-43) | 5.6 | 12.8 | 5000 | 39.1 | 134.2 | 0.33 | 0.62 |
| Ex.(13) | Com.(P-58) | 5.6 | 12.9 | 5000 | 38.7 | 132.3 | 0.33 | 0.61 |
| Ex.(14) | Com.(P-69) | 5.5 | 11.9 | 5000 | 42.1 | 141.1 | 0.33 | 0.62 |
| Ex.(15) | Com.(P-70) | 5.6 | 11.9 | 5000 | 42.2 | 142.9 | 0.33 | 0.61 |
| Ex.(16) | Com.(P-71) | 5.5 | 11.4 | 5000 | 44.0 | 153.8 | 0.33 | 0.62 |
| Ex.(17) | Com.(P-72) | 5.5 | 11.6 | 5000 | 43.0 | 143.0 | 0.33 | 0.61 |
| Ex.(18) | Com.(P-73) | 5.6 | 11.5 | 5000 | 43.5 | 148.9 | 0.33 | 0.62 |
| Ex.(19) | Com.(P-89) | 5.6 | 12.1 | 5000 | 41.5 | 137.1 | 0.33 | 0.62 |
| Ex.(20) | Com.(P-94) | 5.7 | 13.2 | 5000 | 37.9 | 128.3 | 0.33 | 0.61 |
| Ex.(21) | Com.(P-96) | 5.7 | 15.2 | 5000 | 32.8 | 119.7 | 0.33 | 0.61 |
| Ex.(22) | Com.(P-100) | 5.6 | 13.3 | 5000 | 37.5 | 130.6 | 0.33 | 0.62 |
| Ex.(23) | Com.(P-104) | 5.8 | 14.0 | 5000 | 35.7 | 124.0 | 0.33 | 0.62 |
| Ex.(24) | Com.(P-107) | 5.8 | 14.4 | 5000 | 34.8 | 118.5 | 0.33 | 0.61 |
| Ex.(25) | Com.(P-110) | 5.8 | 13.9 | 5000 | 35.9 | 121.5 | 0.33 | 0.61 |
| Ex.(26) | Com.(P-111) | 5.7 | 14.7 | 5000 | 34.1 | 119.2 | 0.33 | 0.62 |
| Ex.(27) | Com.(P-112) | 5.7 | 14.8 | 5000 | 33.7 | 117.5 | 0.33 | 0.62 |
| Ex.(28) | Com.(P-115) | 5.6 | 12.7 | 5000 | 39.4 | 136.9 | 0.33 | 0.61 |
| Ex.(29) | Com.(P-119) | 5.7 | 12.9 | 5000 | 38.9 | 132.0 | 0.33 | 0.61 |
| Ex.(30) | Com.(P-120) | 5.6 | 13.0 | 5000 | 38.5 | 132.9 | 0.33 | 0.61 |
| Ex.(31) | Com.(P-125) | 5.6 | 12.7 | 5000 | 39.4 | 136.7 | 0.33 | 0.62 |
| Ex.(32) | Com.(P-128) | 5.6 | 13.8 | 5000 | 36.3 | 121.2 | 0.33 | 0.62 |
| Ex.(33) | Com.(P-134) | 5.8 | 15.6 | 5000 | 32.1 | 114.4 | 0.33 | 0.62 |

From the results of Table 4, it can be confirmed that the OLEDs employing the inventive compound of the present invention as the hole transport layer material has a relatively low driving voltage, improved luminescent efficiency and improved life span as compared with the OLEDs employing Comparative Compounds 1 to 6 as the hole transport layer material.

Comparing the inventive compound P-6 with Comparative Compounds 3 to 5, they all have the same skeleton but differ in the kind of atoms (S, C, N, O) introduced into the core. It can be seen that the characteristics of the OLEDs are different when a compound having different kinds of atoms introduced into the core is used as a hole transporting layer material. It can be seen that the efficiency and life span of the organic electric element are the most excellent, when the dibenzothiophene in which "S" is introduced into the core is used as the hole transport layer material like the present invention.

It seems that the OLED employing the compound as a hole transport layer material has a high light transmittance, thereby improving the luminous efficiency since it has a deep HOMO energy level and a high refractive index when a dibenzothiophene instead of a carbazole (Example 4) or dibenzofuran (Example 5) is introduced into a heterocyclic core, and the luminous efficiency and life span of the OLED are maximized since the hole is easily moved due to the deep HOMO energy level, so that the charge balance of holes and electrons in the light emitting layer is increased.

Comparing the comparative examples 3 to 5 with the examples of the present invention, it can be seen that the life span and the efficiency of the OLED are remarkably improved when heteroatoms are introduced into the same skeleton. In particular, it is confirmed that the comparative compound 3 comprising Sp$^3$ carbon in the core exhibits lower thermal stability than the compound of the present invention, and thus the heat resistance to joule heat occurring between the organic layers or between the organic layer and the metal electrode and the resistance under high temperature environment were reduced during electroluminescence.

Comparing Comparative Example 2 with the examples using the compounds of the present invention (especially, P-1 and P-6), it can be seen that the driving voltage is lowered and the efficiency and life span are remarkably improved in the embodiment of the present invention. The compounds P-1 and P-6 of the present invention and Comparative Compound 2 are the same in that a substituent diphenylamine (—N(—N(C$_6$H$_6$)$_2$) is bonded to both benzene rings of the dibenzothiophene skeleton, but are different in that one phenyl of diphenylamine of the inventive compounds is further substituted with diphenylamine. That is, it can be seen that the life span and the efficiency of the present invention are remarkably improved when a diamine type is used as a hole transport layer material like an embodiment of the present invention, wherein the diamine type comprised an amine group directly or indirectly bonded to a dibenzothiophene that is directly or indirectly further substituted with an amine substituent (-L$^1$-NAr$^4$Ar$^5$), comparing to Comparative Example 2. It seems that this is because when the compound of the present invention is introduced in an appropriate range without excessively increasing the number of aryl (-L$^1$-NAr$^4$Ar$^5$) substituted with an amine, wherein the amine is substituted with an amine substituent, the HOMO energy level of the hole transport layer is controlled and the hole transport layer has the most appropriate HOMO energy level difference with the light emitting layer, so that the light emission is more easily performed in the light emitting layer.

Comparing Comparative Example 6 with Examples of the present invention, it can be seen that the OLEDs of Examples of the present invention has significantly improved luminous efficiency and life span comparing to the OLEDs of Comparative Example 6. Comparing the compounds used in Comparative Example 6 and Examples of the present invention, it can be seen that Comparative compound 6 and the compounds P-51 and P-58 of the present invention comprise a structure having the same $Ar^2$ and only different $Ar^3$ in the amine group ($-L^3-N(Ar^2)(Ar^3)$) bonded to the dibenzothiophene. That is, Comparative Compound 6 and the compounds P-51 and P-58 of the present invention are the same in that $L^3$ is a single bond and $Ar^2$ is phenyl, but it is different in that $Ar^3$ in Comparative Compound is carbazole derivatives, while $Ar^3$ in compound P-51 of the present invention is a phenyl and $Ar^3$ in compound P-58 of the present invention is a dibenzothiophene. Therefore, it can be seen that even if the structure has the same skeleton, the characteristics of the OLED is different depending on the types of amine groups substituted in the dibenzothiophene core, and luminous efficiency and life span are remarkably improved when the compound of the present invention is used as a hole transporting layer material, compared to compound comprising carbazole (carbazole derivative), wherein $Ar^2$ and/or $Ar^3$ of the compound is the carbazole (carbazole derivative), as a hole transporting layer material. In particular, it can be confirmed that the refractive index of the OLED is higher and the luminous efficiency of the OLED is remarkably improved when the compound P-58 of the present invention, wherein an amine group of the compound P-58 is substituted with a dibenzothiophene substituent, is used as a hole transport layer material, comparing to using the Comparative compound 6, wherein an amine group of the Comparative compound 6 is substituted with a carbazole substituent, as a hole transporting layer material.

On the other hand, in the case of the compound of the present invention, when the linking group $L^1$ connecting the amine and the amine is phenylene, the characteristics of the OLED are different depending on the position where the amine group is bonded to the phenylene. This can be confirmed by comparing the compounds P-1, P-6 and P-11 of the present invention. The amine group of compounds P-1 and P-11 is bonded to the meta or ortho position of a phenylene linker, while the amine group of the compound P-6 is bonded to the para position of a phenylene linker. Comparing Example 1 (using the compound P-1), Example 2 (using the compound P-6) and Example 6 (using the compound P-11) using these compounds as the hole transporting layer material, it can be seen that the luminous efficiency and life span of Example 2 are better. Therefore, it can be seen that the compound in which the amine is bonded to the linking group in the para position is more suitable as the hole transporting layer material when the linking group $L^1$ is phenylene. On the other hand, it can be seen that the compound in which the amine is attached to the linking group in the meta or ortho position has a deeper HOMO energy level than the compound in which the amine is attached to the linking group in the para position when the linking group $L^1$ is phenylene, and thus the compound in which the amine is bonded to the linking group in the meta or ortho position is more suitable as the light-emitting-auxiliary layer material.

Taking all of the above-mentioned characteristics (high refractive index, high thermal stability and deep HOMO energy level) into consideration, it can be seen that the band gap, electrical characteristics, interface characteristics, and the like are largely changed depending on the kind of atoms (S, C, N, O) introduced into the core, whether a aryl ($-L^1-NAr^4Ar^5$) substituted with an amine is further introduced or not as a substituent of amine and what is the kind of an amine substituent in the structure substituted with two amines, and it acts as a main factor for improving the performance.

In the case of the hole transporting layer, it is necessary to grasp the relationship with the light emitting layer (host), and thus it is an object of the present invention to infer the advantageous effect (characteristic) shown by using the compound according to the present invention as a hole transporting layer material, Even ordinary technicians who belong to it will be very difficult.

One skilled in the art, even using a similar core compound, would have much difficulty in inferring the advantageous effect (characteristic) shown by using the compound according to the present invention as a hole transporting layer material since it should be considered in relation with the light emitting layer (host), in the case of the hole transporting layer.

Example 34 Red OLED (an Emission-Auxiliary Layer)

Organic light emitting diodes (OLEDs) were fabricated according to a conventional method by using a compound of the present invention as an emission-auxiliary layer material.

First, an ITO layer (anode) was formed on a glass substrate, and a film of 2-TNATA was vacuum-deposited on the ITO layer to form a hole injection layer with a thickness of 60 nm. Subsequently, NPB was vacuum-deposited with a thickness of 60 nm on the hole injection layer to form a hole transport layer.

Subsequently, a film of the compound P-1 of the present invention was vacuum-deposited on the hole transport layer to form a emission-auxiliary layer with a thickness of 20 nm.

A light emitting layer with a thickness of 30 nm was deposited on the emission-auxiliary layer by using the CBP as a host material and bis-(1-phenylisoquinolyl)iridium(III) acetylacetonate ("(piq)$_2$Ir(acac)") as a dopant material in a weight ratio of 95:5.

Next, a film of BAlq was vacuum-deposited with a thickness of 10 nm on the light emitting layer to form a hole blocking layer, and a film of Alq$_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

Example 35 to Example 104 Red OLED (an Emission-Auxiliary Layer)

The OLEDs were fabricated in the same manner as described in Example 34 except that the compounds P-2 to P-134 of the present invention described in Table 5, instead of the compound P-1 of the present invention, were used as an emission-auxiliary layer material.

Comparative Example 7

The OLED was fabricated in the same manner as described in Example 34 except that an emission-auxiliary layer was not formed.

Comparative Example 8 to Comparative Example 14

The OLEDs were fabricated in the same manner as described in Example 34 except that the Comparative compounds 2 to 8 described in Table 5 instead of the compound P-1 of the present invention were used as an emission-auxiliary layer material.

<Comp. compound 7>

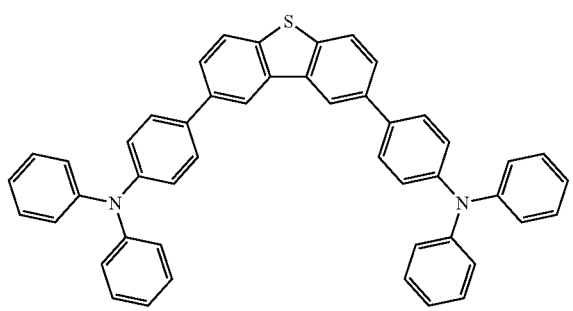

<Comp. compound 8>

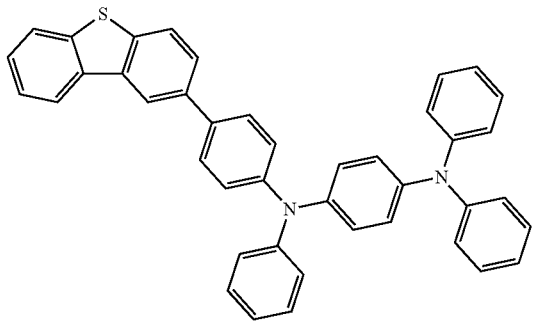

Electruminescence (EL) characteristics were measured with a PR-650 (Photoresearch) by applying a forward bias DC voltage to the OLEDs prepared in Examples 34 to 104 of the present invention and Comparative Examples 7 to 14. And, the T95 life span was measured using a life span measuring apparatus manufactured by Macscience Inc. at reference brightness of 2500 cd/m². The measurement results are shown in Table 5 below.

TABLE 5

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| comp. Ex(7) | — | 6.3 | 33.3 | 2500 | 7.5 | 62.7 | 0.66 | 0.32 |
| comp. Ex(8) | comp. Com2 | 6.5 | 21.2 | 2500 | 11.8 | 83.5 | 0.66 | 0.33 |
| comp. Ex(9) | comp. Com3 | 6.6 | 25.9 | 2500 | 9.7 | 78.6 | 0.66 | 0.32 |
| comp. Ex(10) | comp. Com4 | 6.7 | 30.9 | 2500 | 8.1 | 73.3 | 0.66 | 0.32 |
| comp. Ex(11) | comp. Com5 | 6.5 | 22.3 | 2500 | 11.2 | 101.4 | 0.66 | 0.33 |
| comp. Ex(12) | comp. Com6 | 6.5 | 18.6 | 2500 | 13.4 | 130.9 | 0.66 | 0.33 |
| comp. Ex(13) | comp. Com7 | 6.5 | 21.9 | 2500 | 11.4 | 82.8 | 0.66 | 0.33 |
| comp. Ex(14) | comp. Com8 | 6.6 | 22.9 | 2500 | 10.9 | 80.3 | 0.66 | 0.32 |
| Ex.(34) | Com.(P-1) | 6.4 | 12.5 | 2500 | 20.0 | 136.7 | 0.66 | 0.33 |
| Ex.(35) | Com.(P-2) | 6.5 | 13.3 | 2500 | 18.8 | 132.5 | 0.66 | 0.32 |
| Ex.(36) | Com.(P-3) | 6.5 | 12.5 | 2500 | 20.1 | 136.3 | 0.66 | 0.32 |
| Ex.(37) | Com.(P-4) | 6.4 | 11.6 | 2500 | 21.6 | 138.1 | 0.66 | 0.33 |
| Ex.(38) | Com.(P-5) | 6.4 | 10.9 | 2500 | 23.0 | 139.8 | 0.66 | 0.33 |
| Ex.(39) | Com.(P-6) | 6.5 | 15.2 | 2500 | 16.4 | 120.7 | 0.66 | 0.32 |
| Ex.(40) | Com.(P-11) | 6.4 | 13.4 | 2500 | 18.7 | 127.6 | 0.66 | 0.33 |
| Ex.(41) | Com.(P-12) | 6.5 | 12.0 | 2500 | 20.9 | 138.9 | 0.66 | 0.33 |
| Ex.(42) | Com.(P-13) | 6.4 | 12.4 | 2500 | 20.1 | 136.4 | 0.66 | 0.33 |
| Ex.(43) | Com.(P-14) | 6.4 | 12.6 | 2500 | 19.8 | 136.4 | 0.66 | 0.32 |
| Ex.(44) | Com.(P-15) | 6.5 | 12.8 | 2500 | 19.6 | 136.2 | 0.66 | 0.33 |
| Ex.(45) | Com.(P-16) | 6.4 | 9.8 | 2500 | 25.6 | 154.5 | 0.66 | 0.32 |
| Ex.(46) | Com.(P-17) | 6.4 | 9.6 | 2500 | 26.1 | 159.6 | 0.66 | 0.32 |
| Ex.(47) | Com.(P-18) | 6.3 | 9.7 | 2500 | 25.7 | 153.2 | 0.66 | 0.32 |
| Ex.(48) | Com.(P-20) | 6.4 | 9.5 | 2500 | 26.2 | 161.6 | 0.66 | 0.32 |
| Ex.(49) | Com.(P-21) | 6.4 | 9.3 | 2500 | 26.9 | 168.9 | 0.66 | 0.33 |
| Ex.(50) | Com.(P-29) | 6.3 | 9.5 | 2500 | 26.4 | 160.3 | 0.66 | 0.33 |
| Ex.(51) | Com.(P-31) | 6.4 | 9.5 | 2500 | 26.2 | 160.6 | 0.66 | 0.33 |
| Ex.(52) | Com.(P-32) | 6.3 | 10.1 | 2500 | 24.7 | 149.4 | 0.66 | 0.33 |
| Ex.(53) | Com.(P-33) | 6.4 | 9.9 | 2500 | 25.2 | 152.0 | 0.66 | 0.33 |
| Ex.(54) | Com.(P-34) | 6.5 | 10.9 | 2500 | 22.9 | 140.0 | 0.66 | 0.33 |
| Ex.(55) | Com.(P-36) | 6.4 | 12.6 | 2500 | 19.8 | 135.9 | 0.66 | 0.32 |
| Ex.(56) | Com.(P-39) | 6.4 | 11.1 | 2500 | 22.5 | 138.3 | 0.66 | 0.33 |
| Ex.(57) | Com.(P-46) | 6.5 | 13.6 | 2500 | 18.4 | 124.2 | 0.66 | 0.33 |
| Ex.(58) | Com.(P-47) | 6.5 | 12.3 | 2500 | 20.4 | 136.3 | 0.66 | 0.32 |
| Ex.(59) | Com.(P-48) | 6.5 | 13.1 | 2500 | 19.1 | 132.0 | 0.66 | 0.33 |
| Ex.(60) | Com.(P-51) | 6.4 | 9.4 | 2500 | 26.7 | 165.5 | 0.66 | 0.33 |
| Ex.(61) | Com.(P-52) | 6.3 | 9.3 | 2500 | 26.9 | 165.3 | 0.66 | 0.32 |
| Ex.(62) | Com.(P-53) | 6.3 | 9.4 | 2500 | 26.6 | 166.6 | 0.66 | 0.33 |
| Ex.(63) | Com.(P-55) | 6.4 | 9.1 | 2500 | 27.4 | 171.1 | 0.66 | 0.33 |
| Ex.(64) | Com.(P-56) | 6.4 | 9.3 | 2500 | 27.0 | 167.1 | 0.66 | 0.32 |
| Ex.(65) | Com.(P-57) | 6.3 | 9.3 | 2500 | 26.9 | 167.0 | 0.66 | 0.33 |
| Ex.(66) | Com.(P-58) | 6.3 | 9.1 | 2500 | 27.3 | 171.5 | 0.66 | 0.32 |
| Ex.(67) | Com.(P-59) | 6.4 | 9.2 | 2500 | 27.1 | 168.7 | 0.66 | 0.33 |
| Ex.(68) | Com.(P-60) | 6.3 | 9.2 | 2500 | 27.2 | 168.9 | 0.66 | 0.32 |
| Ex.(69) | Com.(P-61) | 6.3 | 9.3 | 2500 | 27.0 | 168.0 | 0.66 | 0.33 |

TABLE 5-continued

|  | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex.(70) | Com.(P-62) | 6.3 | 8.9 | 2500 | 28.2 | 184.1 | 0.66 | 0.32 |
| Ex.(71) | Com.(P-63) | 6.3 | 9.0 | 2500 | 27.8 | 179.2 | 0.66 | 0.33 |
| Ex.(72) | Com.(P-64) | 6.3 | 9.1 | 2500 | 27.4 | 172.3 | 0.66 | 0.33 |
| Ex.(73) | Com.(P-65) | 6.3 | 9.0 | 2500 | 27.9 | 175.6 | 0.66 | 0.33 |
| Ex.(74) | Com.(P-66) | 6.3 | 9.1 | 2500 | 27.6 | 179.3 | 0.66 | 0.32 |
| Ex.(75) | Com.(P-67) | 6.4 | 9.1 | 2500 | 27.3 | 173.6 | 0.66 | 0.33 |
| Ex.(76) | Com.(P-68) | 6.3 | 9.2 | 2500 | 27.1 | 168.1 | 0.66 | 0.32 |
| Ex.(77) | Com.(P-74) | 6.4 | 9.4 | 2500 | 26.5 | 161.1 | 0.66 | 0.32 |
| Ex.(78) | Com.(P-76) | 6.3 | 9.4 | 2500 | 26.6 | 166.9 | 0.66 | 0.33 |
| Ex.(79) | Com.(P-77) | 6.3 | 9.0 | 2500 | 27.7 | 175.8 | 0.66 | 0.33 |
| Ex.(80) | Com.(P-78) | 6.3 | 9.3 | 2500 | 26.8 | 166.7 | 0.66 | 0.33 |
| Ex.(81) | Com.(P-79) | 6.3 | 9.5 | 2500 | 26.2 | 160.3 | 0.66 | 0.33 |
| Ex.(82) | Com.(P-80) | 6.3 | 9.4 | 2500 | 26.6 | 166.4 | 0.66 | 0.32 |
| Ex.(83) | Com.(P-81) | 6.3 | 9.4 | 2500 | 26.5 | 161.2 | 0.66 | 0.33 |
| Ex.(84) | Com.(P-82) | 6.4 | 9.3 | 2500 | 26.9 | 167.8 | 0.66 | 0.33 |
| Ex.(85) | Com.(P-83) | 6.3 | 9.1 | 2500 | 27.4 | 172.5 | 0.66 | 0.33 |
| Ex.(86) | Com.(P-84) | 6.4 | 10.3 | 2500 | 24.3 | 140.2 | 0.66 | 0.33 |
| Ex.(87) | Com.(P-85) | 6.5 | 10.5 | 2500 | 23.7 | 143.4 | 0.66 | 0.33 |
| Ex.(88) | Com.(P-88) | 6.4 | 10.3 | 2500 | 24.3 | 142.4 | 0.66 | 0.32 |
| Ex.(89) | Com.(P-91) | 6.5 | 10.7 | 2500 | 23.3 | 139.3 | 0.66 | 0.33 |
| Ex.(90) | Com.(P-92) | 6.3 | 9.7 | 2500 | 25.7 | 153.7 | 0.66 | 0.33 |
| Ex.(91) | Com.(P-93) | 6.4 | 10.9 | 2500 | 22.8 | 138.6 | 0.66 | 0.33 |
| Ex.(92) | Com.(P-96) | 6.5 | 15.3 | 2500 | 16.3 | 129.2 | 0.66 | 0.32 |
| Ex.(93) | Com.(P-100) | 6.4 | 12.3 | 2500 | 20.3 | 135.8 | 0.66 | 0.32 |
| Ex.(94) | Com.(P-104) | 6.5 | 13.5 | 2500 | 18.5 | 133.8 | 0.66 | 0.32 |
| Ex.(95) | Com.(P-107) | 6.4 | 15.0 | 2500 | 16.7 | 133.9 | 0.66 | 0.33 |
| Ex.(96) | Com.(P-110) | 6.5 | 15.5 | 2500 | 16.1 | 128.2 | 0.66 | 0.33 |
| Ex.(97) | Com.(P-111) | 6.4 | 13.7 | 2500 | 18.2 | 132.4 | 0.66 | 0.33 |
| Ex.(98) | Com.(P-112) | 6.5 | 14.9 | 2500 | 16.8 | 130.2 | 0.66 | 0.32 |
| Ex.(99) | Com.(P-115) | 6.3 | 11.2 | 2500 | 22.4 | 142.1 | 0.66 | 0.32 |
| Ex.(100) | Com.(P-119) | 6.4 | 11.4 | 2500 | 21.9 | 138.3 | 0.66 | 0.33 |
| Ex.(101) | Com.(P-120) | 6.5 | 11.8 | 2500 | 21.2 | 137.8 | 0.66 | 0.32 |
| Ex.(102) | Com.(P-125) | 6.3 | 11.2 | 2500 | 22.3 | 140.2 | 0.66 | 0.32 |
| Ex.(103) | Com.(P-128) | 6.5 | 13.2 | 2500 | 19.0 | 135.1 | 0.66 | 0.33 |
| Ex.(104) | Com.(P-134) | 6.5 | 15.7 | 2500 | 15.9 | 129.5 | 0.66 | 0.32 |

From the results of Table 5, it can be seen that the OLEDs employing the inventive compound of the present invention as the emission-auxiliary layer material has remarkably improved luminescent efficiency and life span as compared with the OLEDs of Comparative Examples 7 to 14.

It can be confirmed that the OLEDs according to Comparative Examples 8 to 14, wherein an emission-auxiliary layer was formed using the Comparative Compounds 2 to 8, and the Examples of the present invention, wherein an emission-auxiliary layer was formed using the compounds of the present invention, have improved luminescent efficiency and life span, compared to Comparative Example 7 in which an emission-auxiliary layer was not formed, Particularly, the OLEDs according to the Examples of the present invention have remarkably improved luminescent efficiency and life span.

As already mentioned in Table 4 above, it is believed that this is because the types of atoms (S, C, N, O) introduced into the core, whether or not a aryl (-L$^1$-NAr$^4$Ar$^5$) substituted with an amine is further introduced, and the type of amine substituent in the structure substituted with two amines in the hole, in the case of an emission-auxiliary layer (red phosphorescent) as well as a hole transport layer, act as a main factor for improving the performance, and thus it facilitates the charge balance within the light emitting layer due to high refractive index, high T1 value and deep HOMO energy level to efficiently transport holes in the hole transport layer.

Particularly, it was confirmed that the refractive index and T$_g$ value in the case where amine group in the compounds of the present invention is substituted with at least one heterocyclic substituent group such as dibenzothiophene are higher than in the case where amine group in the compounds of the present invention is substituted with only aryl or at least one carbazole, so that the light emitting efficiency and the thermal stability were improved.

On the other hand, in the evaluation results of the above-described OLED fabrication, although the OLED characteristics has been just described for the case where the compound of the present invention is applied to only one of the hole transporting layer and the emission-auxiliary layer, but the compound of the present invention may be used as materials of both the hole transport layer and the emission-auxiliary layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 1:

[Formula 1]

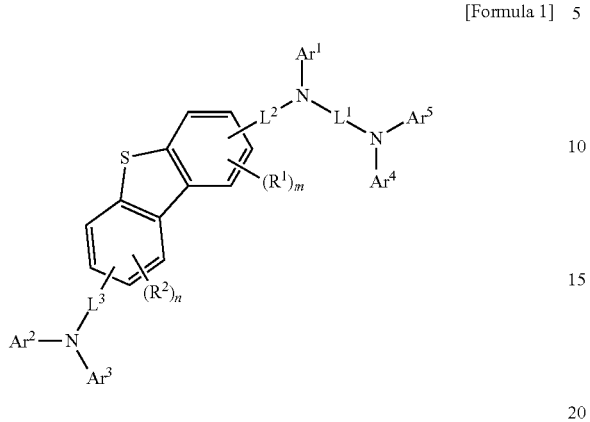

wherein,
$L^1$ is a $C_6$-$C_{60}$ arylene group,
$L^2$ and $L^3$ are each independently selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; and a fused ring formed by a $C_6$-$C_{60}$ aromatic ring and a $C_3$-$C_{60}$ aliphatic ring,
$Ar^1$ to $Ar^5$ are each independently selected from the group consisting of a $C_6$-$C_{60}$ aryl group; a $C_2$-$C_{60}$ heterocyclic group containing at least one heteroatom selected from the group consisting of O, N, S, Se, Si and P; a fluorenyl group; a fused ring formed by a $C_6$-$C_{60}$ aromatic ring and a $C_3$-$C_{60}$ aliphatic ring; a $C_1$-$C_{50}$ alkyl group; a $C_2$-$C_{20}$ alkenyl group; a $C_2$-$C_{20}$ alkynl group; a $C_1$-$C_{30}$ alkoxy group; and a $C_6$-$C_{30}$ aryloxy group, with the proviso that carbazole is excluded from $Ar^2$ and $Ar^3$,
"m" and "n" are each an integer of 0 to 3,
$R^1$ and $R^2$ are each independently selected from the group consisting of deuterium; tritium; halogen; a cyano group; a nitro group; a $C_6$-$C_{60}$ aryl group; a fluorenyl group; a $C_2$-$C_{60}$ heterocyclic group containing at least one heteroatom selected from the group consisting of O, N, S, Se, Si and P; a fused ring formed by a $C_6$-$C_{60}$ aromatic ring and a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group,
when "m" and "n" are each an integer of 2 or more, a plurality of $R^1$s and $R^2$s may be each the same or different from each other, and neighboring $R^1$s and/or neighboring $R^2$s may be linked to each other to form a ring, and
$Ar^1$~$Ar^5$, $R^1$, $R^2$, $L^1$~$L^3$, a ring formed by linking between neighboring $R^1$s, and a ring formed by linking between neighboring $R^2$s may be each substituted with one or more substituents selected from the group consisting of deuterium; halogen; a silane group substituted or unsubstituted with a $C_1$-$C_{20}$ alkyl group or a $C_6$-$C_{20}$ aryl group; a phosphine oxide group substituted or unsubstituted with a $C_1$-$C_{20}$ alkyl group or a $C_6$-$C_{20}$ aryl group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Se, Si and P; a $C_3$-$C_{20}$ cycloalkyl group; a $C_7$-$C_{20}$ arylalkyl group; a $C_8$-$C_{20}$ arylalkenyl group; and

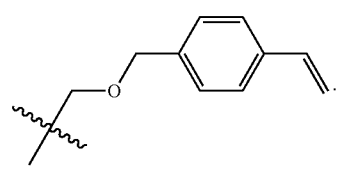 [SMILES: *COCc1ccc(C=C)cc1]

2. The compound of claim 1, wherein Formula 1 is represented by one of Formulas 2 to 5 below:

<Formula 2>

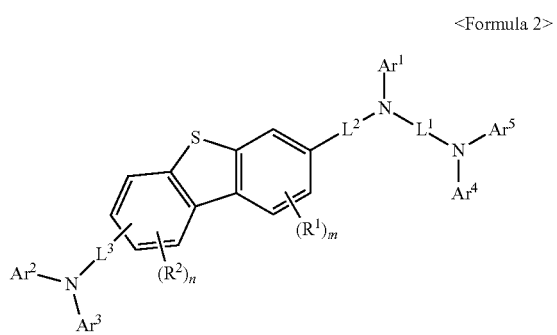

<Formula 3>

<Formula 4>

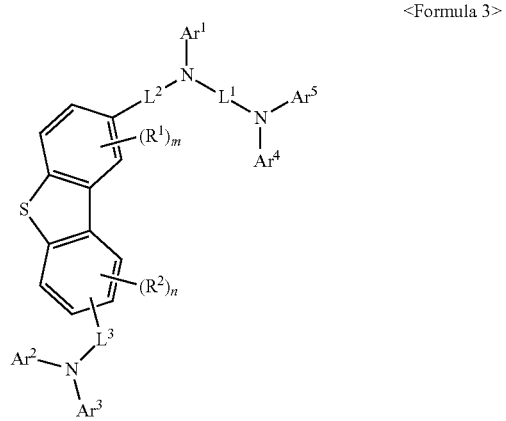

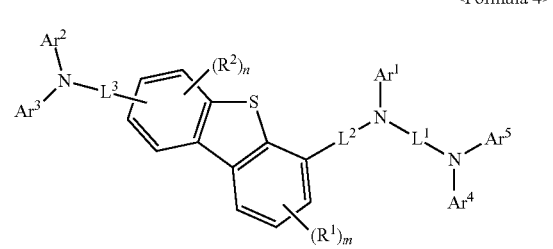

-continued

<Formula 5>

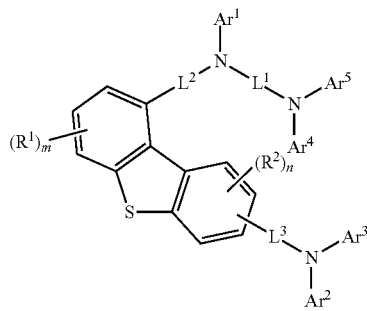

in formulas 2 to 5, $Ar^1 \sim Ar^5$, $R^1$, $R^2$, $L^1 \sim L^3$, m and n are each the same as defined in claim 1.

3. The compound of claim 1, wherein Formula 1 is represented by one of Formulas 6 to 10 below:

<Formula 6>

<Formula 7>

<Formula 8>

<Formula 9>

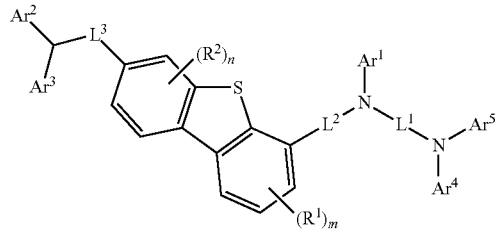

<Formula 10>

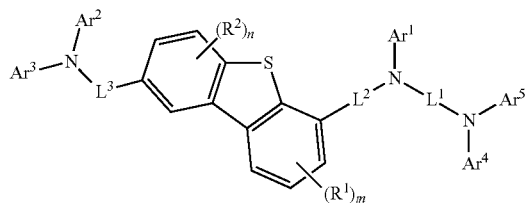

in formulas 6 to 10, $Ar^1 \sim Ar^5$, $R^1$, $R^2$, $L^1 \sim L^3$, m and n are each the same as defined in claim 1.

4. The compound of claim 1, $L^1$ is represented by one of Formulas L1-1 to L1-7 below:

<Formula L1-1>

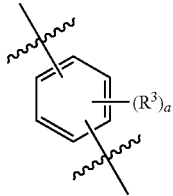

<Formula L1-2>

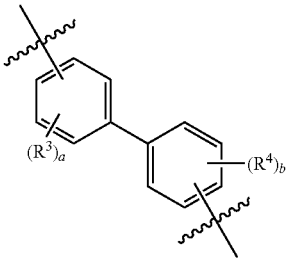

<Formula L1-3>

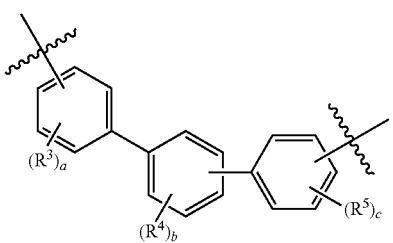

<Formula L1-4>

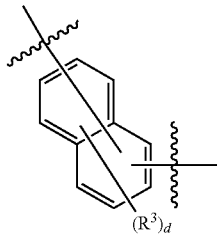

-continued

<Formula L1-5>
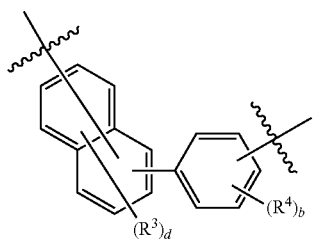

<Formula L1-6>
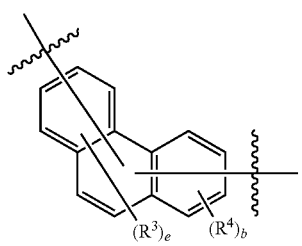

<Formula L1-7>
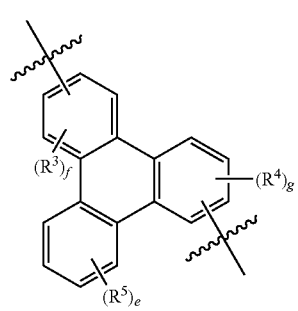

in formulas L1-1 to L1-7,

"a" to "c" are each an integer of 0 to 4, "d" is an integer of 0 to 6, "e" is an integer of 0 to 5, "f" and "g" are each an integer of 0 to 3, and $R^3$ to $R^5$ are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_6$-$C_{60}$ aromatic ring and a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group, and a plurality of $R^3$s to $R^5$s may be each the same or different from each other when "a" to "g" are each an integer of 2 or more.

5. The compound of claim 1, one of $Ar^1$ to $Ar^5$ is represented by Formula 11 below:

<Formula 11>
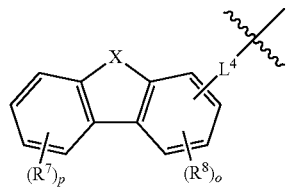

in formula 11,

X is S, Se, O, $C(R^c)(R^d)$ or $N(R^e)$ when at least one of $Ar^1$, $Ar^4$ and $Ar^5$ is Formula 11, and X is S, Se, O or $C(R^c)(R^d)$ when at least one of $Ar^2$ and $Ar^3$ is Formula 11, $R^c$ to $R^e$ are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_6$-$C_{60}$ aromatic ring and a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group, and $R^c$ and $R^d$ may be linked to each other to form a spiro compound, $L^4$ is selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; and a fused ring formed by a $C_6$-$C_{60}$ aromatic ring and a $C_3$-$C_{60}$ aliphatic ring, "o" is an integer of 0 to 3, "p" is an integer of 0 to 4, $R^6$ and $R^7$ are each independently selected from the group consisting of deuterium; tritium; halogen; a cyano group; a nitro group; a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_6$-$C_{60}$ aromatic ring and a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group, and when "o" and "p" are each an integer of 2 or more, a plurality of $R^6$s and $R^7$s may be each the same or different from each other, and adjacent $R^6$s and/or adjacent $R^6$s may be linked to each other to form a ring.

6. The compound of claim 5, at least one of $Ar^1$, $Ar^2$ and $Ar^5$ is the above Formula 11, wherein X is S.

7. The compound of claim 1, wherein Formula 1 is any one of the compounds below:

P-1
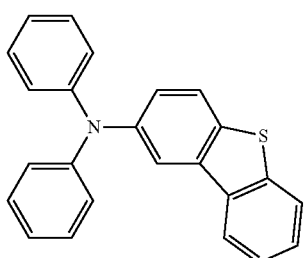
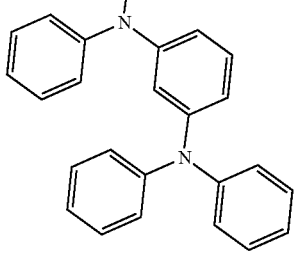

P-2
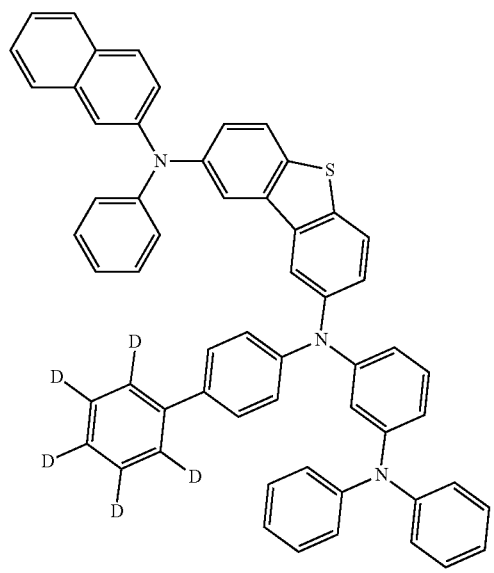
P-3
P-5
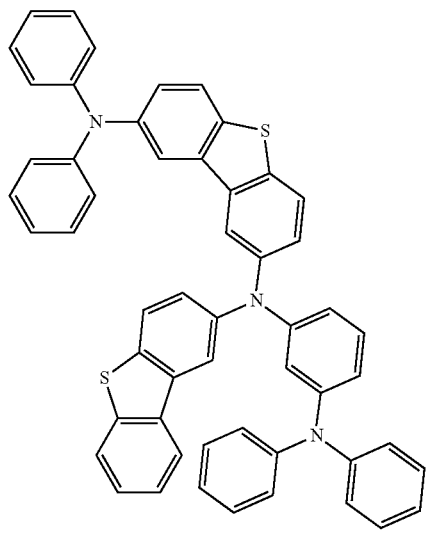
P-6
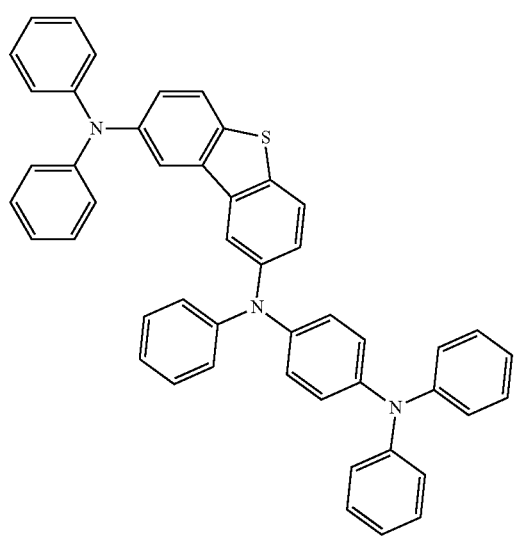
P-4
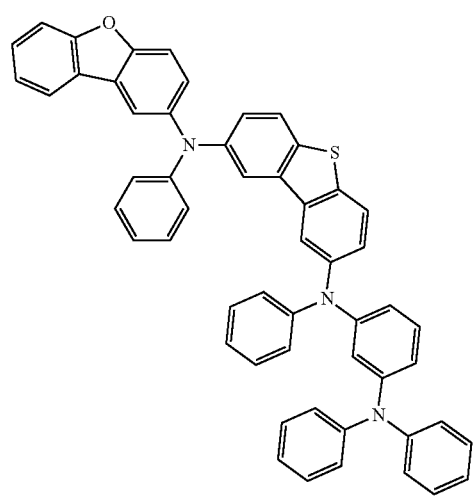
P-7

-continued
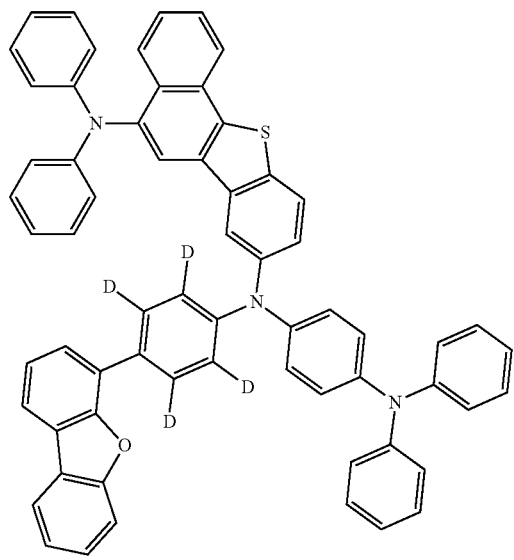
P-8
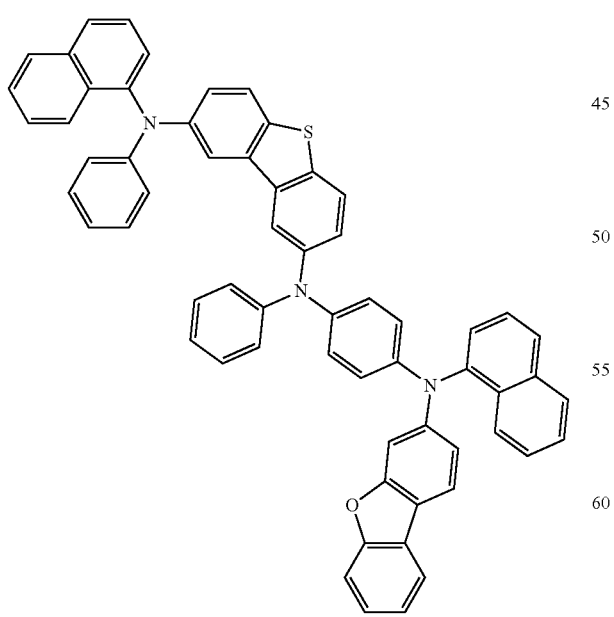
P-9
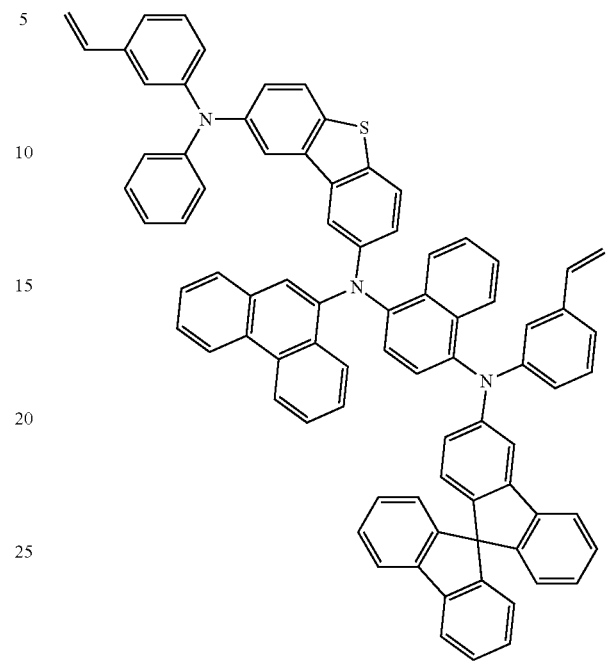
P-10
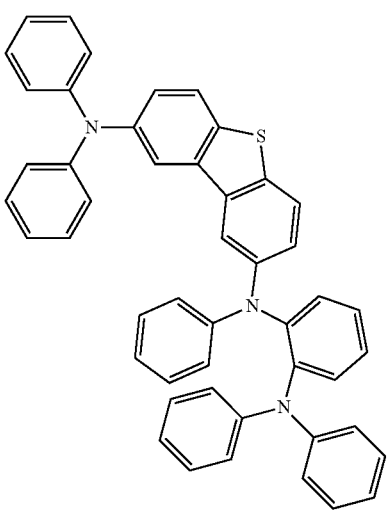
P-11

P-12
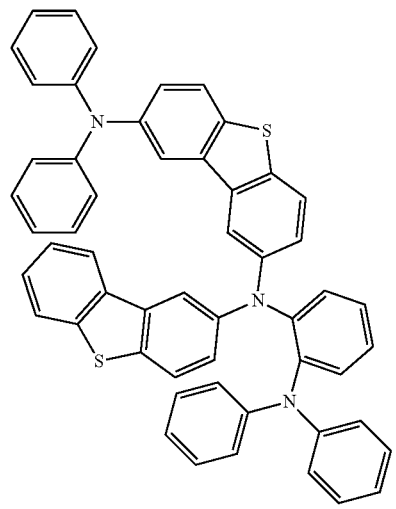
P-13
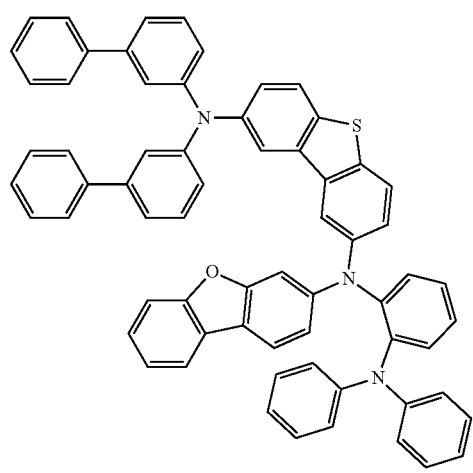
P-14
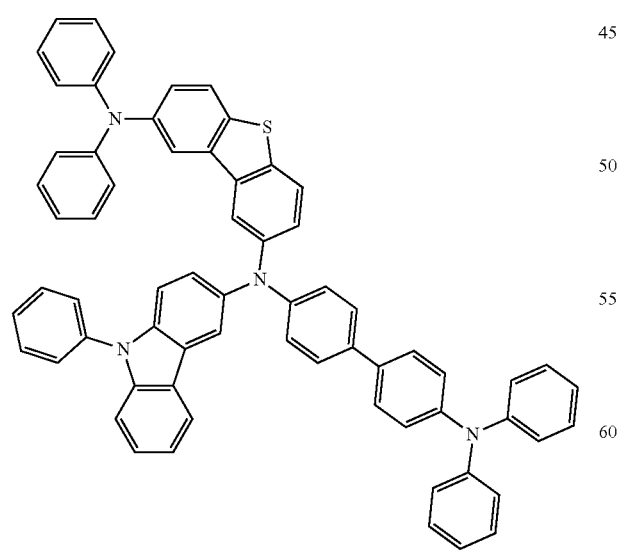
P-15
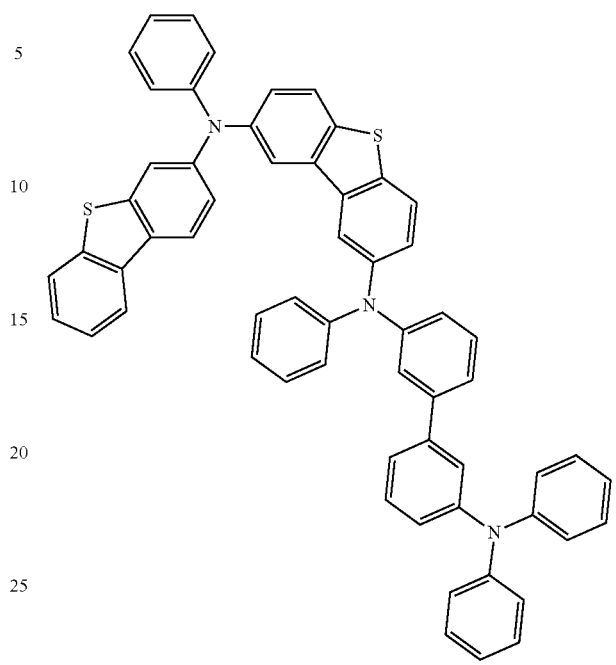
P-16
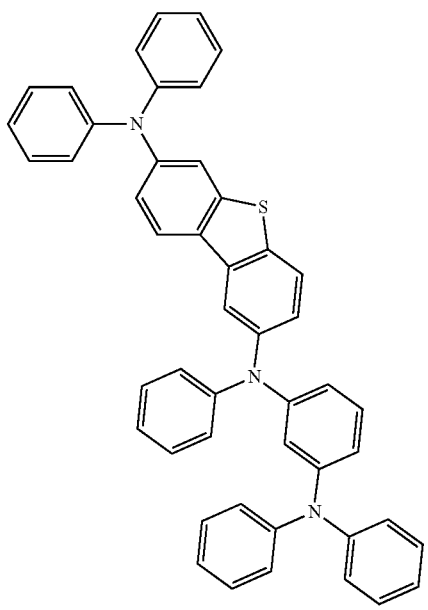

P-17
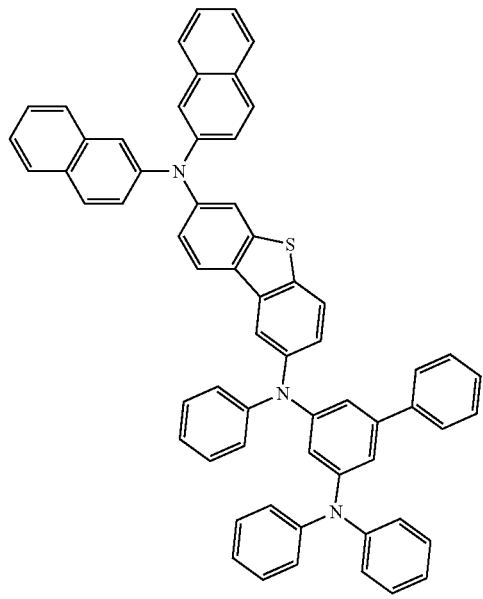
P-18
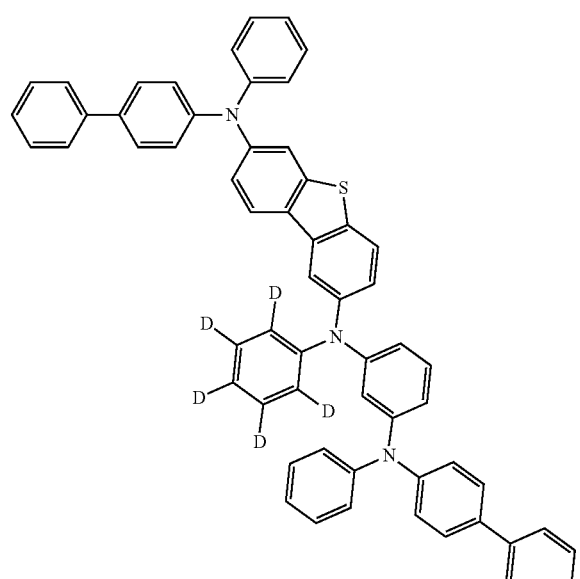
P-19
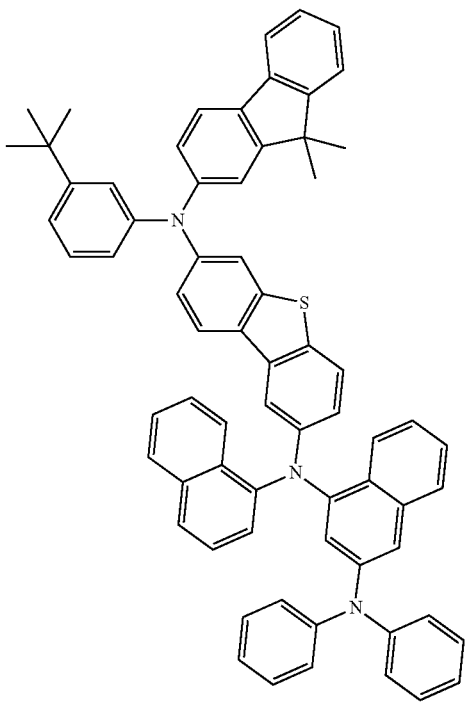
P-20
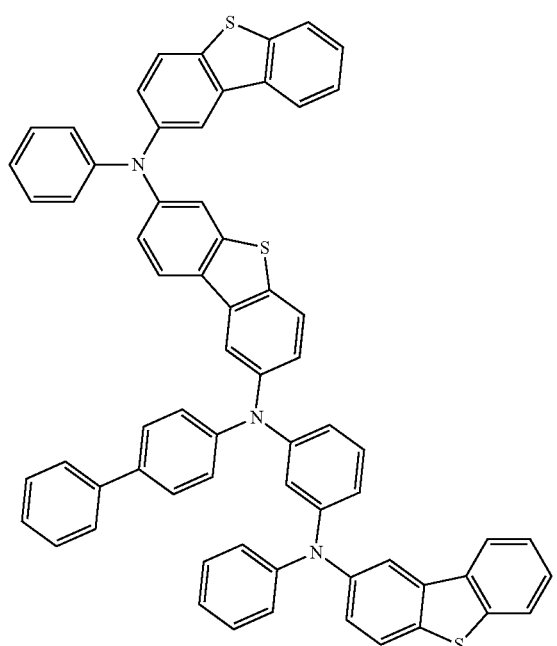

P-21
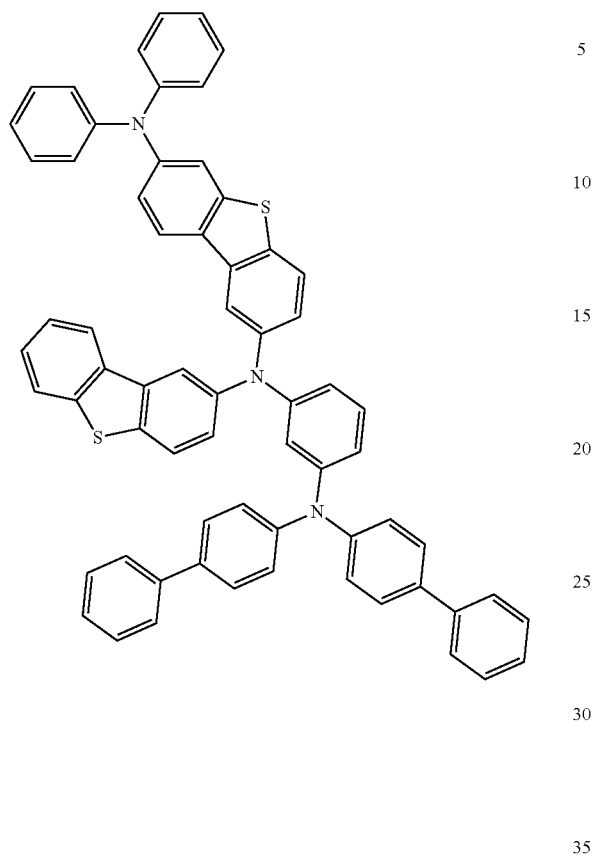
P-22
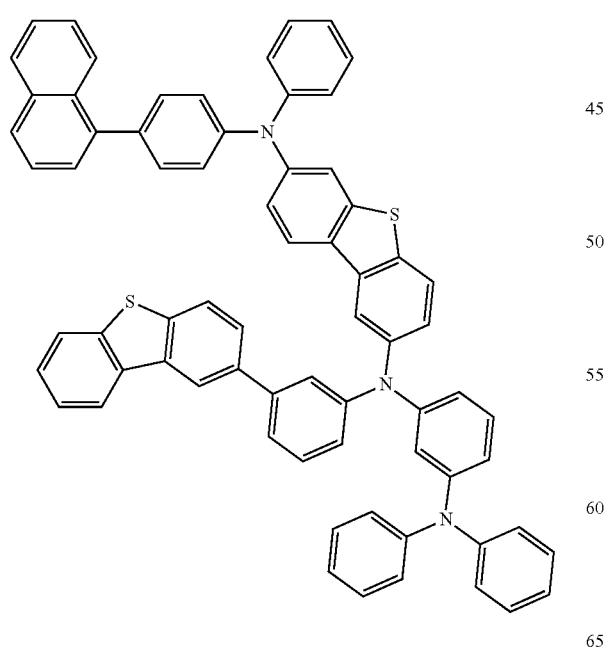
P-23
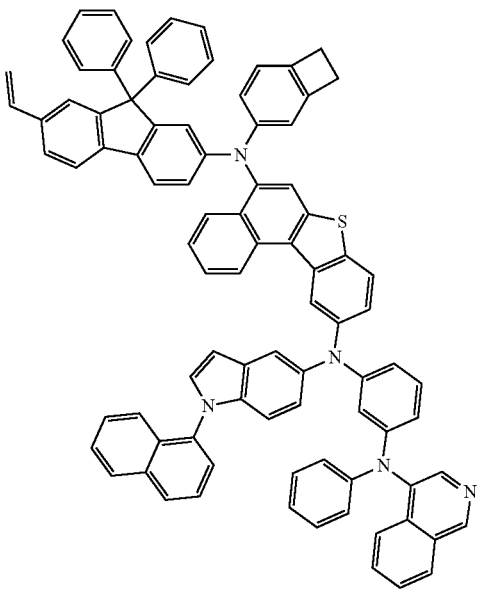
P-24
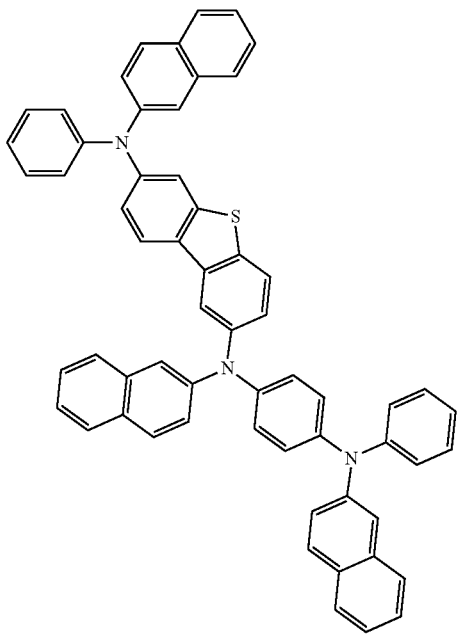

-continued
P-25
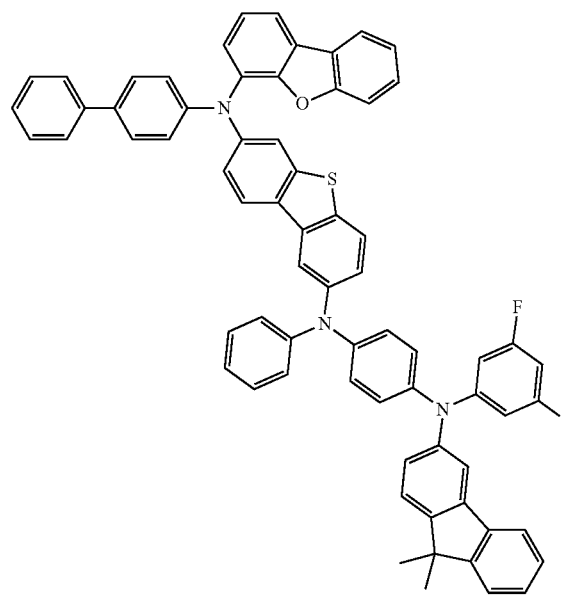
P-27
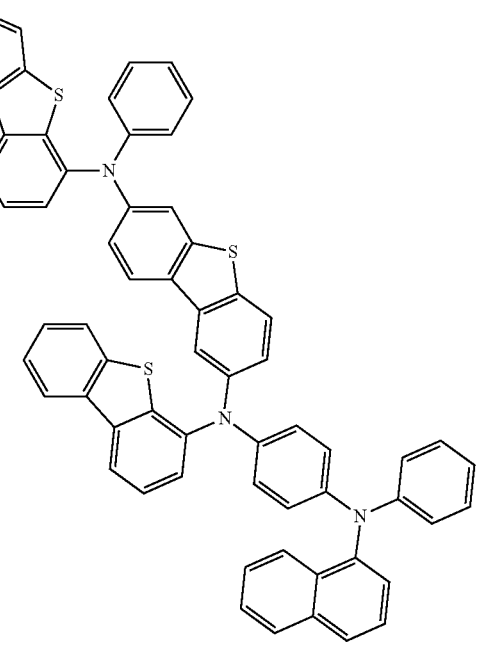
P-26
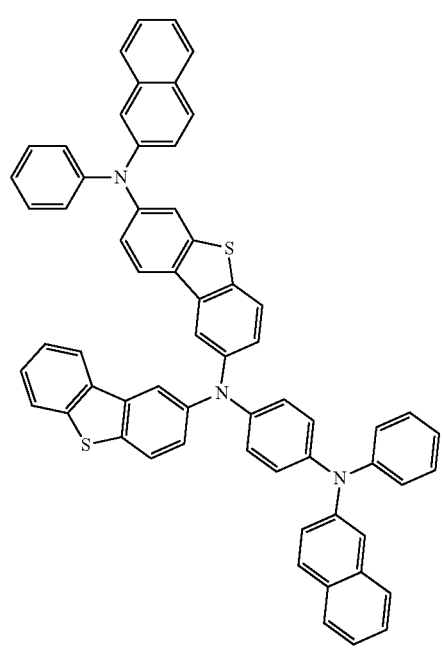
P-28
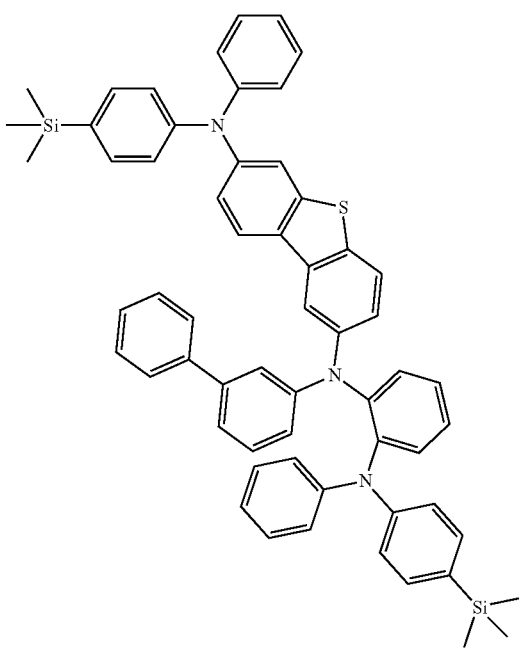

P-29
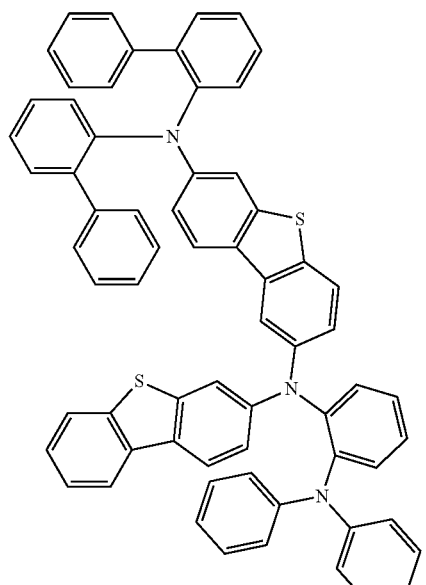
P-31
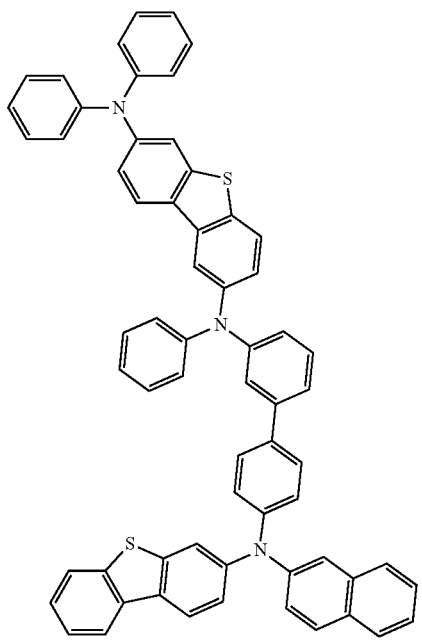
P-30
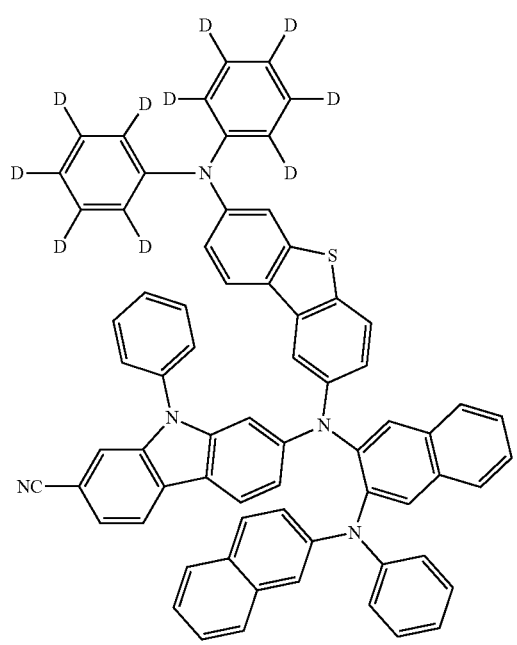
P-32
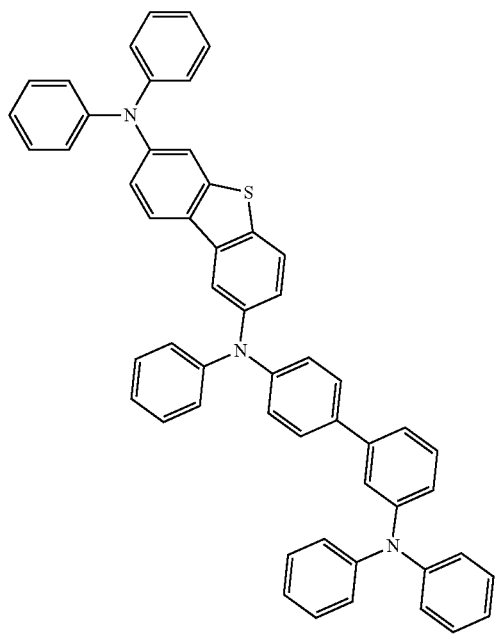

-continued
P-33
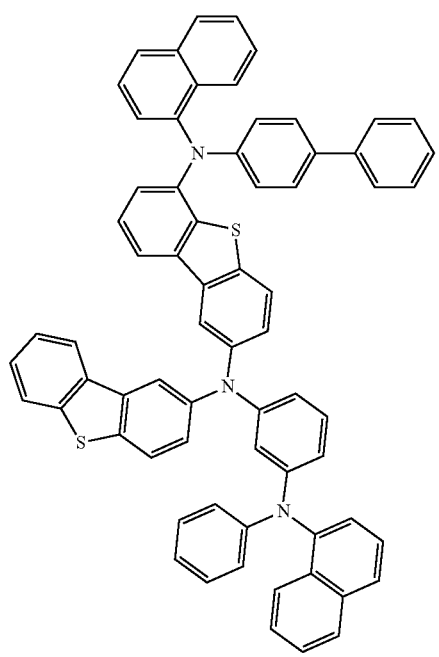
P-34
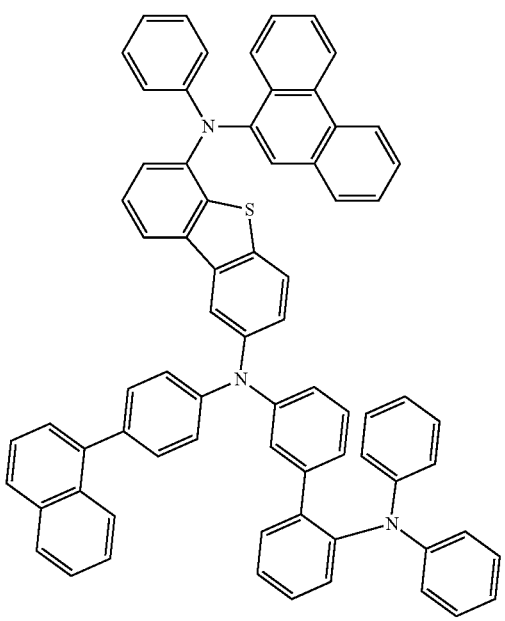
P-35
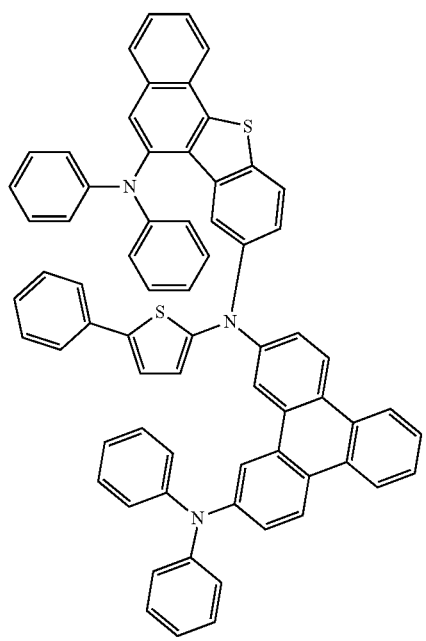
P-36
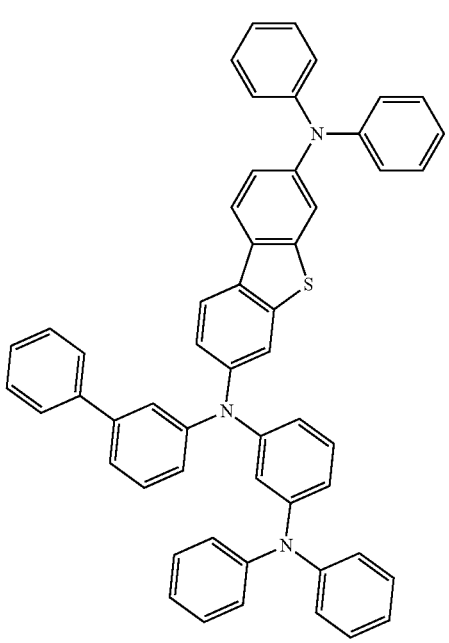

P-37
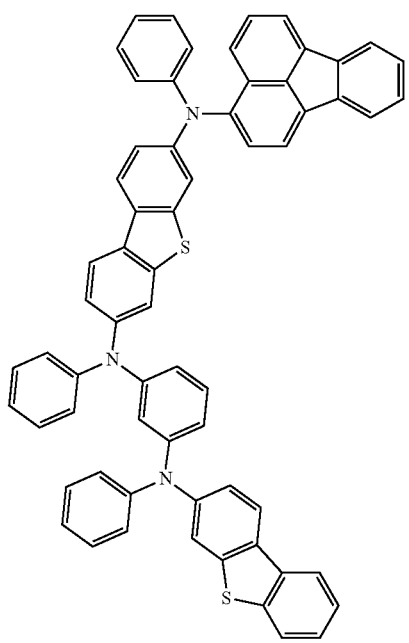
P-38
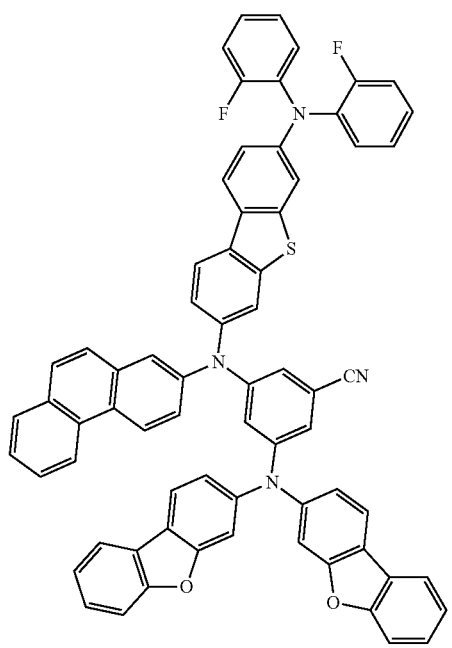
P-39
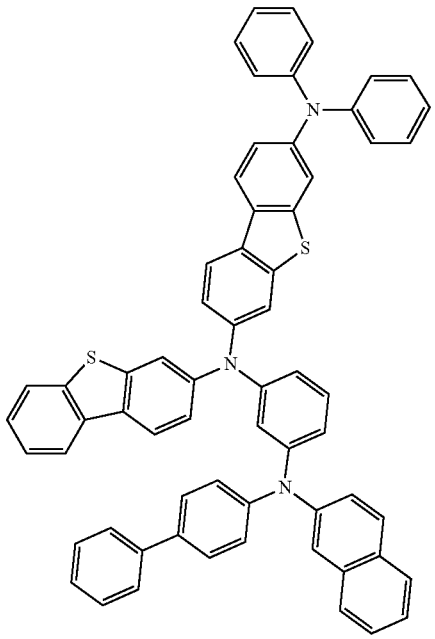
P-40
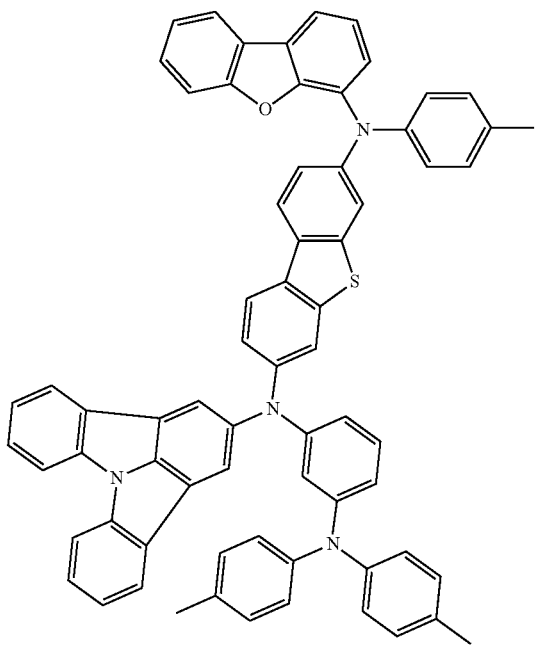

P-41
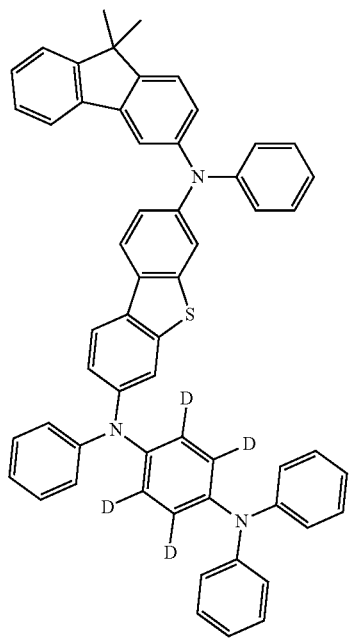
P-43
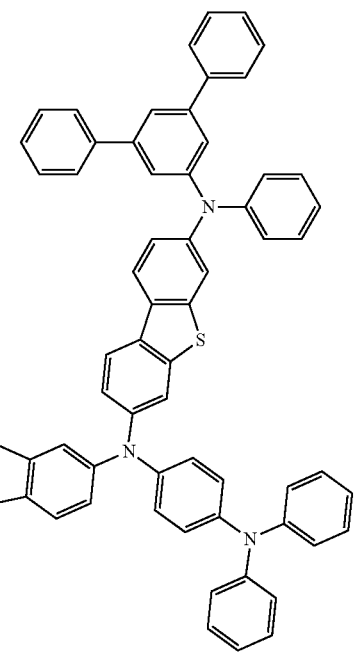
P-42
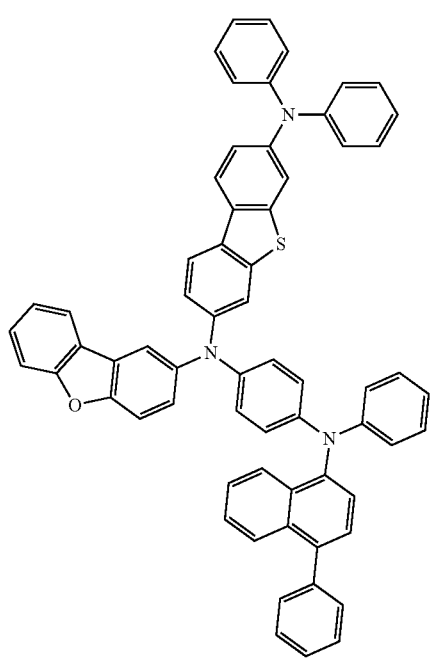
P-44
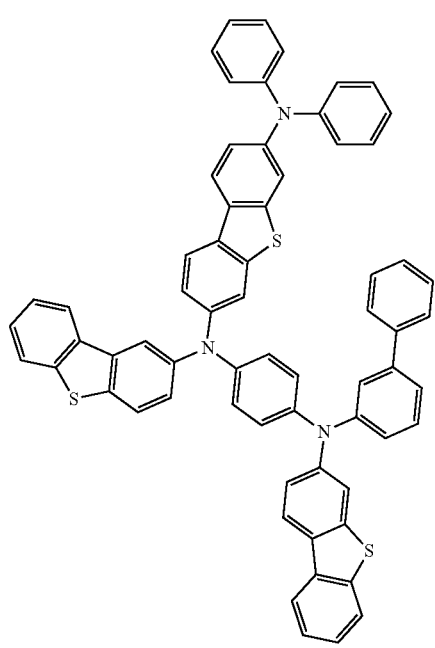

-continued
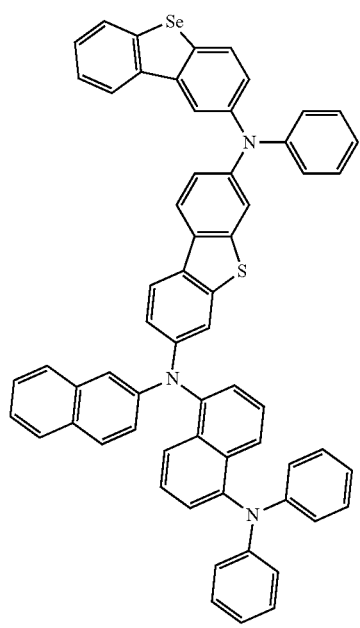
P-45
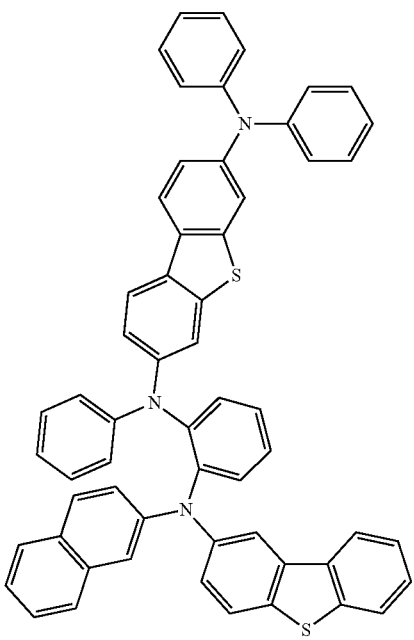
P-47
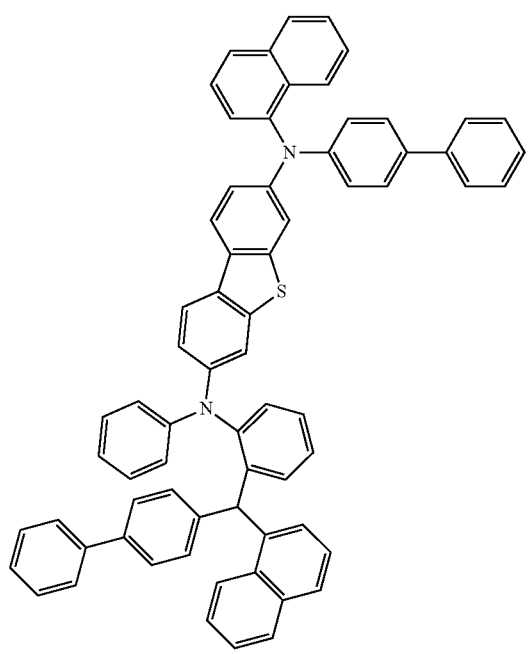
P-46
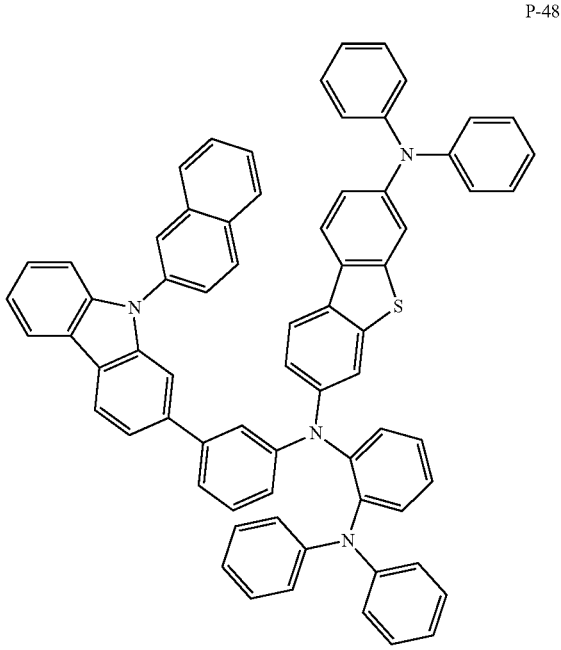
P-48

-continued
P-49
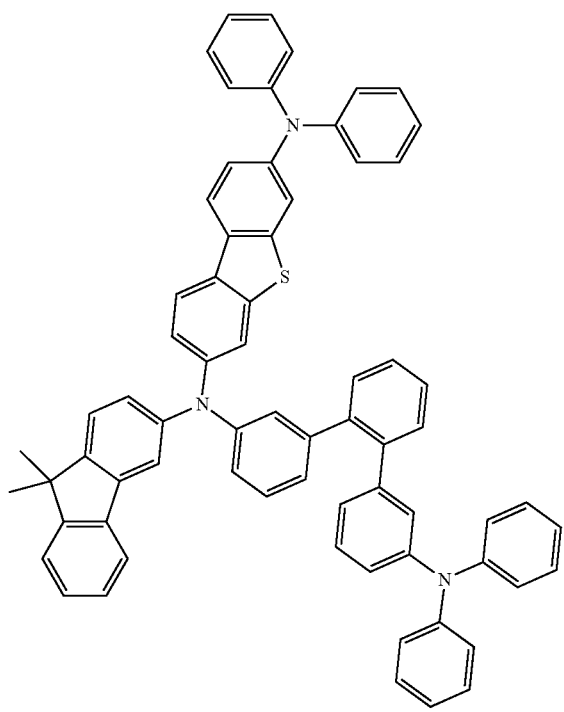
P-50
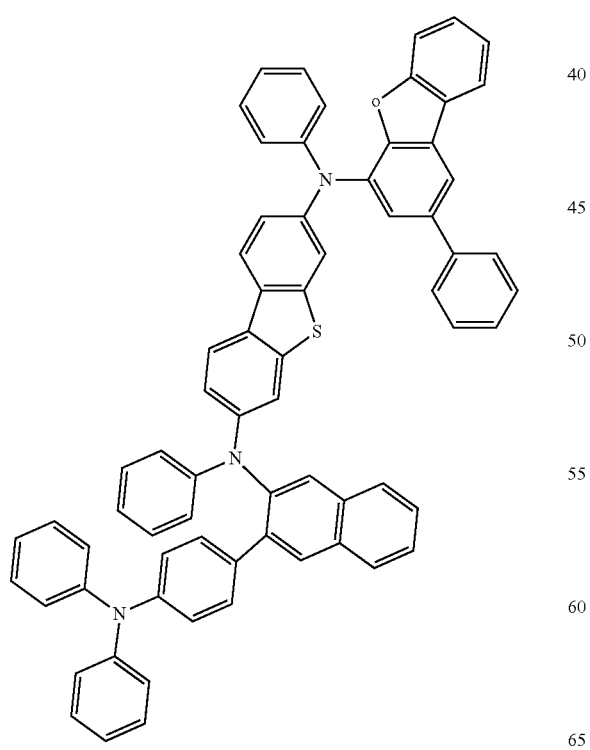
P-51
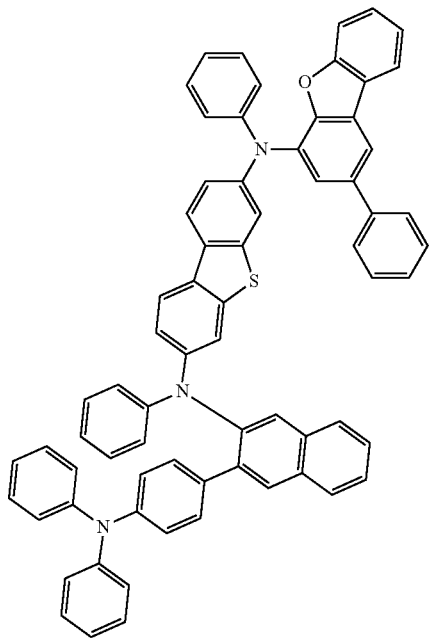
P-52
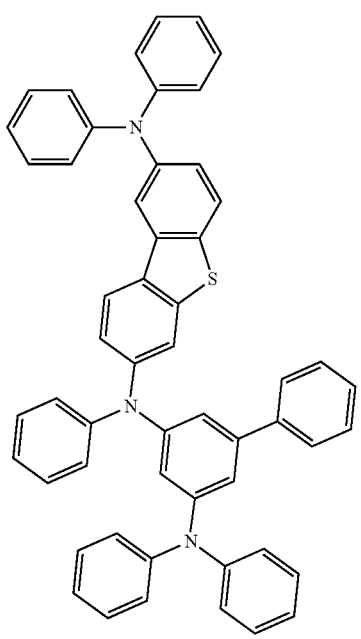

-continued
P-53
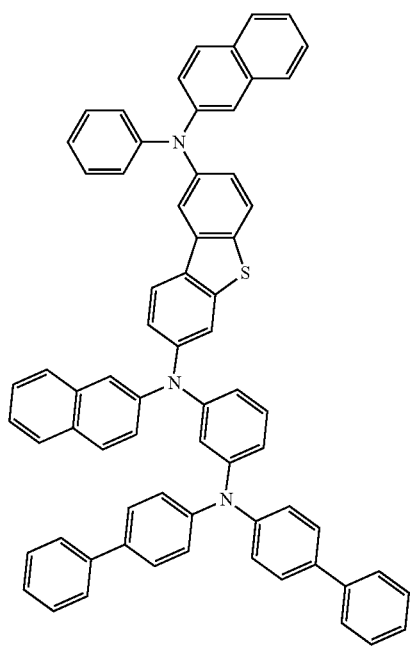
P-55
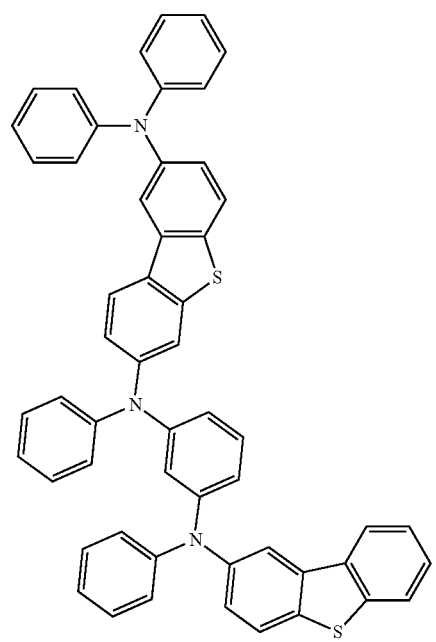
P-54
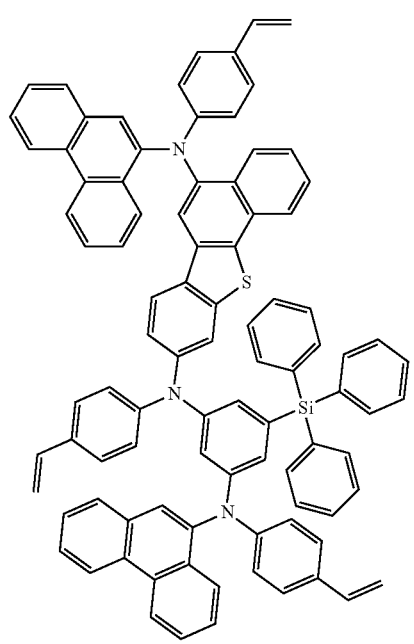
P-56
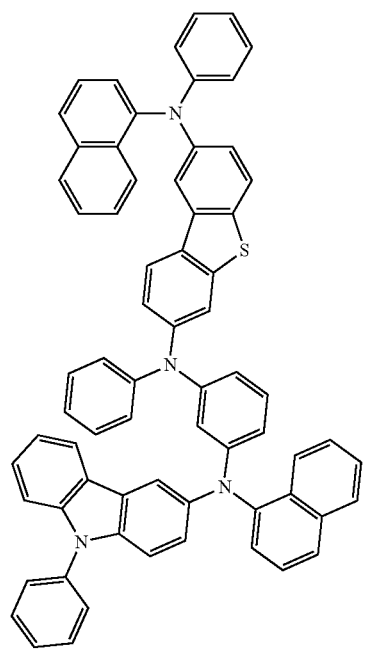

P-57
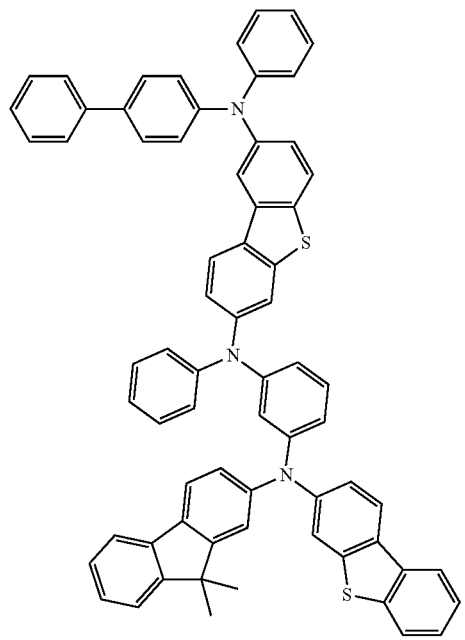
P-58
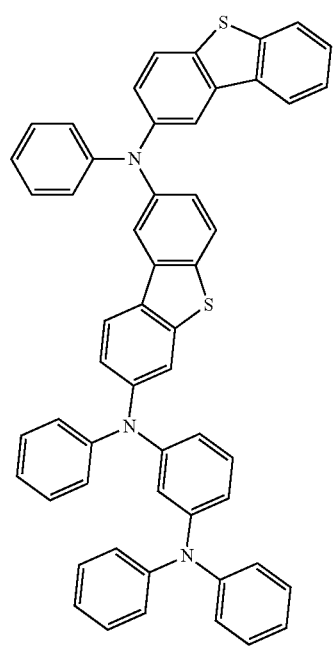
P-59
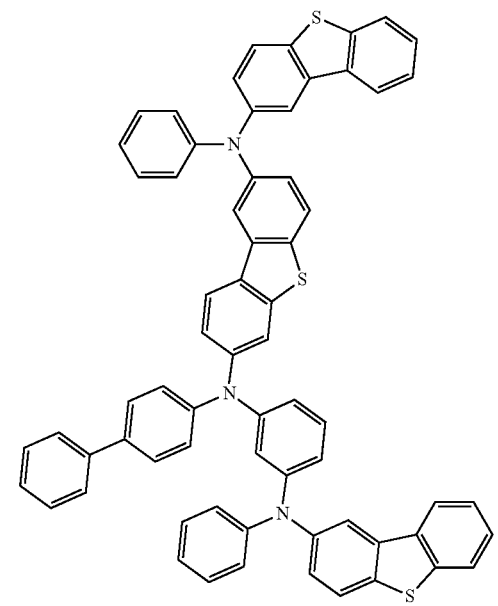
P-60
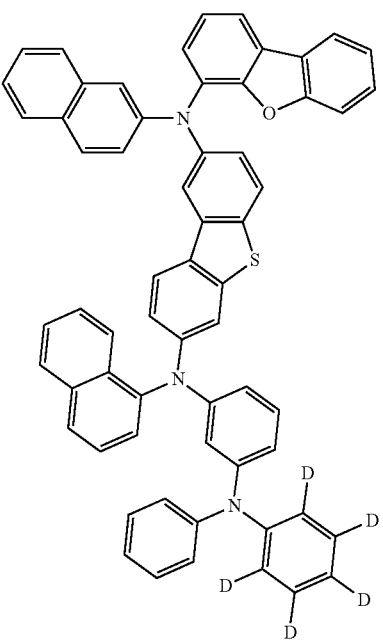

P-61
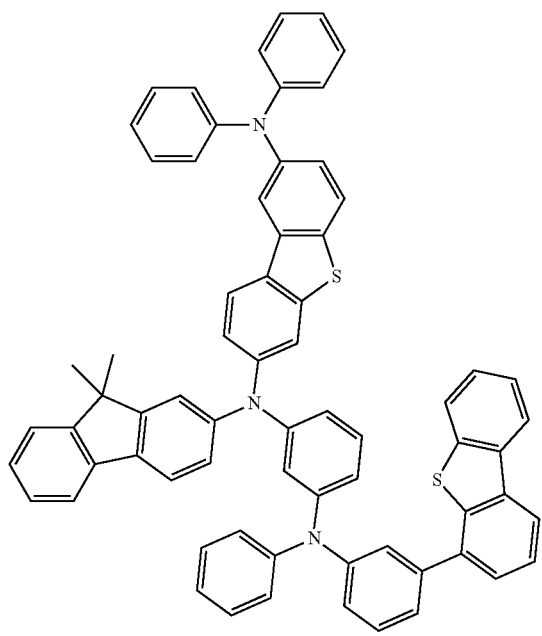
P-63
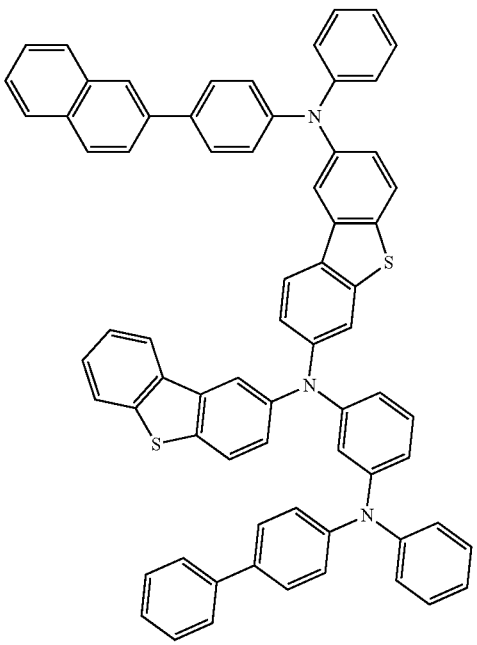
P-62
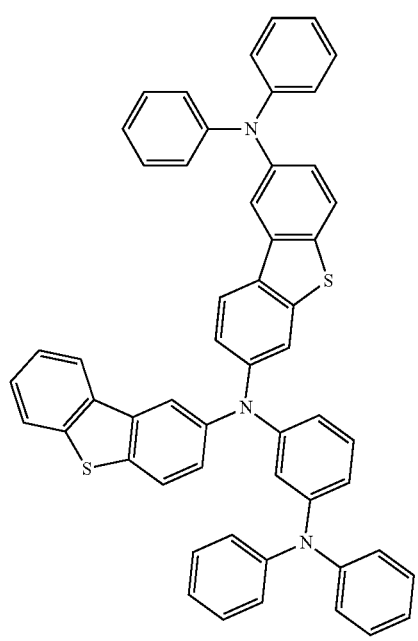
P-64
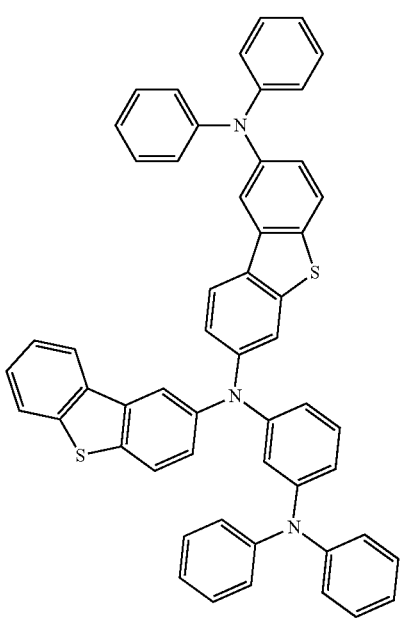

P-65
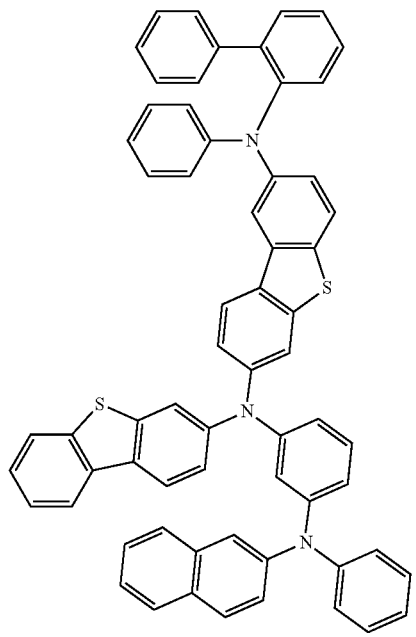
P-66
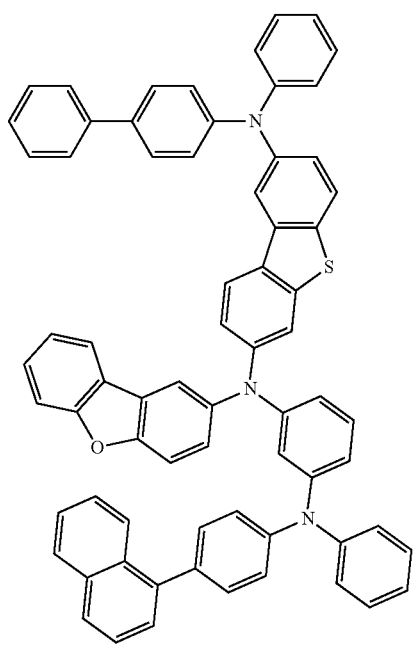
P-67
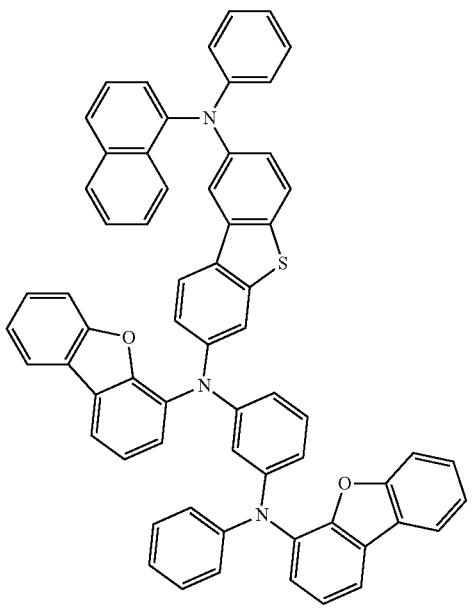
P-68
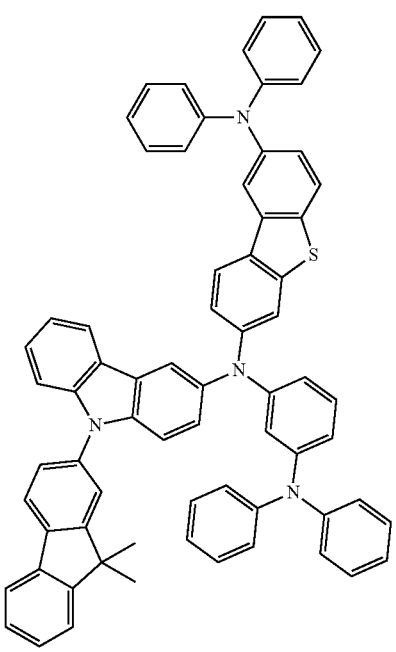

P-69
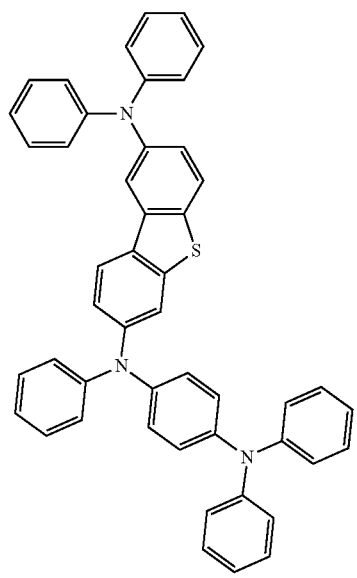
P-71
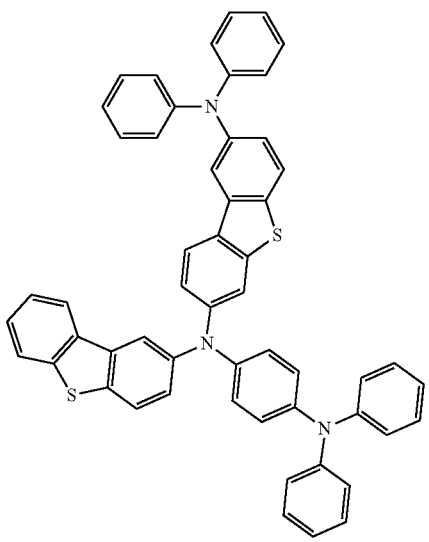
P-70
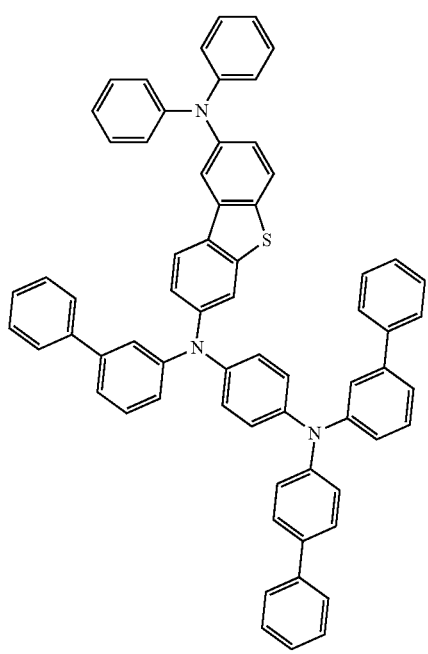
P-72
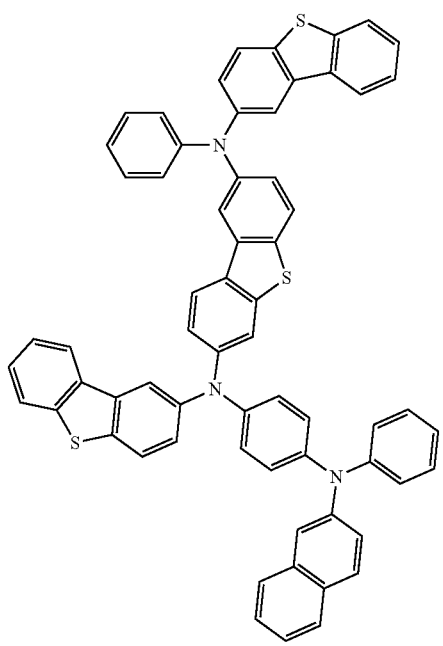

-continued
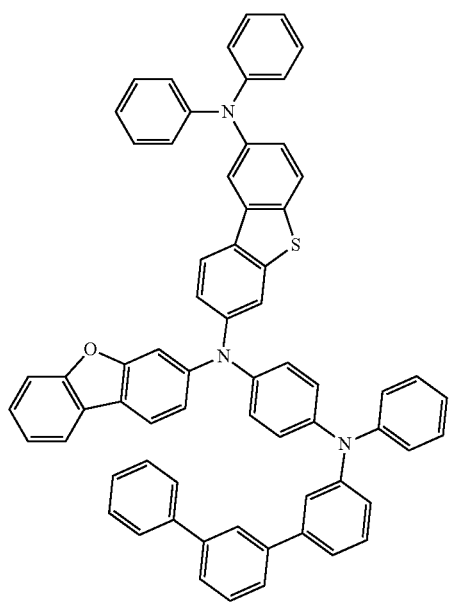
P-73
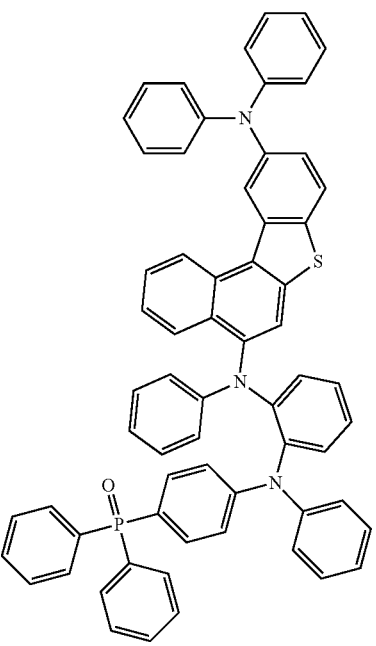
P-75
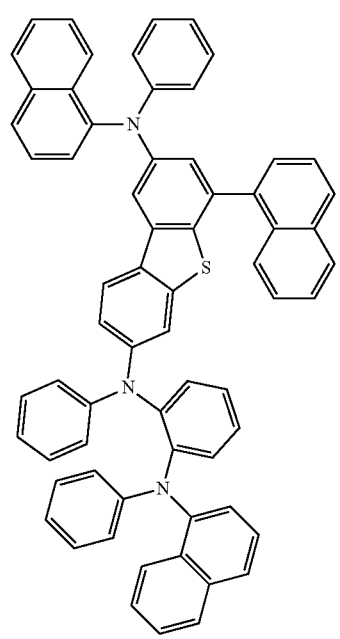
P-74
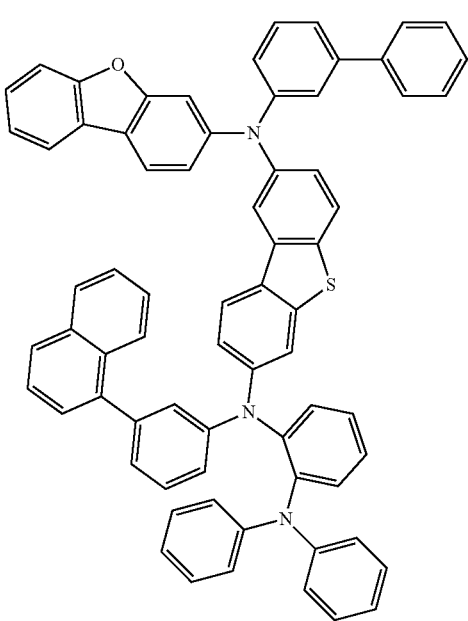
P-76

P-77
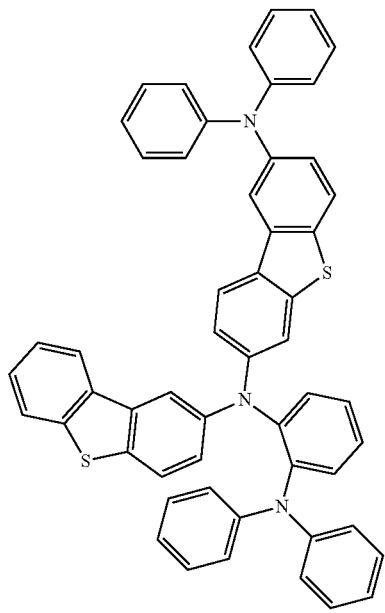
P-78
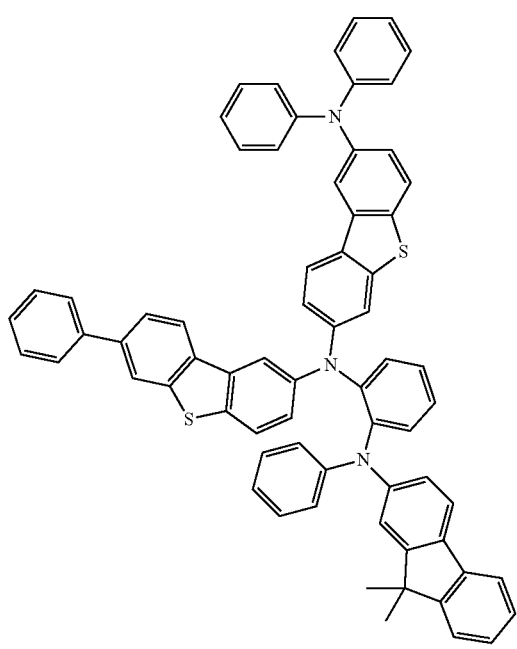
P-79
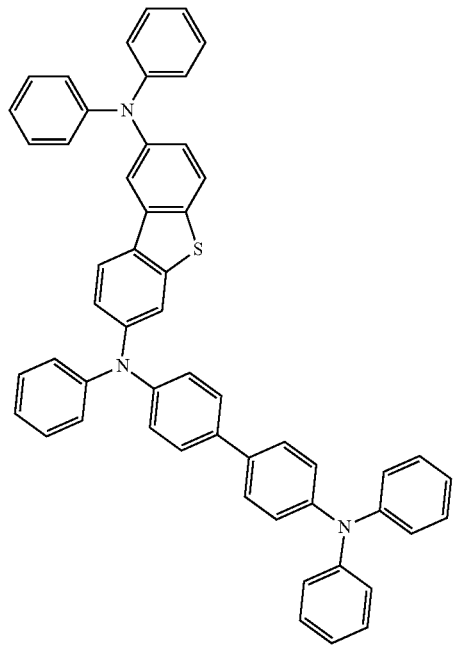
P-80
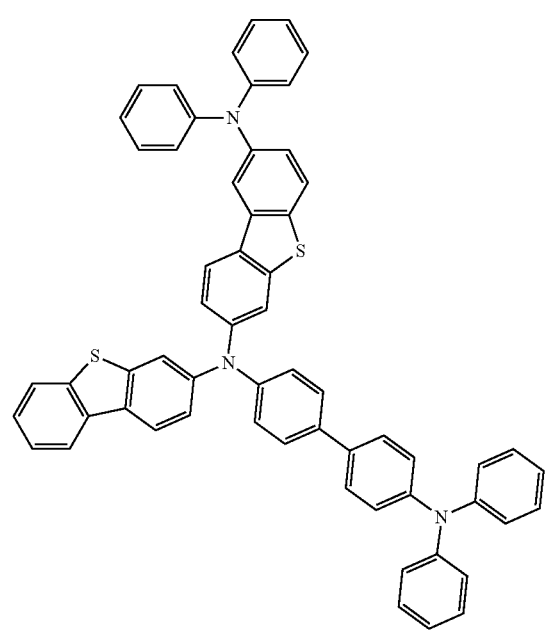

P-81
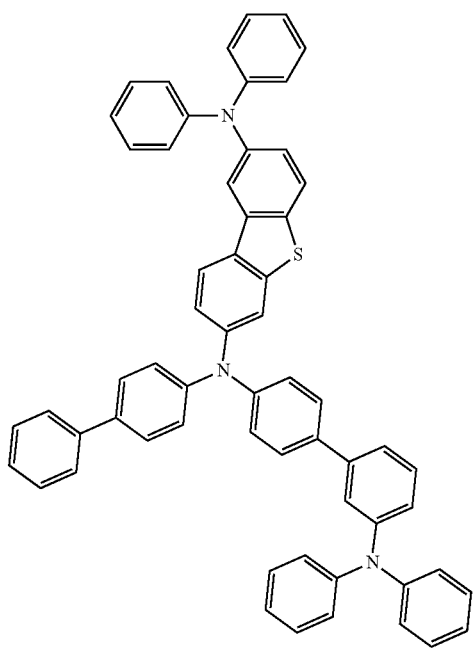
P-83
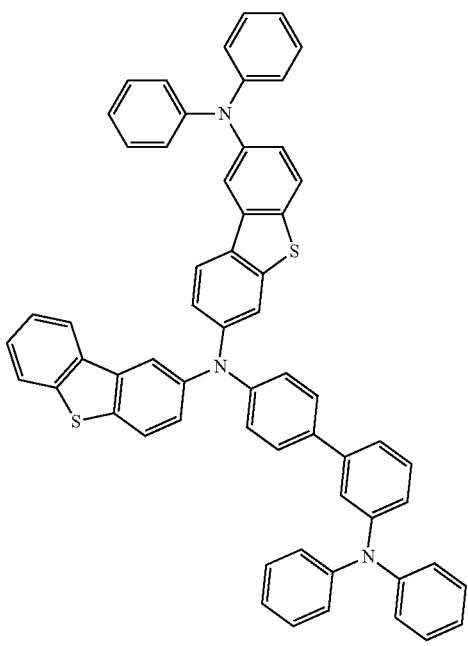
P-82
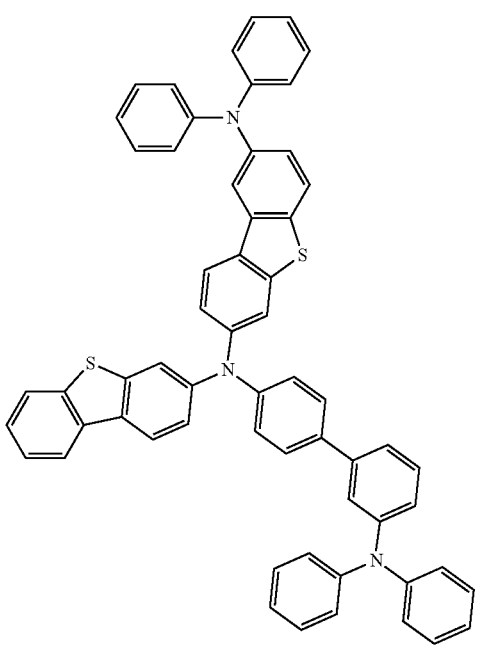
P-84
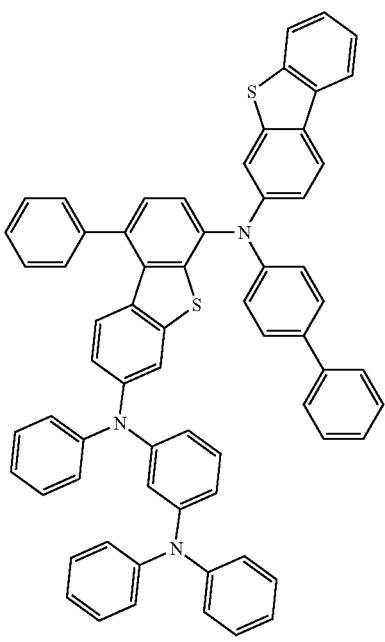

P-85
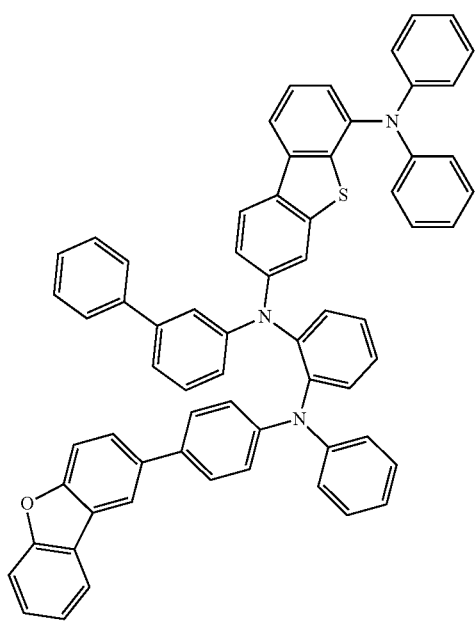
P-87
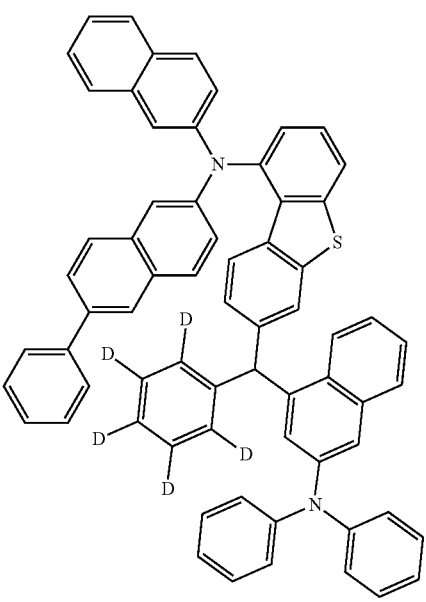
P-86
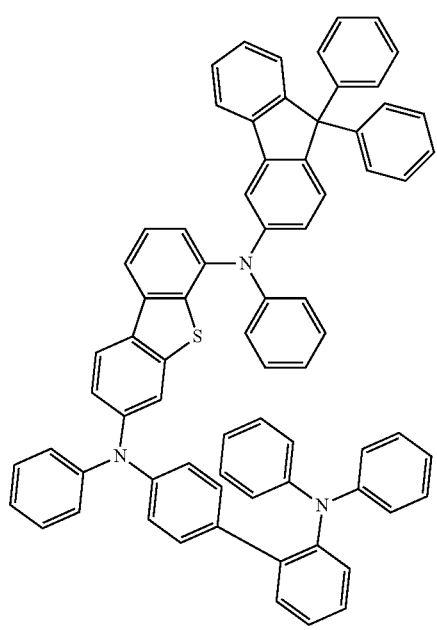
P-88
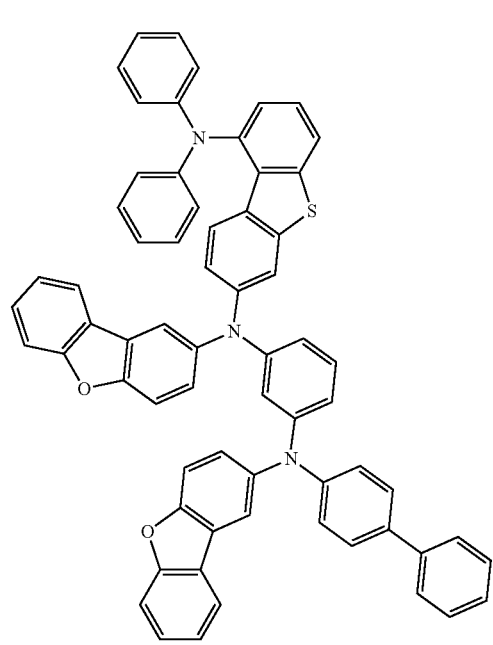

P-89
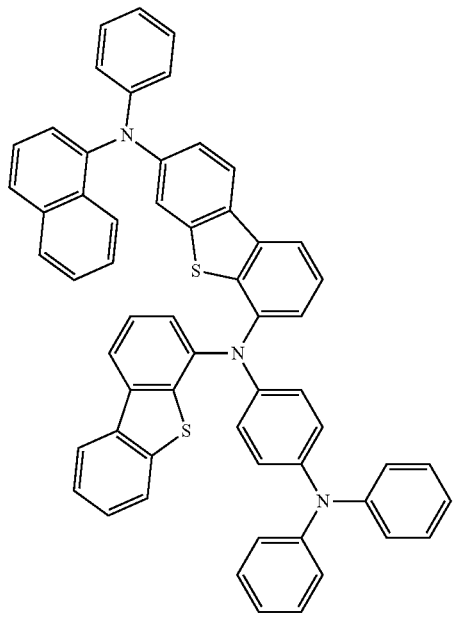
P-90
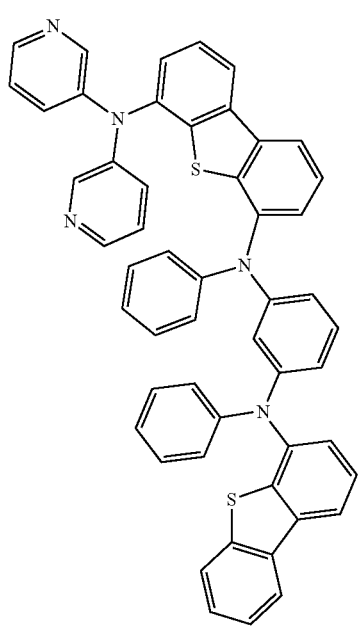
P-91
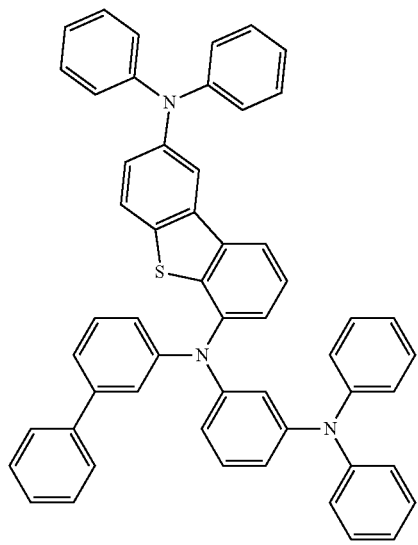
P-92
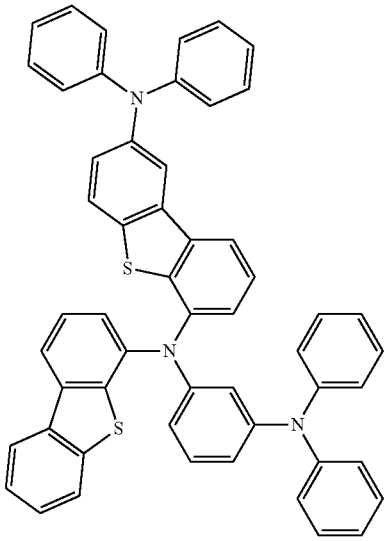

-continued
P-93
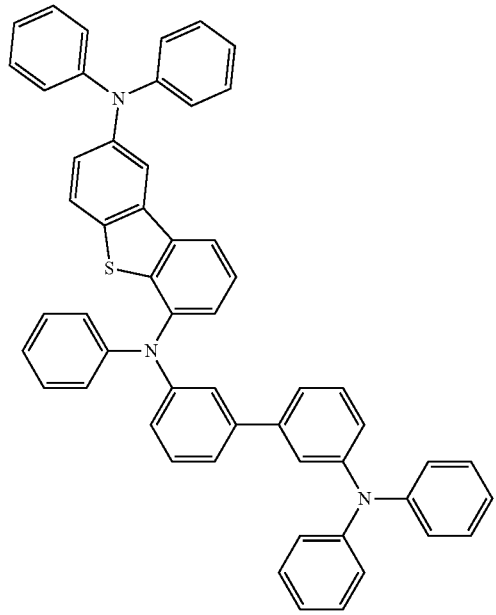
P-94
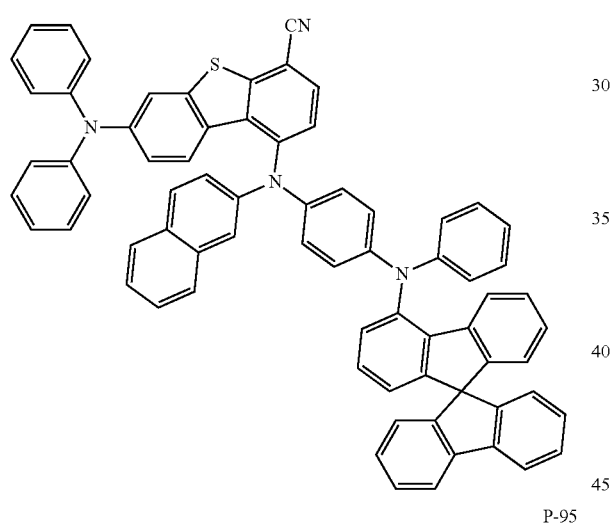
P-95
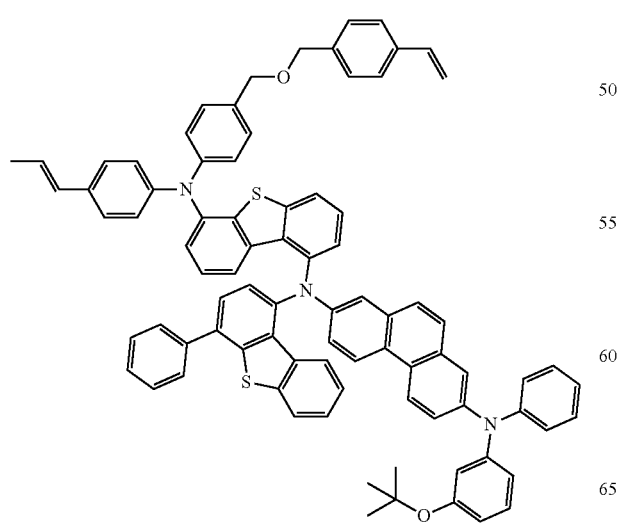
-continued
P-96
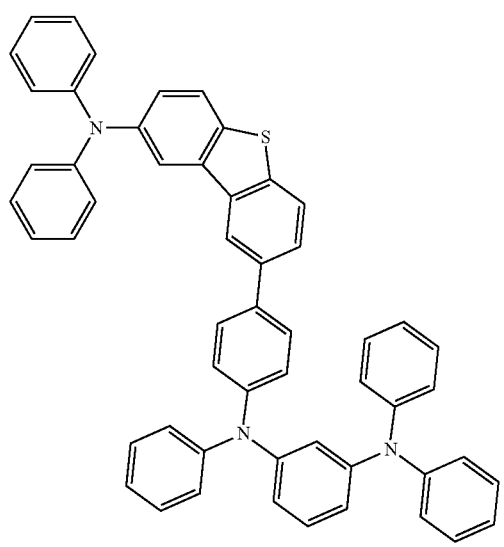
P-97
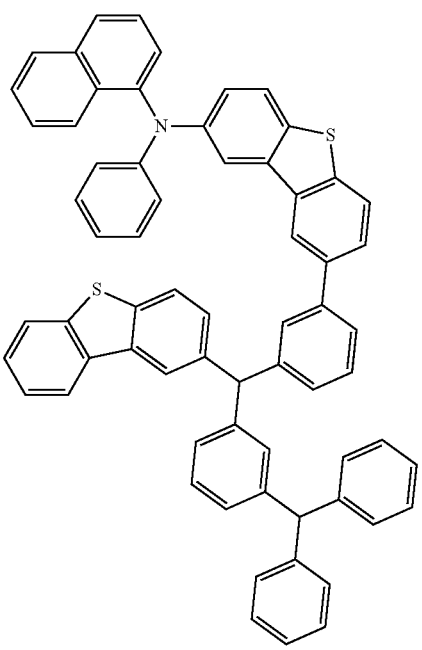

P-98
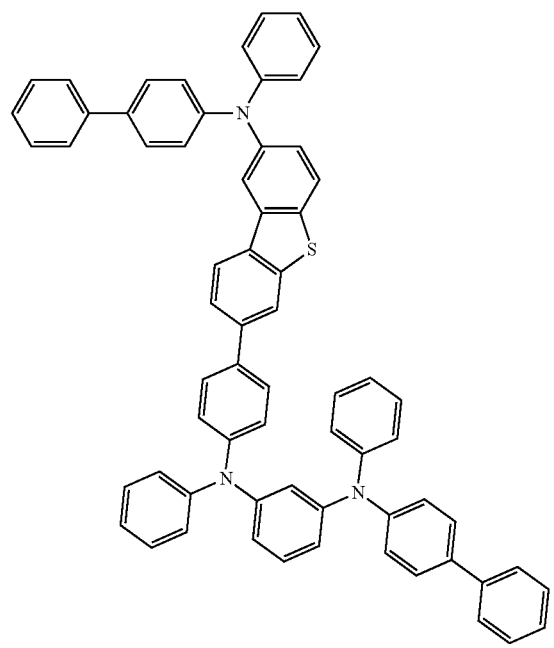
P-100
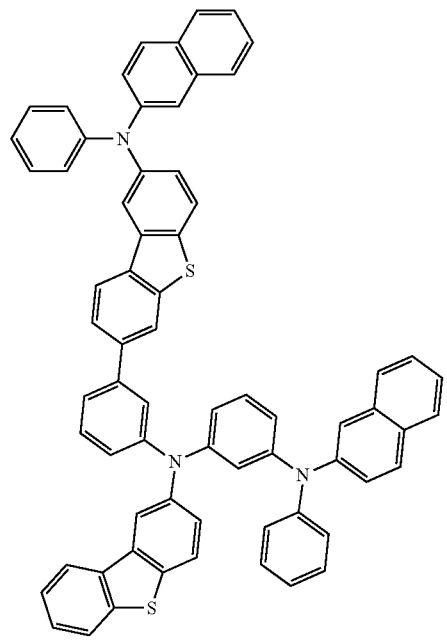
P-99
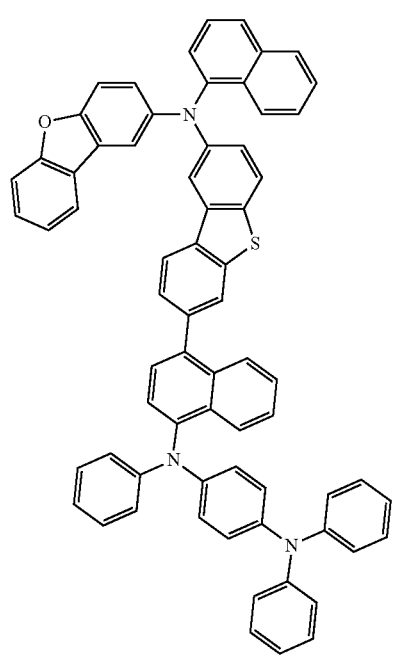
P-101
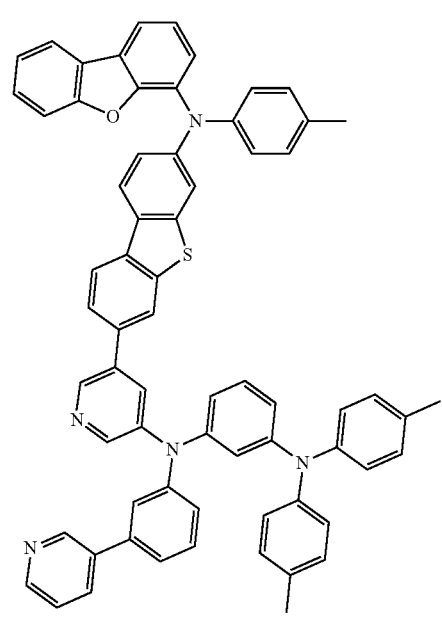

P-102
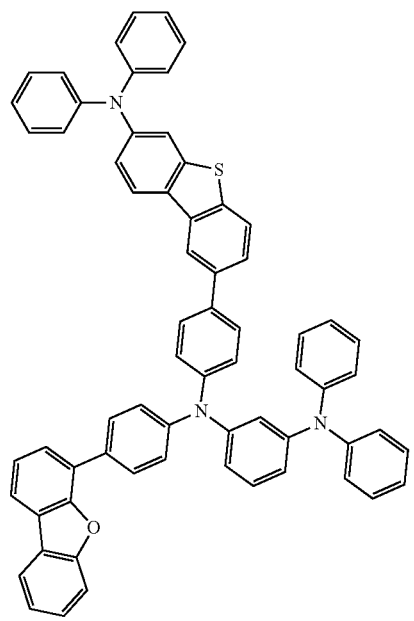
P-103
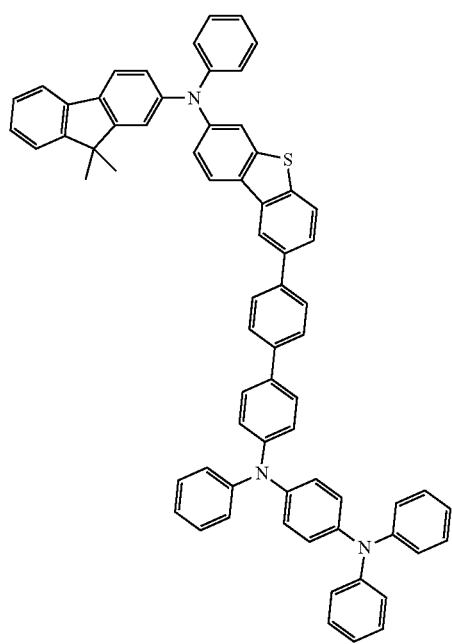
P-104
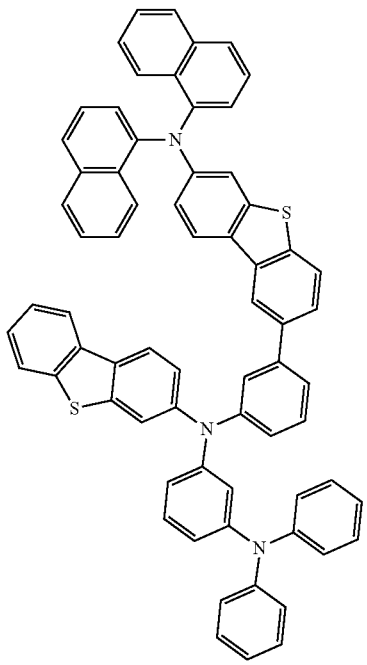
P-105
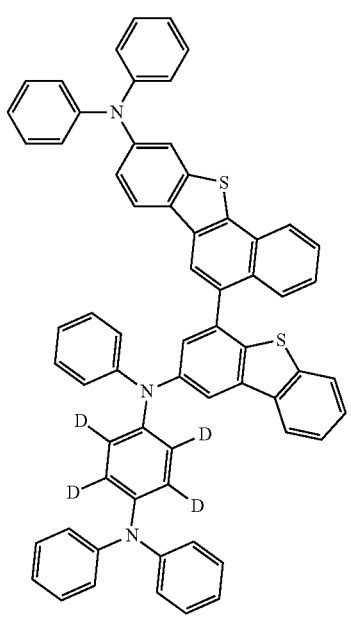

-continued
P-106
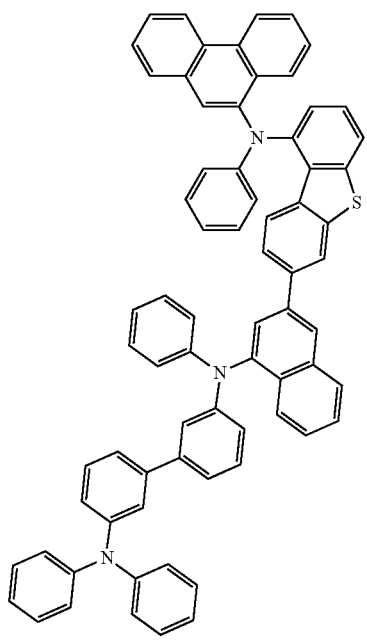
P-107
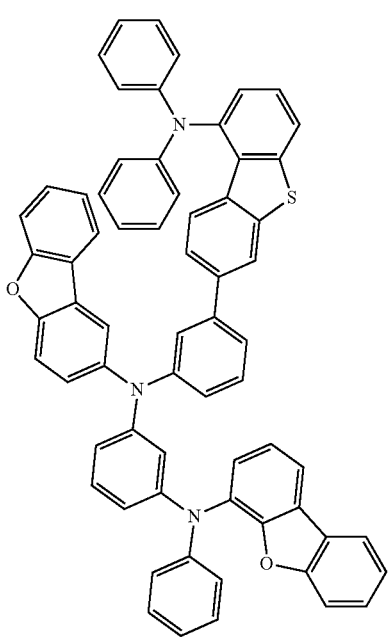
-continued
P-108
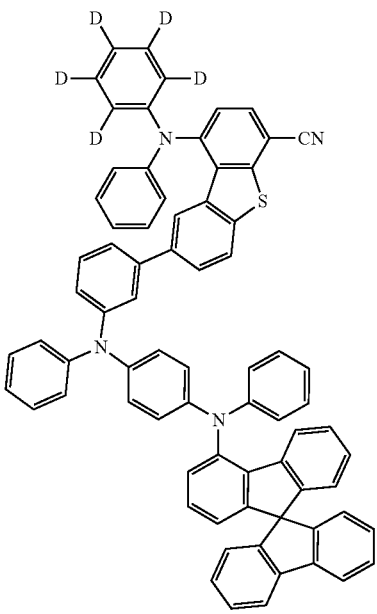
P-109
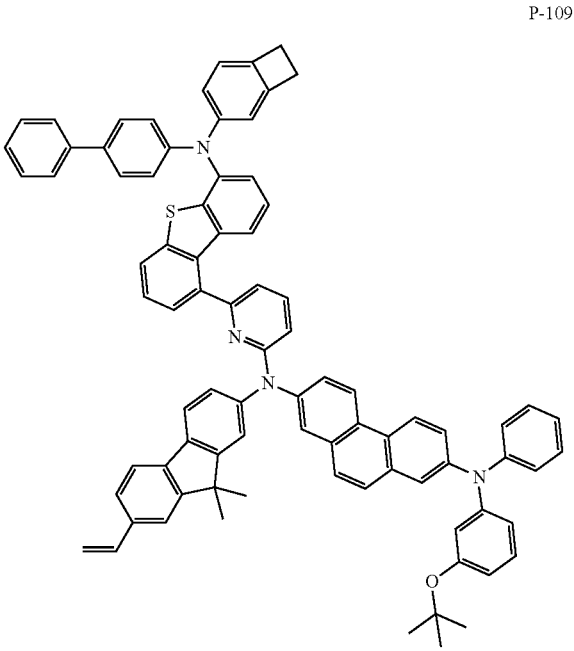

P-110
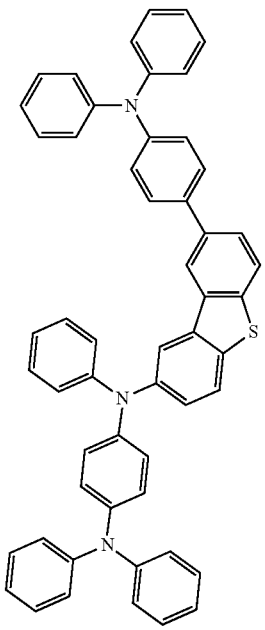
P-112
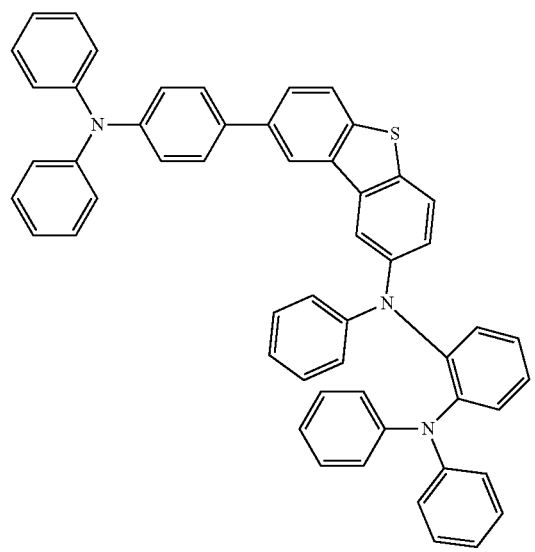
P-111
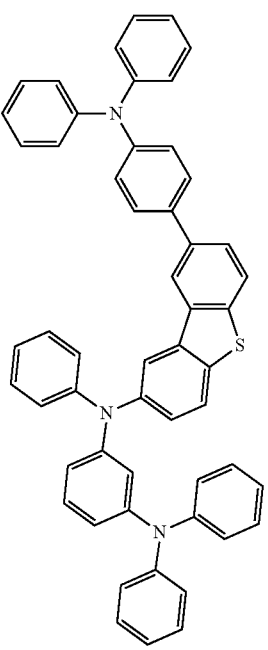
P-113
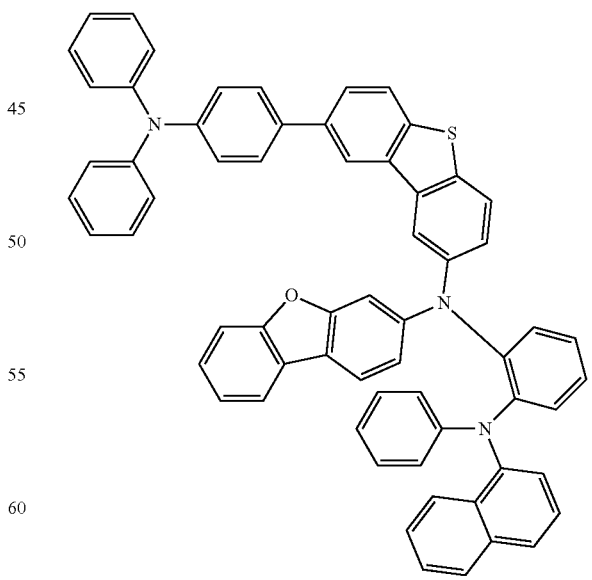

P-114
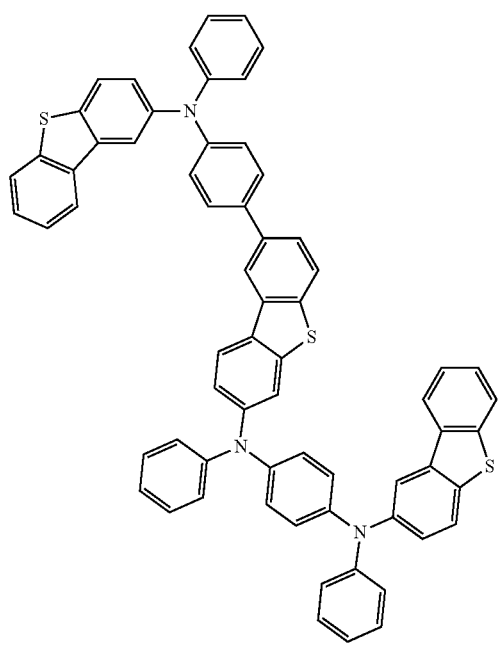
P-116
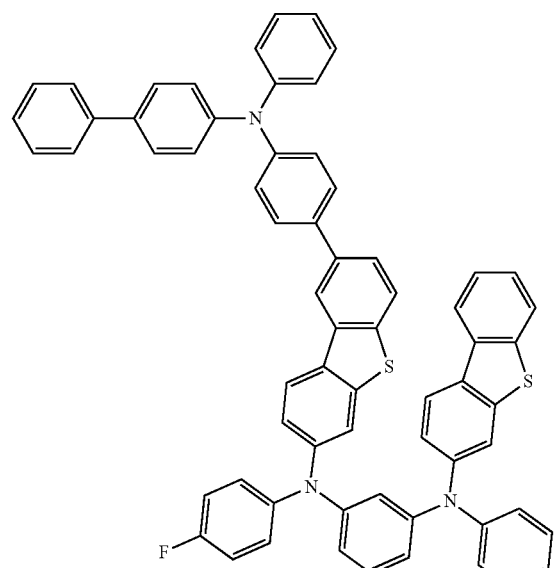
P-115
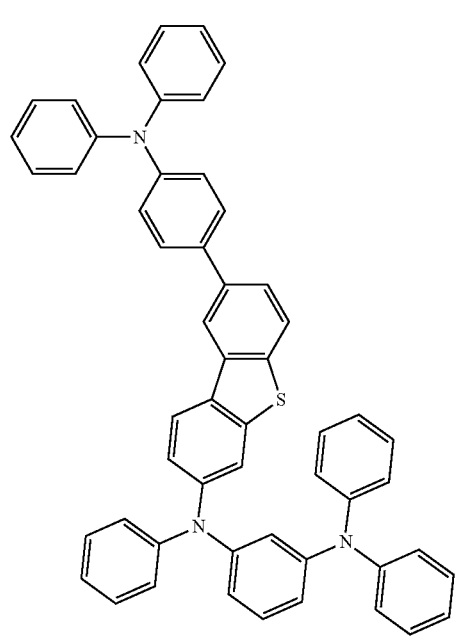
P-117
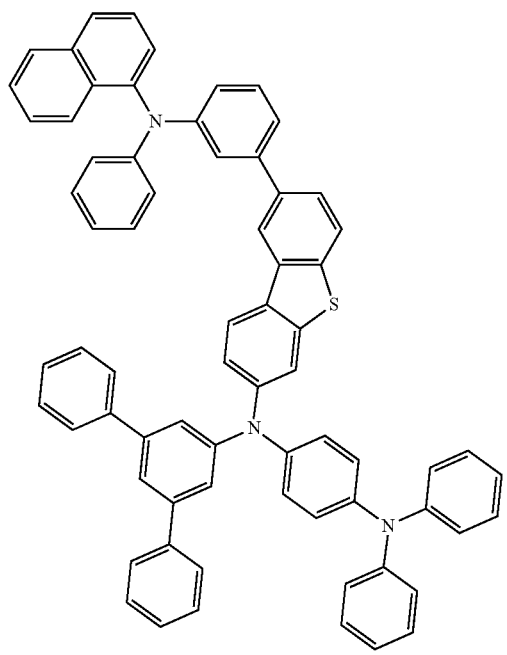

-continued
P-118
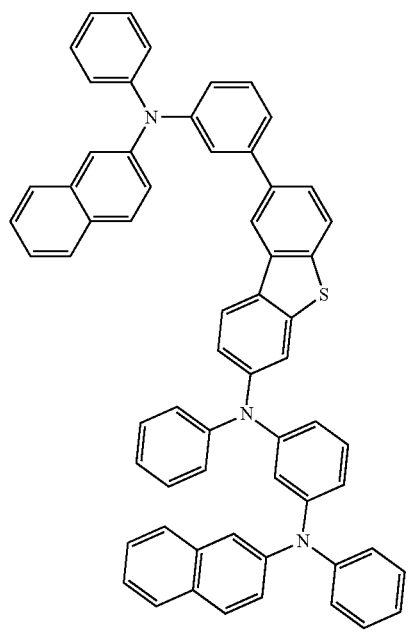
P-120
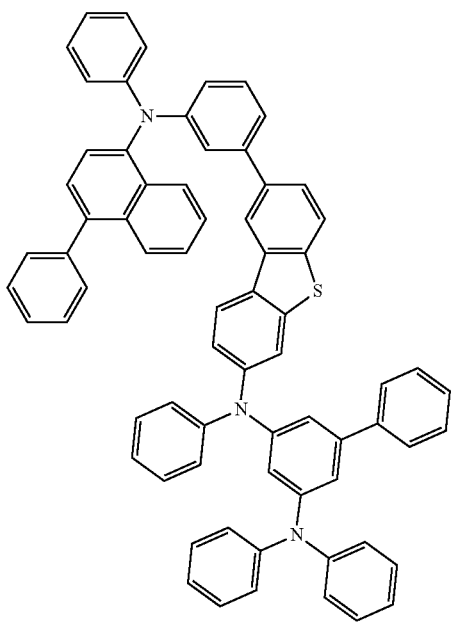
P-119
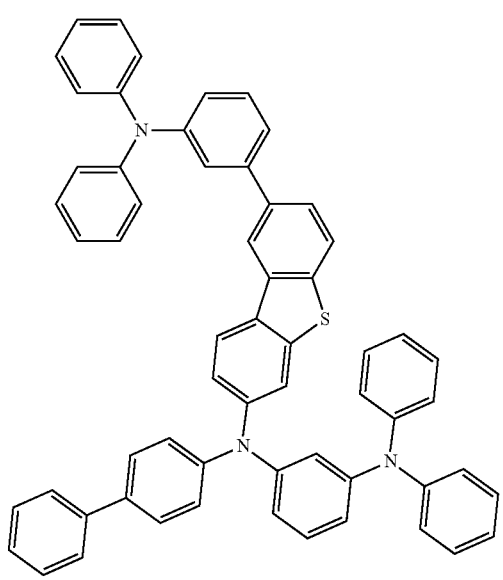
P-121
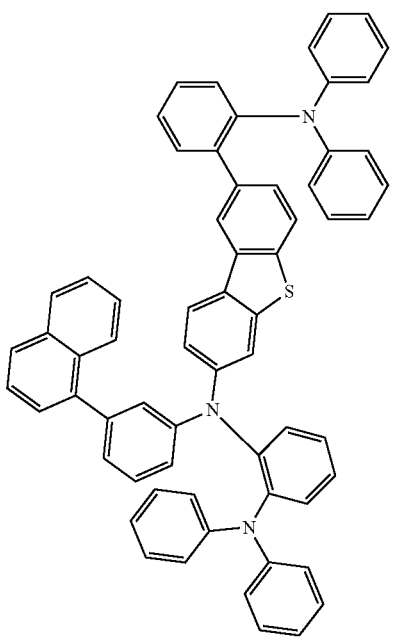

P-122
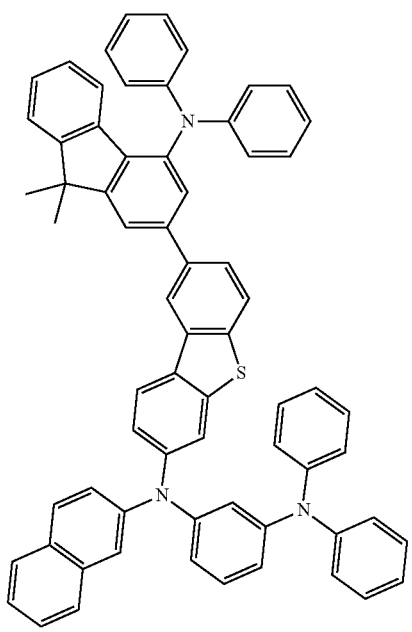
P-123
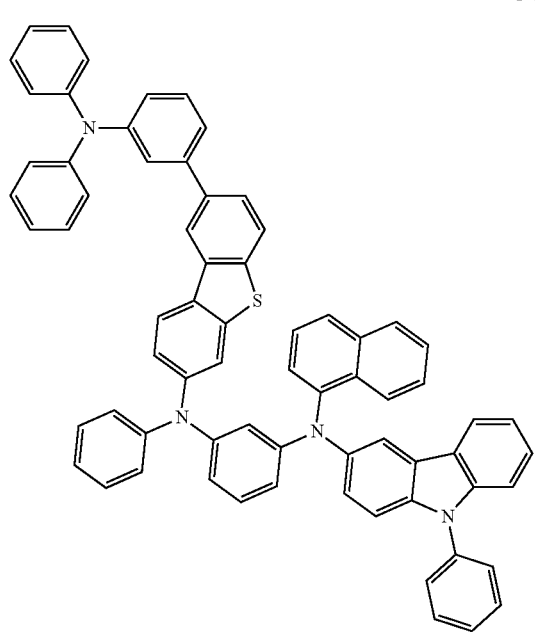
P-124
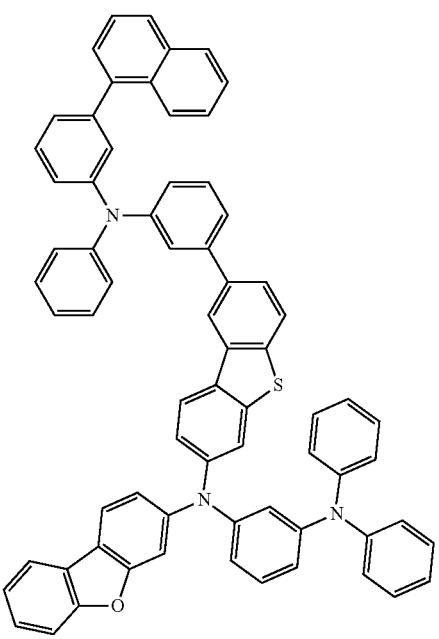
P-125
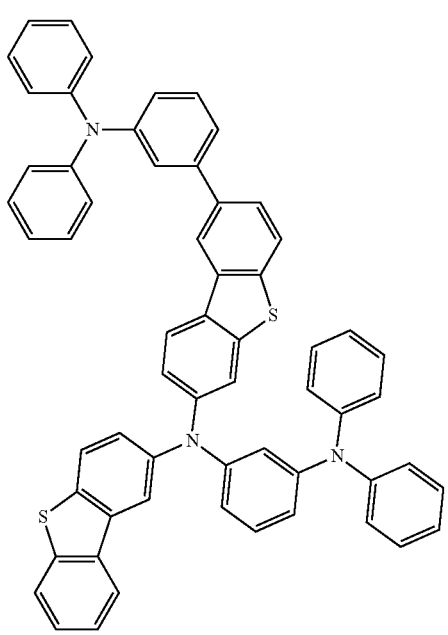

P-126
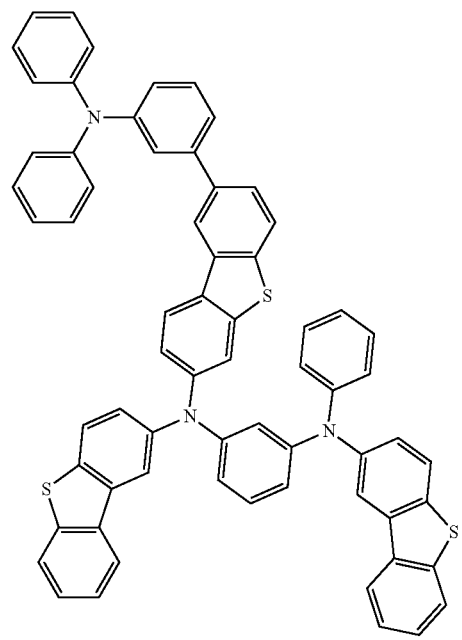
P-128
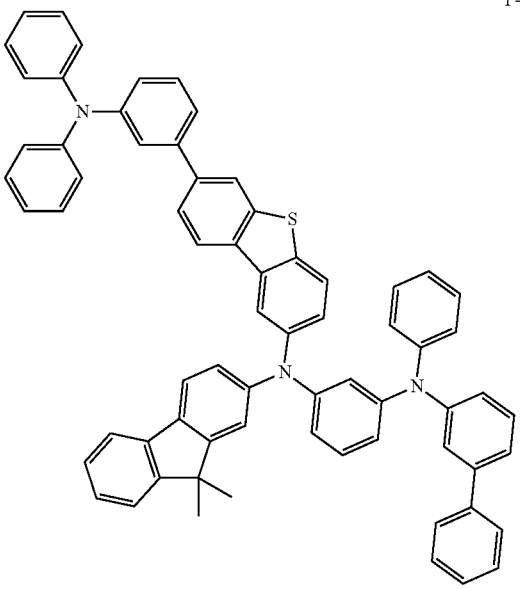
P-127
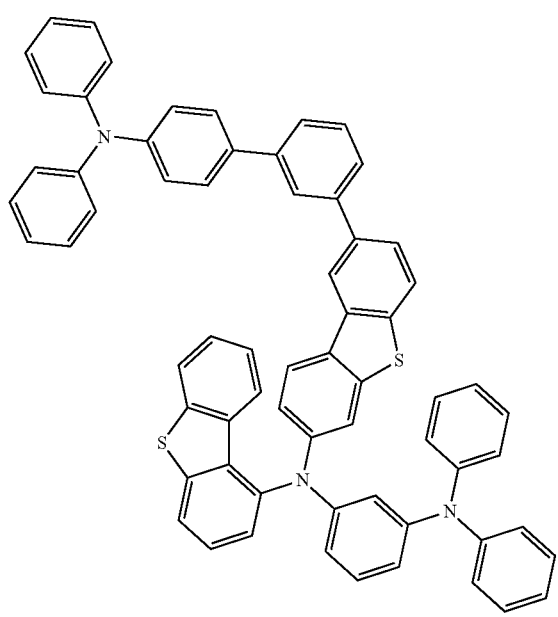
P-129
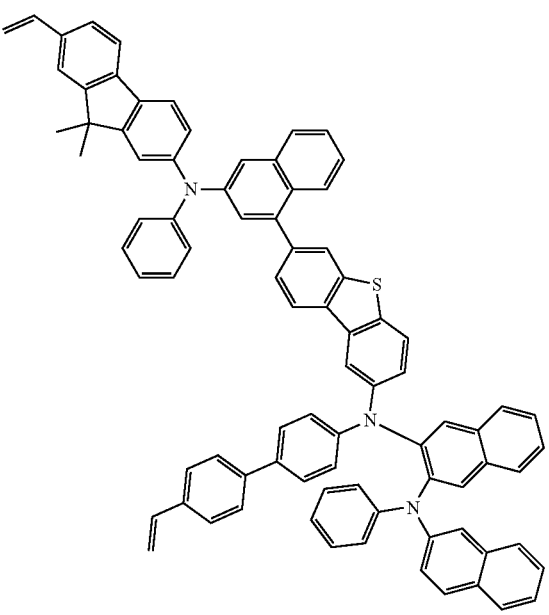

P-130
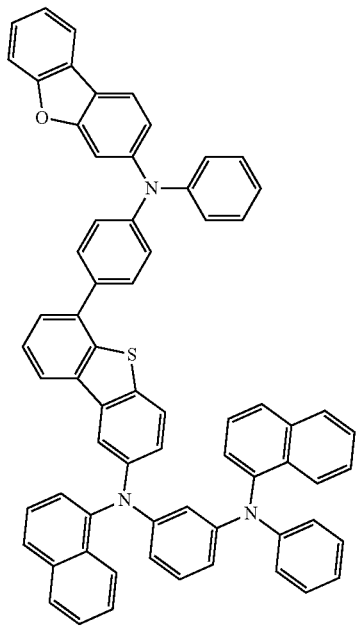
P-131
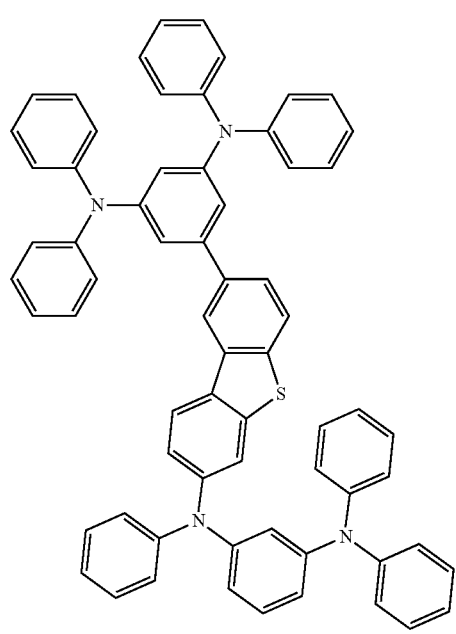
P-132
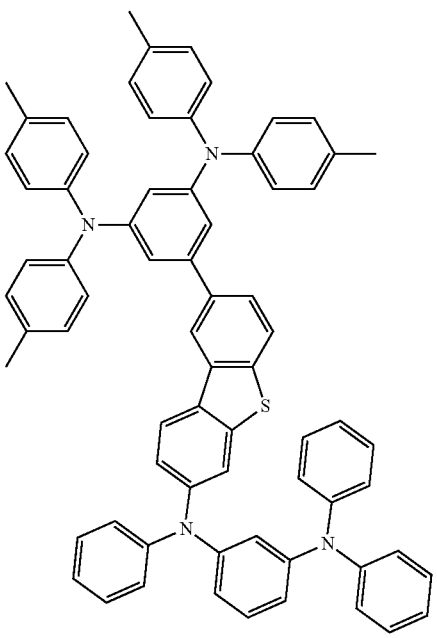
P-133
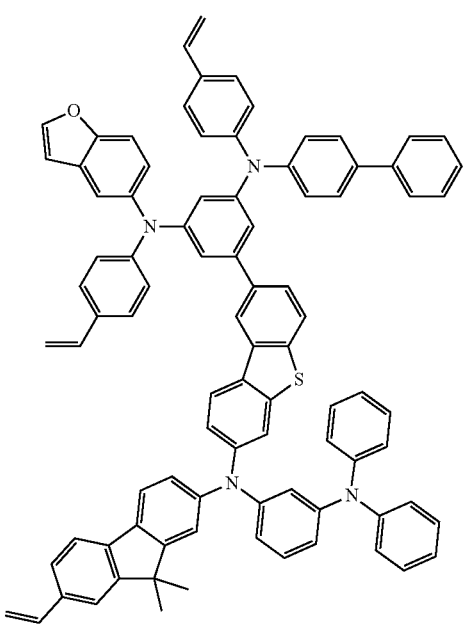

-continued

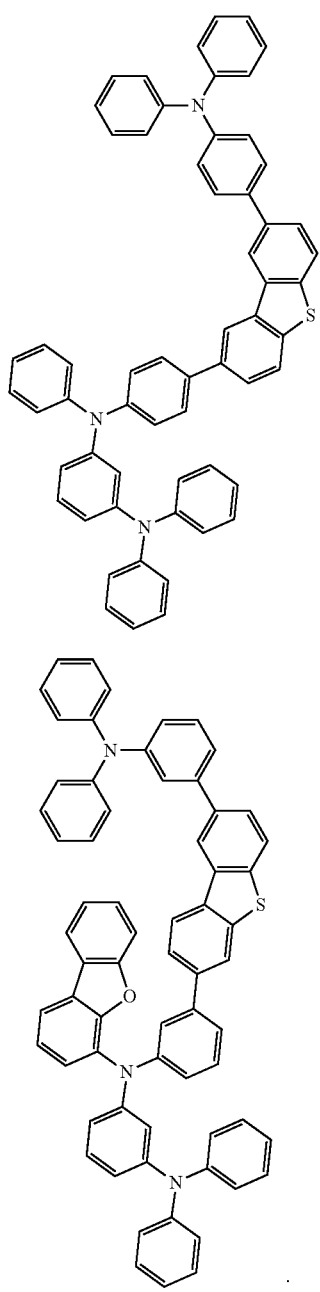

8. An organic electric element comprising a first electrode, a second electrode, and an organic material layer formed between the first electrode and the second electrode, wherein the organic material layer comprises the compound of claim 1.

9. The organic electric element of claim 8, wherein the organic material layer comprises at least one of a hole injection layer, a hole transport layer, an emission-auxiliary layer, an light emitting layer, an electron transport-auxiliary layer, an electron transport layer and an electron injection layer, and at least one of the hole injection layer, the hole transport layer, the emission-auxiliary layer, the light emitting layer, the electron transport-auxiliary layer, the electron transport layer and the electron injection layer contains the compound as a single compound or a mixture of two or more different kinds.

10. The organic electric element of claim 9, wherein the organic layer comprises the light emitting layer and the emission-auxiliary layer, and the light emitting layer includes a phosphorescent red light emitting material, and the compound is contained in the emission-auxiliary layer.

11. The organic electric element of claim 8, wherein the organic material layer is formed by any one of the processes of spin coating, nozzle printing, inkjet printing, slot coating, dip coating and roll-to-roll.

12. An electronic device comprising a display device and a control unit for driving the display device, wherein the display device comprises the organic electric element of claim 8.

13. The electronic device of claim 12, wherein the organic electric element comprises at least one of an organic light emitting diode, an organic solar cell, an organic photo conductor, an organic transistor, and an element for monochromatic or white illumination.

* * * * *